(12) United States Patent
Holder et al.

(10) Patent No.: US 10,913,987 B2
(45) Date of Patent: Feb. 9, 2021

(54) BACTERIA IDENTIFICATION AND ANTIBIOTIC SUSCEPTIBILITY PROFILING DEVICE

(71) Applicant: The Charles Stark Draper Laboratory, Inc., Cambridge, MA (US)

(72) Inventors: Jason W. Holder, Swampscott, MA (US); Jason O. Fiering, Boston, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 51 days.

(21) Appl. No.: 15/470,750

(22) Filed: Mar. 27, 2017

(65) Prior Publication Data

US 2017/0298456 A1 Oct. 19, 2017

Related U.S. Application Data

(60) Provisional application No. 62/314,163, filed on Mar. 28, 2016.

(51) Int. Cl.
*C12Q 1/70* (2006.01)
*B01L 3/00* (2006.01)
(Continued)

(52) U.S. Cl.
CPC .......... *C12Q 1/70* (2013.01); *B01L 3/502753* (2013.01); *B01L 3/502761* (2013.01);
(Continued)

(58) Field of Classification Search
None
See application file for complete search history.

(56) References Cited

U.S. PATENT DOCUMENTS 7,312,085 B2 * 12/2007 Chou ................ B01L 3/502761
422/50
2004/0191859 A1 * 9/2004 Tabacco ............... C12Q 1/6825
435/69.1
(Continued)

FOREIGN PATENT DOCUMENTS

WO   WO-2011014946 A1 *   2/2011    ........ B01L 3/502753
WO   WO-2016/100389       6/2016

OTHER PUBLICATIONS

Wu et al., "Soft inertial microfluidics for high throughput separation of bacteria from human blood cells," Lab Chip 9: 1193-1199 (Year: 2009).*

(Continued)

*Primary Examiner* — M Franco G Salvoza
(74) *Attorney, Agent, or Firm* — Foley & Lardner LLP

(57) ABSTRACT

The system described herein for bacterial identification can be used as a point-of-care or lab-based diagnostic system. In some implementations, the system can be used to detect other foreign agents within blood or other samples. The system can include disposable microfluidic cartridges that are removable from the system. The microfluidic cartridges can receive a sample, such as a blood sample, that is suspected of containing bacterial cells and separate the bacterial cells from the blood sample. Once the bacterial cells are separated from the blood, the system can introduce the recombinant detector bacteriophages into the system that can infect the bacterial cells. The system can then detect the expression of reporter genes from the recombinant detector bacteriophages.

11 Claims, 45 Drawing Sheets

Specification includes a Sequence Listing.

(51) Int. Cl.
*C12N 15/86* (2006.01)
*C12N 7/00* (2006.01)
*C12N 15/11* (2006.01)
*C12N 15/66* (2006.01)
*C12N 15/90* (2006.01)

(52) U.S. Cl.
CPC ............... *C12N 7/00* (2013.01); *C12N 15/11* (2013.01); *C12N 15/66* (2013.01); *C12N 15/86* (2013.01); *C12N 15/902* (2013.01); *C12Y 301/00* (2013.01); *B01L 2200/0652* (2013.01); *B01L 2200/10* (2013.01); *B01L 2300/0627* (2013.01); *B01L 2300/12* (2013.01); *C12N 2310/20* (2017.05); *C12N 2795/10221* (2013.01); *C12N 2795/10243* (2013.01); *C12N 2795/10251* (2013.01); *C12N 2800/80* (2013.01)

(56) References Cited

U.S. PATENT DOCUMENTS

| | | |
|---|---|---|
| 2014/0273180 A1 | 9/2014 | Griswold et al. |
| 2015/0344930 A1 | 12/2015 | Koeris et al. |
| 2016/0010138 A1* | 1/2016 | Shamsheyeva .......... C12Q 1/18 702/19 |
| 2016/0319378 A1 | 11/2016 | Rey |
| 2016/0348187 A1 | 12/2016 | Rey et al. |
| 2017/0152576 A1 | 6/2017 | Rey et al. |
| 2017/0321289 A1 | 11/2017 | Rey et al. |

OTHER PUBLICATIONS

Huh et al., "Microfluidics for flow cytometric analysis of cells and particles," Physiol. Meas. 26: R73-R98 (Year: 2005).*

Zourub et al., "Principles of Bacterial Detection: Biosensors, Recognition Receptors and Microsystems," Springer Science and Business Media (Year: 2008).*

Ai et al., "Separation of *Escherichia coli* Bacteria from Peripheral Blood Mononuclear Cells Using Standing Surface Acoustic Waves," Analytical Chemistry 85: 9126-9134 (Year: 2013).*

Box, et al., "Functional analysis of bacteriophage immunity through a type I-E CRISPR-Cas system in Vibrio cholera and its application in bacteriophage genome engineering", Journal of Bacteriology, vol. 198, No. 3, Feb. 23, 2016.

Cas9-Assisted Targeting of Chromosome segments CATCH enables one-step targeted cloning of large gene clusters, Nature Communications, vol. 6, Sep. 1, 2015.

International Search Report and Written Opinion for PCT/US2017/024369 dated Oct. 9, 2017.

Jia-Wang, et al., "CRISPR/Cas9 nuclease cleavage combined with Gibson assembly for seamless cloning", Biotechniques Rapid Dispatches, vol. 58, No. 4, Apr. 1, 2015.

Kiro, et al., "Efficient engineering of a bacteriophage genome using the type I-E CRISPR-Cas system", RNA Biology, vol. 11, No. 1, Jan. 1, 2014, pp. 42-44.

Marinelli et al., "BRED: A Simple and Powerful Tool for Constructing Mutant and Recombinant Bacteriophage Genomes", PLOS One, vol. 3, No. 12, Dec. 17, 2008, p. e3957, XP055385275.

Martel, et al., "CRISPR-Cas: an efficient tool for genome engineering of virulent bacteriophages", Nucleic Acids Research, vol. 42, No. 14, Jul. 24, 2014.

Ying-Ta Lai, et al., "In Vitro Repair of Gaps in Bacteriophage T7 DNA", Journal of Bacteriology, Dec. 1, 1998, pp. 6193-6202, XP055385229.

Cotta de Almeida (Genome Research 13:2190-2194, 2003) (Year: 2003).

Final Office Action on U.S. Appl. No. 15/470,685 dated Feb. 27, 2020 (10 pages).

Non-Final Office Action on U.S. Appl. No. 15/470,685 dated Aug. 29, 2019 (14 pages).

Sadowski et al., Proc. Nat. Acad. Sci. USA, 73, 3, 692-696 (Year: 1976).

Scearce et al., J. Bact. 173, 2, 869-878 (Year: 1991).

Shen etal. (Genetics 112:441-457, 1986 (Year: 1986).

* cited by examiner

>T7_10A_Nhel_Nluc_LacZa_extraction Enterobacteria phage T7, complete genome (SEQ ID NO.: 1)

CCTCTAGAAATAATTTTGTTTAACTTTAAGAAGGAGATATACATA
TGGTCTTCACACTCGAAGATTTCGTTGGGGACTGGCGACAG
ACAGCCGGCTACAACCTGGACCAAGTCCTTGAACAGGGAG
GTGTGTCCAGTTTGTTTCAGAATCTCGGGGTGTCCGTAACT
CCGATCCAAAGGATTGTCCTGAGCGGTGAAAATGGGCTGAA
GATCGACATCCATGTCATCATCCCGTATGAAGGTCTGAGCG
GCGACCAAATGGGCCAGATCGAAAAATTTTTAAGGTGGTGT
ACCCTGTGGATGATCATCACTTTAAGGTGATCCTGCACTATG
GCACACTGGTAATCGACGGGGTTACGCCGAACATGATCGAC
TATTTCGGACGGCCGTATGAAGGCATCGCCGTGTTCGACGG
CAAAAAGATCACTGTAACAGGGACCCTGTGGAACGGCAAC
AAAATTATCGACGAGCGCCTGATCAACCCCGACGGCTCCCT
GCTGTTCCGAGTAACCATCAACGGAGTGACCGGCTGGCGG
CTGTGCGAACGCATTCTGGCGTAAAGGAGGTAAACATATGA
CCATGATTACGGATTCACTGGCCGTCGTTTTACAACGTCGTG
ACTGGGAAAACCCTGGCGTTACCCAACTTAATCGCCTTGCA
GCACATCCCCCTTTCGCCAGCTGGCGTAATAGCGAAGAGG
CCCGCACCGATCGCCCTTCCCAACAGTTGCGCAGCCTGAA
TGGCGAATGGTAAAAGAGGAGGTATACAATGGCTAGCATGA
CTGGTGGACAGCAAATGGGTACTAACCAAGGT

>DLPEC02_Double_lumi Enterobacteria phage T7, complete genome (SEQ ID NO: 2)
TCTCACAGTGTACGGACCTAAAGTTCCCCCATAGGGGTACCTAAAGCCCAGCCAATCACCTAAAGTCAACCTT
CGGTTGACCTTGAGGGTTCCCTAAGGGTTGGGGATGACCCTTGGGTTTGTCTTTGGGTGTTACCTTGAGTGTCT
CTCTGTGTCCCTATCTGTTACAGTCTCCTAAAGTATCCTCCTAAAGTCACCTCCTAACGTCCATCCTAAAGCCA
ACACCTAAAGCCTACACCTAAAGACCCATCAAGTCAACGCCTATCTTAAAGTTTAAACATAAAGACCAGACCTA
AAGACCAGACCTAAAGACACTACATAAAGACCAGACCTAAAGACGCCTTGTTGTTAGCCATAAAGTGATAACCT
TTAATCATTGTCTTTATTAATACAACTCACTATAAGGAGAGACAACTTAAAGAGACTTAAAAGATTAATTTAAA
ATTTATCAAAAGAGTATTGACTTAAAGTCTAACCTATAGGATACTTACAGCCATCGAGAGGGACACGGCGAAT
AGCCATCCCAATCGACACCGGGGTCAACCGGATAAGTAGACAGCCTGATAAGTCGCACGAAAAACAGGTATTGA
CAACATGAAGTAACATGCAGTAAGATACAAATCGCTAGGTAACACTAGCAGCGTCAACCGGGCGCACAGTGCCT
TCTAGGTGACTTAAGCGCACCACGGCACATAAGGTGAAACAAAACGGTTGACAACATGAAGTAAACACGGTACG
ATGTACCACATGAAACGACAGTGAGTCACCACACTGAAAGGTGATGCGGTCTAACGAAACCTGACCTAAGACGC
TCTTTAACAATCTGGTAAATAGCTCTTGAGTGCATGACTAGCGGATAACTCAAGGGTATCGCAAGGTGCCCTTT
ATGATATTCACTAATAACTGCACGAGGTAACACAAGATGGCTATGTCTAACATGACTTACAACAACGTTTTCGA
CCACGCTTACGAAATGCTGAAAGAAAACATCCGTTATGATGACATCCGTGACACTGATGACCTGCACGATGCTA
TTCACATGGCTGCCGATAATGCAGTTCCGCACTACTACGCTGACATCTTTAGCGTAATGGCAAGTGAGGGCATT
GACCTTGAGTTCGAAGACTCTGGTCTGATGCCTGACACCAAGGACGTAATCCGCATCCTGCAAGCGCGTATCTA
TGAGCAATTAACGATTGACCTCTGGGAAGACGCAGAAGACTTGCTCAATGAATACTTGGAGGAAGTCGAGGAGT
ACGAGGAGGATGAAGAGTAATGTCTACTACCAACGTGCAATACGGTCTGACCGCTCAAACTGTACTTTTCTATA
GCGACATGGTGCGCTGTGGCTTTAACTGGTCACTCGCAATGGCACAGCTCAAAGAACTGTACGAAAACAACAAG
GCAATAGCTTTAGAATCTGCTGAGTGATAGACTCAAGGTCGCTCCTAGCGAGTGGCCTTTATGATTATCACTTT
ACTTATGAGGGAGTAATGTATATGCTTACTATCGGTCTACTCACCGCTCTAGGTCTAGCTGTAGGTGCATCCTT
TGGGAAGGCTTTAGGTGTAGCTGTAGGTTCCTACTTTACCGCTTGCATCATCATAGGAATCATCAAAGGGGCAC
TACGCAAATGATGAAGCACTACGTTATGCCAATCCACACGTCCAACGGGGCAACCGTATGTACACCTGATGGGT
TCGCAATGAAACAACGAATCGAACGCCTTAAGCGTGAACTCCGCATTAACCGCAAGATTAACAAGATAGGTTCC
GGCTATGACAGAACGCACTGATGGCTTAAAGAAAGGTTATATGCCCAATGGCACACTATACGCTGCAAATCGGC
GAATAGTGAGAACTTGGCGAGAGAACAACCTCGAACGCCGCAAGGACAAGAGAGGGCGGCGTGGCATAGACGAA
AGGAAAAGGTTAAAGCCAAGAAACTCGCCGCACTTGAACAGGCACTAGCCAACACACTGAACGCTATCTCATAA
CGAACATAAAGGACACAATGCAATGAACATTACCGACATCATGAACGCTATCGACGCAATCAAAGCACTGCCAA
TCTGTGAACTTGACAAGCGTCAAGGTATGCTTATCGACTTACTGGTCGAGATGGTCAACAGCGAGACGTGTGAT
GGCGAGCTAACCGAACTAAATCAGGCACTTGAGCATCAAGATTGGTGGACTACCTTGAAGTGTCTCACGGCTGA
CGCAGGGTTCAAGATGCTCGGTAATGGTCACTTCTCGGCTGCTTATAGTCACCCGCTGCTACCTAACAGAGTGA
TTAAGGTGGGCTTTAAGAAAGAGGATTCAGGCGCAGCCTATACCGCATTCTGCCGCATGTATCAGGGTCGTCCT
GGTATCCCTAACGTCTACGATGTACAGCGCCACGCTGGATGCTATACGGTGGTACTTGACGCACTTAAGGATTG
CGAGCGTTTCAACAATGATGCCCATTATAAATACGCTGAGATTGCAAGCGACATCATTGATTGCAATTCGGATG
AGCATGATGAGTTAACTGGATGGGATGGTGAGTTTGTTGAAACTTGTAAACTAATCCGCAAGTTCTTTGAGGGC
ATCGCCTCATTCGACATGCATAGCGGGAACATCATGTTCTCAAATGGAGACGTACCATACATCACCGACCCGGT
ATCATTCTCGCAGAAGAAAGACGGTGGCGCATTCAGCATCGACCCTGAGGAACTCATCAAGGAAGTCGAGGAAG
TCGCACGACAGAAAGAAATTGACCGCGCTAAGGCCCGTAAAGAACGTCACGAGGGCGCTTAGAGGCACGCAGA
TTCAAACGTCGCAACCGCAAGGCACGTAAAGCACACAAAGCTAAGCGCGAAAGAATGCTTGCTGCGTGGCGATG
GGCTGAACGTCAAGAACGGCGTAACCATGAGGTAGCTGTAGATGTACTAGGAAGAACCAATAACGCTATGCTCT
GGGTCAACATGTTCTCTGGGGACTTTAAGGCGCTTGAGGAACGAATCGCGCTGCACTGGCGTAATGCTGACCGG
ATGGCTATCGCTAATGGTCTTACGCTCAACATTGATAAGCAACTTGACGCAATGTTAATGGGCTGATAGTCTTA
TCTTACAGGTCATCTGCGGGTGGCCTGAATAGGTACGATTTACTAACTGGAAGAGGCACTAAATGAACACGATT
AACATCGCTAAGAACGACTTCTCTGACATCGAACTGGCTGCTATCCCGTTCAACACTCTGGCTGACCATTACGG
TGAGCGTTTAGCTCGCGAACAGTTGGCCCTTGAGCATGAGTCTTACGAGATGGGTGAAGCACGCTTCCGCAAGA
TGTTTGAGCGTCAACTTAAAGCTGGTGAGGTTGCGGATAACGCTGCCGCCAAGCCTCTCATCACTACCCTACTC
CCTAAGATGATTGCACGCATCAACGACTGGTTTGAGGAAGTGAAAGCTAAGCGCGGCAAGCGCCCGACAGCCTT
CCAGTTCCTGCAAGAAATCAAGCCGGAAGCCGTAGCGTACATCACCATTAAGACCACTCTGGCTTGCCTAACCA

FIG. 5B

```
GTGCTGACAATACAACCGTTCAGGCTGTAGCAAGCGCAATCGGTCGGGCCATTGAGGACGAGGCTCGCTTCGGT
CGTATCCGTGACCTTGAAGCTAAGCACTTCAAGAAAAACGTTGAGGAACAACTCAACAAGCGCGTAGGGCACGT
CTACAAGAAAGCATTTATGCAAGTTGTCGAGGCTGACATGCTCTCTAAGGGTCTACTCGGTGGCGAGGCGTGGT
CTTCGTGGCATAAGGAAGACTCTATTCATGTAGGAGTACGCTGCATCGAGATGCTCATTGAGTCAACCGGAATG
GTTAGCTTACACCGCCAAAATGCTGGCGTAGTAGGTCAAGACTCTGAGACTATCGAACTCGCACCTGAATACGC
TGAGGCTATCGCAACCCGTGCAGGTGCGCTGGCTGGCATCTCTCCGATGTTCCAACCTTGCGTAGTTCCTCCTA
AGCCGTGGACTGGCATTACTGGTGGTGGCTATTGGGCTAACGGTCGTCGTCCTCTGGCGCTGGTGCGTACTCAC
AGTAAGAAAGCACTGATGCGCTACGAAGACGTTTACATGCCTGAGGTGTACAAAGCGATTAACATTGCGCAAAA
CACCGCATGGAAAATCAACAAGAAAGTCCTAGCGGTCGCCAACGTAATCACCAAGTGGAAGCATTGTCCGGTCG
AGGACATCCCTGCGATTGAGCGTGAAGAACTCCCGATGAAACCGGAAGACATCGACATGAATCCTGAGGCTCTC
ACCGCGTGGAAACGTGCTGCCGCTGCTGTGTACCGCAAGGACAAGGCTCGCAAGTCTCGCCGTATCAGCCTTGA
GTTCATGCTTGAGCAAGCCAATAAGTTTGCTAACCATAAGGCCATCTGGTTCCCTTACAACATGGACTGGCGCG
GTCGTGTTTACGCTGTGTCAATGTTCAACCCGCAAGGTAACGATATGACCAAAGGACTGCTTACGCTGGCGAAA
GGTAAACCAATCGGTAAGGAAGGTTACTACTGGCTGAAAATCCACGGTGCAAACTGTGCGGGTGTCGATAAGGT
TCCGTTCCCTGAGCGCATCAAGTTCATTGAGGAAAACCACGAGAACATCATGGCTTGCGCTAAGTCTCCACTGG
AGAACACTTGGTGGGCTGAGCAAGATTCTCCGTTCTGCTTCCTTGCGTTCTGCTTTGAGTACGCTGGGGTACAG
CACCACGGCCTGAGCTATAACTGCTCCCTTCCGCTGGCGTTTGACGGGTCTTGCTCTGGCATCCAGCACTTCTC
CGCGATGCTCCGAGATGAGGTAGGTGGTCGCGCGGTTAACTTGCTTCCTAGTGAAACCGTTCAGGACATCTACG
GGATTGTTGCTAAGAAAGTCAACGAGATTCTACAAGCAGACGCAATCAATGGGACCGATAACGAAGTAGTTACC
GTGACCGATGAGAACACTGGTGAAATCTCTGAGAAAGTCAAGCTGGGCACTAAGGCACTGGCTGGTCAATGGCT
GGCTTACGGTGTTACTCGCAGTGTGACTAAGCGTTCAGTCATGACGCTGGCTTACGGGTCCAAAGAGTTCGGCT
TCCGTCAACAAGTGCTGGAAGATACCATTCAGCCAGCTATTGATTCCGGCAAGGGTCTGATGTTCACTCAGCCG
AATCAGGCTGCTGGATACATGGCTAAGCTGATTTGGGAATCTGTGAGCGTGACGGTGGTAGCTGCGGTTGAAGC
AATGAACTGGCTTAAGTCTGCTGCTAAGCTGCTGGCTGCTGAGGTCAAAGATAAGAAGACTGGAGAGATTCTTC
GCAAGCGTTGCGCTGTGCATTGGGTAACTCCTGATGGTTTCCCTGTGTGGCAGGAATACAAGAAGCCTATTCAG
ACGCGCTTGAACCTGATGTTCCTCGGTCAGTTCCGCTTACAGCCTACCATTAACACCAACAAAGATAGCGAGAT
TGATGCACACAAACAGGAGTCTGGTATCGCTCCTAACTTTGTACACAGCCAAGACGGTAGCCACCTTCGTAAGA
CTGTAGTGTGGGCACACGAGAAGTACGGAATCGAATCTTTTGCACTGATTCACGACTCCTTCGGTACCATTCCG
GCTGACGCTGCGAACCTGTTCAAAGCAGTGCGCGAAACTATGGTTGACACATATGAGTCTTGTGATGTACTGGC
TGATTTCTACGACCAGTTCGCTGACCAGTTGCACGAGTCTCAATTGGACAAAATGCCAGCACTTCCGGCTAAAG
GTAACTTGAACCTCCGTGACATCTTAGAGTCGGACTTCGCGTTCGCGTAACGCCAAATCAATACGACTCACTAT
AGAGGGACAAACTCAAGGTCATTCGCAAGAGTGGCCTTTATGATTGACCTTCTTCCGGTTAATACGACTCACTA
TAGGAGAACCTTAAGGTTTAACTTTAAGACCCTTAAGTGTTAATTAGAGATTTAGGAGATTCAACATGGTCTTC
ACACTCGAAGATTTCGTTGGGGACTGGCGACAGACAGCCGGCTACAACCTGGACCAAGTCCTTGAACAGGGAGG
TGTGTCCAGTTTGTTTCAGAATCTCGGGGTGTCCGTAACTCCGATCCAAAGGATTGTCCTGAGCGGTGAAAATG
GGCTGAAGATCGACATCCATGTCATCATCCCGTATGAAGGTCTGAGCGGCGACCAAATGGGCCAGATCGAAAAA
ATTTTTAAGGTGGTGTACCCTGTGGATGATCATCACTTTAAGGTGATCCTGCACTATGGCACACTGGTAATCGA
CGGGGTTACGCCGAACATGATCGACTATTTCGGACGGCCGTATGAAGGCATCGCCGTGTTCGACGGCAAAAAGA
TCACTGTAACAGGGACCCTGTGGAACGGCAACAAAATTATCGACGAGCGCCTGATCAACCCCGACGGCTCCCTG
CTGTTCCGAGTAACCATCAACGGAGTGACCGGCTGGCGGCTGTGCGAACGCATTCTGGCGTAAAGGAGGTAAAC
ATATGACCATGATTACGGATTCACTGGCCGTCGTTTTACAACGTCGTGACTGGGAAAACCCTGGCGTTACCCAA
CTTAATCGCCTTGCAGCACATCCCCCTTTCGCCAGCTGGCGTAATAGCGAAGAGGCCCGCACCGATCGCCCTTC
CCAACAGTTGCGCAGCCTGAATGGCGAATGGAAATTAAAGAATTACTAAGAGAGGACTTTAAGTATGCGTAACT
TCGAAAGATGACCAAACGTTCTAACCGTAATGCTCGTGACTTCGAGGCAACCAAAGGTCGCAAGTTGAATAAG
ACTAAGCGTGACCGCTCTCACAAGCGTAGCTGGGAGGGTCAGTAAGATGGACGTTTATATAGTGGTAATCTGG
CAGCATTCAAGGCAGCAACAAACAAGCTGTTCCAGTTAGACTTAGCGGTCATTTATGATGACTGGTATGATGCC
TATACAAGAAAGATTGCATACGGTTACGTATTGAGGACAGGAGTGGAAACCTGATTGATACTAGCACCTTCTA
CCACCACGACGAGGACGTTCTGTTCAATATGTGTACTGATTGGTTGAACCATATGTATGACCAGTTGAAGGACT
GGAAGTAATACGACTCAGTATAGGGACAATGCTTAAGGTCGCTCTCTAGGAGTGGCCTTAGTCATTTAACCAAT
AGGAGATAAACATTATGATGAACATTAAGACTAACCCGTTTAAAGCCGTGTCTTTCGTAGAGTCTGCCATTAAG
AAGGCTCTGGATAACGCTGGGTATCTTATCGCTGAAATCAAGTACGATGGTGTACGCGGGAACATCTGCGTAGA
CAATACTGCTAACAGTTACTGGCTCTCTCGTGTATCTAAAACGATTCCGGCACTGGAGCACTTAAACGGGTTTG
ATGTTCGCTGGAAGCGTCTACTGAACGATGACCGTTGCTTCTACAAAGATGGCTTTATGCTTGATGGGGAACTC
ATGGTCAAGGGCGTAGACTTTAACACAGGGTCCGGCCTACTGCGTACCAAATGGACTGACACGAAGAACCAAGA
```

FIG. 5C

```
GTTCCATGAAGAGTTATTCGTTGAACCAATCCGTAAGAAAGATAAAGTTCCCTTTAAGCTGCACACTGGACACC
TTCACATAAAACTGTACGCTATCCTCCCGCTGCACATCGTGGAGTCTGGAGAAGACTGTGATGTCATGACGTTG
CTCATGCAGGAACACGTTAAGAACATGCTGCCTCTGCTACAGGAATACTTCCCTGAAATCGAATGGCAAGCGGC
TGAATCTTACGAGGTCTACGATATGGTAGAACTACAGCAACTGTACGAGCAGAAGCGAGCAGAAGGCCATGAGG
GTCTCATTGTGAAAGACCCGATGTGTATCTATAAGCGCGGTAAGAAATCTGGCTGGTGGAAAATGAAACCTGAG
AACGAAGCTGACGGTATCATTCAGGGTCTGGTATGGGGTACAAAAGGTCTGGCTAATGAAGGTAAAGTGATTGG
TTTTGAGGTGCTTCTTGAGAGTGGTCGTTTAGTTAACGCCACGAATATCTCTCGCGCCTTAATGGATGAGTTCA
CTGAGACAGTAAAAGAGGCCACCCTAAGTCAATGGGGATTCTTTAGCCCATACGGTATTGGCGACAACGATGCT
TGTACTATTAACCCTTACGATGGCTGGGCGTGTCAAATTAGCTACATGGAGGAAACACCTGATGGCTCTTTGCG
GCACCCATCGTTCGTAATGTTCCGTGGCACCGAGGACAACCCTCAAGAGAAATGTAATCACACTGGCTCACCT
TCGGGTGGGCCTTTCTGCGTTTATAAGGAGACACTTTATGTTTAAGAAGGTTGGTAAATTCCTTGCGGCTTTGG
CAGCTATCCTGACGCTTGCGTATATTCTTGCGGTATACCCTCAAGTAGCACTAGTAGTAGTTGGCGCTTGTTAC
TTAGCGGCAGTGTGTGCTTGCGTGTGGAGTATAGTTAACTGGTAATACGACTCACTAAAGGAGGTACACACCAT
GATGTACTTAATGCCATTACTCATCGTCATTGTAGGATGCCTTGCGCTCCACTGTAGCGATGATGATATGCCAG
ATGGTCACGCTTAATACGACTCACTAAAGGAGACACTATATGTTTCGACTTCATTACAACAAAAGCGTTAAGAA
TTTCACGGTTCGCCGTGCTGACCGTTCAATCGTATGTGCGAGCGAGCGCCGAGCTAAGATACCTCTTATTGGTA
ACACAGTTCCTTTGGCACCGAGCGTCCACATCATTATCACCCGTGGTGACTTTGAGAAAGCAATAGACAAGAAA
CGTCCGGTTCTTAGTGTGGCAGTGACCCGCTTCCCGTTCGTCCGTCTGTTACTCAAACGAATCAAGGAGGTGTT
CTGATGGGACTGTTAGATGGTGAAGCCTGGGAAAAGAAAACCCGCCAGTACAAGCAACTGGGTGTATAGCTTG
CTTAGAGAAAGATGACCGTTATCCACACACCTGTAACAAAGGAGCTAACGATATGACCGAACGTGAACAAGAGA
TGATCATTAAGTTGATAGACAATAATGAAGGTCGCCCAGATGATTTGAATGGCTGCGGTATTCTCTGCTCCAAT
GTCCCTTGCCACCTCTGCCCCGCAAATAACGATCAAAAGATAACCTTAGGTGAAATCCGAGCGATGGACCCACG
TAAACCACATCTGAATAAACCTGAGGTAACTCCTACAGATGACCAGCCTTCCGCTGAGACAATCGAAGGTGTCA
CTAAGCCTTCCCACTACATGCTGTTTGACGACATTGAGGCTATCGAAGTGATTGCTCGTTCAATGACCGTTGAG
CAGTTCAAGGGATACTGCTTCGGTAACATCTTAAAGTACAGACTACGTGCTGGTAAGAAGTCAGAGTTAGCGTA
CTTAGAGAAAGACCTAGCGAAAGCAGACTTCTATAAAGAACTCTTTGAGAAACATAAGGATAAATGTTATGCAT
AACTTCAAGTCAACCCCACCTGCCGACAGCCTATCTGATGACTTCACATCTTGCTCAGAGTGGTGCCGAAAGAT
GTGGGAAGAGACATTCGACGATGCGTACATCAAGCTGTATGAACTTTGGAAATCGAGAGGTCAATGACTATGTC
AAACGTAAATACAGGTTCACTTAGTGTGGACAATAAGAAGTTTTGGGCTACCGTAGAGTCCTCGGAGCATTCCT
TCGAGGTTCCAATCTACGCTGAGACCCTAGACGAAGCTCTGGAGTTAGCCGAATGGCAATACGTTCCGGCTGGC
TTTGAGGTTACTCGTGTGCGTCCTTGTGTAGCACCGAAGTAATACGACTCACTATTAGGGAAGACTCCCTCTGA
GAAACCAAACGAAACCTAAAGGAGATTAACATTATGGCTAAGAAGATTTTCACCTCTGCGCTGGGTACCGCTGA
ACCTTACGCTTACATCGCCAAGCCGGACTACGGCAACGAAGAGCGTGGCTTTGGGAACCCTCGTGGTGTCTATA
AAGTTGACCTGACTATTCCCAACAAAGACCCGCGCTGCCAGCGTATGGTCGATGAAATCGTGAAGTGTCACGAA
GAGGCTTATGCTGCTGCCGTTGAGGAATACGAAGCTAATCCACCTGCTGTAGCTCGTGGTAAGAAACCGCTGAA
ACCGTATGAGGGTGACATGCCGTTCTTCGATAACGGTGACGGTACGACTACCTTTAAGTTCAAATGCTACGCGT
CTTTCCAAGACAAGAAGACCAAAGAGACCAAGCACATCAATCTGGTTGTGGTTGACTCAAAAGGTAAGAAGATG
GAAGACGTTCCGATTATCGGTGGTGGCTCTAAGCTGAAAGTTAAATATTCTCTGGTTCCATACAAGTGGAACAC
TGCTGTAGGTGCGAGCGTTAAGCTGCAACTGGAATCCGTGATGCTGGTCGAACTGGCTACCTTTGGTGGCGGTG
AAGACGATTGGGCTGACGAAGTTGAAGAGAACGGCTATGTTGCCTCTGGTTCTGCCAAAGCGAGCAAACCACGC
GACGAAGAAAGCTGGGACGAAGACGACGAAGAGTCCGAGGAAGCAGACGAAGACGGAGACTTCTAAGTGGAACT
GCGGGAGAAAATCCTTGAGCGAATCAAGGTGACTTCCTCTGGGTGTTGGGAGTGGCAGGGCGCTACAACAATA
AAGGGTACGGGCAGGTGTGGTGCAGCAATACCGGAAAGGTTGTCTACTGTCATCGCGTAATGTCTAATGCTCCG
AAAGGTTCTACCGTCCTGCACTCCTGTGATAATCCATTATGTTGTAACCCTGAACACCTATCCATAGGAACTCC
AAAAGAGAACTCCACTGACATGGTAAATAAGGGTCGCTCACACAAGGGGTATAAACTTTCAGACGAAGACGTAA
TGGCAATCATGGAGTCCAGCGAGTCCAATGTATCCTTAGCTCGCACCTATGGTGTCTCCCAACAGACTATTTGT
GATATACGCAAAGGGAGGCGACATGGCAGGTTACGGCGCTAAAGGAATCCGAAAGGTTGGAGCGTTTCGCTCTG
GCCTAGAGGACAAGGTTTCAAAGCAGTTGGAATCAAAAGGTATTAAATTCGAGTATGAAGAGTGGAAAGTGCCT
TATGTAATTCCGGCGAGCAATCACACTTACACTCCAGACTTCTTACTTCCAAACGGTATATTCGTTGAGACAAA
GGGTCTGTGGGAAAGCGATGATAGAAAGAAGCACTTATTAATTAGGGAGCAGCACCCCGAGCTAGACATCCGTA
TTGTCTTCTCAAGCTCACGTACTAAGTTATACAAAGGTTCTCCAACGTCTTATGGAGAGTTCTGCGAAAAGCAT
GGTATTAAGTTCGCTGATAAACTGATACCTGCTGAGTGGATAAAGGAACCCAAGAAGGAGGTCCCCTTTGATAG
ATTAAAAAGGAAAGGAGGAAAGAAATAATGGCTCGTGTACAGTTTAAACAACGTGAATCTACTGACGCAATCTT
TGTTCACTGCTCGGCTACCAAGCCAAGTCAGAATGTTGGTGTCCGTGAGATTCGCCAGTGGCACAAAGAGCAGG
```

FIG. 5D

```
GTTGGCTCGATGTGGGATACCACTTTATCATCAAGCGAGACGGTACTGTGGAGGCAGGACGAGATGAGATGGCT
GTAGGCTCTCACGCTAAGGGTTACAACCACAACTCTATCGGCGTCTGCCTTGTTGGTGGTATCGACGATAAAGG
TAAGTTCGACGCTAACTTTACGCCAGCCCAAATGCAATCCCTTCGCTCACTGCTTGTCACACTGCTGGCTAAGT
ACGAAGGCGCTGTGCTTCGCGCCCATCATGAGGTGGCGCCGAAGGCTTGCCCTTCGTTCGACCTTAAGCGTTGG
TGGGAGAAGAACGAACTGGTCACTTCTGACCGTGGATAATTAATTGAACTCACTAAAGGGAGACCACAGCGGTT
TCCCTTTGTTCGCATTGGAGGTCAAATAATGCGCAAGTCTTATAAACAATTCTATAAGGCTCCGAGGAGGCATA
TCCAAGTGTGGGAGGCAGCCAATGGGCCTATACCAAAAGGTTATTATATAGACCACATTGACGGCAATCCACTC
AACGACGCCTTAGACAATCTCCGTCTGGCTCTCCCAAAAGAAAACTCATGGAACATGAAGACTCCAAAGAGCAA
TACCTCAGGACTAAAGGGACTGAGTTGGAGCAAGGAAAGGGAGATGTGGAGAGGCACTGTAACAGCTGAGGGTA
AACAGCATAACTTTCGTAGTAGAGATCTATTGGAAGTCGTTGCGTGGATTTATAGAACTAGGAGGGAATTGCAT
GGACAATTCGCACGATTCCGATAGTGTATTTCTTTACCACATTCCTTGTGACAACTGTGGGAGTAGTGATGGGA
ACTCGCTGTTCTCTGACGGACACACGTTCTGCTACGTATGCGAGAAGTGGACTGCTGGTAATGAAGACACTAAA
GAGAGGGCTTCAAAACGGAAACCCTCAGGAGGTAAACCAATGACTTACAACGTGTGGAACTTCGGGGAATCCAA
TGGACGCTACTCCGCGTTAACTGCGAGAGGAATCTCCAAGGAAACCTGTCAGAAGGCTGGCTACTGGATTGCCA
AAGTAGACGGTGTGATGTACCAAGTGGCTGACTATCGGGACCAGAACGGCAACATTGTGAGTCAGAAGGTTCGA
GATAAAGATAAGAACTTTAAGACCACTGGTAGTCACAAGAGTGACGCTCTGTTCGGGAAGCACTTGTGGAATGG
TGGTAAGAAGATTGTCGTTACAGAAGGTGAAATCGACATGCTTACCGTGATGGAACTTCAAGACTGTAAGTATC
CTGTAGTGTCGTTGGGTCACGGTGCCTCTGCCGCTAAGAAGACATGCGCTGCCAACTACGAATACTTTGACCAG
TTCGAACAGATTATCTTAATGTTCGATATGGACGAAGCAGGGCGCAAAGCAGTCGAAGAGGCTGCACAGGTTCT
ACCTGCTGGTAAGGTACGAGTGGCAGTTCTTCCGTGTAAGGATGCAAACGAGTGTCACCTAAATGGTCACGACC
GTGAAATCATGGAGCAAGTGTGGAATGCTGGTCCTTGGATTCCTGATGGTGTGGTATCGGCTCTTTCGTTACGT
GAACGAATCCGTGAGCACCTATCGTCCGAGGAATCAGTAGGTTTACTTTTCAGTGGCTGCACTGGTATCAACGA
TAAGACCTTAGGTGCCCGTGGTGGTGAAGTCATTATGGTCACTTCCGGTTCCGGTATGGGTAAGTCAACGTTCG
TCCGTCAACAAGCTCTACAATGGGGCACAGCGATGGGCAAGAAGGTAGGCTTAGCGATGCTTGAGGAGTCCGTT
GAGGAGACCGCTGAGGACCTTATAGGTCTACACAACCGTGTCCGACTGAGACAATCCGACTCACTAAAGAGAGA
GATTATTGAGAACGGTAAGTTCGACCAATGGTTCGATGAACTGTTCGGCAACGATACGTTCCATCTATATGACT
CATTCGCCGAGGCTGAGACGGATAGACTGCTCGCTAAGCTGGCCTACATGCGCTCAGGCTTGGGCTGTGACGTA
ATCATTCTAGACCACATCTCAATCGTCGTATCCGCTTCTGGTGAATCCGATGAGCGTAAGATGATTGACAACCT
GATGACCAAGCTCAAAGGGTTCGCTAAGTCAACTGGGGTGGTGCTGGTCGTAATTTGTCACCTTAAGAACCCAG
ACAAAGGTAAAGCACATGAGGAAGGTCGCCCCGTTTCTATTACTGACCTACGTGGTTCTGGCGCACTACGCCAA
CTATCTGATACTATTATTGCCCTTGAGCGTAATCAGCAAGGCGATATGCCTAACCTTGTCCTCGTTCGTATTCT
CAAGTGCCGCTTTACTGGTGATACTGGTATCGCTGGCTACATGGAATACAACAAGGAAACCGGATGGCTTGAAC
CATCAAGTTACTCAGGGGAAGAAGAGTCACACTCAGAGTCAACAGACTGGTCCAACGACACTGACTTCTGACAG
GATTCTTGATGACTTTCCAGACGACTACGAGAAGTTTCGCTGGAGAGTCCCATTCTAATACGACTCACTAAAGG
AGACACACCATGTTCAAACTGATTAAGAAGTTAGGCCAACTGCTGGTTCGTATGTACAACGTGGAAGCCAAGCG
ACTGAACGATGAGGCTCGTAAAGAGGCCACACAGTCACGCGCTCTGGCGATTCGCTCCAACGAACTGGCTGACA
GTGCATCCACTAAAGTTACCGAGGCTGCCCGTGTGGCAAACCAAGCTCAACAGCTTTCCAAATTCTTTGAGTAA
TCAAACAGGAGAAACCATTATGTCTAACGTAGCTGAAACTATCCGTCTATCCGATACAGCTGACCAGTGGAACC
GTCGAGTCCACATCAACGTTCGCAACGGTAAGGCGACTATGGTTTACCGCTGGAAGGACTCTAAGTCCTCTAAG
AATCACACTCAGCGTATGACGTTGACAGATGAGCAAGCACTGCGTCTGGTCAATGCGCTTACCAAAGCTGCCGT
GACAGCAATTCATGAAGCTGGTCGCGTCAATGAAGCTATGGCTATCCTCGACAAGATTGATAACTAAGAGTGGT
ATCCTCAAGGTCGCCAAAGTGGTGGCCTTCATGAATACTATTCGACTCACTATAGGAGATATTACCATGCGTGA
CCCTAAAGTTATCCAAGCAGAAATCGCTAAACTGGAAGCTGAACTGGAGGACGTTAAGTACCATGAAGCTAAGA
CTCGCTCCGCTGTTCACATCTTGAAGAACTTAGGCTGGACTTGGACAAGACAGACTGGCTGGAAGAAACCAGAA
GTTACCAAGCTGAGTCATAAGGTGTTCGATAAGGACACTATGACCCACATCAAGGCTGGTGATTGGGTTAAGGT
TGACATGGGAGTTGTTGGTGGATACGGCTACGTCCGCTCAGTTAGTGGCAAATATGCACAAGTGTCATACATCA
CAGGTGTTACTCCACGCGGTGCAATCGTTGCCGATAAGACCAACATGATTCACACAGGTTTCTTGACAGTTGTT
TCATATGAAGAGATTGTTAAGTCACGATAATCAATAGGAGAAATCAATATGATCGTTTCTGACATCGAAGCTAA
CGCCCTCTTAGAGAGCGTCACTAAGTTCCACTGCGGGGTTATCTACGACTACTCCACCGCTGAGTACGTAAGCT
ACCGTCCGAGTGACTTCGGTGCGTATCTGGATGCGCTGGAAGCCGAGGTTGCACGAGGCGGTCTTATTGTGTTC
CACAACGGTCACAAGTATGACGTTCCTGCATTGACCAAACTGGCAAAGTTGCAATTGAACCGAGAGTTCCACCT
TCCTCGTGAGAACTGTATTGACACCCTTGTGTTGTCACGTTTGATTCATTCCAACCTCAAGGACACCGATATGG
GTCTTCTGCGTTCCGGCAAGTTGCCCGGAAAACGCTTTGGGTCTCACGCTTTGGAGGCGTGGGGTTATCGCTTA
GGCGAGATGAAGGGTGAATACAAAGACGACTTTAAGCGTATGCTTGAAGAGCAGGGTGAAGAATACGTTGACGG
```

FIG. 5E

```
AATGGAGTGGTGGAACTTCAACGAAGAGATGATGGACTATAACGTTCAGGACGTTGTGGTAACTAAAGCTCTCC
TTGAGAAGCTACTCTCTGACAAACATTACTTCCCTCCTGAGATTGACTTTACGGACGTAGGATACACTACGTTC
TGGTCAGAATCCCTTGAGGCCGTTGACATTGAACATCGTGCTGCATGGCTGCTCGCTAAACAAGAGCGCAACGG
GTTCCCGTTTGACACAAAAGCAATCGAAGAGTTGTACGTAGAGTTAGCTGCTCGCCGCTCTGAGTTGCTCCGTA
AATTGACCGAAACGTTCGGCTCGTGGTATCAGCCTAAAGGTGGCACTGAGATGTTCTGCCATCCGCGAACAGGT
AAGCCACTACCTAAATACCCTCGCATTAAGACACCTAAAGTTGGTGGTATCTTTAAGAAGCCTAAGAACAAGGC
ACAGCGAGAAGGCCGTGAGCCTTGCGAACTTGATACCCGCGAGTACGTTGCTGGTGCTCCTTACACCCCAGTTG
AACATGTTGTGTTTAACCCTTCGTCTCGTGACCACATTCAGAAGAAACTCCAAGAGGCTGGGTGGGTCCCGACC
AAGTACACCGATAAGGGTGCTCCTGTGGTGGACGATGAGGTACTCGAAGGAGTACGTGTAGATGACCCTGAGAA
GCAAGCCGCTATCGACCTCATTAAAGAGTACTTGATGATTCAGAAGCGAATCGGACAGTCTGCTGAGGGAGACA
AAGCATGGCTTCGTTATGTTGCTGAGGATGGTAAGATTCATGGTTCTGTTAACCCTAATGGAGCAGTTACGGGT
CGTGCGACCCATGCGTTCCCAAACCTTGCGCAAATTCCGGGTGTACGTTCTCCTTATGGAGAGCAGTGTCGCGC
TGCTTTTGGCGCTGAGCACCATTTGGATGGGATAACTGGTAAGCCTTGGGTTCAGGCTGGCATCGACGCATCCG
GTCTTGAGCTACGCTGCTTGGCTCACTTCATGGCTCGCTTTGATAACGGCGAGTACGCTCACGAGATTCTTAAC
GGCGACATCCACACTAAGAACCAGATAGCTGCTGAACTACCTACCCGAGATAACGCTAAGACGTTCATCTATGG
GTTCCTCTATGGTGCTGGTGATGAGAAGATTGGACAGATTGTTGGTGCTGGTAAAGAGCGCGGTAAGGAACTCA
AGAAGAAATTCCTTGAGAACACCCCCGCGATTGCAGCACTCCGCGAGTCTATCCAACAGACACTTGTCGAGTCC
TCTCAATGGGTAGCTGGTGAGCAACAAGTCAAGTGGAAACGCCGCTGGATTAAAGGTCTGGATGGTCGTAAGGT
ACACGTTCGTAGTCCTCACGCTGCCTTGAATACCCTACTGCAATCTGCTGGTGCTCTCATCTGCAAACTGTGGA
TTATCAAGACCGAAGAGATGCTCGTAGAGAAAGGCTTGAAGCATGGCTGGGATGGGGACTTTGCGTACATGGCA
TGGGTACATGATGAAATCCAAGTAGGCTGCCGTACCGAAGAGATTGCTCAGGTGGTCATTGAGACCGCACAAGA
AGCGATGCGCTGGGTTGGAGACCACTGGAACTTCCGGTGTCTTCTGGATACCGAAGGTAAGATGGGTCCTAATT
GGGCGATTTGCCACTGATACAGGAGGCTACTCATGAACGAAAGACACTTAACAGGTGCTGCTTCTGAAATGCTA
GTAGCCTACAAATTTACCAAAGCTGGGTACACTGTCTATTACCCTATGCTGACTCAGAGTAAAGAGGACTTGGT
TGTATGTAAGGATGGTAAATTTAGTAAGGTTCAGGTTAAAACAGCCACAACGGTTCAAACCAACACAGGAGATG
CCAAGCAGGTTAGGCTAGGTGGATGCGGTAGGTCCGAATATAAGGATGGAGACTTTGACATTCTTGCGGTTGTG
GTTGACGAAGATGTGCTTATTTTCACATGGGACGAAGTAAAAGGTAAGACATCCATGTGTGTCGGCAAGAGAAA
CAAAGGCATAAAACTATAGGAGAAATTATTATGGCTATGACAAAGAAATTTAAAGTGTCCTTCGACGTTACCGC
AAAGATGTCGTCTGACGTTCAGGCAATCTTAGAGAAAGATATGCTGCATCTATGTAAGCAGGTCGGCTCAGGTG
CGATTGTCCCCAATGGTAAACAGAAGGAAATGATTGTCCAGTTCCTGACACACGGTATGGAAGGATTGATGACA
TTCGTAGTACGTACATCATTTCGTGAGGCCATTAAGGACATGCACGAAGAGTATGCAGATAAGGACTCTTTCAA
ACAATCTCCTGCAACAGTACGGGAGGTGTTCTGATGTCTGACTACCTGAAAGTGCTGCAAGCAATCAAAAGTTG
CCCTAAGACTTTCCAGTCCAACTATGTACGGAACAATGCGAGCCTCGTAGCGGAGGCCGCTTCCCGTGGTCACA
TCTCGTGCCTGACTACTAGTGGACGTAACGGTGGCGCTTGGGAAATCACTGCTTCCGGTACTCGCTTTCTGAAA
CGAATGGGAGGATGTGTCTAATGTCTCGTGACCTTGTGACTATTCCACGCGATGTGTGGAACGATATACAGGGC
TACATCGACTCTCTGGAACGTGAGAACGATAGCCTTAAGAATCAACTAATGGAAGCTGACGAATACGTAGCGGA
ACTAGAGGAGAAACTTAATGGCACTTCTTGACCTTAAACAATTCTATGAGTTACGTGAAGGCTGCGACGACAAG
GGTATCCTTGTGATGGACGGCGACTGGCTGGTCTTCCAAGCTATGAGTGCTGCTGAGTTTGATGCCTCTTGGGA
GGAAGAGATTTGGCACCGATGCTGTGACCACGCTAAGGCCCGTCAGATTCTTGAGGATTCCATTAAGTCCTACG
AGACCCGTAAGAAGGCTTGGGCAGGTGCTCCAATTGTCCTTGCGTTCACCGATAGTGTTAACTGGCGTAAAGAA
CTGGTTGACCCGAACTATAAGGCTAACCGTAAGGCCGTGAAGAAACCTGTAGGGTACTTTGAGTTCCTTGATGC
TCTCTTTGAGCGCGAAGAGTTCTATTGCATCCGTGAGCCTATGCTTGAGGGTGATGACGTTATGGGAGTTATTG
CTTCCAATCCGTCTGCCTTCGGTGCTCGTAAGGCTGTAATCATCTCTTGCGATAAGGACTTTAAGACCATCCCT
AACTGTGACTTCCTGTGGTGTACCACTGGTAACATCCTGACTCAGACCGAAGAGTCCGCTGACTGGTGGCACCT
CTTCCAGACCATCAAGGGTGACATCACTGATGGTTACTCAGGGATTGCTGGATGGGGTGATACCGCCGAGGACT
TCTTGAATAACCCGTTCATAACCGAGCCTAAAACGTCTGTGCTTAAGTCCGGTAAGAACAAAGGCCAAGAGGTT
ACTAAATGGGTTAAACGCGACCCTGAGCCTCATGAGACGCTTTGGGACTGCATTAAGTCCATTGGCGCGAAGGC
TGGTATGACCGAAGAGGATATTATCAAGCAGGGCCAAATGGCTCGAATCCTACGGTTCAACGAGTACAACTTTA
TTGACAAGGAGATTTACCTGTGGAGACCGTAGCGTATATTGGTCTGGGTCTTTGTGTTCTCGGAGTGTGCCTCA
TTTCGTGGGCCTTTGGGACTTAGCCAGAATAATCAAGTCGTTACACGACACTAAGTGATAAACTCAAGGTCCC
TAAATTAATACGACTCACTATAGGGAGATAGGGGCCTTTACGATTATTACTTTAAGATTTAACTCTAAGAGGAA
TCTTTATTATGTTAACACCTATTAACCAATTACTTAAGAACCCTAACGATATTCCAGATGTACCTCGTGCAACC
GCTGAGTATCTACAGGTTCGATTCAACTATGCGTACCTCGAAGCGTCTGGTCATATAGGACTTATGCGTGCTAA
TGGTTGTAGTGAGGCCCACATCTTGGGTTTCATTCAGGGCCTACAGTATGCCTCTAACGTCATTGACGAGATTG
```

FIG. 5F

```
AGTTACGCAAGGAACAACTAAGAGATGATGGGGAGGATTGACACTATGTGTTTCTCACCGAAAATTAAAACTCC
GAAGATGGATACCAATCAGATTCGAGCCGTTGAGCCAGCGCCTCTGACCCAAGAAGTGTCAAGCGTGGAGTTCG
GTGGGTCTTCTGATGAGACGGATACCGAGGGCACCGAAGTGTCTGGACGCAAAGGCCTCAAGGTCGAACGTGAT
GATTCCGTAGCGAAGTCTAAAGCCAGCGGCAATGGCTCCGTCGTATGAAATCTTCCATCCGTAAGTCCGCATT
TGGAGGTAAGAAGTGATGTCTGAGTTCACATGTGTGGAGGCTAAGAGTCGCTTCCGTGCAATCCGGTGGACTGT
GGAACACCTTGGGTTGCCTAAAGGATTCGAAGGACACTTTGTGGGCTACAGCCTCTACGTAGACGAAGTGATGG
ACATGTCTGGTTGCCGTGAAGAGTACATTCTGGACTCTACCGGAAAACATGTAGCGTACTTCGCGTGGTGCGTA
AGCTGTGACATTCACCACAAAGGAGACATTCTGGATGTAACGTCCGTTGTCATTAATCCTGAGGCAGACTCTAA
GGGCTTACAGCGATTCCTAGCGAAACGCTTTAAGTACCTTGCGGAACTCCACGATTGCGATTGGGTGTCTCGTT
GTAAGCATGAAGGCGAGACAATGCGTGTATACTTTAAGGAGGTATAAGTTATGGGTAAGAAAGTTAAGAAGGCC
GTGAAGAAAGTCACCAAGTCCGTTAAGAAAGTCGTTAAGGAAGGGGCTCGTCCGGTTAAACAGGTTGCTGGCGG
TCTAGCTGGTCTGGCTGGTGGTACTGGTGAAGCACAGATGGTGGAAGTACCACAAGCTGCCGCACAGATTGTTG
ACGTACCTGAGAAAGAGGTTTCCACTGAGGACGAAGCACAGACAGAAAGCGGACGCAAGAAAGCTCGTGCTGGC
GGTAAGAAATCCTTGAGTGTAGCCCGTAGCTCCGGTGGCGGTATCAACATTTAATCAGGAGGTTATCGTGGAAG
ACTGCATTGAATGGACCGGAGGTGTCAACTCTAAGGGTTATGGTCGTAAGTGGGTTAATGGTAAACTTGTGACT
CCACATAGGCACATCTATGAGGAGACATATGGTCCAGTTCCAACAGGAATTGTGGTGATGCATATCTGCGATAA
CCCTAGGTGCTATAACATAAAGCACCTTACGCTTGGAACTCCAAAGGATAATTCCGAGGACATGGTTACCAAAG
GTAGACAGGCTAAAGGAGAGGAACTAAGCAAGAAACTTACAGAGTCAGACGTTCTCGCTATACGCTCTTCAACC
TTAAGCCACCGCTCCTTAGGAGAACTGTATGGAGTCAGTCAATCAACCATAACGCGAATACTACAGCGTAAGAC
ATGGAGACACATTTAATGGCTGAGAAACGAACAGGACTTGCGGAGGATGGCGCAAAGTCTGTCTATGAGCGTTT
AAAGAACGACCGTGCTCCCTATGAGACACGCGCTCAGAATTGCGCTCAATATACCATCCCATCATTGTTCCCTA
AGGACTCCGATAACGCCTCTACAGATTATCAAACTCCGTGGCAAGCCGTGGGCGCTCGTGGTCTGAACAATCTA
GCCTCTAAGCTCATGCTGGCTCTATTCCCTATGCAGACTTGGATGCGACTTACTATATCTGAATATGAAGCAAA
GCAGTTACTGAGCGACCCCGATGGACTCGCTAAGGTCGATGAGGGCCTCTCGATGGTAGAGCGTATCATCATGA
ACTACATTGAGTCTAACAGTTACCGCGTGACTCTCTTTGAGGCTCTCAAACAGTTAGTCGTAGCTGGTAACGTC
CTGCTGTACCTACCGGAACCGGAAGGGTCAAACTATAATCCCATGAAGCTGTACCGATTGTCTTCTTATGTGGT
CCAACGAGACGCATTCGGCAACGTTCTGCAAATGGTGACTCGTGACCAGATAGCTTTTGGTGCTCTCCCTGAGG
ACATCCGTAAGGCTGTAGAAGGTCAAGGTGGTGAGAAGAAAGCTGATGAGACAATCGACGTGTACACTCACATC
TATCTGGATGAGGACTCAGGTGAATACCTCCGATACGAAGAGGTCGAGGGTATGGAAGTCCAAGGCTCCGATGG
GACTTATCCTAAAGAGGCTTGCCCATACATCCCGATTCGGATGGTCAGACTAGATGGTGAATCCTACGGTCGTT
CGTACATTGAGGAATACTTAGGTGACTTACGGTCCCTTGAAAATCTCCAAGAGGCTATCGTCAAGATGTCCATG
ATTAGCTCTAAGGTTATCGGCTTAGTGAATCCTGCTGGTATCACCCAGCCACGCCGACTGACCAAAGCTCAGAC
TGGTGACTTCGTTACTGGTCGTCCAGAAGACATCTCGTTCCTCCAACTGGAGAAGCAAGCAGACTTTACTGTAG
CTAAAGCCGTAAGTGACGCTATCGAGGCTCGCCTTTCGTTTGCCTTTATGTTGAACTCTGCGGTTCAGCGTACA
GGTGAACGTGTGACCGCCGAAGAGATTCGGTATGTAGCTTCTGAACTTGAAGATACTTTAGGTGGTGTCTACTC
TATCCTTTCTCAAGAATTACAATTGCCTCTGGTACGAGTGCTCTTGAAGCAACTACAAGCCACGCAACAGATTC
CTGAGTTACCTAAGGAAGCCGTAGAGCCAACCATTAGTACAGGTCTGGAAGCAATTGGTCGAGGACAAGACCTT
GATAAGCTGGAGCGGTGTGTCACTGCGTGGGCTGCACTGGCACCTATGCGGGACGACCCTGATATTAACCTTGC
GATGATTAAGTTACGTATTGCCAACGCTATCGGTATTGACACTTCTGGTATTCTACTCACCGAAGAACAGAAGC
AACAGAAGATGGCCCAACAGTCTATGCAAATGGGTATGGATAATGGTGCTGCTGCGCTGGCTCAAGGTATGGCT
GCACAAGCTACAGCCTTCACCTGAGGCTATGGCTGCTGCCGCTGATTCCGTAGGTTTACAGCCGGGAATTTAATA
CGACTCACTATAGGGAGACCTCATCTTTGAAATGAGCGATGACAAGAGGTTGGAGTCCTCGGTCTTCCTGTAGT
TCAACTTTAAGGAGACAATAATAATGGCTGAATCTAATGCAGACGTATATGCATCTTTGGCGTGAACTCCGCT
GTGATGTCTGGTGGTTCCGTTGAGGAACATGAGCAGAACATGCTGGCTCTTGATGTTGCTGCCCGTGATGGCGA
TGATGCAATCGAGTTAGCGTCAGACGAAGTGGAAACAGAACGTGACCTGTATGACAACTCTGACCCGTTCGGTC
AAGAGGATGACGAAGGCCGCATTCAGGTTCGTATCGGTGATGGCTCTGAGCCGACCGATGTGGACACTGGAGAA
GAAGGCGTTGAGGGCACCGAAGGTTCCGAAGAGTTTACCCCACTGGGCGAGACTCCAGAAGAACTGGTAGCTGC
CTCTGAGCAACTTGGTGAGCACGAAGAGGGCTTCCAAGAGATGATTAACATTGCTGCTGAGCGTGGCATGAGTG
TCGAGACCATTGAGGCTATCCAGCGTGAGTACGAGGAGAACGAAGAGTTGTCCGCCGAGTCCTACGCTAAGCTG
GCTGAAATTGGCTACACGAAGGCTTTCATTGACTCGTATATCCGTGGTCAAGAAGCTCTGGTGGAGCAGTACGT
AAACAGTGTCATTGAGTACGCTGGTGGTCGTGAACGTTTTGATGCACTGTATAACCACCTTGAGACGCACAACC
CTGAGGCTGCACAGTCGCTGGATAATGCGTTGACCAATCGTGACTTAGCGACCGTTAAGGCTATCATCAACTTG
GCTGGTGAGTCTCGCGCTAAGGCGTTCGGTCGTAAGCCAACTCGTAGTGTGACTAATCGTGCTATTCCGGCTAA
ACCTCAGGCTACCAAGCGTGAAGGCTTTGCGGACCGTAGCGAGATGATTAAAGCTATGAGTGACCCTCGGTATC
```

FIG. 5G

```
GCACAGATGCCAACTATCGTCGTCAAGTCGAACAGAAAGTAATCGATTCGAACTTCTGATAGACTTCGAAATTA
ATACGACTCACTATAGGGAGACCACAACGGTTTCCCTCTAGAAATAATTTTGTTTAACTTTAAGAAGGAGATAT
ACATATGGAGGAGATTCAACATGGTCTTCACACTCGAAGATTTCGTTGGGGACTGGCGACAGACAGCCGGCTAC
AACCTGGACCAAGTCCTTGAACAGGGAGGTGTGTCCAGTTTGTTTCAGAATCTCGGGGTGTCCGTAACTCCGAT
CCAAAGGATTGTCCTGAGCGGTGAAAATGGGCTGAAGATCGACATCCATGTCATCATCCCGTATGAAGGTCTGA
GCGGCGACCAAATGGGCCAGATCGAAAAATTTTTAAGGTGGTGTACCCTGTGGATGATCATCACTTTAAGGTG
ATCCTGCACTATGGCACACTGGTAATCGACGGGGTTACGCCGAACATGATCGACTATTTCGGACGGCCGTATGA
AGGCATCGCCGTGTTCGACGGCAAAAAGATCACTGTAACAGGGACCCTGTGGAACGGCAACAAAATTATCGACG
AGCGCCTGATCAACCCCGACGGCTCCCTGCTGTTCCGAGTAACCATCAACGGAGTGACCGGCTGGCGGCTGTGC
GAACGCATTCTGGCGTAAAGGAGGTAAACATATGACCATGATTACGGATTCACTGGCCGTCGTTTTACAACGTC
GTGACTGGGAAAACCCTGGCGTTACCCAACTTAATCGCCTTGCAGCACATCCCCCTTTCGCCAGCTGGCGTAAT
AGCGAAGAGGCCCGCACCGATCGCCCTTCCCAACAGTTGCGCAGCCTGAATGGCGAATGGCATGACTGGTGGAC
AGCAAATGGGTACTAACCAAGGTAAAGGTGTAGTTGCTGCTGGAGATAAACTGGCGTTGTTCTTGAAGGTATTT
GGCGGTGAAGTCCTGACTGCGTTCGCTCGTACCTCCGTGACCACTTCTCGCCACATGGTACGTTCCATCTCCAG
CGGTAAATCCGCTCAGTTCCCTGTTCTGGGTCGCACTCAGGCAGCGTATCTGGCTCCGGGCGAGAACCTCGACG
ATAAACGTAAGGACATCAAACACACCGAGAAGGTAATCACCATTGACGGTCTCCTGACGGCTGACGTTCTGATT
TATGATATTGAGGACGCGATGAACCACTACGACGTTCGCTCTGAGTATACCTCTCAGTTGGGTGAATCTCTGGC
GATGGCTGCGGATGGTGCGGTTCTGGCTGAGATTGCCGGTCTGTGTAACGTGGAAAGCAAATATAATGAGAACA
TCGAGGGCTTAGGTACTGCTACGTAATTGAGACCACTCAGAACAAGGCCGCACTTACCGACCAAGTTGCGCTG
GGTAAGGAGATTATTGCGGCTCTGACTAAGGCTCGTGCGGCTCTGACCAAGAACTATGTTCCGGCTGCTGACCG
TGTGTTCTACTGTGACCCAGATAGCTACTCTGCGATTCTGGCAGCACTGATGCCGAACGCAGCAAACTACGCTG
CTCTGATTGACCCTGAGAAGGGTTCTATCCGCAACGTTATGGGCTTTGAGGTTGTAGAAGTTCCGCACCTCACC
GCTGGTGGTGCTGGTACCGCTCGTGAGGGCACTACTGGTCAGAAGCACGTCTTCCCTGCCAATAAAGGTGAGGG
TAATGTCAAGGTTGCTAAGGACAACGTTATCGGCCTGTTCATGCACCGCTCTGCGGTAGGTACTGTTAAGCTGC
GTGACTTGGCTCTGGAGCGCGCTCGCCGTGCTAACTTCCAAGCGGACCAGATTATCGCTAAGTACGCAATGGGC
CACGGTGGTCTTCGCCCAGAAGCTGCTGGTGCAGTGGTTTTCAAAGTGGAGTAATGCTGGGGGTGGCCTCAACG
GTCGCTGCTAGTCCCGAAGAGGCGAGTGTTACTTCAACAGAAGAAACCTTAACGCCAGCACAGGAGGCCGCACG
CACCCGCGCTGCTAACAAAGCCCGAAAGGAAGCTGAGTTGGCTGCTGCCACCGCTGAGCAATAACTAGCATAAC
CCCTTGGGGCCTCTAAACGGGTCTTGAGGGGTTTTTTGCTGAAAGGAGGAACTATATGCGCTCATACGATATGA
ACGTTGAGACTGCCGCTGAGTTATCAGCTGTGAACGACATTCTGGCGTCTATCGGTGAACCTCCGGTATCAACG
CTGGAAGGTGACGCTAACGCAGATGCAGCGAACGCTCGGCGTATTCTCAACAAGATTAACCGACAGATTCAATC
TCGTGGATGGACGTTCAACATTGAGGAAGGCATAACGCTACTACCTGATGTTTACTCCAACCTGATTGTATACA
GTGACGACTATTTATCCCTAATGTCTACTTCCGGTCAATCCATCTACGTTAACCGAGGTGGCTATGTGTATGAC
CGAACGAGTCAATCAGACCGCTTTGACTCTGGTATTACTGTGAACATTATTCGTCTCCGCGACTACGATGAGAT
GCCTGAGTGCTTCCGTTACTGGATTGTCACCAAGGCTTCCCGTCAGTTCAACAACCGATTCTTTGGGGCACCGG
AAGTAGAGGGTGTACTCCAAGAAGAGGAAGATGAGGCTAGACGTCTCTGCATGGAGTATGAGATGGACTACGGT
GGGTACAATATGCTGGATGGAGATGCGTTCACTTCTGGTCTACTGACTCGCTAACATTAATAAATAAGGAGGCT
CTAATGGCACTCATTAGCCAATCAATCAAGAACTTGAAGGGTGGTATCAGCCAACAGCCTGACATCCTTCGTTA
TCCAGACCAAGGGTCACGCCAAGTTAACGGTTGGTCTTCGGAGACCGAGGGCCTCCAAAAGCGTCCACCTCTTG
TTTTCTTAAATACACTTGGAGACAACGGTGCGTTAGGTCAAGCTCCGTACATCCACCTGATTAACCGAGATGAG
CACGAACAGTATTACGCTGTGTTCACTGGTAGCGGAATCCGAGTGTTCGACCTTTCTGGTAACGAGAAGCAAGT
TAGGTATCCTAACGGTTCCAACTACATCAAGACCGCTAATCCACGTAACGACCTGCGAATGGTTACTGTAGCAG
ACTATACGTTCATCGTTAACCGTAACGTTGTTGCACAGAAGAACACAAAGTCTGTCAACTTACCGAATTACAAC
CCTAATCAAGACGGATTGATTAACGTTCGTGGTGGTCAGTATGGTAGGGAACTAATTGTACACATTAACGGTAA
AGACGTTGCGAAGTATAAGATACCAGATGGTAGTCAACCTGAACACGTAAACAATACGGATGCCCAATGGTTAG
CTGAAGAGTTAGCCAAGCAGATGCGCACTAACTTGTCTGATTGGACTGTAAATGTAGGGCAAGGGTTCATCCAT
GTGACCGCACCTAGTGGTCAACAGATTGACTCCTTCACGACTAAAGATGGCTACGCAGACCAGTTGATTAACCC
TGTGACCCACTACGCTCAGTCGTTCTCTAAGCTGCCACCTAATGCTCCTAACGGCTACATGGTGAAAATCGTAG
GGGACGCCTCTAAGTCTGCCGACCAGTATTACGTTCGGTATGACGCTGAGCGGAAAGTTTGGACTGAGACTTTA
GGTTGGAACACTGAGGACCAAGTTCTATGGGAAACCATGCCACACGCTCTTGTGCGAGCCGCTGACGGTAATTT
CGACTTCAAGTGGCTTGAGTGGTCTCCTAAGTCTTGTGGTGACGTTGACACCAACCCTTGGCCTTCTTTTGTTG
GTTCAAGTATTAACGATGTGTTCTTCTTCCGTAACCGCTTAGGATTCCTTAGTGGGGAGAACATCATATTGAGT
CGTACAGCCAAATACTTCAACTTCTACCCTGCGTCCATTGCGAACCTTAGTGATGACGACCCTATAGACGTAGC
TGTGAGTACCAACCGAATAGCAATCCTTAAGTACGCCGTTCCGTTCTCAGAAGAGTTACTCATCTGGTCCGATG
```

FIG. 5H

```
AAGCACAATTCGTCCTGACTGCCTCGGGTACTCTCACATCTAAGTCGGTTGAGTTGAACCTAACGACCCAGTTT
GACGTACAGGACCGAGCGAGACCTTTTGGGATTGGGCGTAATGTCTACTTTGCTAGTCCGAGGTCCAGCTTCAC
GTCCATCCACAGGTACTACGCTGTGCAGGATGTCAGTTCCGTTAAGAATGCTGAGGACATTACATCACACGTTC
CTAACTACATCCCTAATGGTGTGTTCAGTATTTGCGGAAGTGGTACGGAAAACTTCTGTTCGGTACTATCTCAC
GGGGACCCTAGTAAAATCTTCATGTACAAATTCCTGTACCTGAACGAAGAGTTAAGGCAACAGTCGTGGTCTCA
TTGGGACTTTGGGGAAAACGTACAGGTTCTAGCTTGTCAGAGTATCAGCTCAGATATGTATGTGATTCTTCGCA
ATGAGTTCAATACGTTCCTAGCTAGAATCTCTTTCACTAAGAACGCCATTGACTTACAGGGAGAACCCTATCGT
GCCTTTATGGACATGAAGATTCGATACACGATTCCTAGTGGAACATACAACGATGACACATTCACTACCTCTAT
TCATATTCCAACAATTTATGGTGCAAACTTCGGGAGGGGCAAAATCACTGTATTGGAGCCTGATGGTAAGATAA
CCGTGTTTGAGCAACCTACGGCTGGGTGGAATAGCGACCCTTGGCTGAGACTCAGCGGTAACTTGGAGGGACGC
ATGGTGTACATTGGGTTCAACATTAACTTCGTATATGAGTTCTCTAAGTTCCTCATCAAGCAGACTGCCGACGA
CGGGTCTACCTCCACGGAAGACATTGGGCGCTTACAGTTACGCCGAGCGTGGGTTAACTACGAGAACTCTGGTA
CGTTTGACATTTATGTTGAGAACCAATCGTCTAACTGGAAGTACACAATGGCTGGTGCCCGATTAGGCTCTAAC
ACTCTGAGGGCTGGGAGACTGAACTTAGGGACCGGACAATATCGATTCCCTGTGGTTGGTAACGCCAAGTTCAA
CACTGTATACATCTTGTCAGATGAGACTACCCCTCTGAACATCATTGGGTGTGGCTGGAAGGTAACTACTTAC
GGAGAAGTTCCGGTATTTAATTAAATATTCTCCCTGTGGTGGCTCGAAATTAATACGACTCACTATAGGGAGAA
CAATACGACTACGGGAGGGTTTTCTTATGATGACTATAAGACCTACTAAAAGTACAGACTTTGAGGTATTCACT
CCGGCTCACCATGACATTCTTGAAGCTAAGGCTGCTGGTATTGAGCCGAGTTTCCCTGATGCTTCCGAGTGTGT
CACGTTGAGCCTCTATGGGTTCCCTCTAGCTATCGGTGGTAACTGCGGGGACCAGTGCTGGTTCGTTACGAGCG
ACCAAGTGTGGCGACTTAGTGGAAAGGCTAAGCGAAAGTTCCGTAAGTTAATCATGGAGTATCGCGATAAGATG
CTTGAGAAGTATGATACTCTTTGGAATTACGTATGGGTAGGCAATACGTCCCACATTCGTTTCCTCAAGACTAT
CGGTGCGGTATTCCATGAAGAGTACACACGAGATGGTCAATTTCAGTTATTTACAATCACGAAAGGAGGATAAC
CATATGTGTTGGGCAGCCGCAATACCTATCGCTATATCTGGCGCTCAGGCTATCAGTGGTCAGAACGCTCAGGC
CAAAATGATTGCCGCTCAGACCGCTGCTGGTCGTCGTCAAGCTATGGAAATCATGAGGCAGACGAACATCCAGA
ATGCTGACCTATCGTTGCAAGCTCGAAGTAAACTTGAGGAAGCGTCCGCCGAGTTGACCTCACAGAACATGCAG
AAGGTCCAAGCTATTGGGTCTATCCGAGCGGCTATCGGAGAGAGTATGCTTGAAGGTTCCTCAATGGACCGCAT
TAAGCGAGTCACAGAAGGACAGTTCATTCGGGAAGCCAATATGGTAACTGAGAACTATCGCCGTGACTACCAAG
CAATCTTCGCACAGCAACTTGGTGGTACTCAAAGTGCTGCAAGTCAGATTGACGAAATCTATAAGAGCGAACAG
AAACAGAAGAGTAAGCTACAGATGGTTCTGGACCCACTGGCTATCATGGGGTCTTCCGCTGCGAGTGCTTACGC
ATCCGGTGCGTTCGACTCTAAGTCCACAACTAAGGCACCTATTGTTGCCGCTAAAGGAACCAAGACGGGGAGGT
AATGAGCTATGAGTAAAATTGAATCTGCCCTTCAAGCGGCACAACCGGGACTCTCTCGGTTACGTGGTGGTGCT
GGAGGTATGGGCTATCGTGCAGCAACCACTCAGGCCGAACAGCCAAGGTCAAGCCTATTGGACACCATTGGTCG
GTTCGCTAAGGCTGGTGCCGATATGTATACCGCTAAGGAACAACGAGCACGAGACCTAGCTGATGAACGCTCTA
ACGAGATTATCCGTAAGCTGACCCCTGAGCAACGTCGAGAAGCTCTCAACAACGGGACCCTTCTGTATCAGGAT
GACCCATACGCTATGGAAGCACTCCGAGTCAAGACTGGTCGTAACGCTGCGTATCTTGTGGACGATGACGTTAT
GCAGAAGATAAAAGAGGGTGTCTTCCGTACTCGCGAAGAGATGGAAGAGTATCGCCATAGTCGCCTTCAAGAGG
GCGCTAAGGTATACGCTGAGCAGTTCGGCATCGACCCTGAGGACGTTGATTATCAGCGTGGTTTCAACGGGGAC
ATTACCGAGCGTAACATCTCGCTGTATGGTGCGCATGATAACTTCTTGAGCCAGCAAGCTCAGAAGGGCGCTAT
CATGAACAGCCGAGTGGAACTCAACGGTGTCCTTCAAGACCCTGATATGCTGCGTCGTCCAGACTCTGCTGACT
TCTTTGAGAAGTATATCGACAACGGTCTGGTTACTGGCGCAATCCCATCTGATGCTCAAGCCACACAGCTTATA
AGCCAAGCGTTCAGTGACGCTTCTAGCCGTGCTGGTGGTGCTGACTTCCTGATGCGAGTCGGTGACAAGAAGGT
AACACTTAACGGAGCCACTACGACTTACCGAGAGTTGATTGGTGAGGAACAGTGGAACGCTCTCATGGTCACAG
CACAACGTTCTCAGTTTGAGACTGACGCGAAGCTGAACGAGCAGTATCGCTTGAAGATTAACTCTGCGCTGAAC
CAAGAGGACCCAAGGACAGCTTGGGAGATGCTTCAAGGTATCAAGGCTGAACTAGATAAGGTCCAACCTGATGA
GCAGATGACACCACAACGTGAGTGGCTAATCTCCGCACAGGAACAAGTTCAGAATCAGATGAACGCATGGACGA
AAGCTCAGGCCAAGGCTCTGGACGATTCCATGAAGTCAATGAACAAACTTGACGTAATCGACAAGCAATTCCAG
AAGCGAATCAACGGTGAGTGGGTCTCAACGGATTTTAAGGATATGCCAGTCAACGAGAACACTGGTGAGTTCAA
GCATAGCGATATGGTTAACTACGCCAATAAGAAGCTCGCTGAGATTGACAGTATGGACATTCCAGACGGTGCCA
AGGATGCTATGAAGTTGAAGTACCTTCAAGCGGACTCTAAGGACGGAGCATTCCGTACAGCCATCGGAACCATG
GTCACTGACGCTGGTCAAGAGTGGTCTGCCGCTGTGATTAACGGTAAGTTACCAGAACGAACCCCAGCTATGGA
TGCTCTGCGCAGAATCCGCAATGCTGACCCTCAGTTGATTGCTGCGCTATACCCAGACCAAGCTGAGCTATTCC
TGACGATGGACATGATGGACAAGCAGGGTATTGACCCTCAGGTTATTCTTGATGCCGACCGACTGACTGTTAAG
CGGTCCAAAGAGCAACGCTTTGAGGATGATAAAGCATTCGAGTCTGCACTGAATGCATCTAAGGCTCCTGAGAT
TGCCCGTATGCCAGCGTCACTGCGCGAATCTGCACGTAAGATTTATGACTCCGTTAAGTATCGCTCGGGGAACG
```

FIG. 5I

```
AAAGCATGGCTATGGAGCAGATGACCAAGTTCCTTAAGGAATCTACCTACACGTTCACTGGTGATGATGTTGAC
GGTGATACCGTTGGTGTGATTCCTAAGAATATGATGCAGGTTAACTCTGACCCGAAATCATGGGAGCAAGGTCG
GGATATTCTGGAGGAAGCACGTAAGGGAATCATTGCGAGCAACCCTTGGATAACCAATAAGCAACTGACCATGT
ATTCTCAAGGTGACTCCATTTACCTTATGGACACCACAGGTCAAGTCAGAGTCCGATACGACAAAGAGTTACTC
TCGAAGGTCTGGAGTGAGAACCAGAAGAAACTCGAAGAGAAAGCTCGTGAGAAGGCTCTGGCTGATGTGAACAA
GCGAGCACCTATAGTTGCCGCTACGAAGGCCCGTGAAGCTGCTGCTAAACGAGTCCGAGAGAAACGTAAACAGA
CTCCTAAGTTCATCTACGGACGTAAGGAGTAACTAAAGGCTACATAAGGAGGCCCTAAATGGATAAGTACGATA
AGAACGTACCAAGTGATTATGATGGTCTGTTCCAAAAGGCTGCTGATGCCAACGGGGTCTCTTATGACCTTTTA
CGTAAAGTCGCTTGGACAGAATCACGATTTGTGCCTACAGCAAAATCTAAGACTGGACCATTAGGCATGATGCA
ATTTACCAAGGCAACCGCTAAGGCCCTCGGTCTGCGAGTTACCGATGGTCCAGACGACGACCGACTGAACCCTG
AGTTAGCTATTAATGCTGCCGCTAAGCAACTTGCAGGTCTGGTAGGGAAGTTTGATGGCGATGAACTCAAAGCT
GCCCTTGCGTACAACCAAGGCGAGGGACGCTTGGGTAATCCACAACTTGAGGCGTACTCTAAGGGAGACTTCGC
ATCAATCTCTGAGGAGGGACGTAACTACATGCGTAACCTTCTGGATGTTGCTAAGTCACCTATGGCTGGACAGT
TGGAAACTTTTGGTGGCATAACCCCAAAGGGTAAAGGCATTCCGGCTGAGGTAGGATTGGCTGGAATTGGTCAC
AAGCAGAAAGTAACACAGGAACTTCCTGAGTCCACAAGTTTTGACGTTAAGGGTATCGAACAGGAGGCTACGGC
GAAACCATTCGCCAAGGACTTTTGGGAGACCCACGGAGAAACACTTGACGAGTACAACAGTCGTTCAACCTTCT
TCGGATTCAAAAATGCTGCCGAAGCTGAACTCTCCAACTCAGTCGCTGGGATGGCTTTCCGTGCTGGTCGTCTC
GATAATGGTTTTGATGTGTTTAAAGACACCATTACGCCGACTCGCTGGAACTCTCACATCTGGACTCCAGAGGA
GTTAGAGAAGATTCGAACAGAGGTTAAGAACCCTGCGTACATCAACGTTGTAACTGGTGGTTCCCCTGAGAACC
TCGATGACCTCATTAAATTGGCTAACGAGAACTTTGAGAATGACTCCCGCGCTGCCGAGGCTGGCCTAGGTGCC
AAACTGAGTGCTGGTATTATTGGTGCTGGTGTGGACCCGCTTAGCTATGTTCCTATGGTCGGTGTCACTGGTAA
GGGCTTTAAGTTAATCAATAAGGCTCTTGTAGTTGGTGCCGAAAGTGCTGCTCTGAACGTTGCATCCGAAGGTC
TCCGTACCTCCGTAGCTGGTGGTGACGCAGACTATGCGGGTGCTGCCTTAGGTGGCTTTGTGTTTGGCGCAGGC
ATGTCTGCAATCAGTGACGCTGTAGCTGCTGGACTGAAACGCAGTAAACCAGAAGCTGAGTTCGACAATGAGTT
CATCGGTCCTATGATGCGATTGGAAGCCCGTGAGACAGCACGAAACGCCAACTCTGCGGACCTCTCTCGGATGA
ACACTGAGAACATGAAGTTTGAAGGTGAACATAATGGTGTCCCTTATGAGGACTTACCAACAGAGAGAGGTGCC
GTGGTGTTACATGATGGCTCCGTTCTAAGTGCAAGCAACCCAATCAACCCTAAGACTCTAAAAGAGTTCTCCGA
GGTTGACCCTGAGAAGGCTGCGCGAGGAATCAAACTGGCTGGGTTCACCGAGATTGGCTTGAAGACCTTGGGGT
CTGACGATGCTGACATCCGTAGAGTGGCTATCGACCTCGTTCGCTCTCCTACTGGTATGCAGTCTGGTGCCTCA
GGTAAGTTCGGTGCAACAGCTTCTGACATCCATGAGAGACTTCATGGTACTGACCAGCGTACTTATAATGACTT
GTACAAAGCAATGTCTGACGCTATGAAAGACCCTGAGTTCTCTACTGGCGGCGCTAAGATGTCCCGTGAAGAAA
CTCGATACACTATCTACCGTAGAGCGGCACTAGCTATTGAGCGTCCAGAACTACAGAAGGCACTCACTCCGTCT
GAGAGAATCGTTATGGACATCATTAAGCGTCACTTTGACACCAAGCGTGAACTTATGGAAAACCCAGCAATATT
CGGTAACACAAAGGCTGTGAGTATCTTCCCTGAGAGTCGCCACAAAGGTACTTACGTTCCTCACGTATATGACC
GTCATGCCAAGGCGCTGATGATTCAACGCTACGGTGCCGAAGGTTTGCAGGAAGGGATTGCCCGCTCATGGATG
AACAGCTACGTCTCCAGACCTGAGGTCAAGGCCAGAGTCGATGAGATGCTTAAGGAATTACACGGGGTGAAGGA
AGTAACACCAGAGATGGTAGAGAAGTACGCTATGGATAAGGCTTATGGTATCTCCCACTCAGACCAGTTCACCA
ACAGTTCCATAATAGAAGAGAACATTGAGGGCTTAGTAGGTATCGAGAATAACTCATTCCTTGAGGCACGTAAC
TTGTTTGATTCGGACCTATCCATCACTATGCCAGACGGACAGCAATTCTCAGTGAATGACCTAAGGGACTTCGA
TATGTTCCGCATCATGCCAGCGTATGACCGCCGTGTCAATGGTGACATCGCCATCATGGGGTCTACTGGTAAAA
CCACTAAGGAACTTAAGGATGAGATTTTGGCTCTCAAAGCGAAAGCTGAGGGAGACGGTAAGAAGACTGGCGAG
GTACATGCTTTAATGGATACCGTTAAGATTCTTACTGGTCGTGCTAGACGCAATCAGGACACTGTGTGGGAAAC
CTCACTGCGTGCCATCAATGACCTAGGGTTCTTCGCTAAGAACGCCTACATGGGTGCTCAGAACATTACGGAGA
TTGCTGGGATGATTGTCACTGGTAACGTTCGTGCTCTAGGGCATGGTATCCCAATTCTGCGTGATACACTCTAC
AAGTCTAAACCAGTTTCAGCTAAGGAACTCAAGGAACTCCATGCGTCTCTGTTCGGGAAGGAGGTGGACCAGTT
GATTCGGCCTAAACGTGCTGACATTGTGCAGCGCCTAAGGGAAGCAACTGATACCGGACCTGCCGTGGCGAACA
TCGTAGGGACCTTGAAGTATTCAACACAGGAACTGGCTGCTCGCTCTCCGTGGACTAAGCTACTGAACGGAACC
ACTAACTACCTTCTGGATGCTGCGCGTCAAGGTATGCTTGGGGATGTTATTAGTGCCACCCTAACAGGTAAGAC
TACCCGCTGGGAGAAGAAGGCTTCCTTCGTGGTGCCTCCGTAACTCCTGAGCAGATGGCTGGCATCAAGTCTC
TCATCAAGGAACATATGGTACGCGGTGAGGACGGGAAGTTTACCGTTAAGGACAAGCAAGCGTTCTCTATGGAC
CCACGGGCTATGGACTTATGGAGACTGGCTGACAAGGTAGCTGATGAGGCAATGCTGCGTCCACATAAGGTGTC
CTTACAGGATTCCCATGCGTTCGGAGCACTAGGTAAGATGGTTATGCAGTTTAAGTCTTTCACTATCAAGTCCC
TTAACTCTAAGTTCCTGCGAACCTTCTATGATGGATACAAGAACAACCGAGCGATTGACGCTGCGCTGAGCATC
ATCACCTCTATGGGTCTCGCTGGTGGTTTCTATGCTATGGCTGCACACGTCAAAGCATACGCTCTGCCTAAGGA
```

FIG. 5J

```
GAAACGTAAGGAGTACTTGGAGCGTGCACTGGACCCAACCATGATTGCCCACGCTGCGTTATCTCGTAGTTCTC
AATTGGGTGCTCCTTTGGCTATGGTTGACCTAGTTGGTGGTGTTTTAGGGTTCGAGTCCTCCAAGATGGCTCGC
TCTACGATTCTACCTAAGGACACCGTGAAGGAACGTGACCCAAACAAACCGTACACCTCTAGAGAGGTAATGGG
CGCTATGGGTTCAAACCTTCTGGAACAGATGCCTTCGGCTGGCTTTGTGGCTAACGTAGGGGCTACCTTAATGA
ATGCTGCTGGCGTGGTCAACTCACCTAATAAAGCAACCGAGCAGGACTTCATGACTGGTCTTATGAACTCCACA
AAAGAGTTAGTACCGAACGACCCATTGACTCAACAGCTTGTGTTGAAGATTTATGAGGCGAACGGTGTTAACTT
GAGGGAGCGTAGGAAATAATACGACTCACTATAGGGAGAGGCGAAATAATCTTCTCCCTGTAGTCTCTTAGATT
TACTTTAAGGAGGTCAAATGGCTAACGTAATTAAAACCGTTTTGACTTACCAGTTAGATGGCTCCAATCGTGAT
TTTAATATCCCGTTTGAGTATCTAGCCCGTAAGTTCGTAGTGGTAACTCTTATTGGTGTAGACCGAAAGGTCCT
TACGATTAATACAGACTATCGCTTTGCTACACGTACTACTATCTCTCTGACAAAGGCTTGGGGTCCAGCCGATG
GCTACACGACCATCGAGTTACGTCGAGTAACCTCCACTACCGACCGATTGGTTGACTTTACGGATGGTTCAATC
CTCCGCGCGTATGACCTTAACGTCGCTCAGATTCAAACGATGCACGTAGCGGAAGAGGCCCGTGACCTCACTAC
GGATACTATCGGTGTCAATAACGATGGTCACTTGGATGCTCGTGGTCGTCGAATTGTGAACCTAGCGAACGCCG
TGGATGACCGCGATGCTGTTCCGTTTGGTCAACTAAAGACCATGAACCAGAACTCATGGCAAGCACGTAATGAA
GCCTTACAGTTCCGTAATGAGGCTGAGACTTTCAGAAACCAAGCGGAGGGCTTTAAGAACGAGTCCAGTACCAA
CGCTACGAACACAAAGCAGTGGCGCGATGAGACCAAGGGTTTCCGAGACGAAGCCAAGCGGTTCAAGAATACGG
CTGGTCAATACGCTACATCTGCTGGGAACTCTGCTTCCGCTGCGCATCAATCTGAGGTAAACGCTGAGAACTCT
GCCACAGCATCCGCTAACTCTGCTCATTTGGCAGAACAGCAAGCAGACCGTGCGGAACGTGAGGCAGACAAGCT
GGAAAATTACAATGGATTGGCTGGTGCAATTGATAAGGTAGATGGAACCAATGTGTACTGGAAAGGAAATATTC
ACGCTAACGGGCGCCTTTACATGACCACAAACGGTTTTGACTGTGGCCAGTATCAACAGTTCTTTGGTGGTGTC
ACTAATCGTTACTCTGTCATGGAGTGGGGAGATGAGAACGGATGGCTGATGTATGTTCAACGTAGAGAGTGGAC
AACAGCGATAGGCGGTAACATCCAGTTAGTAGTAAACGGACAGATCATCACCCAAGGTGGAGCCATGACCGGTC
AGCTAAAATTGCAGAATGGGCATGTTCTTCAATTAGAGTCCGCATCCGACAAGGCGCACTATATTCTATCTAAA
GATGGTAACAGGAATAACTGGTACATTGGTAGAGGGTCAGATAACAACAATGACTGTACCTTCCACTCCTATGT
ACATGGTACGACCTTAACACTCAAGCAGGACTATGCAGTAGTTAACAAACACTTCCACGTAGGTCAGGCCGTTG
TGGCCACTGATGGTAATATTCAAGGTACTAAGTGGGGAGGTAAATGGCTGGATGCTTACCTACGTGACAGCTTC
GTTGCGAAGTCCAAGGCGTGGACTCAGGTGTGGTCTGGTAGTGCTGGCGGTGGGGTAAGTGTGACTGTTTCACA
GGATCTCCGCTTCCGCAATATCTGGATTAAGTGTGCCAACAACTCTTGGAACTTCTTCCGTACTGGCCCCGATG
GAATCTACTTCATAGCCTCTGATGGTGGATGGTTACGATTCCAAATACACTCCAACGGTCTCGGATTCAAGAAT
ATTGCAGACAGTCGTTCAGTACCTAATGCAATCATGGTGGAGAACGAGTAATTGGTAAATCACAAGGAAAGACG
TGTAGTCCACGGATGGACTCTCAAGGAGGTACAAGGTGCTATCATTAGACTTTAACAACGAATTGATTAAGGCT
GCTCCAATTGTTGGGACGGGTGTAGCAGATGTTAGTGCTCGACTGTTCTTTGGGTTAAGCCTTAACGAATGGTT
CTACGTTGCTGCTATCGCCTACACAGTGGTTCAGATTGGTGCCAAGGTAGTCGATAAGATGATTGACTGGAAGA
AAGCCAATAAGGAGTGATATGTATGGAAAAGGATAAGAGCCTTATTACATTCTTAGAGATGTTGGACACTGCGA
TGGCTCAGCGTATGCTTGCGGACCTTTCGGACCATGAGCGTCGCTCTCCGCAACTCTATAATGCTATTAACAAA
CTGTTAGACCGCCACAAGTTCCAGATTGGTAAGTTGCAGCCGGATGTTCACATCTTAGGTGGCCTTGCTGGTGC
TCTTGAAGAGTACAAAGAGAAAGTCGGTGATAACGGTCTTACGGATGATGATATTTACACATTACAGTGATATA
CTCAAGGCCACTACAGATAGTGGTCTTTATGGATGTCATTGTCTATACGAGATGCTCCTACGTGAAATCTGAAA
GTTAACGGGAGGCATTATGCTAGAATTTTTACGTAAGCTAATCCCTTGGGTTCTCGCTGGGATGCTATTCGGGT
TAGGATGGCATCTAGGGTCAGACTCAATGGACGCTAAATGGAAACAGGAGGTACACAATGAGTACGTTAAGAGA
GTTGAGGCTGCGAAGAGCACTCAAAGAGCAATCGATGCGGTATCTGCTAAGTATCAAGAAGACCTTGCCGCGCT
GGAAGGGAGCACTGATAGGATTATTTCTGATTTGCGTAGCGACAATAAGCGGTTGCGCGTCAGAGTCAAAACTA
CCGGAACCTCCGATGGTCAGTGTGGATTCGAGCCTGATGGTCGAGCCGAACTTGACGACCGAGATGCTAAACGT
ATTCTCGCAGTGACCCAGAAGGGTGACGCATGGATTCGTGCGTTACAGGATACTATTCGTGAACTGCAACGTAA
GTAGGAAATCAAGTAAGGAGGCAATGTGTCTACTCAATCCAATCGTAATGCGCTCGTAGTGGCGCAACTGAAAG
GAGACTTCGTGGCGTTCCTATTCGTCTTATGGAAGGCGCTAAACCTACCGGTGCCCACTAAGTGTCAGATTGAC
ATGGCTAAGGTGCTGGCGAATGGAGACAACAAGAAGTTCATCTTACAGGCTTTCCGTGGTATCGGTAAGTCGTT
CATCACATGTGCGTTCGTTGTGTGGTCCTTATGGAGAGACCCTCAGTTGAAGATACTTATCGTATCAGCCTCTA
AGGAGCGTGCAGACGCTAACTCCATCTTTATTAAGAACATCATTGACCTGCTGCCATTCCTATCTGAGTTAAAG
CCAAGACCCGGACAGCGTGACTCGGTAATCAGCTTTGATGTAGGCCCAGCCAATCCTGACCACTCTCCTAGTGT
GAAATCAGTAGGTATCACTGGTCAGTTAACTGGTAGCCGTGCTGACATTATCATTGCGGATGACGTTGAGATTC
CGTCTAACAGCGCAACTATGGGTGCCCGTGAGAAGCTATGGACTCTGGTTCAGGAGTTCGCTGCGTTACTTAAA
CCGCTGCCTTCCTCTCGCGTTATCTACCTTGGTACACCTCAGACAGAGATGACTCTCTATAAGGAACTTGAGGA
TAACCGTGGGTACACAACCATTATCTGGCCTGCTCTGTACCCAAGGACACGTGAAGAGAACCTCTATTACTCAC
```

```
AGCGTCTTGCTCCTATGTTACGCGCTGAGTACGATGAGAACCCTGAGGCACTTGCTGGGACTCCAACAGACCCA
GTGCGCTTTGACCGTGATGACCTGCGCGAGCGTGAGTTGGAATACGGTAAGGCTGGCTTTACGCTACAGTTCAT
GCTTAACCCTAACCTTAGTGATGCCGAGAAGTACCCGCTGAGGCTTCGTGACGCTATCGTAGCGGCCTTAGACT
TAGAGAAGGCCCCAATGCATTACCAGTGGCTTCCGAACCGTCAGAACATCATTGAGGACCTTCCTAACGTTGGC
CTTAAGGGTGATGACCTGCATACGTACCACGATTGTTCCAACAACTCAGGTCAGTACCAACAGAAGATTCTGGT
CATTGACCCTAGTGGTCGCGGTAAGGACGAAACAGGTTACGCTGTGCTGTACACACTGAACGGTTACATCTACC
TTATGGAAGCTGGAGGTTTCCGTGATGGCTACTCCGATAAGACCCTTGAGTTACTCGCTAAGAAGGCAAAGCAA
TGGGGAGTCCAGACGGTTGTCTACGAGAGTAACTTCGGTGACGGTATGTTCGGTAAGGTATTCAGTCCTATCCT
TCTTAAACACCACAACTGTGCGATGGAAGAGATTCGTGCCCGTGGTATGAAAGAGATGCGTATTTGCGATACCC
TTGAGCCAGTCATGCAGACTCACCGCCTTGTAATTCGTGATGAGGTCATTAGGGCCGACTACCAGTCCGCTCGT
GACGTAGACGGTAAGCATGACGTTAAGTACTCGTTGTTCTACCAGATGACCCGTATCACTCGTGAGAAAGGCGC
TCTGGCTCATGATGACCGATTGGATGCCCTTGCGTTAGGCATTGAGTATCTCCGTGAGTCCATGCAGTTGGATT
CCGTTAAGGTCGAGGGTGAAGTACTTGCTGACTTCCTTGAGGAACACATGATGCGTCCTACGGTTGCTGCTACG
CATATCATTGAGATGTCTGTGGGAGGAGTTGATGTGTACTCTGAGGACGATGAGGGTTACGGTACGTCTTTCAT
TGAGTGGTGATTTATGCATTAGGACTGCATAGGGATGCACTATAGACCACGGATGGTCAGTTCTTTAAGTTACT
GAAAAGACACGATAAATTAATACGACTCACTATAGGGAGAGGAGGGACGAAAGGTTACTATATAGATACTGAAT
GAATACTTATAGAGTGCATAAAGTATGCATAATGGTGTACCTAGAGTGACCTCTAAGAATGGTGATTATATTGT
ATTAGTATCACCTTAACTTAAGGACCAACATAAAGGGAGGAGACTCATGTTCCGCTTATTGTTGAACCTACTGC
GGCATAGAGTCACCTACCGATTTCTTGTGGTACTTTGTGCTGCCCTTGGGTACGCATCTCTTACTGGAGACCTC
AGTTCACTGGAGTCTGTCGTTTGCTCTATACTCACTTGTAGCGATTAGGGTCTTCCTGACCGACTGATGGCTCA
CCGAGGGATTCAGCGGTATGATTGCATCACACCACTTCATCCCTATAGAGTCAAGTCCTAAGGTATACCCATAA
AGAGCCTCTAATGGTCTATCCTAAGGTCTATACCTAAAGATAGGCCATCCTATCAGTGTCACCTAAAGAGGGTC
TTAGAGAGGGCCTATGGAGTTCCTATAGGGTCCTTTAAAATATACCATAAAAATCGAGTGACTATCTCACAGT
GTACGGACCTAAAGTTCCCCCATAGGGGGTACCTAAAGCCCAGCCAATCACCTAAAGTCAACCTTCGGTTGACC
TTGAGGGTTCCCTAAGGGTTGGGATGACCCTTGGGTTTGTCTTTGGGTGTTACCTTGAGTGTCTCTCTGTGTC
CCT
```

>K1-S Insert DNA (SEQ ID NO: 3)
CAACGTCGTGCCATGAAGAAACCTTCTGCATCTTCTGCGTAAAGAGGAGATATACAATGGTCTTCACACTCGAAGA
TTTCGTTGGGGACTGGCGACAGACAGCCGGCTACAACCTGGACCAAGTCCTTGAACAGGGAGGTGTGTCCAGTTT
GTTTCAGAATCTCGGGGTGTCCGTAACTCCGATCCAAAGGATTGTCCTGAGCGGTGAAAATGGGCTGAAGATCGA
CATCCATGTCATCATCCCGTATGAAGGTCTGAGCGGCGACCAAATGGGCCAGATCGAAAAAATTTTTAAGGTGGT
GTACCCTGTGGATGATCATCACTTTAAGGTGATCCTGCACTATGGCACACTGGTAATCGACGGGGTTACGCCGAAC
ATGATCGACTATTTCGGACGGCCGTATGAAGGCATCGCCGTGTTCGACGGCAAAAAGATCACTGTAACAGGGACC
CTGTGGAACGGCAACAAAATTATCGACGAGCGCCTGATCAACCCCGACGGCTCCCTGCTGTTCCGAGTAACCATCA
ACGGAGTGACCGGCTGGCGGCTGTGCGAACGCATTCTGGCGTAAGCAGGTTAATATCTTAGTATAAACAAGGGCA
GACTTAGGTTTGTCCTTAGTGTATTCCAAAGGAGGTAACATGCTGAAAGATGGTTGGGTTTCATATGACCCTACAG
ACCCTAAGAATTGGCTACAGGTTATCGCTATAGCTTGTGCAGGTAGCCTATTGGCTGCCCTGATGTATTCATTATGG
ATGTACACAAAGTAACCAAAGTCAAAATTTTGATGTAGGCGTGTGTCAGCTCTCTCGCCCTCGCCCTCGCCGGGTT
GTCCCCATAGGGTGGCCTGAGGGAATCCGTCTTCGACGGGCAGGGCTGATGTACTCCTTGTCTAGTACAAGGGAG
GCGGAGGGAACGCCTAGGGAGGCCTAGGAATGGCTTAGTGGTGGACAAGGTGATTACCTTAGTGAAGCCTCTTA
GTGCATTCCTGAGGCCATTCAGGGCGTTTATGAGGGATTGACAGGGTGTGAGGGCGTGGGCTA

FIG. 13A

>Recombinant detector K1-5 phage (SEQ ID NO: 4)
TCGCCCTCGCCCTCGCCGGGTTGTCCCCATAGGGTGGCCTGAGGGAATCCGTCTTCGACGGGCAGGGCTGATGTACTCCTTGTCTAGTACAA
GGGAGGCGGAGGGAACGCCTAGGGAGGCCTAGGAATGGCTTAGTGGTGGACAAGGTGATTACCTTAGTGAAGCCTCTTAGTGCATTCCTGA
GGCCATTCAGGGCGTTTATGAGGGATTGACAGGGTGTGAGGGCGTGGGCTATCTGTTCCTTTGCTCCTCACTTCGTTCGTCGCTGCGGTAGCC
TGATGTGTACCTTAGGTTATTCCTTGATGGATAGCTTAGGTTAGCCTTAGTGGATTACCTTAGTTAAAGCCTTAGTGCTTCACTTAGTATCAGCT
TAGTAGTGTACCTTAGTAAGTCTTAGTGTCTTCTCTTAGTGATTGCACATGCAAGCATGTAAGATGCTAATAGGTCGCGGTCGGCAGACCGCT
AAAGAAAGAGAATGGTAATAAGATGCAGTAGGAGGAACACCAGAAGCCTAGCCAACCTAAGCTATCCTAGCTCTATATCTATTGCTTTTCCTT
AGTCTAACACGTTAGACAACCTATCTTATTCTTAGTGATGGTAACTTAGTGTTGACAAGATAATCTTAGTGTAATACTATGCATCACGTAGGCG
GTGCTGAGGCACCTAGTAGCCAGCTAGTAAGGCATACGAAGAGACTAGCGCTTACATTGCTCTTTAACAATTTGCTTAGTGTAACCTATGTAT
GCCGTGGTTAACTACTTATTGAATGAGGTATTAACTATGACATTAAATAACCGTGAACTGTCCGTTCTCTTCACTCTGTTGTGCTACATGATTCG
TAACAACGAATTACTTACAGATGATGAGTTAGCCTTGTATCACCGCTTTCTTAACGAAGGTTGGACCGATACAGTTAATCAATACCGTAACATG
ATAGATGAGTTGAGGGAGGGTAAATAATGTATCAACATGAGGTATTCTTTGAATCAGCTAGCGAAGCTATTCGCTTCCGTGATGATATGATG
CAAGCTGGTGTAGGCGTTGATGTGTATCACTATTTGATAGATTACGACACTGAATATCACCGAGTTACCTTAGTATCTGAGTATGACAACCAA
GTCATTACTGAGTATCTAGGCAGTGAAGATTACGATTACGATGAAGTAATCACGACAAATCTCTAAATTAACTGTTGACAGCCACGGCATACA
AGGTTACATTAAGCATCAAGACGGCGACGTCTTTAAACATCCCGCTCTTTAACAATACGGTTTGTGTCTTGATAGGCTAACTAACTAACTAAGG
TAATTATCATGAAAGGGTTAATTTGTGTAGAACGTATGGTCAATGGTAAACTTGAAATATTACCACTGGAAAACCAATCTAGCTTCAAAGAGT
GGTATGGCTGTTTCTCACTGATTTAAGGTAAAGGCTGGCACTAGTCAGCCTATCAAGGCGCAAACCAAGCTCTTTAACAATTTGGATGGTAGC
TTCTTAGTCTGGATAGGTTAAACCTAGGAGATTCTCTTGAGTCTCCTATAATGTAACCTAACTAACTAAATGAGGATTAAATCATGGAACGCAA
TGCTAACGCTTACTACAACCTTCTGGCTGCAACTGTTGAAGCATTCAACGAGCGTATTCAGTTTGATGAGATTCGCGAAGGTGATGATTACTCT
GATGCACTACATGAGGTTGTAGACAGCAATGTTCCAGTTTATTACAGCGAAATCTTTACAGTGATGGCTGCTGATGGTATTGATGTTGATTTT
GAGGATGCTGGTTTGATTCCTGACACGAAGGATGTAACCAAGATTCTACAAGCTCGCATCTATGAAGCTCTTTATAATGATGTACCAAATGAC
AGCGATGTAGTTTGGTGTGAAGGCGAAGAAGAGGAAGAATAAGGATGGAAAAGCAATATAACTTTATCTTTTCAGACGGTGTAACCCTGAA
GTGTTCCCTACGATTCGCACAAATTCGTGAGGAAGTACTAGGCACTACATCAAACTATTTAGCTGACACTATAAGAGAAGGCTTAACAAGGC
GTTACTAAGGTAGCGCCTGATTAAACTTTCACTTACTAGGAGTTGAGATTATGAAAACCTTGATTGGATGCTTCTTGTTGGCTTCTCTTGCTCT
GGCATTTACCGCTAAAGCTGGTTATGACGCTTATAAAGTAGAACAAGCCCAGCAAGACTGGGCCAAAAAAAGTTCAACTTGTGCAGAAGA
GCAACACCTACGAGTACTGCAACAAAACACTAAGACACTTATGGAAAGAGTAACTAGCCTATAGCCCACCTGAGTGGGCTATGTGATATTTAC
TTAACACTATATAAGGTGATTACTATGACTACTGAAAACACCCTCGTGTCTGTCCGTGAAGCTGCAACGCTGAAATCAAGCAACATTTAGAC
AATATCGGCACTTCTTACATCAAAGTAGGGGCTTGTCTGAATGAGTTACGCGGAGACTTTGAAGGTCAAAAAGAGTTTTTAGCCTATGTTGAA
GCAGAGTTTGCCATTAAGAAGGCACAATGTTACAAGCTGATGAGTGTAGCCCGTGTCTTTGAAGGCGATGATCGCTTTAAAGGCGTGGCGAT
GCGTGTAATGCTGGCGCTTGTTCCTTTCGCTGATGAAAATATAATCATGGAGAAGGCCGCAGAACTCGCCGCAAATGGCAAGCTGGACACTA
ATGCCGTAAACGCCCTGATTGAACCTAAGAAAGAGTCAAAGGCCGAAACGGTACAATCTAAGGCTGAGACAGTAAAACCGCAGGAGAACGC
GACTGAGTCCGCAGAATCACATGAAATGCAAGCGCCGCAGGTAGTGCCACCCGCGAGCGAGCAGGAGTCCGACGAATCAGCACCTTGGGAA
GAGGAAAGCAAACCGGAAGCGCCAAAGGCAGCTCCGATGGATAACACGGCTAATACTGAGAATGCCGCTATTGCTGGTCTGCTGGCACAAA
TTAAAGCACTGACTGAGCAATTACAGGCAGCCAATGACCGCATCGCCTCCTTAAGTAGCGCACGCGAAAGCAAGAAGGCATCCGCACCTATG
CTGCCGCAGTTCAAATCTTCCTGCTTCTACGCTCGCTTAGGCTTGAGCGCGGAGGAGGCAACGAAGAAAACAGCAGTTAACAAGGCACGCCG
CGAACTGGTTAAGCTGGGATACGGTGAAGGCCATGAGGCATGGCCCTTAATCTCTGAGGCAGTAGAAGAGTTGACTAAGTAACCTTATCGGT
GGCATCTTCTTAGGTGTCACCTATTAAGGTTTCTTTCACTAGGAGTAAACAAGATGCAAGGCCTACACGCTATTCAACTTCAACTTGAAGAAGA
AATGTTTAACGGCGGTATCCGTCGCTTTGAAGCGGACCAACAACGCCAGATTGCATCCGGTAATGAATCAGACACGGCATGGAATCGCCGCT
TATTGTCCGAGTTAATCGCGCCAATGGCTGAAGGTATTCAGGCATACAAGGAAGAGTATGAAGGTAAAAGAGGCCGTGCACCGCGTGCATT
AGCTTTCATTAACTGCGTAGAAAACGAAGTGGCAGCATATATCACGATGAAAATCGTTATGGATATGCTGAACACGGATGTAACCTTGCAGG
CTATAGCCATGAATGTAGCTGACCGCATTGAGGACCAAGTACGTTTTAGCAAGCTGGAAGGTCACGCCGCCAAATACTTTGAAAAAGTTAAG
AAGTCACTTAAGGCAAGTAAGACTAAATCATATCGCCATGCGCACAACGTAGCGGTAGTGGCTGAGAAGTCAGTAGCTGACCGTGACGCTGA
TTTCTCCCGCTGGGAGGCATGGCCTAAAGACACCTTGCTGCAAATTGGGATGACCTTGCTTGAAATCTTAGAGAATAGCGTATTCTTCAACGG
GCAACCTGTCTTCCTCCGCACCTTGCGCACTAATGGCGGCAAACATGGTGTTTACTACCTACAGACTAGTGAACACGTAGGTGAGTGGATAAC
TGCATTCAAAGAGCACGTAGCGCAACTGAGTCCTGCCTATGCTCCTTGCGTCATCCCTCCGCGTCCGTGGGTATCACCTTTTAACGGCGGTTTC
CACACTGAGAAAGTAGCAAGCCGTATTCGTCTGGTAAAAGGAAACCGCGAACACGTCCGCAAGCTGACCAAAAAGCAAATGCCAGAGGTTT
ACAAGGCTGTTAACGCGTTGCAGGCGACTAAATGGCAGGTTAACAAGGAAGTTTTACAGGTTGTGGAAGACGTCATCCGTCTAGACCTAGGT
TATGGTGTACCTTCCTTTAAACCACTCATTGACCGCGAGAACAAGCCAGCTAATCCAGTGCCGCTAGAATTTCAGCACCTACGGGGCCGTGAA
CTGAAAGAAATGCTTACGCCGGAACAATGGCAAGCCTTTATCAACTGGAAAGGTGAATGTACTAAGCTGTACACCGCTGAAACTAAGCGCGG
AAGCAAATCGGCGGCAACCGTTCGCATGGTTGGTCAGGCCCGTAAATATAGCCAGTTCGACGCAATCTACTTCGTGTATGCACTGGACAGCC
GCAGCCGCGTCTACGCGCAATCTAGCACACTCTCACCGCAATCAAATGACTTGGGCAAGGCCTTGCTCCGTTTTACCGAAGGGCAGCGTCTTG
ATAGCGCTGAGGCGCTTAAGTGGTTTTTGGTGAACGGGGCTAATAACTGGGGTTGGGATAAGAAAACTTTTGACGTGCGCACCGCTAACGTG

FIG. 13B

```
CTGGATAGTGAATTTCAAGACATGTGCCGCGACATTGCAGCGGATCCGCTGACCTTCACTCAATGGGTAAATGCCGACTCCCCTTACGGCTTC
CTTGCATGGTGCTTTGAATATGCGCGTTATCTGGATGCACTGGATGAAGGCACGCAAGACCAATTCATGACGCACCTCCCAGTCCATCAAGAT
GGTAGTTGTTCTGGTATCCAGCACTACAGTGCTATGCTACGCGATGCAGTAGGTGCGAAAGCAGTAAACCTTAAGCCCTCTGACTCTCCTCAA
GATATTTATGGTGCCGTTGCGCAGGTAGTAATTCAGAAGAATTATGCATACATGAATGCAGAGGATGCGGAAACCTTCACTTCTGGCAGCGT
GACTTTAACAGGTGCGGAGCTGCGTAGTATGGCTAGTGCGTGGGATATGATAGGAATCACTCGCGGCCTGACCAAAAAGCCCGTAATGACA
CTACCTTATGGCAGCACACGTCTAACCTGCCGTGAGTCAGTGATTGATTATATCGTTGATTTAGAAGAAAAAGAGGCCCAACGGGCTATTGCG
GAAGGGCGTACCGCCAATCCTGTACACCCTTTTGATAATGACCGTAAAGACAGCCTGACACCTAGCGCAGCTTATAACTATATGACAGCTTTA
ATCTGGCCTTCTATTTCGGAAGTGGTTAAAGCCCCTATAGTGGCAATGAAAATGATTCGTCAGCTTGCCCGTTTCGCAGCTAAAAGGAATGAA
GGCTTAGAGTATACCCTGCCTACTGGCTTCATCTTGCAACAAAAGATTATGGCTACTGATATGCTCCGCGTATCTACTTGCTTGATGGGAGAAA
TCAAGATGAGTCTACAGATTGAAACAGACGTAGTGGATGAAACGGCAATGATGGGCGCTGCTGCTCCTAACTTTGTGCATGGTCATGATGCC
AGCCACCTTATCTTAACAGTCTGCGACCTTGTTGATAAAGGGATTACATCTATCGCAGTTATTCATGACTCTTTTGGCACTCATGCAGGCCGTA
CAGCCGACCTTCGTGATAGCTTAAGGGCAGAAATGGTGAAGATGTATCAAGGCCGTAATGCACTGCAAAGCCTGCTAGATGAGCACGAAGA
ACGCTGGTTAGTTGATACCGGAATACAAGTACCAGAGCAAGGGGAGTTTGACCTTAACGAAATCTTAGTTTCAGACTATTGCTTCGCATAATA
TTAATAGGCCATTCCTTCGGGAGTGGCCTTTCTTTTACCTACTACCTGTAACATTTCATTAACATAAAAGTGTCTCACATGTGAGACTTATTTAC
CGGACACTATAGGATAGCCGTCGGAGACGGGAAAGAAAGGGAAGATAAAGGATATAAAGGAAGTAATAGGTATTAAAGGTTATATAGGTT
ATCTAGGAATACCTATTACCTTCCTTCCTCTTATTACCACTCAGAGGAAGGGCAGACCTAGGTTGTCTCACATGTGAGACTTCGTATTTACC
GGACAGTATAGATAAGATTAACTCACTTTGGAGATTTAACCATGCGCAACTTTGAGAAGATGGCCCGTAAAGCTAACCGTTTTGACATGGAA
GAGGGGCAGAAGAAAGGCAAGAAGCTGAATAAGCCTGTCCGTGACCGTGCATCTAAACGCGCTGCGTGGGAGTTCTAAGTTATGGCTATTA
TTCAGAATGTACCGTGTCCTGCCTGTCAAAAGAATGGACATGATATTACTGGCAACCATCTCATGATATTTGATGATGGTGCCGGCTACTGTA
ATCGTGGACACTTTCATGATAATGGTAGACCTTACTATCACAAGCCGGAAGGTGGCATCGAGATAACCGAGTTATCTATTACTGGCAATATCA
AATATACACCTTCTCAATTCAAAGAAATGGAGAAGGAAGGGAAGATAAGCGACCCTAAATTACGTGCCATCGCACTTGGTGGTATGCGTATG
AAAGACCGTTGGGAGGTCATGAATGAACAAGAAAGGGCAGAGCAAGAAGCAGAGTGGAAACTTGATGTTGAATGGTTCCTCACGCTTAAGC
GTAAGAACCTTGTTTCCAGGCACATTCGCGGCGACATTTGCGCATTGTATGATGTACGTGTTGGGCACGATGAAGAGGGTAGAGTCTCACGG
CATTACTATCCGCGCTTCGAAAAGGTGAGCTAGTAGGCGCTAAGTGTCGCACATTACCTAAAGATTTTAAGTTTGGTCATTTAGGTAAACTCT
TTGGTATGCAAGATCTTTTCGGTATGAATACTTTGTCTCACGTGTTAGACAAGGGAAGACGAAAGGATTGCTTGCTCATTGTCGGCGGCGAAC
TGGATGCACTAGCAGCGCAGCAGATGCTCCTTGATTCTGCCAAGGGTACTAAGTGGGAAGGCCAGCCATACCATGTATGGTCTGTCAACAAA
GGCGAGTCTTGCCTTGAAGAGATAGTGCAGAACCGTGAGCATATCGCCCAATTCAAGAAGATTATATGGGGTTTTGATGGAGATGAGGTAG
GGCAGAAGCAGAATCAGCAAGCGGCTCGCCTGTTTCCTGGTAAATCCTATATCCTTGAATACCCCTCTGGTTGCAAAGATGCTAACAAGGCAT
TGATGGCTGGCAAGGCTAAAGAATTTGTAGATGCATGGTTTAATGCCAAGTCATCTGATGAAGTCTTTGGTAGCCAGATTAAATCTATCGCAT
CTCAAAGGGATAAGCTCAAGGCTGCACGTCCAGAGCAAGGACTGTCATGGCCTTGGCCTAAGCTGAACAAGGTAACGCTAGGTATTCGTAAG
AACCAGCTTATCATTGTAGGTGCAGGGTCTGGTGTAGGTAAGACTGAGTTCCTTCGTGAAGTAGTTAAGCACCTCATTGAAGAACACGGTGA
ATCTGTAGGCATCATTTCTACAGAAGACCCGATGGTCAAGGTGTCCCGTGCTTTTATCGGCAAGTGGATTGATAAGCGTATTGAGTTACCTCC
AACCAACGACCCGAAAGAAGACGGATACCGTGAGGTGTTCGACTATACCGAGGAAGAAGCTAACGCCGCCATTGATTATGTAGCTGATACA
GGTAAGCTGTTTGTAGCTGACCTAGAGGGTGACTATTCGATGGAAAAGGTAGAGCAAACTTGCCTAGAGTTTGAGGCTATGGGTATTTCTAA
TATCATCATTGATAACTTAACGGGGATTAAATTAGATGAGCGTGCTTTTGGTGGGAAGGTTGGTGCACTTGATGAATGCGTCAAGCGGATTG
GTACTATCAAAGACCGACACCCGGTTACTATATTCCTTGTATCACACCTTACACGTCCTCCGGCAAACCGTACCCAACACGAAGAAGGTGGCG
AAGTTATCCTTTCTGACTTCCGAGGCTCAGGCGCTATCGGATTCTGGGCATCTTACGCCTTGGGGATTGAGCGTAATACAAGAGCTGAAACGC
TTGACGAAAGGACTACCACGTACATCTCATGTGTCAAAGACCGCGACCAAGGTATCTACACTGGAACCAAGGTCATGCTTAAGGGTGACATT
CAAACCGGACGTTTAATGGAACCACAAGCCCGTACTAAGTCATTTGATACAGGTGAAGCAAGGCAACAAGAAGTACCAGATTTACCGGATAC
TATAGAAGAGACTACCTTCGATGAAGAAGTGAGTTCTGATTAGTGTATTTATCAGGCTTGTCTCACATGTGAGACAGGCTCTTATTAAGTAC
ATTAAATAACTGGAGATTGATTATGTATAACTTAGTGTTGAATGTAGGTGACTTTGTACGCAACATCAAGAAAGATTCAAGTCGCTATCTTTGC
CGTGGTGTTGTAACCCTTTGTAGGTGAGAACCTGTATTATGTAGAATATCGCAGTGGTGTTAAGCAATATTACCACAAGAAGACAGCACATAAA
TATCTTGAAAAGATTGTAGAGATAAACAATCAATGTAAGTGCATACATGATGAGGTTTGCGATAAATGTGCTCGCCAGATGCTTAAGAATTTC
CTAGCTCCTCTTTATTATGGTGCTGGTCCTCAAACACTAGCAGAGTGCATGGCAGAAAAGAAAACCACACTCAAGAAAGAGCGTCGCAATGT
AATCACTGGTAAGACTCAAAGTGAGATGATTAAGCAATGTGGCACTGCATTAGGTGTTACACAGTTTAATACTCGTGCATTGGGTAAATCCAC
AGGACAAGCTATGGTAAAGATTGGAGAAGCCATGATGCATCCAAATGTACCTGTGCGAATCATGGATGTTGACCATGCAATCACAGAACAAG
GTACGCAACGACGTGTAATTAATAAGCATTTTGCCGACACTATAGAAGGCATTATTCGTAAGCAAGGGTTGAAAGGTCTTCACATCTTAAATG
GTGAAGAATTACTGTACCTACCTATCGTTACTGAAGAAACATACGTGAATATCTAAGGAGTTAATCATGACTAAGGTATTAATTTATATGCGT
GGACCTCATAAATGCTATGCAGTTGTAGCACCAAATGGTGTTAAGCCTTATCGTACTTCAAAAAGATTGGCATTAATAGGTGCTAGTAGTAGT
GCAAGTTTCCAAATGGAACTTTTGGTCATTGGACTGAAAGGCAATTCCGTGAGGATTTTAAAGTCATTGGCAGCTTCATGGTGAAATATGCA
GAATAAACATAGTCTTAGAATGTTCGATGGTCATGAAAACCTGCAAGCCAAGATTACTAACCAAGCCTTCCTGTTCGCACAGTTAACTATGGC
TGAGGCTAAGAAGAATAGTCTCACTCGTGAACAGGTTATCAAGGAGGCCACTTGGGAACCACACCAAGGTAAATATATGGGCCACAAATTAA
CTGTAACACGCAGTCGATAAGTCAAGGGTTGTCCAACGTGTTGGACAGCCTTTCATCATATTGATTGGGAGGTATTAAATGACTAAGTTTACT
ATGCAAGACCTCATTAAATTACGTGATGAAATAGAATCACCGGAAGTTAATACAGAGTTTCACTACATTGATCCACGAGATAAACGAGAGATT
```

FIG. 13C

CCTGATTATCAGATTGAGACGGAGTTAATGTATGAAGATTATTGATTGGAAGAAGGAAGCAGAAGGCCGTATCCTAGTGATGGATGCGGAG
GCTAAAGGCCTGCTGGGTGCTATCCGCTACGGTCATCGTGAAGATGTACACATTATTTGCTGCATGGACTTGCTCACCACTGAGGAGTTCCTC
TTCTTCGACCCATATGAGATGCGTGACCCTGAAGCAAGGGAACACTTGAAAGAGTGGGAAGGCCATCAAGATGGGACCTTGGTTGATGGTG
TTAACTTCCTAAAGCACTGTGAAGCCATCGTCTCACAGAACTTCCTAGGCTATGACGGGCTTCTCTTTGAGAAAGCCTTCCCTGACATCTGGAA
GGGATTTAACTACACCGAGAGGCGCGGCAAGGGCAGACTACGTGCTGACTTGTGTCCGGTACGCGTCATGGATACGCTGGTCATGAGTCGC
CTGTTAAACCCAGATAGACGCCTTCCTCCGCAAGCATATGCCAAAGGTATGGGTAACGTTGCCCCTCACTCAATTGAGGCGCACGGCATTCGT
ATAGGCCGTTATAAGCCGGAGAACGAGGATTGGTCTAAACTAACTGACCACATGGTACATCGTGTACGCGAGGACGTGGCGATAGGCCGTG
ACCTATTCCTCTGGCTATTTAACGGAGAATGGACGGAGCACAAACGCCGTGGCGTGAATAAACGCACTGGCCTAGGTATTGAGACAGCCTTC
CACATGGAGTCCATTGTGACGCTGGAGATGAGCCGTCAGGCCGAGCGTGGATTCCGTCTGGATATAGATAAAGCATTAGCACGATGCGAGG
AATTGGACGCTAAGATTGATGAGACAGTCGCAGCGTTCCGTCCGCACATGCCTATGCGTATCAAGTCTAAACCTTTTAAACCGGAAGAAAAG
AATGAAGTATGCCAACGCGCAAATGAGTATGGAGCTAGCAACAATATACCTACTGTCCTTGACCCCTCTCACTTTCTTCACGCAGAGAGACGA
GGAGATCGCAAGACAGTATGGAGTGTCACTACTAAGTCTGGTGATTGGTCGGCTAGCGTCAAGAAAGACTTTCCTCACCTTAGAGGAAACCG
TAATGACACGCCAAGTGTCAAGTGGATTGGCGCTTACTCGCCTGTTACTTTCGAAGAGATTCCCTTGGGTAACAGGGATACAGTTAAGCAAGT
GCTCTATGATTATGGATGGAAAGGTGTTGAATTTAACGATACCGAGCAAGCGCATCTCGATGAGCATGGCGTATTACCCAAGCCTTGGAGTG
GGAAGATAAATGAAAAGTCCCTTACTTTATGGCAAGAGAGAGCCGCACGTGAAGGTAAAACAGTCCCTGATTGGTGCTTGGGTATCGCTGCA
TGGTACATACTCGTATCCCGTCGTGGTCAGATCCTCAACCGTGGTGACGTTGAAGCCTTCGACCAGAAGGGGGTGTGGCCTTCGCAAGCTGG
TATACGAAAGTGTCGCGGCCTTGTACCTGTAGCATTTAACAAGGAGTTAGGAATCAATGCGCAGCAATACTACGAAAGGTACGGATGCTGGC
CTACGTCAGACAAGGATGACGGAGAATGGCGTGTGCCAGCTATTGCTATTAGTATTGGAACTTCTACGTTCCGTATGCGTCATCGTAACGTGG
TTAATATTCCTGCCCGTGGCTTGTATCCTTTACGTGATTTATTCATAGCAGGGAAAGGCAAGCTAATCCTTGGTTGTGACGGTGCAGGTCTTGA
ACTGCGTGTCCTGTCTCACTTCATGAATGACCCTGAGTACCAAGAGATTGTACTGCACGGTGATATTCATACGCATAACCAGATGAAGGCTGG
TCTTCCTAAGCGTGATATGGCGAAGACATTTATATATGCCTTCCTATATGGGTCTGGTATAGCTAACCTTGCAGCAGTATGTGGTGTTACTGAG
GAAGAAATGGAGGAAGTTGTGGCAAGATTTGAGGTTGAACTACCATCTCTTGCACGTCTTCGTGAGAATGTTATCGCACAAGGTAACAAGTT
TGGCTACCTACAAGCACCTGATGGTCATTGGGTCGCATCCGTATGTCTGGTGGTGAACTTAAAGAACACACTATGCTTAACGTACTACTCCA
GATGACTGGTTCTCTGTGTATGAAATACGCATTGGTCAGAGCGTTTGCAGTGATGCGCAAGGAAGGTGTGGCCTTAGATAGCATGGGAAACC
CTTGCGGTATAGCTAACGTGCACGATGAAATCCAGATGGAAGTCCCTGAAGATGAGGTCTTGTATCTCAACTACGACTTGCCTTTCACCTTAG
AAGGGTTCGAAACAGAGAAGGCTGCTGTGAAAGCAGTGTTCGATGCAGAGGAGAAACGTGTTCATGTGGATTCTGAAGGACGTATGTGGTC
TGCTGCAAATCTCGTTAGTGTTGATGCTGGTGTACTTCATTGCCAGCGTCGTTATCACCGTGCAGGGCATATCATTGCCGACGCAATGACCTG
GGCGGGTCAGTACCTGAAGATGCGTTGTCCGATGGCAGGTGAGTATAAGATTGGTGCAAGTTGGAAGGAAACACTGATGGACAGGTTTG
ATATTGTTTGCCTATTCTCTACCTTCTTTCTTATATTCCTTATGCTTGCTTGCTATGGAAGTATGCGATTAGATATACCTGATGAAGAGGAGGGT
TACGATTGATGCAGGCATCTTTTATTATTCTTGGAGTCATATTATTTATGGTAGTATTCTGGGCTTTCTCTGGCATTGACCCAGATTGTGATGGT
AACTACGACTGAGTTATACTCAAGGTCACTTACGAGTGGCCTTTATGAATAACTTATTCCTACTTATTTTGTCTAACATGATTTACTGGACACTA
TAGAAGGAAAGCATAGGTAATCTAGGTTTATAAGGTAGTATAGGTAATTAAGTAAATATAGGAGATATAAATATGTCTATGGTAACTACTCTG
GTATTCGTGGCTCAATACTTTCGTGGTCTTGCTAATAAGTTCAAGTCCAAGGCTATCAAAGCTATTGAGGCTCGCATCGAAGCAGTACAGGCA
GAGCAAGTTAAAGTTGAAGAACATCGTAGTTCTCAAATGATTGACTGTCATAACCGCTACTATGCATCTCGTGATGAACTAAATGCACGTCAA
GTCAAAGAGGTAGAAGATATGCTGGCACGTCACCAGCAAGAGCGTGACAGCCTGAAAGCTGAATTTGAAGAGAACAAGGCATCAATTGCTC
TTGTACATCAAGCTGCATCTGACAGTCTGAAGAAAGAGATTGTTATGCTGGAAATCGAACTGGATAACCTGACCAAATAAGGGGGGGTTATG
ATGGAAGAAGTAATTCAAGCTAAACATGTAGGTATTATCTTTCGCGATCTAGAGCAGCGTAAAGTTGCAGGTCATACTCGTCTGGCTAAAGA
GGAAGACACCGCAATCACTACTGTAGAACAAGCAGATGCCTATCGTGGACCAGAGTTCACTCAAGGTGAAACTTGTCACCAATTGAGCCTAT
CAATTTGTGACACTATGGCTATTGTAAATGTGCAAGAAGTCGAAGAGGGTGAGTGTGTCAGTTACATCTACCCTTTAGATACTATTGCACGCA
TTAAGGTAATCCATAAGTAATTACTAGACACTATAGAACAATAGGTCGGCTTAGTTCGGCCTATGATTGTAAAGTGTTGTTGATGTTAACCA
TTGTGCATCTTGCACAACCCGATACCGTATAGGGCTTTCTAGTGAGTACATGCTTGTGCTCAGTACAAAGCTAACTGACAATAGGAGACTAAA
TAAATGGCACGTGGTGATTTTGATTTTGGTGCTCAGGTTACTAAATCTGAAGGTAAAGTCTTTAAGAATCCAGAAGTAGGTGATCATGAAGCA
GTAATCTCTGGCATCATTCATGTTGGTTCCTTCCAAGACATCTTTAAGAAAGGTAATACCACTGAAGTTAAGAAGCCAGCAAACTTTGTTCTGG
TTAAGATTGTCCTGATGGGTGACGATGACAAGAACGAAGATGGTTCTCGCATGGAACAATGGATGGCTGTGCCTCTGAAGTCTGGTGATAAG
GCAACACTGACTAAGTTCCTGAATGCAGTTGACCCTAAAGAGTTGCTGGGTGGCTTCGATGATTTCATTGGTGAATGCCTGACTGCAACGATG
GTCGGTTCTGGTGATAAGAATGACGATGGCTCATTCAAGTATGTTAACTGGAAGGGATTTGGTGGTATGCCGGACAAGCTGAAGAAACTGGT
CATTGCTCAGGTTGAAGAGGAAGGTCTGTCTATGACAGGTCACATTACCTTCGACAAGCTGACCAAAGAAATCCTTGATGACATCCCAGCCAA
CTTGGTGCGTCAATACTTCCTGAACGAGACGCCTCGTGGTAAGAACCTGTCTGTTGCTGGTTCTCACGTAGAAGCAATCATTAAAGCTGCTCG
TGAAGAAGACCCAGAATGGAAGAAGGCTAAGAAGAAAGACGAGGAAGATGCTACCCCAGCTAATCGTAAATCTCTGGATACTGGTGAGTCT
GTTCCACAGGAAGTACCTGAAGCAGAAGATACTCCTGCACCGGAGATGGATGAGGACGCGGAATATTAAGGAGAAAGGATGAAAGTACAA
ATCGTAACCCTGCACTGCAAGAAAGGAATTACAACTCTTGGCGGCAACACTTTTCACTCCTTCTCTGAAGGGGACACATATGCCGACCTGCAC
TACATCTGGCGCGACGGACAGCACGTGGTGAACTACAGCGACCCAGCTACGGGGAAACGCCACGGCGTATCGCTTCCGGCGCATGACATTG
CTCAGGTGAACACAGTTTTATAAAGTCTCACGTGTGAGACAAATCGGTGTCCGGTATTTACTGGACACTATAGAAGAGAAGAATTTTAATCGG
CGATAATGCCATAACCAACAAAAGGAGAATTTAATATGTTCAAGATTGAAACTATCGTAAACCGTGTTGTTAAAGGTGCTGCTCTGGTATCCG

FIG. 13D

```
TTGAGTCTTTCATTATCGTCGATGAAACTGATCAACTGGTAGCTGGTACTAAGGCTTACGATACCCGTGAAGAAGCTCAGGCTAAGATTGACA
GCATGGGTAACTTCGCTGCTGGTCTGGAGTTCGCTCGTGCTTGCTTCCCTGAGCAGGCTGACAAAGCTCAGATTGGTAAGGCTAATATCGTAG
CTGAATATCTGGATTGGGTTGCTGCTGGTAAACCAGTGAAAGAAGTTAAGGCTGCTGAAGAAGCTGAAGCTCCAGCAGAAGAAGTAGCTGC
ACCGGAAACTCCGGTAAGTGAAGAGGAAGAATTTTGATAATAGCAGGTGTTGCCTCTGTTAGTCCTAGCTGACTATCACGCTCACCTCATCTA
ATGCCCTGTCTGCCTTAGTGTAGGCAGGGTCTTTTGCGTAATAGTTATTGGAGAATGAATTATGCCGACTATTGAATCTCGAATTGAACTGGA
CATTAGCTACAATGCAATCACCAGACAGTATATTGGGGTTGCCTATGATTACAAAACTGGTGAGAAGCTAGTGGAGGTGAGACAATGGGATG
ACTATTGGTTAAGACAGAACCTCCATGATGCGGTGTCCTCCTTCCTGAAGGAGTGGCCTACATGCGACCAAACTTCGACTTCGGAGCTACAGT
ATCGGAAGACAATAACCTGTTGCTGTGGCCAACTGAAGGTAATCGAATCGCTTTAATAGATGCTGATATGTTACCTTACATCATAGGGTATAC
AATCAGTGATATGACTTATGTACGAGCCACAACTCGTGTTAAGTCAGGGCAAGTCCCCTCAATCAAAGATACACCTGAGTGTAAGCAAGCGT
GTGACCGTGTGAACTCCTTGCTTAACTCTTGGGTGTATGCAGCAGAATGTGATGCAGCTAAGTTGTTCATGACGAAATCAGAAGCTAACTTCC
GTGTCCGCCTAGCATTCACCAAGCCTTATAAAGGTCAACGTAAGACCGAGAAGCCTCCATTCTTCTATGAATTGCGAGAGCATCTCTTAGAGG
TTCACGGTGCAATCTTGGCAGATGGAGAGGAAGCAGATGACCTCATGAGTATCGCACAATGGGACAGCCACCGCCGCTTCCAGCAAGATACA
GGTAACGAGTTCCCTATCGGTAGTCCAGAGCATAAAGCATTCTCTGATACTTGCATCGTTTCCTTGGATAAGGATTTGATGATTGTTCCCGGTT
GGCATCTACAGCCGGGTCAAGAGAAGAAATGGGTAGAGCCTATGGGTTGGCTTGAGCTACGCCGTAAGGCTAATGGGCAAGTCAAAGATCT
AAAAGGTGCTGGCCTCATGTTCCACTATGCACAGATGATTATCGGTGATGATATTGATAACTATGCTGGCATACCAGGTCGTGGTGCTAAATA
TGCCTATGATCTTCTCAAAGATTGTAAGACAGAGAAAGAGTTGTACATGGCAGTGCTGGGTGCTTACAAGGCTAAGTTCGGGCATGGACAAG
TTAAAATTAAGAATTACCGAGGTGGTTATCGTATCGGCAAAGCCTTTGACCTAATGCTTGAGTGTGGTCGCTTATCTCACATGGCAAGATTCA
AGGGTGATATATGGCGAGCCGATAAGAACCCAATCTTGTGGGGAGATGATGCGGAATGGTTAGCAAATTAAAATCATCGGAGGTGGCAGCT
TATAAGAAGGAATTGCTAGATAAGCAAGGATGGAAATGCCCTCTGTGTGGCGGCAGTCTCAAAGCTGTCACACCTGTAAACCGTGTACTTGA
CCATGACCATGAGACAGGATTCTGCCGCGCTGTTGTATGCCGAGGCTGCAATGGTGCGGAAGGGAAGATTAAGGGTGTTATCTCTGGTTATG
GTAAGGCTGGTAACAACCGTTACTTCCAGCTTCAATGGTTAGAGCGACTATATGAATACTGGAAGTTACATAGTACGCCTCAGACAGATAAGT
TATATCACAAACATCAAACGGAGGCAGAGAAGCGCGAGGCTAAGAACCGTAAGGCACGCCTTGCTTATGCAAGAAAGAAGGAGGTTAAAGT
TGGGTAAGCTGCGCAGCTTGTACAAAGACTCCGAGGTACTTGATGCAATCGAGCAAGCTACCGACGAGAAAGGTAATGTTAACTACAATGAG
ATGGCACGTGTATTATCGTGTCATACTGTGGGTAAGAAGATTACCCGCCAGTTGGCTCGATACTGGCATGGTCAATTCAAGAAGACCAAGAA
GAATGGTGATTACTACCAGACCCTTCTGCAAGAAGATAAGCGTATCAAAGAAGAGCGTAAGCTCAGGACTCCTGACCGCTACGAGGATTTGG
CTATTGTGCCATTGCCTGACTCGCCTCATCGAAGTGTACTGGTGATCCCTGATACTCATGCACCTTATGAGCACCCAGATACCCTAGAGTTCCT
TGCAGCCGTGGCAGCACGTTACCGTCCAGACACAGTGGTACACCTAGGAGATGAGGCAGACAAACATGCCCTGTCATTCCACGATTCGGACC
CAAATCTGGATAGTGCTGGCATGGAGTTAGAGAAGGCTCGTATCTTCATGCACAAATTGCACAAGATGTTCCCTGTGATGCGCCTGTGTCACT
CTAACCACGGCTCTATGCACTTCCGTAAGGCAAGCGCCAAAGGCATCCCTGTGCAATACCTGCGCACCTATCGTGAAGTCTTCTTCCCGCAGG
GAGGTGGCGACCAGTGGGATTGGCAACATACGCACGTCCTTGAGTTGCCGAATGGTGAACAAGTGGCATTCAAGCATCAACCTGCTGGCTCT
GTCCTAGCAGATGCAGCGCATGAGCGTATGAACCTTGTGTGTGGTCACTTGCACGGTAAGATGTCTGTGGAGTACGCACGTAATACACATGA
ACAGTATTGGGCTGTGCAAGGTGGCTGCTTAATTGATGAGTCATCCCGTGCATTTGCCTATGGTCGTGAGTCTAAATACAAGCCAGCATTAGG
TTGTGTGGTCATTCTGGAGGGTGTGCCTCACATTGTCCCGATGCAAACCAATAGCGACAACCGTTGGATTGGCAAGATTTAGTTGACACTATA
GAACAAAGGGCTAGGTAAGACTTTATCGGCTGGCGTATCCAAATGATATTGCACTAGCCCTTGATTGTATAGTGAATGGAGGATTCAATATGT
CACACTATGAATGTAAGAAGTGTCATAAGCGTTATGATTACTGTACTTGTGGTCAAGAGAAAACATCTTTTAAAGTTGGAGACAAGGTATTTC
GTAATGAAAAGATTCGATTCCTTGGAATCAATACTGCAAAGAAGCTGGTATTGACCCTGATAGCCCTGTAACCATAGATGATATTGATGGCA
TTAACTTGTGCTTTCGTGAGGTGAGGGGTACAGGTTGGGATTCCAAAAAATTCAAACTTGCATCTGATAAGTTAGACAACAATATGGTAATTA
AGCCTAAGCACTACGAGTTCTTTGATGGCGTAGAGGCAATCACTATCATTGCCCGCAGTATGACCGAGAAGCAATTCGCTGGCTATTGCATGG
GTAATGCTTTGAAGTACCGTCTACGTGCAGGTAAGAAGTTCAACACTGAAGAAGACCTGAAGAAAGCAGATTACTACAAAGAGTTATTCCAG
AAGCATCGTCACGAATGTATTGATGAGGATATTTGATATGAATATCTTTGAGTTCCTAGGTCTTCCAGAAGACCACCGCAATCACCCATTCATG
CTGGTGAAGCATCGCGGTGAAGTTCCTGAGAAGAAATTAACTTTTCCATGTTATGCACAGGTGAAACGAGATGGTATCTTTTCTGCTGTTGTT
GTTCGCACTGATGGTGTCGTTGGCATTTTGGTCGCACTGGTAAGAAATTGGCAAACACTGAAGGACTCGAACAAGCCTTTGCTACCTTTCCG
GTTGGCATTTATCTTGGTGAGCTTCAGTCTATGGCCATTGATATCTACCTTGAGGCAATCTCTGGGGTTGTGAACCCCAATCGCACTGAGCCAC
TTGATTTCATAGGCCAGCAGATTAAAGACAACCTGTATATCGACTTCTTCGATATGTTAACTATTAAGGCATTCCATGATGGATTCACTGATGT
TTCTTATCTCAAACGTTACGATGCTTTACATCGTCGTATCGGCGCTCATCTTAGCGGGTGCAACGCTATCCTTCCTATCACTCCTTGCCATAATG
AGCGAGAAGTTGAAGCGTTTGCGCAAGAGCAAATAGATGCAGGACGTGAGGGTGCTGTATTCAAACTGGACTGCGATTATGAAGCAGGACA
CAAAGGTTATCGTCAGACTAAAGAAGTCCGTAAGGTAACCTATGACCTTACTTGTATTGGCTTTGAAGAAGGTAAAGGCAAATACAAAGGTA
AGGTAGCTAACCCTCATTTTCAAATGGAAAGGAGGCAAGACAATCAAAGCTATGTTAGGTAAGGGGTGGACTCATGCAGATGCAGAGCAGAT
GTTCCACGACATTAAACATGGTGGACGATTGAATGTCATTGGTAAAATCTTTGAAGTCAAAGGTCTTCAGGATTCAAGCAAGGGCAACATTCG
TCTGCCCAAAGCGGGAGAATTAAGACATGACAAAGATGAACCAGATTTCTTTTGATAGCATGAAGGCAACTCGTGCAGTTGAGGTAGCAGAA
GCTATCTTCGAAACTTTATCCTGTGGCATGGAAGTGCCATATACTTTACTTGCTGATGCAGAAGAACTTGGTCTTTCTGTAGAAGCTATCCAAG
AGAAGGTTGACGAATTATATGGTACAGACGAAGAAGAAACCGACGATTTCATTTGAAGGAATGGAGATGCTTGAGATGATTCTCAAGCCTTC
TTCTCCTAAGGTGACTAAGACTCATGAAGAGTTAATCGTTGATGAAGTTAAGCGTTACATCATGGATTGTGTCAGAGCACAACTGGTGGTCCA
ATGATACGTCCAGCCTCCTTCCTAGATATTCCTGAGATTATAAACCTTGGGAATAAATATGTGGAAGAGGAAGTCAAGGTTGTAGCCCACCAC
```

FIG. 13E

```
TCAGCCTCATGGAATGCAGAACAAAGTGCCATAACCTTTGTGCATCTCTTAATAGAGACCCACCACTCAGCCTCATGGAATGCAGAACAAAGT
GCACATAACCTTTGTGCATCTCTTAGTAGAGAAGATTTATCCCTATGGGTTGCTGTAGATGAAGGGCAGATTGTAGGGTTCCTGTGGGCTGGC
TATCACGAGTTGGCCCCTTGGACACCTGTAAGAGTTGCCTCTGACATTCTCTTTTATATTATACCAGAGAGGCGAGGAACACTACTTGGTATGC
GTCTCATCAAAGCCCTAAAGCAATGGGCTAGTGATAATGAATGCTCTGAGGTTCGCCTGTCTATCGCCTCTGGTATTAATGAAGAACGTGTCG
GACGTATGTATAAGCGACTTGGCTTTGAACCGTTTGGCACTGTGTATAACCTGAAGTTCTAAGGAGATAACATGGGTGTTGTAAAGAAAGCA
TTTAAGGCTATCGGTCTTGCTCAAGATGCACCACGTATTGAAGCCAAAGTCCCAGCACAGCAGCTTGAGCGTAAGCCTGAGACTGAAGCTGA
AGATATTCAAATTGGTGCAGGGGATGATGCTACTGCATCTGCAAAAGGTAAGCGTGGCCTTGTCCGTCCGGTAGCTTCTAGCTTGAAGGTGT
AATATGAAACAGAGCATAGATTTGGAGTATGGAGGTAAGCGGTCTAAGATACCTAAGCTATGGGAGAAGTTCTCCAATAAACGTAGCTCTTT
CCTTGATAGGGCGAAGCATTACTCCAAATTAACCTTGCCCTATCTGATGAATGACAAAGGTGATAACGAGACTTCGCAGAATGGATGGCAAG
GTGTAGGTGCTCAGGCAACCAACCATCTAGCCAACAAGCTAGCGCAAGTACTATTCCCTGCACAGCGTTCCTTCTTCCGTGTAGACTTAACTGC
ACAAGGTGAGAAGGTTCTTAATCAGCGTGGCCTGAAGAAGACAGAGCTAGCTACCATCTTCGCTCAAGTGGAAACACGGGCAATGAAAGAG
TTAGAGCAACGTCAATTCCGGCCTGCTGTAGTAGAAGCATTTAAGCATCTTATTGTTGCTGGCAGCTGTATGCTATACAAGCCGAGCAAAGGT
GCAATCAGTGCTATCCCAATGCATCACTACGTAGTTAACCGTGATACCAATGGCGACCTGTTAGACATTATCTTGCTACAAGAGAAAGCCTTAC
GTACCTTTGACCCAGCTACACGTGCGGTAGTAGAGGTTGGCCTGAAAGGTAAGAAGTGCAAGGAAGATGACAGCGTTAAGCTGTACACACA
TGCTAAGTATCTTGGTGATGGATTTTGGGAACTCAAGCAATCTGCTGATGATATCCCTGTGGGTAAGGTGAGTAAAATCAAATCAGAAAAGC
TACCTTTCATCCCATTAACTTGGAAGCGAAGCTATGGTGAGGATTGGGGTCGACCTCTTGCAGAGGATTACTCCGGTGATTTATTCGTTATCCA
ATTCTTATCTGAAGCGGTTGCCCGTGGTGCTGCGCTGATGGCAGATATCAAGTACCTGATTCGTCCTGGTGCTCAAACTGATGTTGACCACTTT
GTTAACTCTGGCACTGGTGAGGTTGTCACTGGTGTAGAAGAAGACATCCATATTGTACAGTTAGGTAAGTACGCAGACCTCACACCTATTAGC
GCGGTTCTAGAGGTATACACTCGCCGTATCGGTGTTGTCTTCATGATGGAGACAATGACACGCCGTGACGCCGAACGTGTTACTGCTGTAGA
AATCCAGCGAGATGCGTTAGAGATTGAGCAGAACATGGGTGGTGTATACTCCCTCTTTGCTACTACTATGCAATCGCCAGTAGCGATGTGGG
GTCTGCTGGAGGCAGGGGAGTCCTTCACTAGTGACTTAGTGGACCCTGTGATTATCACAGGTATTGAAGCTTTAGGACGCATGGCTGAGTTG
GATAAACTGGCTAACTTTGCTCAGTATATGTCACTGCCATTACAATGGCCTGAGCCTGTCCTAGCTGCTGTGAAATGGCCTGACTATATGGATT
GGGTGCGTGGTCAAATCTCTGCTGAACTGCCGTTCCTTAAATCGGCTGAAGAGATGGCACAAGAACAGGAAGCACAGATGCAAGCACAGCA
AGCACAGATGCTTGAAGAAGGTGTGGCTAAGGCCGTGCCGGGTGTAATTCAACAAGAACTTAAGGAGGCGTAATGTCTTTCTCATTTACTGA
ACCGTCAACCACTCACCCTACTGCTGAAGAGGGTCCGGTAGAAACCAAGGAGGTAACAACTGATGCTGCTACTACTGATGCTCCTGCTGACG
CTGGCACTTCTGTACAAGATGACAATGCTGGTGCACAACCTACTGAAGACACCGGAGGAGAAGCTTCTGGACAGCCTTCAGAAAAAGGAGA
CAATGGCGGAGAGAATGGTGAACCTAAGCCAGATGATACCGCGACCGACACTGAGGAAGTGCAATACTTCTTCGGAGAACATGAAGTAACA
GTAGACATCCCACAGGATGTAACTGACAGCCTTAAAGAGAAAGGCATTGATGCCAAGCAGGTTGCCAAGGAACTCTATTCCAAAGGTGGCAA
GTTTGAACTGTCAGATGCAACCAAGCAGAAATTGTATGATGCTTTTGGCAAGTTTGCGGTAGATGCTTACCTATCAGGTCTAAAGGCTCAAAA
TGAAGCCTTCTTCCTGAAAGAAGCCAACGCAGCTAAAGAGTTGGAAGCAGCTAACACCCAACGCTTCTCTGATGTTTCTAAGGAAATTGGTGG
CGAAGAAGGTTGGTCCCGTCTTGAGGAGTGGGCACTTGAAGCGCTGTCTGATGACGAACTAATGGCATTCAATGCGGTGATGGAATCTGGC
AACCAGTACCTGCAACAATATGCTGTTCGTGAACTGGAGGGTCGTCGTAAGCAGGCACAGGGGGATGATAAGCCATCCCTGATTGAGCCATC
AGCACCTGCTAAGGCTAATGAAGAGAATGGCCCACTGACGCGAGATCAGTACGTTCAAGCAATCGCAACTCTTAGCCAGAAGTACGGCAATG
ACCGTAAAGCTATGGCAGAAGCTCAGGCTAAACTGGACGCCCGTCGCCGTGCTGGCATGGCTCGCGGTATCTAATTCAGTATTTACTGGACA
CTATAGAAGGGAGAAAAGTTCTCCCTAGTTATCAATTTGATTTATAAGGAGATTATAATACATGTCTACACCGAATACTCTGACTAACGTTGCT
GTATCTGCGTCCGGTGAGGTTGACAGCCTTCTCATTGAGAAGTTTAATGGTAAGGTCAATGAGCAGTACCTGAAAGGTGAGAACATTCTGTC
CTACTTTGATGTACAAACTGTTACTGGCACTAACACAGTGAGCAACAAATATTTGGGCGAAACTGAGTTGCAGGTGCTAGCACCGGGTCAGT
CCCCTAATGCCACCCCTACTCAGGCGGATAAAAACCAGTTGGTAATTGATACCACTGTCATTGCTCGTAACACTGTGGCTCACATCCACGATGT
ACAAGGTGACATCGATAGCCTGAAACCAAACTGGCTATGAACCAAGCCAAGCAACTGAAACGTCTGGAAGACCAGATGGCAATTCAGCAG
ATGCTGTTAGGCGGTATTGCTAACACCAAGGCCGAACGTAACAAGCCGCGTGTTAAAGGGCATGGCTTCTCTATCAACGTTAACGTAACTGA
GAGTGAAGCACTGGCTAACCCTCAGTATGTTATGGCTGCGGTAGAGTATGCTCTGGAGCAACAGCTTGAGCAGGAAGTGGACATCTCTGATG
TAGCTATCATGATGCCGTGGAAGTTCTTCAATGCTTTGCGTGATGCAGACCGAATTGTAGATAAGACTTACACTATCAGCCAGTCTGGTGCAA
CCATTAATGGCTTCGTTCTCTCTTCTTATAACTGCCCTGTGATCCCGTCTAACCGATTCCCTACCTTCGCTCAGGATCAGGCTCACCACCTGTTGT
CTAATGAAGATAACGGCTATCGTTATGACCCTATCGCAGAGATGAATGGTGCAGTTGCTGTTCGTTCACTTCCGACGCACTGCTGGTGGGTC
GTACCATTGAAGTGACTGGTGACATCTTCTATGAAGAAAAGAGAAGACTTATTACATTGACACCTTCATGGCTGAGGGTGCAATCCCTGACC
GTTGGGAAGCAGTGTCTGTAGTTACCACTAAACGTGATGCAACTACTGGTGATGCTGGAGGTCCTGGTGATGATCACGCAACCGTACTGGCT
CGTGCACAGCGTAAGGCTGTATATGTCAAAACCGAAGGTGCTGCGGCTGCATTCTGCTGCCCCAGCAGGTATCCAAGCGGAAGACCTTGT
AGCGGCGGTACGTGCTGTAATGGCAAATGACATTAAGCCGACTGCAATGAAACCTACTGAGTAACACCTATGCCCTATCTACCTTGCGTAGGT
AGGGTTCTTTTTGTTAGGAGGATTCATGCCTGTAATTAGACAAACCAGTAAATTAGGACATATGATGGAAGATGTGGCCTTCCAGATTATTGA
TAGTAAGCTGGAAGCGGTAAACTTGTGTATGCGAGCTATTGGTCGTGAGGGTGTGGATTCCCTGACTCAGGGGACTTGGACGCAGAAGAT
GCAAGCAAAATGATCGACATCGTATCCCAGCGGTTCCAGTACAACAAGGAGGTGGCTGGTGGTTCAATCGTGAACCAAACTGGCAACTTGC
ACCAGACACTAACGGTGAAGTTAATTTACCTAACAACTGCCTAGCAGTATTGCAGTGTTATGCTTTAGGTGAAAAGAAAGTACCTATGACTAT
GCGAGCAGGTAAGCTCTACTCTACTTGGAGTCACACCTTTGATATGCGTAAGCATGTTAATGCTAATGGTATGATTCGTCTTACCTTACTCACC
TTACTACCCTACGAGCATCTACCTACAAGTGTAATGCAGGCTATTGCCTATCAAGCTGCTGTAGAGTTTATTGTGTCTAAGGATGCAGATCAGA
```

FIG. 13F

```
CTAAGCTAGCCACTGCGCAGCAGATAGCCACTCAGCTTCTTATGGATGTACAATCTGAGCAAATGTCACAGAAGCGATTAAACATGCTGGTAC
ATAACCCTACTCAGCGTCAGTTTGGTATCATGGCTGGTGGCTCTCAGAATGTACCTGCTTACTCTCATTCACCTTATGAGAGTTGGGCGCTCCG
TCCGTGGGAGGATCGTTAATGGAAGTACAAGGTTCATTAGGTAGACAAATCCAAGGGATTAGCCAGCAGCCGCCAGCGGTACGCTTGGATG
GTCAGTGCACAGCTATGGTTAATATGATACCTGATGTAGTGAATGGTACTCAATCACGCATGGGTACAACTCATATTGCAAAGATACTTGATG
CGGGGACTGATGACATGGCTACTCATCATTATCGCAGAGGTGATGGTGATGAAGAGTATTTCTTCACGTTGAAGAAAGGACAAGTTCCTGAG
ATATTTGATAAGTATGGGCGCAAATGTAATGTGACTTCACAAGATGCACCTATGACCTACCTCTCTGAGGTTGTTAATCCAAGGGAAGATGTG
CAATTCATGACGATAGCTGATGTTACTTTCATGCTTAATCGTAGGAAAGTAGTTAAAGCTAGTAGCAGGAAGTCACCTAAAGTTGGAAACAAA
GCCATTGTGTTTTGTGCGTATGGTCAATATGGTACATCTTATTCCATTGTAATTAATGGGGCCAACGCTGCTAGTTTTAAAACACCGGATGGTG
GAAGTGCAGACCATGTTGAACAAATTCGAACTGAACGTATCACTTCTGAATTGTACTCTAAGTTGCAGCAATGGAGCGGTGTGAGTGACTAT
GAAATACAAAGAGACGGTACTAGTATATTTATCGAGAGACGGGATGGTGCTAGCTTTACAATAACAACCACCGATGGTGCAAAAGGTAAGG
ACTTAGTGGCTATCAAGAATAAAGTTAGCTCTACTGACCTACTCCCTTCTCGTGCGCCTGCTGGTTATAAAGTACAAGTGTGGCCTACTGGCAG
CAAACCTGAGTCTCGTTACTGGCTGCAAGCTGAGCCTAAAGAGGGAAACCTTGTGTCTTGGAAAGAAACAATAGCTGCTGATGTATTACTTG
GGTTTGATAAAGGCACAATGCCTTACATTATTGAACGTACAGATATCATCAACGGCATAGCTCAATTCAAGATAAGACAAGGTGATTGGGAA
GATCGTAAAGTAGGGGATGACTTGACTAACCCTATGCCCTCTTTTATTGATGAGGAAGTACCCCAGACAATAGGTGGAATGTTCATGGTGCA
GAACCGCCTATGCTTTACAGCAGGTGAAGCGGTTATTGCTTCTCGTACATCATACTTCTTCGATTTCTTTCGTTATACGGTTATCTCTGCATTGG
CAACTGACCCCTTTGATATTTTCTCAGATGCTAGTGAAGTCTACCAGCTAAAACATGCAGTGACCTTAGATGGCGCTACCGTGTTGTTCTCTGA
TAAGTCACAATTCATACTGCCAGGCGATAAGCCTTTAGAGAAGTCAAATGCACTGCTTAAGCCTGTTACAACATTTGAAGTGAACAATAAAGT
GAAGCCAGTAGTAACTGGTGAATCGGTAATGTTTGCCACTAATGATGGTTCTTACTCTGGTGTACGAGAGTTCTATACAGACTCTTATAGTGA
CACTAAGAAGGCACAAGCAATCACAAGTCATGTGAATAAACTCATCGAAGGTAACATTACCAACATGGCAGCAAGCACCAATGTCAACAGGT
TACTTGTCACTACCGATAAGTATCGTAACATAATCTACTGCTACGATTGGTTATGGCAAGGAACAGACCGTGTACAATCAGCATGGCATGTAT
GGAAGTGGCCTATAGGTACAAAGGTGCGAGGTATGTTTTATTCTGGTGAATTACTTTACCTGCTCCTTGAGCGAGGAGATGGCGTGTATCTG
GAGAAGATGGACATGGGTGATGCACTAACCTACGGTTTGAATGACCGCATCAGAATGGATAGGCAAGCAGAGTTAGTCTTCAAGCATTTCAA
AGCAGAAGATGAATGGGTATCTGAGCCGCTCCCTTGGGTTCCTACTAACCCAGAACTTTTAGATTGCATCTTAATCGAGGGTTGGGATTCATA
TATTGGCGGCTCTTTCTTATTCAAGTACAACCCTAGTGACAATACTTTGTCTACAACCTTTGATATGTATGATGACAGCCATGTAAAAGCGAAG
GTTATTGTTGGTCAGATTTACCCTCAAGAGTTTGAACCTACGCCTGTGGTTATCAGAGACAATCAAGACCGTGTATCCTACATTGATGTACCAG
TTGTAGGATTGGTTCACCTTAATCTTGACATGTACCCCGATTTCTCCGTAGAAGTTAAGAATGTGAAGAGTGGTAAAGTACGTAGAGTATTAG
CGTCAAACCGTATAGGTGGTGCTCTCAATAATACAGTAGGCTATGTTGAACCGAGAGAAGGTGTCTTCAGATTTCCACTGAGAGCTAAGAGC
ACGGATGTTGTTTATCGTATTATTGTAGAGTCACCTCACACATTCCAGCTTCGTGATATTGAGTGGGAAGGGAGCTACAATCCAACCAAAAGG
AGGGTCTAATGGCTATAGGTTCAGCCGTTATGGCTGGTATGTCTTCTATTGGTAGCATGTTTGCAGGCAGTGGTGCAGCAGCCGCTGCTGGA
GGTGCTGCCGCAGGTGGCGGAGGTTTGCTAGGTTCACTAGGTGGATTCCTAAGTGGCTCTACTGCTGGTTTCTCTAATGCTGGCCTTCTTGGT
GCTGGCCTTCAAGGGTTAGGCTTGATTGGTGATCTATTTGGTGGAAGTGATGAAGCCAAGGCGATGAAGAAAGCACAAGAAGAGCAATGGC
GGCAGCAGCTTATTGCTACACAAGAGGCGTACAAGACAGTGGCAGACGCAGAACGTTCTGCTGCTAAACAATATCATGCAGATGCAATCAGT
AATCAGGCTTCACTGCTACAGCAGCGAGCACAGGTTGCATTACTTGCTGGGGCTACTGGTACTGGTGGTAATTCTGTGTCCTCTATGCTTAAT
GACTTAGCAGCAGATGGCGGCAGGAACCAGAGTACTATCATTGATAACTATGAGAATCAGAAGATTAATTTCACCAACCAGCTTAAGTCTATC
CAACGTGGTGGTCAGATGCAGATGCGTGAGTTTAAGAAGCCTTCTGCTATGAATACCTTGGTTAAAGGTATTCCAAGTCTGGCATCTGCCTAT
GTAACTGGTAGTAAGTCTGGCAAGGCATTGGGTAAAGCCTTAACTGATTCTCGCACATATTCATCTGGAACAAGAGGTATTTAATGGCAATTG
AGCGACAAGCAGTACAAGGTCTGCCACAAGTGCAGGCCACTTCTCCTAATGTCATGACCTTTGCACCTCAACAAGTGGGAGGTGTGGAGGCT
GGCGTGGCTTCTACCTCCGGTAGTAGGTTTATCGAAGACCTTATTCGTGCAGCAAGCAGCGTGGCTGATGTTACCACTGGTATCCTTAATCAG
AAGATTGAGGAAGATAAGGTTGTTCAAATGGAACGGGCATATAACGGATTAATGCCTTCTGAGGATGCAACTCGTGGTGGCGCTCGTGCTAA
CATGCTTGTCAAAGCTCAACTGCTAGCTAATGATGAAGCAGCACGAATGAAAGACATGGCTACTCGTTTCCAAGGAACGGATGACGAATGGA
CACAACTTATGGTTGACTCTCGTAATGAGATGCAGAATAAGCTGTTCCAGCAATACCCTGAGTTGCAAGGTGACAAAGATACTATGCGTATGG
TCACTAATGTCTTCCAAGAACAGCAGCCTCAGATTTGGGCTACACGAACCCAGCATAAACTTGACCGTGAACAAGCAGACCGTGAGGATACCT
TTGACGGGCGAGTGGCTTCTACTTGGGATTCTAATATTGACCCTGAAGCCTCTGGCTATGCTTTACAGGAACGAATCCGCGAAGGTCTTACTC
AAGGATTACTACCTGAACAGATGTACAAGAAGTTAGTCCAGCGAGCAATTTCACTTGCACAAGGCGGTGATGTTAGCATGGCTGAAGCCCTG
AAGTATGTGAAGGACGATAAGGGTGTTTCTGTTTATGCTAAGAATCCACAGCTTATCACAGCCATCACTAGTGGTAATGCAGTTTGGGCTAGG
AATAATGTAGCTGATGTAACTCGTATGTCTTTCGAAGTTAAAGAATCCACCTTGCAGGTGATTTAACTGATGAAGAATTGTTGGAACGAGCA
CAGCACATTAATAATCTGACAGGTAACTCTGTCTTCTCTAATCCAGAACTAGAGGCACTGATGCGCCAACGGGCTAAGCAGAATGCAGAGCTA
GGTGCAATGCAGGATATGCGACGTGAGCTTTACTCCGACCGCCTGACTGGCTTCCAAGGTAAGACTGATAAAGAGAAGAAGGCTTACATTGA
TGTTATCAAACAGGATAGCCAACTTTATGCAGACCAGCAAATCAAACAACGTGGCTTGGACCCTTACAGTCAAGAGGCTGAAGCTATTCGTG
GTGCAGTGGAAGTGCAGCGCCTGCAATTCATGAACTCCAAAGGCTTAGTGGATGATACCTTTGAGTCTCGTATCAAAGCCATGGAATCTATGC
TATCGCCTGAGCACTTTGCCAAGGGCGAACCACAGGAGTTGATGACTATTCGCCAGTTGTGGGAACAGTTACCAGAAGAGAGCCGAGGTGT
CTTTGGTGACACGGTGAATGGCTACATGGATAACTACAACACTGCACTACAAATGGGAGAGACACCTTTGCAGGCTGCAAGGTTTGCGCGTA
AAGCACAGCAGAAATTCTCTCGTACTGAGAAGGAAACCAAGAAGTTCAACTCAGCTATTGGAGATGCACTGGATGAGGTATCTGGTGCTGGC
TGGTTTGATGGTAAAACCGAAGTGTCAGACTTAGGTAAAGCTATTGCGGAAGAAGAGTTACGAGCTAAGGCCAATATGTTGTGGTCTAGTGG
```

FIG. 13G

```
TATGCGTAACATGGATTCCATCAAGAAGGCTTTAATTACTTGGGGCAATAAACGCTACACTCAATCAGAGGATGCAAAGACTTCCGGTGGCTA
TTTCATTAAAGGTGATTACACTTCTGCATCTGATATGCTTATGTCAGTTGGGAAAGGCGTAAACCCTACCGATGTACCTCTGGCGCTTGGTAGG
TATGTAGAAACACAGATGCCAGAATTGAAGAAGGAGCTTCAAGAGGGGGAAACTAAAGATGATATATACATTGATTACAATGAACAGAAAG
GTACTTTCGTGATTCGTGCTGGTGCAGCAGGTCGCCCTCTTTCTGGAGTAATCCCTGTAACCTCTTTAGATACCACTTCACTACTAGATTCTGCC
TATCAGAAGAAAGTAGAGGAACGAGATAAAGGCGAGTATGTTCACCCGTATCGTACAGATATTGGTGCACAAGAGCCTATGCCAGCTAAACC
AACTGCCAAAGATATTGGTAAATTTGGACTAGCTAACTTCCTCATGTCTTCTGCTTTTGCTTCTGGTGAGAATCTGCCTTCTAACTTCGAGATTA
ACTATCGAGGTAATATGCAACAATTCTATGACAAGCTAGCTATGGATGAGAATAAAGATAAAGTTGGCTTTAATAAGGCAACTGGAACCTTTA
CTCCATATAAAGACGCTCACGGTGAGTCTATCGGTTACGGTCATTTCTTAACGGAAGAAGAGAAGCGAAACGGGTATATTAAGATTGGCGAT
GAACTAGTTCCCTATCGAGGGTCTATGTCTCAGCTTACAGAGAGCAAGGCTCGCGCTCTTATGGAGCAAGATGCTAAGAAGCATGTGCCTCCT
ACTCGTGACTGGAAGATTCCGTTTGACCAGATGCACCCTGCACAGCAACGTGGCTTGATGGATTTAAGCTACAATTTAGGTAAAGGTGGAAT
CCAGAACTCACCGCGTGCTCTTGCTGCATTCAAAGCTGGTAAGCTTACGGAGGGCTTTATCGAAATGCTGGGCACTGCATCAAGTGAAGGTA
AGCGTATTCCTGGCCTACTGAAGCGACGCGCTGAGGCATACAATATGGCATCTGCTGGTGGTGTGCCTAAGATTACCGAAGTGGAGACTCGT
GAAGATGGCTCCATGTGGGTTAGGTTTGGTGGACCTATGCCAGCAGGTTCTGTCTCGGCATGGACTCATAAACGTATTGGCGCGGATGGTTG
GTATCAGGTTTATGAGGCTGCACCTACCAAGTTAGCTAAAGATTCTAAGGTAGGTAAAGTTAAGTTGTAGTACCTAACTCAAGGCTTGTCTCA
CATGTGAGACAGGTCTTTATGATAGGCACTATGGAGGAATTATGGAACAAGACATTAAGACTAATTGGGCTGGATATGTCCAGTCTACTCCT
GAGCCGTTTTCTATTGAGGCGGCTCCGGTATCGGCTCCTACGATACGCCAGCGTAATGAGTTACAAGAGCAAGTTCTTGAAGCTAAAGCTGA
CGCTGATATCTTAGGTGCTGTAGGTGCTGCCTTCCAGAATGAGTGGTTGGCATTCGGAGGCAAGCGGTGGTATGACCGTGCCACTGCTGATT
TCACACCTCAACCAGACTTTGAGATACAACCTGAGCAACGTGAAGCACTACGTTTCAAATATGGTACGGATATGATGCAGACAATCACTGAGG
GTGTTCGTTCTGAGGATGAATTGAACTTCCGTATTCAGAATGCGGATGAAGACCTTGAGCGCAATAAGCGCATTGCTCAGGCTGGCTGGGTT
GGCTCTGTGGCGACGATTGGCGCTGCTGTGCTTGACCCTGTGGGATGGGTTGCCTCTATTCCAACCGGTGGTGCCGCTAAAGTTGGACTCGT
AGGCCGTGCTGTGCGTGGCGCTATCGCCGCTGGCGTGAGTAATGCCGCTATTGAATCCGTATTGGTCCAAGGTGACATGACTCGTGATTTAG
ATGACATTATGGTAGCACTGGGTTCCGGTATGGCTATGGGTGGCGTTATTGGCGCTGTAGCGCGTGGTAGGGCCACTAAGCTCAGTGAGCAA
GGTGATGACAGGGCTGCTAGCATTGTGCGCAGTGCAGACGCAGGGGACCGCTATGTTCGTGCTGTTGCCGATGACAGTATCGGTGCGATGC
GTGTTAAGGGCGCAGAGGTTCTCACTGAGGGTGTATTCGATATCTCCAGTAAGAGTGAAGACCTACTGAAAACCTTGCAACGAGAAGGTAAT
GCGATTGATATGACACCTCGCCGTTGGGCTGGAACTATGTCTGCCCTCGGTACTGTCGTGCACTCATCTAAAGATGCAAGTATCCGAGGCCTT
GGTGCTCGTCTGTTTGAATCCCCACAAGGTCTAGGTATGCAGAAGGCATCTGCTAGTCTTATGCAGAATACTAACTTAAATCGCCTGAAATCT
GCTGATATGAACCGCTTCAATGATGGGTTTGATTTGTGGCTTAAAGAGAATAATATCAATCCAGTAGCAGGGCATACCAACTCTCATTATGTA
CAGCAATACAATGAAAAGGTGTGGGAGGCAGTGCGTATTGGCATGGATGAGTCTACACCTAAATCTATCCGCATGGCTGCTGAGGGACAAC
AGGCTATGTACAGAGAGGCGCTGGCTTTACGTCAACGTTCTGGTGAAGCGGGATTTGAAAAGGTAAAAGCCGACAACAAATATATGCCTGAT
ATCTTTGATAGTATGAAAGCCAGACGTCAATTCGATATGCACGATAAAGAAGACATCATCGAACTTTTCTCTCGTGCCTACCAGAATGGCGCT
CGTAAGATTCCAAAGGAAGCAGCAGATGAGATTGCACGAGCACAGGTAAATCGCGTTGCTGATGCTACCTTAACTGGAAAGCTTAGTTTTGA
AAAGGCAATGTCAGGTCAGACTAAGGCAGAGTATGAAGCTATCATGCGTAAGGCAGGCTTCAGTGATGAAGAAATTGAAAAGATGATAGAA
GCTCTGGATAACAAAGAAACCAGAGATAACATCTCTAACCGAGCTAAAATGAGTTTAGGATTAGATGTTACTCAAGAATACAATGGCATTCGT
ATGCGTGACTTCATGAATACCAACGTGGAAGAGCTAACAGATAACTATATGAAGGAAGCAGCAGGTGGCGCTGCATTGGCTCGCCAAGGCTT
CTCTACCTATCAGGCTGCACTTAATGCAATTGACCTTGTAGAGCGAAATGCACGAAACGCGGCTAAGGATAGCAAGGCTAGTTTGGCATTAG
ATGAAGAGATTCGTCAGATGCGAGAAGGTCTTCGCCTGATTATGGGCAAGTCGATTGATGCAGACCCACAGGCTATATCTACTAAGATGATG
CGTCGTGGTCGTGATATCACAGGTGTGCTTCGCTTAGGTCAAATGGGCTTCGCACAGCTAGGTGAACTTGCCAACTTTATGGGTGAATTTGGT
ATTGCTGCAACTACTATGGCTTTAGGTAAGCAATTCCGCTTCACCTCTAAGGCGTTGCGTAATGGCGATGGCTTCTTCCGAGATAAGAACTTA
GCTGAGGTTGAGAGAATGGTGGGGTACATTGGTGAGGATAACTGGCTAACAACTAAGGGTGCACGTCCTGATGAATTTGGTGATGTAACCA
CAGTAAGAGGGATGATGGCTCACTTTGACCAATCCATGAACTCAATACGTCGTGCTCAAACCAACCTATCACTCTTCCGCATGGCACAGGGTT
CTCTGGAGCGAATGACTAATAGGCAAATAGCTTTGTCTTTCATTGACCACCTTGAAGGCAAGAAGATTATTCCTCAGAAGAAACTGGAGGAAC
TTGGTCTTACTCAGGAGTTCATGACTAACCTACAGAAGCACTATGATGCTAACTCTAAAGGTTCTGGCTTGCTTGGCTTTGATACAATGCCTTA
TGCCATGGGTGAAACTTTAGCTAATGCTATTCGTCGTAAGCAGGTCTAATCATCCAACGTAACTTCATTGGTGATGAAGGTATCTGGATGAA
CAAAGCACTAGGTAAGACATTTGCACAGCTTAAGTCATTCTCTCTTGTATCTGGTGAGAAGCAATTTGGTCGAGGGATTCGCCACGATAAAT
TGGTCTTGCTAAGAAGACAGCTTACGGGTTTGCTTTGGGTTCAATAGTGTATGCGGCAAAAGCCTATGTGAACTCTATTGGGCGAGAAGACC
AAGATGAATATTTGGAAGAGAAGTTATCGCCTAAAGGGTTGGCCTTTGGTGCAATGGGTATGATGAGTACAACTGCTGTATTTAGTCTAGGT
GGAGATTTCTTAGGTGGCCTAGGTGTTCTACCTTCCGAACTCATTCAATCACGCTATGAAGCAGGTTTCCAAAGTAAGGGTCTGATTGACCAA
ATACCTCTGGTTGGCGTTGGTGCAGATGCAGTAAATCTGGCTAACTCAATCAAGAAGTATGCAGAAGGTGACACAGAAGGTGTAGATATCGC
TAAGCGAGCACTCCGTCTTGTGCCACTTACCAATATAATAGGTGTCCAAAACGCATTGCGTTATGGCTTAGATGAACTGGAGGATTGATGAGT
TATACTTTCACAGAACATACAGCCAATGGTACGCAAGTCACCTATCCTTTTAGCTTTGCTGGTAGGGATAAAGGGTTATCTTCGTGCCTCAGATG
TGATAGTGGAGTCTCTTCAAGGTAACACTTGGATTGAAGTTACATCTGGCTGGCAACTAACTGGCACGCACCAGATTACTTTTGATGTAGCAC
CAGTTGCAGGTTTGAAGTTCCGTATTCGAAGGGAAGTACAAAAAGAATATCCATACGCTGAGTTTGACCGTGGTGTTACCTTGGATATGAAG
TCTTTAAATGGTTCTTTCATTCATATACTGGAGATTACACAGGAGTTACTTGACGGGTTTTATCCAGAAGGATACTTCATTAAACAGAATGTAA
GCTGGGGCGGCAATAAGATTACTGATTTGGCTGATGGCACAAATCCGGGAGATGCAGTAAATAAAGGGCAGCTTGATGCCATCGACAAGAA
```

FIG. 13H

```
GCATACAGATTGGAACGCCAAACAGGACATTGAGATTGCTGGCCTTAAGGCTGGTATGACTTCTGGTATTGCGCACAGAACTGTTCCTTGGTA
CACGATAGCCCAAGGTGGTGAGATTTCCGTAAAACCACCTTATGAATTTCAAGATGCACTAGTTTTCCTTAATGGGGTATTGCAGCACCAAAT
TGTAGGCGCATACTCTATAAGCAACAACACTATCACTTTCGCAGAGCCGCTTGTGGCTGGTACAGAGGTGTATGTGCTGATTGGTAGTCGTGT
GGCTACATCTGAACCTAATATTCAGTTGGAGTTGAACTTTGACTTAGTAGAAGGCCAACAAGTAGTACAGATTGGCTCTGCATTTAAGTACAT
TGAGGTCTACCTTGATGGATTATTACAACCTAAACTTGCTTATCAGGTAGACGGTGACATTGTTACTTTCTCAGAAAGAGTACCAGAATGCCG
GATGACTGCTAAGATTATCACAGCATAAGGAGGTGGGATGATTAACTCCGAACTGGTAGATAGTGGTGTGAAGCTTGCGCCACCTGCACTCA
TATCAGGTGGGTACTTCCTCGGTATCAGTTGGGATAATTGGGTGTTAATAGCAACATTCATTTATACCGTGTTGCAAATTGGGGACTGGTTTT
ATAATAAGTTCAAGATTTGGAGGGAGAAGCGTGAGCGTACACAATAAACATGCAGCTACAGAGGACGAGGTTGGCATTCTGCATGGTGCTA
TTACCAAAATCTTCAATAAGAAAGCACAGGCAATACTGGACACTATAGAAGAAGACCCTGATGCAGCATTACATTTAGTGTCTGGTAAGGATA
TTGGTGCGATGTGTAAGTGGGTTCTTGATAACGGCATTACCGCCACACCTGCTGCACAGCAGGAAGAGTCCAAGTTATCTAAGCGCCTCAAG
GCTATCCGAGAGGCATCCAGTGGTAAGATAATTCAATTCACTAAGGAGGATTGATGGCTAAGGCAAGAGAATCACAAGCGGAGGCTCTTGC
CAGATGGGAGATGCTACAGGAGTTACAGCAGACCTTTCCTTACACCGCGGAAGGTTTGCTTCTCTTTGCAGATACAGTTATTCATAACTTAATT
GCAGGCAACCCTCATCTGATTCGTATGCAGGCGGATATCTTGAAGTTCCTATTTTACGGACACAAGTACCGCCTCATCGAAGCGCCTCGTGGT
ATCGCTAAGACAACACTATCAGCAATCTATACGGTATTCCGTATTATTCATGAACCGCATAAGCGTATCATGGTTGTGTCCCAAAACGCCAAGC
GAGCAGAGGAAATCGCAGGTTGGGTAGTTAAAATCTTCCGTGGCTTAGACTTTCTTGAGTTTATGCTGCCGGATATCTACGCTGGGGACCGT
GCATCCGTTAAGGCGTTTGAGATTCATTACACCCTACGTGGTAGTGATAAGTCTCCTTCTGTATCCTGTTACTCAATCGAAGCAGGTATGCAGG
GTGCTCGTGCTGATATTATTCTAGCGGATGACGTAGAGTCGATGCAGAATGCTCGTACGGCAGCGGGCCGTGCCTTGCTTGAGGAGCTGACT
AAGGAGTTTGAATCTATCAACCAGTTTGGGGATATCATTTACCTTGGTACACCTCAGAACGTAAACTCTATCTACAACAACCTACCTGCTCGTG
GTTACTCTGTTCGTATCTGGACTGCGCGTTACCCTTCAGTAGAGCAAGAGCAATGTTATGGCGACTTCCTTGCACCTATGATTGTTCAAGATAT
GAAGGACAACCCAGCACTTCGCTCAGGGTACGGGTTGGATGGTAATAGTGGTGCACCTTGTGCCCCTGAAATGTATGATGATGAAGTCCTGA
TTGAGAAGGAAATCTCTCAGGGTGCTGCTAAGTTCCAGCTTCAGTTCATGCTTAACACTCGCATGATGGATGCTGACAGATACCCATTACGCC
TGAACAATCTAATCTTCACCTCGTTTGGTACAGAGGAAGTCCCTGTGATGCCTACGTGGAGTAATGATTCCATAAACATCATTGGTGATGCAC
CTAAGTATGGTAACAAGCCTACGGATTTCATGTACAGACCTGTAGCTCGCCCATATGAATGGGGTGCTGTCTCCCGCAAGATTATGTATATTG
ACCCTGCGGGTGGTGGTAAGAACGGAGATGAGACGGGTGTAGCCATCGTATTCCTGCACGGCACATTCATTTATGTGTATCAGTGCTTTGGT
GTACCTGGCGGATACCGAGAGTCGTCCCTGAATCGCATTGTGCAGGCCGCAAAGCAGGCGGGTGTTAAAGAGGTATTCATTGAGAAGAACT
TTGGTCATGGCGCGTTTGAGGCGGTAATTAAGCCGTACTTTGAACGAGAGTGGCCTGTAACTCTGGAAGAGGATTACGCCACCGGACAGAA
AGAGTTGCGTATCATTGAGACGCTGGAGCCGCTCATGGCAGCCCATAGGCTTATCTTCAATGCAGAGATGGTGAAGTCAGACTTTGAGTCGG
TACAGCACTATCCGCTTGAACTACGCATGTCCTACAGTCTTTTCAATCAAATGTCGAACATAACGATTGAGAAGAACAGCCTCCGGCACGATG
ACCGCCTAGACGCCCTGTATGGCGCTATACGGCAATTAACTTCTCAGATAGACTATGACGAGGTTACACGGATTAATCGCCTCAGAGCGCAG
GAGATGCGCGATTACATCCATGCTATGAACACACCTCATCTACGCAGGGCAATGCTATATGGAGATTACGGTACTGAGCGAAGAGTGACCAA
CACTTCCGTAGCGATGCAGCAGCGAGTTTACGGGCAGAACTACCGAAATAAATCGGCAAGCAGAAATACACTTTCTGCAAGGATTTCAAGGA
CTTATTAATTACTGGACACTATAGAAGGAAGGCCCAGATAATAAGAGAAAATAAGGTAATATATATATAGGTTAACCTAGGTTATATAGGT
ATGCCTTAGTATGGGTGTACTCCTGTACACCCTATTCCTTACTACCTTACTATATTTACATAATAGGAGAGAGACAATGGCTAATGATTATAGT
AGTCAACCATTAACAGGTAAGTCTAAGAGAAAGCAGGTACAACCTGTAAGTGAAGAACTAATGCTTCCGGTGCTCAAAAAAGAGGAAGTTA
GTAAGAAAAGCAATGTTATTAATGATGCCACCAAATCAGGTAAACAGAAAGGGGCCATGGTGTGCCTTGAAGTGAAAGGTGGTGTATTGAA
GATTGCTATCGCGGTTGATGGCAAAGAAGATTCAGAGTGGAAGTTAGTAACAGTGGAACCAACTGTTAACCCAGTTTAAGATAAGGAGGAA
GATTACATGGCTAAATATGGTACTACAGGTTCTGTTACTGGTCAGGCTTTTCGAGTAAAAGCAGTACAAACTATTGCAACGGCAATCCCGATG
CCTGTTGTTAAAGAAGAAGACCTTAAGAGTAAAGACCACCCTATCAACATCAAACATTTATCAGGTAAACAGAAAGGTGCAATGGTTGCTCTT
GAGAAAGGTGACACAACCTTACATATTGCTGTTGCACGTGGTAGTGAACCCACAGACCCTTGGGATGTAACTGGTATGGAAAGGACGCTGT
TACTCCAGCAGGGGTATAATAATGCTTAATAAATACTTCAAGCGTAAAGAGTTTGCTTGCCGTTGTGGGTGCGGTACATCCACTGTTGATGCT
GAATTACTACAGGTAGTCACAGATGTGCGTGAGCACTTTGGTTCTCCTGTAGTTATCACTTCGGGTCATCGCTGTGCTAAGCACAATGCCAAT
GTAGGTGGCGCTAAGAACTCCATGCATCTTACTGGTAAGGCTGCTGACATTAAAGTGTCTGGCATATTACCTTCTGAAGTGCATAAGTATCTT
ACTAGCAAATACCAAGGCAAGTATGGTATAGGTAAGTATAACTCCTTCACTCACATCGATGTACGGGATGGTTGTGCGCGATGGTAAGATGT
GTTGAATGGTGTGAGCGTATGGTTGCCCAAGCTGCCGAGGATGGCAACTATGATGACTGGAAGAACTACTCTGACTTGTTAGCTCAATGGAA
AGGGAGATGCAATGAAAAAGCTGTTTAAGTCTAAGAAGGTTGTAGGTGCACTGGTTGCACTTGTTATTGCTCTTGTTTCTGTAGGTCTTGGTG
TAGACCTTGGCTCTGGCACGGAATCCTCTGTGACAGATGTGGTCTGCCAAGTGATCACCTGTGAATAAGTTTCTAGAAGTTCTGGCAGGTCTT
ATTGGCCTGCTTGTCTCTGCTAAGAAGAAACAAGAAGAGAAGGAGGCACAAAGTGAAGCGAATCATGTTAGTGACAACCCTTCTGATTGGTT
CGCTGACCACTTCCGGGTGTCAGCAGGCGTTACCAGAGAAAGCAATGGTGAAACCTCTGAGGCCGACGCTGACGGCAGTTTACGAGGTAGA
CGATAAGGTCTGCTTTAGTAAGCCTGACGCTACAAAACTTGGTTTGTACATTCTCTCGCTAGAACGCGGATACAATTAATACATAGCTTTATGT
ATCAGTGTCTTACGATTTACTGGACACTATAGAAGAGGTAAGATAGCGCCGTTCTTTTGAGCGGCCTATTACTAGCCAATCTTCATAGGGAGG
GTTGGAAAGTAATAGGAGATAGCATGGCTAAATTAACCAAACCTAATACTGAAGGAATCTTGCATAAAGGACAATCTTTGTATGAGTACCTTG
ATGCGAGAGTTTTAACATCAAAGCCGTTTGGTGCTGCAGGTGACGCCACTACTGATGATACGGAGGGTTATAGCTGCTTCATTAAACTCTCAGA
AAGCTGTCACAGTCTCAGATGGTGTATTCTCTAGCTCTGGTATTAACAGTAATTACTGTAACTTAGACGGCAGGGGTAGTGGCGTGCTAAGTC
ACCGTTCAAGTACAGGTAACTACTTAGTATTTAACAATCTACGTGCAGGTCGCTTAAGTAATATTACGGTAGAAAAGTAATAAGGCGACTGATA
```

FIG. 13I

CAACTCAGGGACAGCAGGTATCCCTTGCTGGTGGAAGTGATGTTACTGTAAGTGACGTTAACTTCTCAAACGTTAAAGGTACTGGTTTCAGTT
TAATCGCATACCCTAATGATGCGCCACCTGATGGACTTATGATTAAAGGCATTCGAGGTAGCTATTCCGGCTATGCTACTAATAAGGCAGCCG
GATGCGTACTTGCTGATTCCTCAGTTAACTCCCTCATAGATAACGTCATTGCTAAGAACTACCCTCAGTTCGGAGCAGTAGAGTTGAAAGGTA
CAGCCAGTTACAACATAGTCAGTAATGTTATAGGGACAGATTGCCAGCATGTAACTTACAACGGCACTGAAGGGCCAATAGCTCCTTCTAATA
ACCTTATCAAGGGGGTGATGGCTAATAACCCTAAGTATGCAGCGGTTGTTGCAGGCAAAGGAAGTACGAACTTAATCTCAGACGTGCTCGTA
GATTACTCAACTTCTGATGCTAGGCAGGCTCATGGTGTTACAGTAGAGGGTTCTGATAACGTCATAAATAATGTGCTTATGTCAGGATGTGAT
GGTACTAACTCTTTAGGACAAGGGCAGACTGCTACAATTGCACGCTTTATAGGTACAGCTAATAACAACTATGCGTCTGTATTTCCTAGCTACA
GTGCTACAGGTGTTATTACTTTCGAATCCGGCTCTACCCGTAACTTCGTAGAGGTAAAGCACCCTGGCAGGAGAAACGACCTTCTCAGTTCTG
CTAGTACTATTGACGGTGCAGCTACTATTGACGGCACTAGTAATAGTAACGTAGTGCACGCACCTGCCTTAGGGCAGTACATAGGTAGTATGT
CAGGTAGGTTCGAATGGCGGATTAAGTCCATGTCACTCCCTTCAGGCGTTCTTACTTCTGCTGATAAGTACAGAATGCTTGGAGATGGTGCTG
TGTCATTAGCTGTAGGTGGGGGCACTTCTTCTCAAGTTCGCCTATTTACTTCTGATGGTACTTCTCGGACAGTGTCCCTCACCAACGGTAACGT
GCGTCTTTCTACCAGTAGCACAGGCTTTTTGCAGTTAGGTGCTGATGCAATGACCCCAGACAGTACTGGTACATACGCATTAGGTTCCGCCAG
CCGAGCATGGTCTGGCGGTTTTACTCAAGCAGCATTCACTGTTACCTCAGATGCTCGGTGTAAAACAGAACCTCTTACTATCTCAGATGCCTTA
CTGGATGCTTGGTCTGAAGTTGACTTTGTGCAGTTTCAGTATTTGGATCGTGTTGAGGAGAAGGGTGCAGACTCAGCTAGATGGCACTTCGG
TATCATCGCTCAGCGAGCTAAGGAGGCTTTCGAACGTCACGGTATAGATGCACATCGCTATGGCTTCTTGTGCTTCGACAGTTGGGATGATGT
ATACGAGGAAGATGCCAATGGCTCTCGTAAACTGATTACACCAGCAGGTTCCCGCTACGGTATTCGTTACGAGGAAGTACTGATATTAGAGG
CTGCGTTGATGCGGCGGACTATTAAGCGTATGCAGGAAGCACTAGCTTCCCTGCCTAAGTAAGCAACAGGCAGTGCGTAAGCACTGCTTTTA
GCGCAACTTTTCTTAAAGGTTATCACGGTGGTAGCCTTTCAGAAAAGGAGGTTACATGATTCAAAGACTAGGTTCTTCATTAGTTAAATTCAA
GAGTAAAATAGCAGGTGCAATCTGGCGTAACTTGGATGACAAGCTCACCGAGGTTGTATCGCTTAAAGATTTTGGAGCCAAAGGTGATGGTA
AGACAAACGACCAAGATGCAGTAAATGCAGCGATGGCTTCAGGTAAGAGAATTGACGGTGCTGGTGCTACTTACAAAGTATCATCTTTACCT
GATATGGAGCGATTCTATAACACCCGCTTCGTATGGGAACGTTTAGCAGGTCAACCTCTTTACTATGTGAGTAAAGGTTTTATCAATGGTGAA
CTATATAAAATCACGGATAACCCTTATTACAATGCTTGGCCTCAAGACAAAGCGTTTGTATATGAGAACGTGATATATGCACCTTACATGGGTA
GTGACCGTCATGGTGTTAGTCGTCTGCATGTATCATGGGTTAAGTCTGGTGACGATGGTCAAACATGGTCTACTCCAGAGTGGTTAACTGATC
TGCATCCAGATTACCCTACAGTGAACTATCATTGTATGAGTATGGGTGTATGTCGCAACCGTCTGTTTGCCATGATTGAAACACGTACTTTAGC
CAAGAACAAACTAACCAATTGTGCATTGTGGGATCGCCCTATGTCTCGTAGTCTGCATCTTACTGGTGGTATCACTAAGGCTGCAAATCAGCA
ATATGCAACAATACATGTACCAGATCACGGACTATTCGTGGGCGATTTTGTTAACTTCTCTAATTCTGCGGTAACAGGTGTATCAGGTGATATG
ACTGTTGCAACGGTAATAGATAAGGACAACTTCACGGTTCTTACACCTAACCAGCAGACTTCAGATTTGAATAACGCTGGAAAGAGTTGGCAC
ATGGGTACTTCTTTCCATAAGTCTCCATGGCGTAAGACAGATCTTGGTCTAATCCCTAGTGTCACAGAGGTGCATAGCTTTGCTACTATTGATA
ACAATGGCTTTGTTATGGGCTATCATCAAGGTGATGTAGCTCCACGAGAAGTTGGTCTTTTCTACTTCCCTGATGCTTTCAATAGCCCATCTAAT
TATGTTCGTCGTCAGATACCATCTGAGTATGAACCAGATGCGTCAGAGCCATGCATCAAGTACTATGACGGTGTATTATACCTTATCACTCGTG
GCACTCTTGGTGACAGACTTGGAAGCTCTTTGCATCGTAGTAGAGATATAGGTCAGACTTGGGAGTCACTGAGATTTCCACATAATGTTCATC
ATACTACCCTACCTTTTGCTAAAGTAGGAGATGACCTTATTATGTTTGGTTCAGAACGTGCAGAAAATGAATGGGAAGCAGGTGCACCAGAT
GATCGTTACAAGGCATCTTATCCTCGTACCTTCTATGCACGATTGAATGTAAACAATTGGAATGCAGATGATATTGAATGGGTTAACATCACA
GACCAAATCTATCAAGGTGACATTGTGAACTCTAGTGTAGGTGTAGGTTCGGTAGTAGTTAAAGCAGCTACATTTACTATATCTTTGGTGGC
GAAAACCATTTCAACCCAATGACTTATGGTGACAACAAAGGTAAAGACCCATTTAAAGGTCATGGACACCCTACTGATATATACTGCTATAAG
ATGCAGATTGCAAATGACAATCGTGTATCTCGTAAGTTTACATATGGTGCAACTCCGGGTCAAGCTATACCTACTTTCATGGGTACTGATGGA
ATACGAAATATCCCTGCACCTTTGTATTTCTCAGATAACATTGTTACGAGGATACTAAAGTTGGACACTTAACACTTAAAGCAAGCACAAGTT
CCAATATACGATCTGAAGTGCAGATGGAAGGTGAATATGGCTTTATTGGCAAGTCTGTTCCAAAGGACAACCCAACTGGTCAACGTTTGATTA
TTTGTGGTGGAGAAGAGACTTCGTCCTCTTCAGGTGCACAGATAACTTTGCACGGCTCTAATTCAAGTAAGGCTAATCGTATCACTTATAACG
GAAATGAGCACCTATTCCAAGGTGCACCAATCATGCCTGCTGTAGATAACCAGTTTGCTGCTGGTGGACCTAGTAACCGATTCACTACCATCT
ACCTAGGTAGTGACCCTGTTACAACTTCAGATGCTGACCACAAGTACAGTATCTCTAGTATTAATACCAAGGTGTTAAAGGCTTGGAGCAGGG
TTGGTTTTAAACAGTATGGTTTGAATAGTGAAGCAGAGAGGGACCTTGATAGCATACACTTCGGTGTCTTGGCTCAGGATATTGTAGCTGCTT
TTGAAGCTGAAGGGTTGGATGCCATTAAGTATGGAATTGTGTCCTTCGAAGAAGGTAGGTACGGTGTGAGGTATAGTGAAGTTCTAATACTA
GAGGCTGCTTATACTCGTTATCGTTTAGACAAGTTAGAGGAGATGTATGCCACTAATAAAATCAGTTAAGCAAGCTGCTGTACTCCAGAACAC
AGAAGAGCTTATTCAATCAGGACGTGACCCTAAGCAGGCTTATGCCATTGCCAAGGATGTTCAACGTCGTGCCATGAAGAAACCTTCTGCATC
TTCTGCGTAAAGAGGAGATATACAATGGTCTTCACACTCGAAGATTTCGTTGGGGACTGGCGACAGACAGCCGGCTACAACCTGGACCAAGT
CCTTGAACAGGGAGGTGTGTCCAGTTTGTTTCAGAATCTCGGGGTGTCCGTAACTCCGATCCAAAGGATTGTCCTGAGCGGTGAAAATGGGC
TGAAGATCGACATCCATGTCATCATCCCGTATGAAGGTCTGAGCGGCGACCAAATGGGCCAGATCGAAAAATTTTTAAGGTGGTGTACCCT
GTGGATGATCATCACTTTAAGGTGATCCTGCACTATGGCACACTGGTAATCGACGGGGTTACGCCGAACATGATCGACTATTTCGGACGGCC
GTATGAAGGCATCGCCGTGTTCGACGGCAAAAAGATCACTGTAACAGGGACCCTGTGGAACGGCAACAAAATTATCGACGAGCGCCTGATC
AACCCCGACGGCTCCCTGCTGTTCCGAGTAACCATCAACGGAGTGACCGGCTGGCGGCTGTGCGAACGCATTCTGGCGTAAGCAGGTTAATA
TCTTAGTATAAACAAGGGCAGACTTAGGTTTGTCCTTAGTGTATTCCAAAGGAGGTAACATGCTGAAAGATGGTTGGGTTTCATATGACCCTA
CAGACCCTAAGAATTGGCTACAGGTTATCGCTATAGCTTGTGCAGGTAGCCTATTGGCTGCCCTGATGTATTCATTATGGATGTACACAAAGT
AACCAAAGTCAAAATTTTGATGTAGGCGTGTGTCAGCTCTCTCGCCCCTCGCCCTCGCCGGGTTGTCCCCATAGGGTGGCCTGAGGGAATCCGT

CTTCGACGGGCAGGGCTGATGTACTCCTTGTCTAGTACAAGGGAGGCGGAGGGAACGCCTAGGGAGGCCTAGGAATGGCTTAGTGGTGGA
CAAGGTGATTACCTTAGTGAAGCCTCTTAGTGCATTCCTGAGGCCATTCAGGGCGTTTATGAGGGATTGACAGGGTGTGAGGGCGTGGGCTA

>DLPEC01_T7_cut_and_nluc_insert Enterobacteria phage T7, complete genome
(SEQ ID NO: 5)

```
TCTCACAGTGTACGGACCTAAAGTTCCCCCATAGGGGGTACCTAAAGCCCAGCCAATCACCTAAAGTCAACCTT
CGGTTGACCTTGAGGGTTCCCTAAGGGTTGGGGATGACCCTTGGGTTTGTCTTTGGGTGTTACCTTGAGTGTCT
CTCTGTGTCCCTATCTGTTACAGTCTCCTAAAGTATCCTCCTAAAGTCACCTCCTAACGTCCATCCTAAAGCCA
ACACCTAAAGCCTACACCTAAAGACCCATCAAGTCAACGCCTATCTTAAAGTTTAAACATAAAGACCAGACCTA
AAGACCAGACCTAAAGACACTACATAAAGACCAGACCTAAAGACGCCTTGTTGTTAGCCATAAAGTGATAACCT
TTAATCATTGTCTTTATTAATACAACTCACTATAAGGAGAGACAACTTAAAGAGACTTAAAAGATTAATTTAAA
ATTTATCAAAAAGAGTATTGACTTAAAGTCTAACCTATAGGATACTTACAGCCATCGAGAGGGACACGGCGAAT
AGCCATCCCAATCGACACCGGGTCAACCGGATAAGTAGACAGCCTGATAAGTCGCACGAAAAACAGGTATTGA
CAACATGAAGTAACATGCAGTAAGATACAAATCGCTAGGTAACACTAGCAGCGTCAACCGGGCGCACAGTGCCT
TCTAGGTGACTTAAGCGCACCACGGCACATAAGGTGAAACAAAACGGTTGACAACATGAAGTAAACACGGTACG
ATGTACCACATGAAACGACAGTGAGTCACCACACTGAAAGGTGATGCGGTCTAACGAAACCTGACCTAAGACGC
TCTTTAACAATCTGGTAAATAGCTCTTGAGTGCATGACTAGCGGATAACTCAAGGGTATCGCAAGGTGCCCTTT
ATGATATTCACTAATAACTGCACGAGGTAACACAAGATGGCTATGTCTAACATGACTTACAACAACGTTTTCGA
CCACGCTTACGAAATGCTGAAAGAAAACATCCGTTATGATGACATCCGTGACACTGATGACCTGCACGATGCTA
TTCACATGGCTGCCGATAATGCAGTTCCGCACTACTACGCTGACATCTTTAGCGTAATGGCAAGTGAGGGCATT
GACCTTGAGTTCGAAGACTCTGGTCTGATGCCTGACACCAAGGACGTAATCCGCATCCTGCAAGCGCGTATCTA
TGAGCAATTAACGATTGACCTCTGGGAAGACGCAGAAGACTTGCTCAATGAATACTTGGAGGAAGTCGAGGAGT
ACGAGGAGGATGAAGAGTAATGTCTACTACCAACGTGCAATACGGTCTGACCGCTCAAACTGTACTTTTCTATA
GCGACATGGTGCGCTGTGGCTTTAACTGGTCACTCGCAATGGCACAGCTCAAAGAACTGTACGAAAACAACAAG
GCAATAGCTTTAGAATCTGCTGAGTGATAGACTCAAGGTCGCTCCTAGCGAGTGGCCTTTATGATTATCACTTT
ACTTATGAGGGAGTAATGTATATGCTTACTATCGGTCTACTCACCGCTCTAGGTCTAGCTGTAGGTGCATCCTT
TGGGAAGGCTTTAGGTGTAGCTGTAGGTTCCTACTTTACCGCTTGCATCATCATAGGAATCATCAAAGGGCAC
TACGCAAATGATGAAGCACTACGTTATGCCAATCCACACGTCCAACGGGGCAACCGTATGTACACCTGATGGGT
TCGCAATGAAACAACGAATCGAACGCCTTAAGCGTGAACTCCGCATTAACCGCAAGATTAACAAGATAGGTTCC
GGCTATGACAGAACGCACTGATGGCTTAAAGAAAGGTTATATGCCCAATGGCACACTATACGCTGCAAATCGGC
GAATAGTGAGAACTTGGCGAGAGAACAACCTCGAACGCCGCAAGGACAAGAGAGGGCGGCGTGGCATAGACGAA
AGGAAAAGGTTAAAGCCAAGAAACTCGCCGCACTTGAACAGGCACTAGCCAACACACTGAACGCTATCTCATAA
CGAACATAAAGGACACAATGCAATGAACATTACCGACATCATGAACGCTATCGACGCAATCAAAGCACTGCCAA
TCTGTGAACTTGACAAGCGTCAAGGTATGCTTATCGACTTACTGGTCGAGATGGTCAACAGCGAGACGTGTGAT
GGCGAGCTAACCGAACTAAATCAGGCACTTGAGCATCAAGATTGGTGGACTACCTTGAAGTGTCTCACGGCTGA
CGCAGGGTTCAAGATGCTCGGTAATGGTCACTTCTCGGCTGCTTATAGTCACCCGCTGCTACCTAACAGAGTGA
TTAAGGTGGGCTTTAAGAAAGAGGATTCAGGCGCAGCCTATACCGCATTCTGCCGCATGTATCAGGGTCGTCCT
GGTATCCCTAACGTCTACGATGTACAGCGCCACGCTGGATGCTATACGGTGGTACTTGACGCACTTAAGGATTG
CGAGCGTTTCAACAATGATGCCCATTATAAATACGCTGAGATTGCAAGCGACATCATTGATTGCAATTCGGATG
AGCATGATGAGTTAACTGGATGGGATGGTGAGTTTGTTGAAACTTGTAAACTAATCCGCAAGTTCTTTGAGGGC
ATCGCCTCATTCGACATGCATAGCGGGAACATCATGTTCTCAAATGGAGACGTACCATACATCACCGACCCGGT
ATCATTCTCGCAGAAGAAAGACGGTGGCGCATTCAGCATCGACCCTGAGGAACTCATCAAGGAAGTCGAGGAAG
TCGCACGACAGAAGAAATTGACCGCGCTAAGGCCCGTAAAGAACGTCACGAGGGGCGCTTAGAGGCACGCAGA
TTCAAACGTCGCAACCGCAAGGCACGTAAAGCACACAAAGCTAAGCGCGAAAGAATGCTTGCTGCGTGGCGATG
GGCTGAACGTCAAGAACGGCGTAACCATGAGGTAGCTGTAGATGTACTAGGAAGAACCAATAACGCTATGCTCT
GGGTCAACATGTTCTCTGGGGACTTTAAGGCGCTTGAGGAACGAATCGCGCTGCACTGGCGTAATGCTGACCGG
ATGGCTATCGCTAATGGTCTTACGCTCAACATTGATAAGCAACTTGACGCAATGTTAATGGGCTGATAGTCTTA
TCTTACAGGTCATCTGCGGGTGGCCTGAATAGGTACGATTTACTAACTGGAAGAGGCACTAAATGAACACGATT
AACATCGCTAAGAACGACTTCTCTGACATCGAACTGGCTGCTATCCCGTTCAACACTCTGGCTGACCATTACGG
TGAGCGTTTAGCTCGCGAACAGTTGGCCCTTGAGCATGAGTCTTACGAGATGGGTGAAGCACGCTTCCGCAAGA
TGTTTGAGCGTCAACTTAAAGCTGGTGAGGTTGCGGATAACGCTGCCGCCAAGCCTCTCATCACTACCCTACTC
CCTAAGATGATTGCACGCATCAACGACTGGTTTGAGGAAGTGAAAGCTAAGCGCGGCAAGCGCCCGACAGCCTT
```

FIG. 14B

```
CCAGTTCCTGCAAGAAATCAAGCCGGAAGCCGTAGCGTACATCACCATTAAGACCACTCTGGCTTGCCTAACCA
GTGCTGACAATACAACCGTTCAGGCTGTAGCAAGCGCAATCGGTCGGGCCATTGAGGACGAGGCTCGCTTCGGT
CGTATCCGTGACCTTGAAGCTAAGCACTTCAAGAAAAACGTTGAGGAACAACTCAACAAGCGCGTAGGGCACGT
CTACAAGAAAGCATTTATGCAAGTTGTCGAGGCTGACATGCTCTCTAAGGGTCTACTCGGTGGCGAGGCGTGGT
CTTCGTGGCATAAGGAAGACTCTATTCATGTAGGAGTACGCTGCATCGAGATGCTCATTGAGTCAACCGGAATG
GTTAGCTTACACCGCCAAAATGCTGGCGTAGTAGGTCAAGACTCTGAGACTATCGAACTCGCACCTGAATACGC
TGAGGCTATCGCAACCCGTGCAGGTGCGCTGGCTGGCATCTCTCCGATGTTCCAACCTTGCGTAGTTCCTCCTA
AGCCGTGGACTGGCATTACTGGTGGTGGCTATTGGGCTAACGGTCGTCGTCCTCTGGCGCTGGTGCGTACTCAC
AGTAAGAAAGCACTGATGCGCTACGAAGACGTTTACATGCCTGAGGTGTACAAAGCGATTAACATTGCGCAAAA
CACCGCATGGAAAATCAACAAGAAAGTCCTAGCGGTCGCCAACGTAATCACCAAGTGGAAGCATTGTCCGGTCG
AGGACATCCCTGCGATTGAGCGTGAAGAACTCCCGATGAAACCGGAAGACATCGACATGAATCCTGAGGCTCTC
ACCGCGTGGAAACGTGCTGCCGCTGCTGTGTACCGCAAGGACAAGGCTCGCAAGTCTCGCCGTATCAGCCTTGA
GTTCATGCTTGAGCAAGCCAATAAGTTTGCTAACCATAAGGCCATCTGGTTCCCTTACAACATGGACTGGCGCG
GTCGTGTTTACGCTGTGTCAATGTTCAACCCGCAAGGTAACGATATGACCAAAGGACTGCTTACGCTGGCGAAA
GGTAAACCAATCGGTAAGGAAGGTTACTACTGGCTGAAAATCCACGGTGCAAACTGTGCGGGTGTCGATAAGGT
TCCGTTCCCTGAGCGCATCAAGTTCATTGAGGAAAACCACGAGAACATCATGGCTTGCGCTAAGTCTCCACTGG
AGAACACTTGGTGGGCTGAGCAAGATTCTCCGTTCTGCTTCCTTGCGTTCTGCTTTGAGTACGCTGGGGTACAG
CACCACGGCCTGAGCTATAACTGCTCCCTTCCGCTGGCGTTTGACGGGTCTTGCTCTGGCATCCAGCACTTCTC
CGCGATGCTCCGAGATGAGGTAGGTGGTCGCGCGGTTAACTTGCTTCCTAGTGAAACCGTTCAGGACATCTACG
GGATTGTTGCTAAGAAAGTCAACGAGATTCTACAAGCAGACGCAATCAATGGGACCGATAACGAAGTAGTTACC
GTGACCGATGAGAACACTGGTGAAATCTCTGAGAAAGTCAAGCTGGGCACTAAGGCACTGGCTGGTCAATGGCT
GGCTTACGGTGTTACTCGCAGTGTGACTAAGCGTTCAGTCATGACGCTGGCTTACGGGTCCAAAGAGTTCGGCT
TCCGTCAACAAGTGCTGGAAGATACCATTCAGCCAGCTATTGATTCCGGCAAGGGTCTGATGTTCACTCAGCCG
AATCAGGCTGCTGGATACATGGCTAAGCTGATTTGGGAATCTGTGAGCGTGACGGTGGTAGCTGCGGTTGAAGC
AATGAACTGGCTTAAGTCTGCTGCTAAGCTGCTGGCTGCTGAGGTCAAAGATAAGAAGACTGGAGAGATTCTTC
GCAAGCGTTGCGCTGTGCATTGGGTAACTCCTGATGGTTTCCCTGTGTGGCAGGAATACAAGAAGCCTATTCAG
ACGCGCTTGAACCTGATGTTCCTCGGTCAGTTCCGCTTACAGCCTACCATTAACACCAACAAAGATAGCGAGAT
TGATGCACACAAACAGGAGTCTGGTATCGCTCCTAACTTTGTACACAGCCAAGACGGTAGCCACCTTCGTAAGA
CTGTAGTGTGGGCACACGAGAAGTACGGAATCGAATCTTTTGCACTGATTCACGACTCCTTCGGTACCATTCCG
GCTGACGCTGCGAACCTGTTCAAAGCAGTGCGCGAAACTATGGTTGACACATATGAGTCTTGTGATGTACTGGC
TGATTTCTACGACCAGTTCGCTGACCAGTTGCACGAGTCTCAATTGGACAAAATGCCAGCACTTCCGGCTAAAG
GTAACTTGAACCTCCGTGACATCTTAGAGTCGGACTTCGCGTTCGCGTAACGCCAAATCAATACGACTCACTAT
AGAGGGACAAACTCAAGGTCATTCGCAAGAGTGGCCTTTATGATTGACCTTCTTCCGGTTAATACGACTCACTA
TAGGAGAACCTTAAGGTTTAACTTTAAGACCCTTAAGTGTTAATTAGAGATTTAAGGAGATTCAACATGGTCTT
CACACTCGAAGATTTCGTTGGGGACTGGCGACAGACAGCCGGCTACAACCTGGACCAAGTCCTTGAACAGGGAG
GTGTGTCCAGTTTGTTTCAGAATCTCGGGGTGTCCGTAACTCCGATCCAAAGGATTGTCCTGAGCGGTGAAAAT
GGGCTGAAGATCGACATCCATGTCATCATCCCGTATGAAGGTCTGAGCGGCGACCAAATGGGCCAGATCGAAAA
AATTTTTAAGGTGGTGTACCCTGTGGATGATCATCACTTTAAGGTGATCCTGCACTATGGCACACTGGTAATCG
ACGGGGTTACGCCGAACATGATCGACTATTTCGGACGGCCGTATGAAGGCATCGCCGTGTTCGACGGCAAAAAG
ATCACTGTAACAGGGACCCTGTGGAACGGCAACAAAATTATCGACGAGCGCCTGATCAACCCCGACGGCTCCCT
GCTGTTCCGAGTAACCATCAACGGAGTGACCGGCTGGCGGCTGTGCAACGCATTCTGGCGTAAAGGAGGTAAA
CATATGACCATGATTACGGATTCACTGGCCGTCGTTTTACAACGTCGTGACTGGGAAAACCCTGGCGTTACCCA
ACTTAATCGCCTTGCAGCACATCCCCCTTTCGCCAGCTGGCGTAATAGCGAAGAGGCCCGCACCGATCGCCCTT
CCCAACAGTTGCGCAGCCTGAATGGCGAATGGTAAAAATTAAAGAATTACTAAGAGAGGACTTTAAGTATGCGT
AACTTCGAAAAGATGACCAAACGTTCTAACCGTAATGCTCGTGACTTCGAGGCAACCAAAGGTCGCAAGTTGAA
TAAGACTAAGCGTGACCGCTCTCACAAGCGTAGCTGGGAGGGTCAGTAAGATGGGACGTTTATATAGTGGTAAT
CTGGCAGCATTCAAGGCAGCAACAAACAAGCTGTTCCAGTTAGACTTAGCGGTCATTTATGATGACTGGTATGA
TGCCTATACAAGAAAAGATTGCATACGGTTACGTATTGAGGACAGGAGTGGAAACCTGATTGATACTAGCACCT
TCTACCACCACGACGAGGACGTTCTGTTCAATATGTGTACTGATTGGTTGAACCATATGTATGACCAGTTGAAG
GACTGGAAGTAATACGACTCAGTATAGGGACAATGCTTAAGGTCGCTCTCTAGGAGTGGCCTTAGTCATTTAAC
CAATAGGAGATAAACATTATGATGAACATTAAGACTAACCCGTTTAAAGCCGTGTCTTTCGTAGAGTCTGCCAT
TAAGAAGGCTCTGGATAACGCTGGGTATCTTATCGCTGAAATCAAGTACGATGGTGTACGCGGGAACATCTGCG
TAGACAATACTGCTAACAGTTACTGGCTCTCTCGTGTATCTAAAACGATTCCGGCACTGGAGCACTTAAACGGG
TTTGATGTTCGCTGGAAGCGTCTACTGAACGATGACCGTTGCTTCTACAAAGATGGCTTTATGCTTGATGGGA
```

FIG. 14C

```
ACTCATGGTCAAGGGCGTAGACTTTAACACAGGGTCCGGCCTACTGCGTACCAAATGGACTGACACGAAGAACC
AAGAGTTCCATGAAGAGTTATTCGTTGAACCAATCCGTAAGAAAGATAAAGTTCCCTTTAAGCTGCACACTGGA
CACCTTCACATAAAACTGTACGCTATCCTCCCGCTGCACATCGTGGAGTCTGGAGAAGACTGTGATGTCATGAC
GTTGCTCATGCAGGAACACGTTAAGAACATGCTGCCTCTGCTACAGGAATACTTCCCTGAAATCGAATGGCAAG
CGGCTGAATCTTACGAGGTCTACGATATGGTAGAACTACAGCAACTGTACGAGCAGAAGCGAGCAGAAGGCCAT
GAGGGTCTCATTGTGAAAGACCCGATGTGTATCTATAAGCGCGGTAAGAAATCTGGCTGGTGGAAAATGAAACC
TGAGAACGAAGCTGACGGTATCATTCAGGGTCTGGTATGGGGTACAAAAGGTCTGGCTAATGAAGGTAAAGTGA
TTGGTTTTGAGGTGCTTCTTGAGAGTGGTCGTTTAGTTAACGCCACGAATATCTCTCGCGCCTTAATGGATGAG
TTCACTGAGACAGTAAAAGAGGCCACCCTAAGTCAATGGGGATTCTTTAGCCCATACGGTATTGGCGACAACGA
TGCTTGTACTATTAACCCTTACGATGGCTGGGCGTGTCAAATTAGCTACATGGAGGAAACACCTGATGGCTCTT
TGCGGCACCCATCGTTCGTAATGTTCCGTGGCACCGAGGACAACCCTCAAGAGAAAATGTAATCACACTGGCTC
ACCTTCGGGTGGGCCTTTCTGCGTTTATAAGGAGACACTTTATGTTTAAGAAGGTTGGTAAATTCCTTGCGGCT
TTGGCAGCTATCCTGACGCTTGCGTATATTCTTGCGGTATACCCTCAAGTAGCACTAGTAGTAGTTGGCGCTTG
TTACTTAGCGGCAGTGTGTGCTTGCGTGTGGAGTATAGTTAACTGGTAATACGACTCACTAAAGGAGGTACACA
CCATGATGTACTTAATGCCATTACTCATCGTCATTGTAGGATGCCTTGCGCTCCACTGTAGCGATGATGATATG
CCAGATGGTCACGCTTAATACGACTCACTAAAGGAGACACTATATGTTTCGACTTCATTACAACAAAAGCGTTA
AGAATTTCACGGTTCGCCGTGCTGACCGTTCAATCGTATGTGCGAGCGAGCGCCGAGCTAAGATACCTCTTATT
GGTAACACAGTTCCTTTGGCACCGAGCGTCCACATCATTATCACCCGTGGTGACTTTGAGAAAGCAATAGACAA
GAAACGTCCGGTTCTTAGTGTGGCAGTGACCCGCTTCCCGTTCGTCCGTCTGTTACTCAAACGAATCAAGGAGG
TGTTCTGATGGGACTGTTAGATGGTGAAGCCTGGGAAAAGAAAACCCGCCAGTACAAGCAACTGGGTGTATAG
CTTGCTTAGAGAAAGATGACCGTTATCCACACACCTGTAACAAAGGAGCTAACGATATGACCGAACGTGAACAA
GAGATGATCATTAAGTTGATAGACAATAATGAAGGTCGCCCAGATGATTTGAATGGCTGCGGTATTCTCTGCTC
CAATGTCCCTTGCCACCTCTGCCCCGCAAATAACGATCAAAAGATAACCTTAGGTGAAATCCGAGCGATGGACC
CACGTAAACCACATCTGAATAAACCTGAGGTAACTCCTACAGATGACCAGCCTTCCGCTGAGACAATCGAAGGT
GTCACTAAGCCTTCCCACTACATGCTGTTTGACGACATTGAGGCTATCGAAGTGATTGCTCGTTCAATGACCGT
TGAGCAGTTCAAGGGATACTGCTTCGGTAACATCTTAAAGTACAGACTACGTGCTGGTAAGAAGTCAGAGTTAG
CGTACTTAGAGAAAGACCTAGCGAAAGCAGACTTCTATAAGAACTCTTTGAGAAACATAAGGATAAATGTTAT
GCATAACTTCAAGTCAACCCCACCTGCCGACAGCCTATCTGATGACTTCACATCTTGCTCAGAGTGGTGCCGAA
AGATGTGGGAAGAGACATTCGACGATGCGTACATCAAGCTGTATGAACTTTGGAAATCGAGAGGTCAATGACTA
TGTCAAACGTAAATACAGGTTCACTTAGTGTGGACAATAAGAAGTTTTGGGCTACCGTAGAGTCCTCGGAGCAT
TCCTTCGAGGTTCCAATCTACGCTGAGACCCTAGACGAAGCTCTGGAGTTAGCCGAATGGCAATACGTTCCGGC
TGGCTTTGAGGTTACTCGTGTGCGTCCTTGTGTAGCACCGAAGTAATACGACTCACTATTAGGGAAGACTCCCT
CTGAGAAACCAAACGAAACCTAAAGGAGATTAACATTATGGCTAAGAAGATTTTCACCTCTGCGCTGGGTACCG
CTGAACCTTACGCTTACATCGCCAAGCCGGACTACGGCAACGAAGAGCGTGGCTTTGGGAACCCTCGTGGTGTC
TATAAAGTTGACCTGACTATTCCCAACAAAGACCCGCGCTGCCAGCGTATGGTCGATGAAATCGTGAAGTGTCA
CGAAGAGGCTTATGCTGCTGCCGTTGAGGAATACGAAGCTAATCCACCTGCTGTAGCTCGTGGTAAGAAACCGC
TGAAACCGTATGAGGGTGACATGCCGTTCTTCGATAACGGTGACGGTACGACTACCTTTAAGTTCAAATGCTAC
GCGTCTTTCCAAGACAAGAAGACCAAAGAGACCAAGCACATCAATCTGGTTGTGGTTGACTCAAAAGGTAAGAA
GATGGAAGACGTTCCGATTATCGTGGTGGCTCTAAGCTGAAAGTTAAATATTCTCTGGTTCCATACAAGTGGA
ACACTGCTGTAGGTGCGAGCGTTAAGCTGCAACTGGAATCCGTGATGCTGGTCGAACTGGCTACCTTTGGTGGC
GGTGAAGACGATTGGGCTGACGAAGTTGAAGAGAACGGCTATGTTGCCTCTGGTTCTGCCAAAGCGAGCAAACC
ACGCGACGAAGAAAGCTGGGACGAAGACGACGAAGAGTCCGAGGAAGCAGACGAAGACGGAGACTTCTAAGTGG
AACTGCGGGAGAAAATCCTTGAGCGAATCAAGGTGACTTCCTCTGGGTGTTGGGAGTGGCAGGGCGCTACGAAC
AATAAAGGGTACGGGCAGGTGTGGTGCAGCAATACCGGAAAGGTTGTCTACTGTCATCGCGTAATGTCTAATGC
TCCGAAAGGTTCTACCGTCCTGCACTCCTGTGATAATCCATTATGTTGTAACCCTGAACACCTATCCATAGGAA
CTCCAAAAGAGAACTCCACTGACATGGTAAATAAGGTCGCTCACACAAGGGTATAAACTTTCAGACGAAGAC
GTAATGGCAATCATGGAGTCCAGCGAGTCCAATGTATCCTTAGCTCGCACCTATGGTGTCTCCCAACAGACTAT
TTGTGATATACGCAAAGGGAGGCGACATGGCAGGTTACGGCGCTAAAGGAATCCGAAAGGTTGGAGCGTTTCGC
TCTGGCCTAGAGGACAAGGTTTCAAAGCAGTTGGAATCAAAAGGTATTAAATTCGAGTATGAAGAGTGGAAAGT
GCCTTATGTAATTCCGGCGAGCAATCACACTTACACTCCAGACTTCTTACTTCCAAACGGTATATTCGTTGAGA
CAAAGGGTCTGTGGGAAAGCGATGATAGAAAGAAGCACTTATTAATTAGGGAGCAGCACCCCGAGCTAGACATC
CGTATTGTCTTCTCAAGCTCACGTACTAAGTTATACAAAGGTTCTCCAACGTCTTATGGAGAGTTCTGCGAAAA
GCATGGTATTAAGTTCGCTGATAAACTGATACCTGCTGAGTGGATAAAGGAACCCAAGAAGGAGGTCCCCTTTG
ATAGATTAAAAAGGAAAGGAGGAAAGAAATAATGGCTCGTGTACAGTTTAAACAACGTGAATCTACTGACGCAA
```

FIG. 14D

```
TCTTTGTTCACTGCTCGGCTACCAAGCCAAGTCAGAATGTTGGTGTCCGTGAGATTCGCCAGTGGCACAAAGAG
CAGGGTTGGCTCGATGTGGGATACCACTTTATCATCAAGCGAGACGGTACTGTGGAGGCAGGACGAGATGAGAT
GGCTGTAGGCTCTCACGCTAAGGGTTACAACCACAACTCTATCGGCGTCTGCCTTGTTGGTGGTATCGACGATA
AAGGTAAGTTCGACGCTAACTTTACGCCAGCCCAAATGCAATCCCTTCGCTCACTGCTTGTCACACTGCTGGCT
AAGTACGAAGGCGCTGTGCTTCGCGCCCATCATGAGGTGGCGCCGAAGGCTTGCCCTTCGTTCGACCTTAAGCG
TTGGTGGGAGAAGAACGAACTGGTCACTTCTGACCGTGGATAATTAATTGAACTCACTAAAGGGAGACCACAGC
GGTTTCCCTTTGTTCGCATTGGAGGTCAAATAATGCGCAAGTCTTATAAACAATTCTATAAGGCTCCGAGGAGG
CATATCCAAGTGTGGGAGGCAGCCAATGGGCCTATACCAAAAGGTTATTATATAGACCACATTGACGGCAATCC
ACTCAACGACGCCTTAGACAATCTCCGTCTGGCTCTCCCAAAAGAAAACTCATGGAACATGAAGACTCCAAAGA
GCAATACCTCAGGACTAAAGGGACTGAGTTGGAGCAAGGAAAGGGAGATGTGGAGAGGCACTGTAACAGCTGAG
GGTAAACAGCATAACTTTCGTAGTAGAGATCTATTGGAAGTCGTTGCGTGGATTTATAGAACTAGGAGGGAATT
GCATGGACAATTCGCACGATTCCGATAGTGTATTTCTTTACCACATTCCTTGTGACAACTGTGGGAGTAGTGAT
GGGAACTCGCTGTTCTCTGACGGACACACGTTCTGCTACGTATGCGAGAAGTGGACTGCTGGTAATGAAGACAC
TAAAGAGAGGGCTTCAAAACGGAAACCCTCAGGAGGTAAACCAATGACTTACAACGTGTGGAACTTCGGGGAAT
CCAATGGACGCTACTCCGCGTTAACTGCGAGAGGAATCTCCAAGGAAACCTGTCAGAAGGCTGGCTACTGGATT
GCCAAAGTAGACGGTGTGATGTACCAAGTGGCTGACTATCGGGACCAGAACGGCAACATTGTGAGTCAGAAGGT
TCGAGATAAAGATAAGAACTTTAAGACCACTGGTAGTCACAAGAGTGACGCTCTGTTCGGGAAGCACTTGTGGA
ATGGTGGTAAGAAGATTGTCGTTACAGAAGGTGAAATCGACATGCTTACCGTGATGGAACTTCAAGACTGTAAG
TATCCTGTAGTGTCGTTGGGTCACGGTGCCTCTGCCGCTAAGAAGACATGCGCTGCCAACTACGAATACTTTGA
CCAGTTCGAACAGATTATCTTAATGTTCGATATGGACGAAGCAGGGCGCAAAGCAGTCGAAGAGGCTGCACAGG
TTCTACCTGCTGGTAAGGTACGAGTGGCAGTTCTTCCGTGTAAGGATGCAAACGAGTGTCACCTAAATGGTCAC
GACCGTGAAATCATGGAGCAAGTGTGGAATGCTGGTCCTTGGATTCCTGATGGTGTGGTATCGGCTCTTTCGTT
ACGTGAACGAATCCGTGAGCACCTATCGTCCGAGGAATCAGTAGGTTTACTTTTCAGTGGCTGCACTGGTATCA
ACGATAAGACCTTAGGTGCCCGTGGTGGTGAAGTCATTATGGTCACTTCCGGTTCCGGTATGGGTAAGTCAACG
TTCGTCCGTCAACAAGCTCTACAATGGGGCACAGCGATGGGCAAGAAGGTAGGCTTAGCGATGCTTGAGGAGTC
CGTTGAGGAGACCGCTGAGGACCTTATAGGTCTACACAACCGTGTCCGACTGAGACAATCCGACTCACTAAAGA
GAGAGATTATTGAGAACGGTAAGTTCGACCAATGGTTCGATGAACTGTTCGGCAACGATACGTTCCATCTATAT
GACTCATTCGCCGAGGCTGAGACGGATAGACTGCTCGCTAAGCTGGCCTACATGCGCTCAGGCTTGGGCTGTGA
CGTAATCATTCTAGACCACATCTCAATCGTCGTATCCGCTTCTGGTGAATCCGATGAGCGTAAGATGATTGACA
ACCTGATGACCAAGCTCAAAGGGTTCGCTAAGTCAACTGGGGTGGTGCTGGTCGTAATTTGTCACCTTAAGAAC
CCAGACAAAGGTAAAGCACATGAGGAAGGTCGCCCCGTTTCTATTACTGACCTACGTGGTTCTGGCGCACTACG
CCAACTATCTGATACTATTATTGCCCTTGAGCGTAATCAGCAAGGCGATATGCCTAACCTTGTCCTCGTTCGTA
TTCTCAAGTGCCGCTTTACTGGTGATACTGGTATCGCTGGCTACATGGAATACAACAAGGAAACCGGATGGCTT
GAACCATCAAGTTACTCAGGGGAAGAAGAGTCACACTCAGAGTCAACAGACTGGTCCAACGACACTGACTTCTG
ACAGGATTCTTGATGACTTTCCAGACGACTACGAGAAGTTTCGCTGGAGAGTCCCATTCTAATACGACTCACTA
AAGGAGACACACCATGTTCAAACTGATTAAGAAGTTAGGCCAACTGCTGGTTCGTATGTACAACGTGGAAGCCA
AGCGACTGAACGATGAGGCTCGTAAAGAGGCCACACAGTCACGCGCTCTGGCGATTCGCTCCAACGAACTGGCT
GACAGTGCATCCACTAAAGTTACCGAGGCTGCCCGTGTGGCAAACCAAGCTCAACAGCTTTCCAAATTCTTTGA
GTAATCAAACAGGAGAAACCATTATGTCTAACGTAGCTGAAACTATCCGTCTATCCGATACAGCTGACCAGTGG
AACCGTCGAGTCCACATCAACGTTCGCAACGGTAAGGCGACTATGGTTTACCGCTGGAAGGACTCTAAGTCCTC
TAAGAATCACACTCAGCGTATGACGTTGACAGATGAGCAAGCACTGCGTCTGGTCAATGCGCTTACCAAAGCTG
CCGTGACAGCAATTCATGAAGCTGGTCGCGTCAATGAAGCTATGGCTATCCTCGACAAGATTGATAACTAAGAG
TGGTATCCTCAAGGTCGCCAAAGTGGTGGCCTTCATGAATACTATTCGACTCACTATAGGAGATATTACCATGC
GTGACCCTAAAGTTATCCAAGCAGAAATCGCTAAACTGGAAGCTGAACTGGAGGACGTTAAGTACCATGAAGCT
AAGACTCGCTCCGCTGTTCACATCTTGAAGAACTTAGGCTGGACTTGGACAAGACAGACTGGCTGGAAGAAACC
AGAAGTTACCAAGCTGAGTCATAAGGTGTTCGATAAGGACACTATGACCCACATCAAGGCTGGTGATTGGGTTA
AGGTTGACATGGGAGTTGTTGGTGGATACGGCTACGTCCGCTCAGTTAGTGGCAAATATGCACAAGTGTCATAC
ATCACAGGTGTTACTCCACGCGGTGCAATCGTTGCCGATAAGACCAACATGATTCACACAGGTTTCTTGACAGT
TGTTTCATATGAAGAGATTGTTAAGTCACGATAATCAATAGGAGAAATCAATATGATCGTTTCTGACATCGAAG
CTAACGCCCTCTTAGAGAGCGTCACTAAGTTCCACTGCGGGGTTATCTACGACTACTCCACCGCTGAGTACGTA
AGCTACCGTCCGAGTGACTTCGGTGCGTATCTGGATGCGCTGGAAGCGAGGTTGCACGAGGCGGTCTTATTGT
GTTCCACAACGGTCACAAGTATGACGTTCCTGCATTGACCAAACTGGCAAAGTTGCAATTGAACCGAGAGTTCC
ACCTTCCTCGTGAGAACTGTATTGACACCCTTGTGTTGTCACGTTTGATTCATTCCAACCTCAAGGACACCGAT
ATGGGTCTTCTGCGTTCCGGCAAGTTGCCCGGAAAACGCTTTGGGTCTCACGCTTTGGAGGCGTGGGGTTATCG
```

FIG. 14E

```
CTTAGGCGAGATGAAGGGTGAATACAAAGACGACTTTAAGCGTATGCTTGAAGAGCAGGGTGAAGAATACGTTG
ACGGAATGGAGTGGTGGAACTTCAACGAAGAGATGATGGACTATAACGTTCAGGACGTTGTGGTAACTAAAGCT
CTCCTTGAGAAGCTACTCTCTGACAAACATTACTTCCCTCCTGAGATTGACTTTACGGACGTAGGATACACTAC
GTTCTGGTCAGAATCCCTTGAGGCCGTTGACATTGAACATCGTGCTGCATGGCTGCTCGCTAAACAAGAGCGCA
ACGGGTTCCCGTTTGACACAAAAGCAATCGAAGAGTTGTACGTAGAGTTAGCTGCTCGCCGCTCTGAGTTGCTC
CGTAAATTGACCGAAACGTTCGGCTCGTGGTATCAGCCTAAAGGTGGCACTGAGATGTTCTGCCATCCGCGAAC
AGGTAAGCCACTACCTAAATACCCTCGCATTAAGACACCTAAAGTTGGTGGTATCTTTAAGAAGCCTAAGAACA
AGGCACAGCGAGAAGGCCGTGAGCCTTGCGAACTTGATACCCGCGAGTACGTTGCTGGTGCTCCTTACACCCCA
GTTGAACATGTTGTGTTTAACCCTTCGTCTCGTGACCACATTCAGAAGAAACTCCAAGAGGCTGGGTGGGTCCC
GACCAAGTACACCGATAAGGGTGCTCCTGTGGTGGACGATGAGGTACTCGAAGGAGTACGTGTAGATGACCCTG
AGAAGCAAGCCGCTATCGACCTCATTAAAGAGTACTTGATGATTCAGAAGCGAATCGGACAGTCTGCTGAGGGA
GACAAAGCATGGCTTCGTTATGTTGCTGAGGATGGTAAGATTCATGGTTCTGTTAACCCTAATGGAGCAGTTAC
GGGTCGTGCGACCCATGCGTTCCCAAACCTTGCGCAAATTCCGGGTGTACGTTCTCCTTATGGAGAGCAGTGTC
GCGCTGCTTTTGGCGCTGAGCACCATTTGGATGGGATAACTGGTAAGCCTTGGGTTCAGGCTGGCATCGACGCA
TCCGGTCTTGAGCTACGCTGCTTGGCTCACTTCATGGCTCGCTTTGATAACGGCGAGTACGCTCACGAGATTCT
TAACGGCGACATCCACACTAAGAACCAGATAGCTGCTGAACTACCTACCCGAGATAACGCTAAGACGTTCATCT
ATGGGTTCCTCTATGGTGCTGGTGATGAGAAGATTGGACAGATTGTTGGTGCTGGTAAAGAGCGCGGTAAGGAA
CTCAAGAAGAAATTCCTTGAGAACACCCCGCGATTGCAGCACTCCGCGAGTCTATCCAACAGACACTTGTCGA
GTCCTCTCAATGGGTAGCTGGTGAGCAACAAGTCAAGTGGAAACGCCGCTGGATTAAAGGTCTGGATGGTCGTA
AGGTACACGTTCGTAGTCCTCACGCTGCCTTGAATACCCTACTGCAATCTGCTGGTGCTCTCATCTGCAAACTG
TGGATTATCAAGACCGAAGAGATGCTCGTAGAGAAAGGCTTGAAGCATGGCTGGGATGGGACTTTGCGTACAT
GGCATGGGTACATGATGAAATCCAAGTAGGCTGCCGTACCGAAGAGATTGCTCAGGTGGTCATTGAGACCGCAC
AAGAAGCGATGCGCTGGGTTGGAGACCACTGGAACTTCCGGTGTCTTCTGGATACCGAAGGTAAGATGGGTCCT
AATTGGGCGATTTGCCACTGATACAGGAGGCTACTCATGAACGAAAGACACTTAACAGGTGCTGCTTCTGAAAT
GCTAGTAGCCTACAAATTTACCAAAGCTGGGTACACTGTCTATTACCCTATGCTGACTCAGAGTAAAGAGGACT
TGGTTGTATGTAAGGATGGTAAATTTAGTAAGGTTCAGGTTAAAACAGCCACAACGGTTCAAACCAACACAGGA
GATGCCAAGCAGGTTAGGCTAGGTGGATGCGGTAGGTCCGAATATAAGGATGGAGACTTTGACATTCTTGCGGT
TGTGGTTGACGAAGATGTGCTTATTTTCACATGGGACGAAGTAAAAGGTAAGACATCCATGTGTGTCGGCAAGA
GAAACAAAGGCATAAAACTATAGGAGAAATTATTATGGCTATGACAAAGAAATTTAAAGTGTCCTTCGACGTTA
CCGCAAAGATGTCGTCTGACGTTCAGGCAATCTTAGAGAAAGATATGCTGCATCTATGTAAGCAGGTCGGCTCA
GGTGCGATTGTCCCCAATGGTAAACAGAAGGAAATGATTGTCCAGTTCCTGACACACGGTATGGAAGGATTGAT
GACATTCGTAGTACGTACATCATTTCGTGAGGCCATTAAGGACATGCACGAAGAGTATGCAGATAAGGACTCTT
TCAAACAATCTCCTGCAACAGTACGGGAGGTGTTCTGATGTCTGACTACCTGAAAGTGCTGCAAGCAATCAAAA
GTTGCCCTAAGACTTTCCAGTCCAACTATGTACGGAACAATGCGAGCCTCGTAGCGGAGGCCGCTTCCCGTGGT
CACATCTCGTGCCTGACTACTAGTGGACGTAACGGTGGCGCTTGGGAAATCACTGCTTCCGGTACTCGCTTTCT
GAAACGAATGGGAGGATGTGTCTAATGTCTCGTGACCTTGTGACTATTCCACGCGATGTGTGGAACGATATACA
GGGCTACATCGACTCTCTGGAACGTGAGAACGATAGCCTTAAGAATCAACTAATGGAAGCTGACGAATACGTAG
CGGAACTAGAGGAGAAACTTAATGGCACTTCTTGACCTTAAACAATTCTATGAGTTACGTGAAGGCTGCGACGA
CAAGGGTATCCTTGTGATGGACGGCGACTGGCTGGTCTTCCAAGCTATGAGTGCTGCTGAGTTTGATGCCTCTT
GGGAGGAAGAGATTTGGCACCGATGCTGTGACCACGCTAAGGCCCGTCAGATTCTTGAGGATTCCATTAAGTCC
TACGAGACCCGTAAGAAGGCTTGGGCAGGTGCTCCAATTGTCCTTGCGTTCACCGATAGTGTTAACTGGCGTAA
AGAACTGGTTGACCCGAACTATAAGGCTAACCGTAAGGCCGTGAAGAAACCTGTAGGGTACTTTGAGTTCCTTG
ATGCTCTCTTTGAGCGCGAAGAGTTCTATTGCATCCGTGAGCCTATGCTTGAGGGTGATGACGTTATGGGAGTT
ATTGCTTCCAATCCGTCTGCCTTCGGTGCTCGTAAGGCTGTAATCATCTCTTGCGATAAGGACTTTAAGACCAT
CCCTAACTGTGACTTCCTGTGGTGTACCACTGGTAACATCCTGACTCAGACCGAAGAGTCCGCTGACTGGTGGC
ACCTCTTCCAGACCATCAAGGGTGACATCACTGATGGTTACTCAGGGATTGCTGGATGGGGTGATACCGCCGAG
GACTTCTTGAATAACCCGTTCATAACCGAGCCTAAAACGTCTGTGCTTAAGTCCGGTAAGAACAAAGGCCAAGA
GGTTACTAAATGGGTTAAACGCGACCCTGAGCCTCATGAGACGCTTTGGGACTGCATTAAGTCCATTGGCGCGA
AGGCTGGTATGACCGAAGAGGATATTATCAAGCAGGGCCAAATGGCTCGAATCCTACGGTTCAACGAGTACAAC
TTTATTGACAAGGAGATTTACCTGTGGAGACCGTAGCGTATATTGGTCTGGGTCTTTGTGTTCTCGGAGTGTGC
CTCATTTCGTGGGCCTTTGGGACTTAGCCAGAATAATCAAGTCGTTACACGACACTAAGTGATAAACTCAAGG
TCCCTAAATTAATACGACTCACTATAGGGAGATAGGGCCTTTACGATTATTACTTTAAGATTTAACTCTAAGA
GGAATCTTTATTATGTTAACACCTATTAACCAATTACTTAAGAACCCTAACGATATTCCAGATGTACCTCGTGC
AACCGCTGAGTATCTACAGGTTCGATTCAACTATGCGTACCTCGAAGCGTCTGGTCATATAGGACTTATGCGTG
```

FIG. 14F

```
CTAATGGTTGTAGTGAGGCCCACATCTTGGGTTTCATTCAGGGCCTACAGTATGCCTCTAACGTCATTGACGAG
ATTGAGTTACGCAAGGAACAACTAAGAGATGATGGGGAGGATTGACACTATGTGTTTCTCACCGAAAATTAAAA
CTCCGAAGATGGATACCAATCAGATTCGAGCCGTTGAGCCAGCGCCTCTGACCCAAGAAGTGTCAAGCGTGGAG
TTCGGTGGGTCTTCTGATGAGACGGATACCGAGGGCACCGAAGTGTCTGGACGCAAAGGCCTCAAGGTCGAACG
TGATGATTCCGTAGCGAAGTCTAAAGCCAGCGGCAATGGCTCCGCTCGTATGAAATCTTCCATCCGTAAGTCCG
CATTTGGAGGTAAGAAGTGATGTCTGAGTTCACATGTGTGGAGGCTAAGAGTCGCTTCCGTGCAATCCGGTGGA
CTGTGGAACACCTTGGGTTGCCTAAAGGATTCGAAGGACACTTTGTGGGCTACAGCCTCTACGTAGACGAAGTG
ATGGACATGTCTGGTTGCCGTGAAGAGTACATTCTGGACTCTACCGGAAAACATGTAGCGTACTTCGCGTGGTG
CGTAAGCTGTGACATTCACCACAAAGGAGACATTCTGGATGTAACGTCCGTTGTCATTAATCCTGAGGCAGACT
CTAAGGGCTTACAGCGATTCCTAGCGAAACGCTTTAAGTACCTTGCGGAACTCCACGATTGCGATTGGGTGTCT
CGTTGTAAGCATGAAGGCGAGACAATGCGTGTATACTTTAAGGAGGTATAAGTTATGGGTAAGAAAGTTAAGAA
GGCCGTGAAGAAAGTCACCAAGTCCGTTAAGAAAGTCGTTAAGGAAGGGGCTCGTCCGGTTAAACAGGTTGCTG
GCGGTCTAGCTGGTCTGGCTGGTGGTACTGGTGAAGCACAGATGGTGGAAGTACCACAAGCTGCCGCACAGATT
GTTGACGTACCTGAGAAAGAGGTTTCCACTGAGGACGAAGCACAGACAGAAAGCGGACGCAAGAAAGCTCGTGC
TGGCGGTAAGAAATCCTTGAGTGTAGCCCGTAGCTCCGGTGGCGGTATCAACATTTAATCAGGAGGTTATCGTG
GAAGACTGCATTGAATGGACCGGAGGTGTCAACTCTAAGGGTTATGGTCGTAAGTGGGTTAATGGTAAACTTGT
GACTCCACATAGGCACATCTATGAGGAGACATATGGTCCAGTTCCAACAGGAATTGTGGTGATGCATATCTGCG
ATAACCCTAGGTGCTATAACATAAAGCACCTTACGCTTGGAACTCCAAAGGATAATTCCGAGGACATGGTTACC
AAAGGTAGACAGGCTAAAGGAGAGGAACTAAGCAAGAAACTTACAGAGTCAGACGTTCTCGCTATACGCTCTTC
AACCTTAAGCCACCGCTCCTTAGGAGAACTGTATGGAGTCAGTCAATCAACCATAACGCGAATACTACAGCGTA
AGACATGGAGACACATTTAATGGCTGAGAAACGAACAGGACTTGCGGAGGATGGCGCAAAGTCTGTCTATGAGC
GTTTAAAGAACGACCGTGCTCCCTATGAGACACGCGCTCAGAATTGCGCTCAATATACCATCCCATCATTGTTC
CCTAAGGACTCCGATAACGCCTCTACAGATTATCAAACTCCGTGGCAAGCCGTGGGCGCTCGTGGTCTGAACAA
TCTAGCCTCTAAGCTCATGCTGGCTCTATTCCCTATGCAGACTTGGATGCGACTTACTATATCTGAATATGAAG
CAAAGCAGTTACTGAGCGACCCCGATGGACTCGCTAAGGTCGATGAGGGCCTCTCGATGGTAGAGCGTATCATC
ATGAACTACATTGAGTCTAACAGTTACCGCGTGACTCTCTTTGAGGCTCTCAAACAGTTAGTCGTAGCTGGTAA
CGTCCTGCTGTACCTACCGGAACCGGAAGGGTCAAACTATAATCCCATGAAGCTGTACCGATTGTCTTCTTATG
TGGTCCAACGAGACGCATTCGGCAACGTTCTGCAAATGGTGACTCGTGACCAGATAGCTTTTGGTGCTCTCCCT
GAGGACATCCGTAAGGCTGTAGAAGGTCAAGGTGGTGAGAAGAAAGCTGATGAGACAATCGACGTGTACACTCA
CATCTATCTGGATGAGGACTCAGGTGAATACCTCCGATACGAAGAGGTCGAGGGTATGGAAGTCCAAGGCTCCG
ATGGGACTTATCCTAAAGAGGCTTGCCCATACATCCCGATTCGGATGGTCAGACTAGATGGTGAATCCTACGGT
CGTTCGTACATTGAGGAATACTTAGGTGACTTACGGTCCCTTGAAAATCTCCAAGAGGCTATCGTCAAGATGTC
CATGATTAGCTCTAAGGTTATCGGCTTAGTGAATCCTGCTGGTATCACCCAGCCACGCCGACTGACCAAAGCTC
AGACTGGTGACTTCGTTACTGGTCGTCCAGAAGACATCTCGTTCCTCCAACTGGAGAAGCAAGCAGACTTTACT
GTAGCTAAAGCCGTAAGTGACGCTATCGAGGCTCGCCTTTCGTTTGCCTTTATGTTGAACTCTGCGGTTCAGCG
TACAGGTGAACGTGTGACCGCCGAAGAGATTCGGTATGTAGCTTCTGAACTTGAAGATACTTTAGGTGGTGTCT
ACTCTATCCTTTCTCAAGAATTACAATTGCCTCTGGTACGAGTGCTCTTGAAGCAACTACAAGCCACGCAACAG
ATTCCTGAGTTACCTAAGGAAGCCGTAGAGCCAACCATTAGTACAGGTCTGGAAGCAATTGGTCGAGGACAAGA
CCTTGATAAGCTGGAGCGGTGTGTCACTGCGTGGGCTGCACTGGCACCTATGCGGGACGACCCTGATATTAACC
TTGCGATGATTAAGTTACGTATTGCCAACGCTATCGGTATTGACACTTCTGGTATTCTACTCACCGAAGAACAG
AAGCAACAGAAGATGGCCCAACAGTCTATGCAAATGGGTATGGATAATGGTGCTGCTGCGCTGGCTCAAGGTAT
GGCTGCACAAGCTACAGCTTCACCTGAGGCTATGGCTGCTGCCGCTGATTCCGTAGGTTACAGCCGGGAATTT
AATACGACTCACTATAGGGAGACCTCATCTTTGAAATGAGCGATGACAAGAGGTTGGAGTCCTCGGTCTTCCTG
TAGTTCAACTTTAAGGAGACAATAATAATGGCTGAATCTAATGCAGACGTATATGCATCTTTTGGCGTGAACTC
CGCTGTGATGTCTGGTGGTTCCGTTGAGGAACATGAGCAGAACATGCTGGCTCTTGATGTTGCTGCCCGTGATG
GCGATGATGCAATCGAGTTAGCGTCAGACGAAGTGGAAACAGAACGTGACCTGTATGACAACTCTGACCCGTTC
GGTCAAGAGGATGACGAAGGCCGCATTCAGGTTCGTATCGGTGATGGCTCTGAGCCGACCGATGTGGACACTGG
AGAAGAAGGCGTTGAGGGCACCGAAGGTTCCGAAGAGTTTACCCCACTGGGCGAGACTCCAGAAGAACTGGTAG
CTGCCTCTGAGCAACTTGTGAGCACGAAGAGGGCTTCCAAGAGATGATTAACATTGCTGCTGAGCGTGGCATG
AGTGTCGAGACCATTGAGGCTATCCAGCGTGAGTACGAGGAGAACGAAGAGTTGTCCGCCGAGTCCTACGCTAA
GCTGGCTGAAATTGGCTACACGAAGGCTTTCATTGACTCGTATATCCGTGGTCAAGAAGCTCTGGTGGAGCAGT
ACGTAAACAGTGTCATTGAGTACGCTGGTGGTCGTGAACGTTTTGATGCACTGTATAACCACCTTGAGACGCAC
AACCCTGAGGCTGCACAGTCGCTGGATAATGCGTTGACCAATCGTGACTTAGCGACCGTTAAGGCTATCATCAA
CTTGGCTGGTGAGTCTCGCGCTAAGGCGTTCGGTCGTAAGCCAACTCGTAGTGTGACTAATCGTGCTATTCCGG
```

FIG. 14G

```
CTAAACCTCAGGCTACCAAGCGTGAAGGCTTTGCGGACCGTAGCGAGATGATTAAAGCTATGAGTGACCCTCGG
TATCGCACAGATGCCAACTATCGTCGTCAAGTCGAACAGAAAGTAATCGATTCGAACTTCTGATAGACTTCGAA
ATTAATACGACTCACTATAGGGAGACCACAACGGTTTCCCTCTAGAAATAATTTTGTTTAACTTTAAGAAGGAG
ATATACATATGGCTAGCATGACTGGTGGACAGCAAATGGGTACTAACCAAGGTAAAGGTGTAGTTGCTGCTGGA
GATAAACTGGCGTTGTTCTTGAAGGTATTTGGCGGTGAAGTCCTGACTGCGTTCGCTCGTACCTCCGTGACCAC
TTCTCGCCACATGGTACGTTCCATCTCCAGCGGTAAATCCGCTCAGTTCCCTGTTCTGGGTCGCACTCAGGCAG
CGTATCTGGCTCCGGGCGAGAACCTCGACGATAAACGTAAGGACATCAAACACACCGAGAAGGTAATCACCATT
GACGGTCTCCTGACGGCTGACGTTCTGATTTATGATATTGAGGACGCGATGAACCACTACGACGTTCGCTCTGA
GTATACCTCTCAGTTGGGTGAATCTCTGGCGATGGCTGCGGATGGTGCGGTTCTGGCTGAGATTGCCGGTCTGT
GTAACGTGGAAAGCAAATATAATGAGAACATCGAGGGCTTAGGTACTGCTACCGTAATTGAGACCACTCAGAAC
AAGGCCGCACTTACCGACCAAGTTGCGCTGGGTAAGGAGATTATTGCGGCTCTGACTAAGGCTCGTGCGGCTCT
GACCAAGAACTATGTTCCGGCTGCTGACCGTGTGTTCTACTGTGACCCAGATAGCTACTCTGCGATTCTGGCAG
CACTGATGCCGAACGCAGCAAACTACGCTGCTCTGATTGACCCTGAGAAGGGTTCTATCCGCAACGTTATGGGC
TTTGAGGTTGTAGAAGTTCCGCACCTCACCGCTGGTGGTGCTGGTACCGCTCGTGAGGGCACTACTGGTCAGAA
GCACGTCTTCCCTGCCAATAAAGGTGAGGGTAATGTCAAGGTTGCTAAGGACAACGTTATCGGCCTGTTCATGC
ACCGCTCTGCGGTAGGTACTGTTAAGCTGCGTGACTTGGCTCTGGAGCGCGCTCGCCGTGCTAACTTCCAAGCG
GACCAGATTATCGCTAAGTACGCAATGGGCCACGGTGGTCTTCGCCCAGAAGCTGCTGGTGCAGTGGTTTTCAA
AGTGGAGTAATGCTGGGGGTGGCCTCAACGGTCGCTGCTAGTCCCGAAGAGGCGAGTGTTACTTCAACAGAAGA
AACCTTAACGCCAGCACAGGAGGCCGCACGCACCCGCGCTGCTAACAAAGCCCGAAAGGAAGCTGAGTTGGCTG
CTGCCACCGCTGAGCAATAACTAGCATAACCCCTTGGGGCCTCTAAACGGGTCTTGAGGGGTTTTTTGCTGAAA
GGAGGAACTATATGCGCTCATACGATATGAACGTTGAGACTGCCGCTGAGTTATCAGCTGTGAACGACATTCTG
GCGTCTATCGGTGAACCTCCGGTATCAACGCTGGAAGGTGACGCTAACGCAGATGCAGCGAACGCTCGGCGTAT
TCTCAACAAGATTAACCGACAGATTCAATCTCGTGGATGGACGTTCAACATTGAGGAAGGCATAACGCTACTAC
CTGATGTTTACTCCAACCTGATTGTATACAGTGACGACTATTTATCCCTAATGTCTACTTCCGGTCAATCCATC
TACGTTAACCGAGGTGGCTATGTGTATGACCGAACGAGTCAATCAGACCGCTTTGACTCTGGTATTACTGTGAA
CATTATTCGTCTCCGCGACTACGATGAGATGCCTGAGTGCTTCCGTTACTGGATTGTCACCAAGGCTTCCCGTC
AGTTCAACAACCGATTCTTTGGGGCACCGGAAGTAGAGGGTGTACTCCAAGAAGAGGAAGATGAGGCTAGACGT
CTCTGCATGGAGTATGAGATGGACTACGGTGGGTACAATATGCTGGATGGAGATGCGTTCACTTCTGGTCTACT
GACTCGCTAACATTAATAAATAAGGAGGCTCTAATGGCACTCATTAGCCAATCAATCAAGAACTTGAAGGGTGG
TATCAGCCAACAGCCTGACATCCTTCGTTATCCAGACCAAGGGTCACGCCAAGTTAACGGTTGGTCTTCGGAGA
CCGAGGGCCTCCAAAAGCGTCCACCTCTTGTTTTCTTAAATACACTTGGAGACAACGGTGCGTTAGGTCAAGCT
CCGTACATCCACCTGATTAACCGAGATGAGCACGAACAGTATTACGCTGTGTTCACTGGTAGCGGAATCCGAGT
GTTCGACCTTTCTGGTAACGAGAAGCAAGTTAGGTATCCTAACGGTTCCAACTACATCAAGACCGCTAATCCAC
GTAACGACCTGCGAATGGTTACTGTAGCAGACTATACGTTCATCGTTAACCGTAACGTTGTTGCACAGAAGAAC
ACAAAGTCTGTCAACTTACCGAATTACAACCCTAATCAAGACGGATTGATTAACGTTCGTGGTGGTCAGTATGG
TAGGGAACTAATTGTACACATTAACGGTAAAGACGTTGCGAAGTATAAGATACCAGATGGTAGTCAACCTGAAC
ACGTAAACAATACGGATGCCCAATGGTTAGCTGAAGAGTTAGCCAAGCAGATGCGCACTAACTTGTCTGATTGG
ACTGTAAATGTAGGGCAAGGGTTCATCCATGTGACCGCACCTAGTGGTCAACAGATTGACTCCTTCACGACTAA
AGATGGCTACGCAGACCAGTTGATTAACCCTGTGACCCACTACGCTCAGTCGTTCTCTAAGCTGCCACCTAATG
CTCCTAACGGCTACATGGTGAAAATCGTAGGGGACGCCTCTAAGTCTGCCGACCAGTATTACGTTCGGTATGAC
GCTGAGCGGAAAGTTTGGACTGAGACTTTAGGTTGGAACACTGAGGACCAAGTTCTATGGGAAACCATGCCACA
CGCTCTTGTGCGAGCCGCTGACGGTAATTTCGACTTCAAGTGGCTTGAGTGGTCTCCTAAGTCTTGTGGTGACG
TTGACACCAACCCTTGGCCTTCTTTTGTTGGTTCAAGTATTAACGATGTGTTCTTCTTCCGTAACCGCTTAGGA
TTCCTTAGTGGGAGAACATCATATTGAGTCGTACAGCCAAATACTTCAACTTCTACCCTGCGTCCATTGCGAA
CCTTAGTGATGACGACCCTATAGACGTAGCTGTGAGTACCAACCGAATAGCAATCCTAAGTACGCCGTTCCGT
TCTCAGAAGAGTTACTCATCTGGTCCGATGAAGCACAATTCGTCCTGACTGCCTCGGGTACTCTCACATCTAAG
TCGGTTGAGTTGAACCTAACGACCCAGTTTGACGTACAGGACCGAGCGAGACCTTTTGGGATTGGGCGTAATGT
CTACTTTGCTAGTCCGAGGTCCAGCTTCACGTCCATCCACAGGTACTACGCTGTGCAGGATGTCAGTTCCGTTA
AGAATGCTGAGGACATTACATCACACGTTCCTAACTACATCCCTAATGGTGTGTTCAGTATTTGCGGAAGTGGT
ACGGAAAACTTCTGTTCGGTACTATCTCACGGGGACCCTAGTAAAATCTTCATGTACAAATTCCTGTACCTGAA
CGAAGAGTTAAGGCAACAGTCGTGGTCTCATTGGACTTTGGGGAAAACGTACAGGTTCTAGCTTGTCAGAGTA
TCAGCTCAGATATGTATGTGATTCTTCGCAATGAGTTCAATACGTTCCTAGCTAGAATCTCTTTCACTAAGAAC
GCCATTGACTTACAGGGAGAACCCTATCGTGCCTTTATGGACATGAAGATTCGATACACGATTCCTAGTGGAAC
ATACAACGATGACACATTCACTACCTCTATTCATATTCCAACAATTTATGGTGCAAACTTCGGGAGGGGCAAAA
```

FIG. 14H

```
TCACTGTATTGGAGCCTGATGGTAAGATAACCGTGTTTGAGCAACCTACGGCTGGGTGGAATAGCGACCCTTGG
CTGAGACTCAGCGGTAACTTGGAGGGACGCATGGTGTACATTGGGTTCAACATTAACTTCGTATATGAGTTCTC
TAAGTTCCTCATCAAGCAGACTGCCGACGACGGGTCTACCTCCACGGAAGACATTGGGCGCTTACAGTTACGCC
GAGCGTGGGTTAACTACGAGAACTCTGGTACGTTTGACATTTATGTTGAGAACCAATCGTCTAACTGGAAGTAC
ACAATGGCTGGTGCCCGATTAGGCTCTAACACTCTGAGGGCTGGGAGACTGAACTTAGGGACCGGACAATATCG
ATTCCCTGTGGTTGGTAACGCCAAGTTCAACACTGTATACATCTTGTCAGATGAGACTACCCCTCTGAACATCA
TTGGGTGTGGCTGGGAAGGTAACTACTTACGGAGAAGTTCCGGTATTTAATTAAATATTCTCCCTGTGGTGGCT
CGAAATTAATACGACTCACTATAGGGAGAACAATACGACTACGGGAGGGTTTTCTTATGATGACTATAAGACCT
ACTAAAAGTACAGACTTTGAGGTATTCACTCCGGCTCACCATGACATTCTTGAAGCTAAGGCTGCTGGTATTGA
GCCGAGTTTCCCTGATGCTTCCGAGTGTGTCACGTTGAGCCTCTATGGGTTCCCTCTAGCTATCGGTGGTAACT
GCGGGGACCAGTGCTGGTTCGTTACGAGCGACCAAGTGTGGCGACTTAGTGGAAAGGCTAAGCGAAAGTTCCGT
AAGTTAATCATGGAGTATCGCGATAAGATGCTTGAGAAGTATGATACTCTTTGGAATTACGTATGGGTAGGCAA
TACGTCCCACATTCGTTTCCTCAAGACTATCGGTGCGGTATTCCATGAAGAGTACACACGAGATGGTCAATTTC
AGTTATTTACAATCACGAAAGGAGGATAACCATATGTGTTGGGCAGCCGCAATACCTATCGCTATATCTGGCGC
TCAGGCTATCAGTGGTCAGAACGCTCAGGCCAAAATGATTGCCGCTCAGACCGCTGCTGGTCGTCGTCAAGCTA
TGGAAATCATGAGGCAGACGAACATCCAGAATGCTGACCTATCGTTGCAAGCTCGAAGTAAACTTGAGGAAGCG
TCCGCCGAGTTGACCTCACAGAACATGCAGAAGGTCCAAGCTATTGGGTCTATCCGAGCGGCTATCGGAGAGAG
TATGCTTGAAGGTTCCTCAATGGACCGCATTAAGCGAGTCACAGAAGGACAGTTCATTCGGGAAGCCAATATGG
TAACTGAGAACTATCGCCGTGACTACCAAGCAATCTTCGCACAGCAACTTGGTGGTACTCAAAGTGCTGCAAGT
CAGATTGACGAAATCTATAAGAGCGAACAGAAACAGAAGAGTAAGCTACAGATGGTTCTGGACCCACTGGCTAT
CATGGGTCTTCCGCTGCGAGTGCTTACGCATCCGGTGCGTTCGACTCTAAGTCCACAACTAAGGCACCTATTG
TTGCCGCTAAAGGAACCAAGACGGGGAGGTAATGAGCTATGAGTAAAATTGAATCTGCCCTTCAAGCGGCACAA
CCGGGACTCTCTCGGTTACGTGGTGGTGCTGGAGGTATGGGCTATCGTGCAGCAACCACTCAGGCCGAACAGCC
AAGGTCAAGCCTATTGGACACCATTGGTCGGTTCGCTAAGGCTGGTGCCGATATGTATACCGCTAAGGAACAAC
GAGCACGAGACCTAGCTGATGAACGCTCTAACGAGATTATCCGTAAGCTGACCCCTGAGCAACGTCGAGAAGCT
CTCAACAACGGGACCCTTCTGTATCAGGATGACCCATACGCTATGGAAGCACTCCGAGTCAAGACTGGTCGTAA
CGCTGCGTATCTTGTGGACGATGACGTTATGCAGAAGATAAAAGAGGGTGTCTTCCGTACTCGCGAAGAGATGG
AAGAGTATCGCCATAGTCGCCTTCAAGAGGGCGCTAAGGTATACGCTGAGCAGTTCGGCATCGACCCTGAGGAC
GTTGATTATCAGCGTGGTTTCAACGGGACATTACCGAGCGTAACATCTCGCTGTATGGTGCGCATGATAACTT
CTTGAGCCAGCAAGCTCAGAAGGGCGCTATCATGAACAGCCGAGTGGAACTCAACGGTGTCCTTCAAGACCCTG
ATATGCTGCGTCGTCCAGACTCTGCTGACTTCTTTGAGAAGTATATCGACAACGGTCTGGTTACTGGCGCAATC
CCATCTGATGCTCAAGCCACACAGCTTATAAGCCAAGCGTTCAGTGACGCTTCTAGCCGTGCTGGTGGTGCTGA
CTTCCTGATGCGAGTCGGTGACAAGAAGGTAACACTTAACGGAGCCACTACGACTTACCGAGAGTTGATTGGTG
AGGAACAGTGGAACGCTCTCATGGTCACAGCACAACGTTCTCAGTTTGAGACTGACGCGAAGCTGAACGAGCAG
TATCGCTTGAAGATTAACTCTGCGCTGAACCAAGAGGACCCAAGGACAGCTTGGGAGATGCTTCAAGGTATCAA
GGCTGAACTAGATAAGGTCCAACCTGATGAGCAGATGACACCACAACGTGAGTGGCTAATCTCCGCACAGGAAC
AAGTTCAGAATCAGATGAACGCATGGACGAAAGCTCAGGCCAAGGCTCTGGACGATTCCATGAAGTCAATGAAC
AAACTTGACGTAATCGACAAGCAATTCCAGAAGCGAATCAACGGTGAGTGGGTCTCAACGGATTTTAAGGATAT
GCCAGTCAACGAGAACACTGGTGAGTTCAAGCATAGCGATATGGTTAACTACGCCAATAAGAAGCTCGCTGAGA
TTGACAGTATGGACATTCCAGACGGTGCCAAGGATGCTATGAAGTTGAAGTACCTTCAAGCGGACTCTAAGGAC
GGAGCATTCCGTACAGCCATCGGAACCATGGTCACTGACGCTGGTCAAGAGTGGTCTGCCGCTGTGATTAACGG
TAAGTTACCAGAACGAACCCCAGCTATGGATGCTCTGCGCAGAATCCGCAATGCTGACCCTCAGTTGATTGCTG
CGCTATACCCAGACCAAGCTGAGCTATTCCTGACGATGGACATGATGGACAAGCAGGGTATTGACCCTCAGGTT
ATTCTTGATGCCGACGACTGACTGTTAAGCGGTCCAAAGAGCAACGCTTTGAGGATGATAAAGCATTCGAGTC
TGCACTGAATGCATCTAAGGCTCCTGAGATTGCCCGTATGCCAGCGTCACTGCGCGAATCTGCACGTAAGATTT
ATGACTCCGTTAAGTATCGCTCGGGGAACGAAAGCATGGCTATGGAGCAGATGACCAAGTTCCTTAAGGAATCT
ACCTACACGTTCACTGGTGATGATGTTGACGGTGATACCGTTGGTGTGATTCCTAAGAATATGATGCAGGTTAA
CTCTGACCCGAAATCATGGGAGCAAGGTCGGGATATTCTGGAGGAAGCACGTAAGGGAATCATTGCGAGCAACC
CTTGGATAACCAATAAGCAACTGACCATGTATTCTCAAGGTGACTCCATTTACCTTATGGACACCACAGGTCAA
GTCAGAGTCCGATACGACAAAGAGTTACTCTCGAAGGTCTGGAGTGAGAACCAGAAGAAACTCGAAGAGAAAGC
TCGTGAGAAGGCTCTGGCTGATGTGAACAAGCGAGCACCTATAGTTGCCGCTACGAAGGCCCGTGAAGCTGCTG
CTAAACGAGTCCGAGAGAAACGTAAACAGACTCCTAAGTTCATCTACGGACGTAAGGAGTAACTAAAGGCTACA
TAAGGAGGCCCTAAATGGATAAGTACGATAAGAACGTACCAAGTGATTATGATGGTCTGTTCCAAAAGGCTGCT
GATGCCAACGGGGTCTCTTATGACCTTTTACGTAAAGTCGCTTGGACAGAATCACGATTTGTGCCTACAGCAAA
```

FIG. 14I

```
ATCTAAGACTGGACCATTAGGCATGATGCAATTTACCAAGGCAACCGCTAAGGCCCTCGGTCTGCGAGTTACCG
ATGGTCCAGACGACGACCGACTGAACCCTGAGTTAGCTATTAATGCTGCCGCTAAGCAACTTGCAGGTCTGGTA
GGGAAGTTTGATGGCGATGAACTCAAAGCTGCCCTTGCGTACAACCAAGGCGAGGGACGCTTGGGTAATCCACA
ACTTGAGGCGTACTCTAAGGGAGACTTCGCATCAATCTCTGAGGAGGGACGTAACTACATGCGTAACCTTCTGG
ATGTTGCTAAGTCACCTATGGCTGGACAGTTGGAAACTTTTGGTGGCATAACCCCAAAGGGTAAAGGCATTCCG
GCTGAGGTAGGATTGGCTGGAATTGGTCACAAGCAGAAAGTAACACAGGAACTTCCTGAGTCCACAAGTTTTGA
CGTTAAGGGTATCGAACAGGAGGCTACGGCGAAACCATTCGCCAAGGACTTTTGGGAGACCCACGGAGAAACAC
TTGACGAGTACAACAGTCGTTCAACCTTCTTCGGATTCAAAAATGCTGCCGAAGCTGAACTCTCCAACTCAGTC
GCTGGGATGGCTTTCCGTGCTGGTCGTCTCGATAATGGTTTTGATGTGTTTAAAGACACCATTACGCCGACTCG
CTGGAACTCTCACATCTGGACTCCAGAGGAGTTAGAGAAGATTCGAACAGAGGTTAAGAACCCTGCGTACATCA
ACGTTGTAACTGGTGGTTCCCCTGAGAACCTCGATGACCTCATTAAATTGGCTAACGAGAACTTTGAGAATGAC
TCCCGCGCTGCCGAGGCTGGCCTAGGTGCCAAACTGAGTGCTGGTATTATTGGTGCTGGTGTGGACCCGCTTAG
CTATGTTCCTATGGTCGGTGTCACTGGTAAGGGCTTTAAGTTAATCAATAAGGCTCTTGTAGTTGGTGCCGAAA
GTGCTGCTCTGAACGTTGCATCCGAAGGTCTCCGTACCTCCGTAGCTGGTGGTGACGCAGACTATGCGGGTGCT
GCCTTAGGTGGCTTTGTGTTTGGCGCAGGCATGTCTGCAATCAGTGACGCTGTAGCTGCTGGACTGAAACGCAG
TAAACCAGAAGCTGAGTTCGACAATGAGTTCATCGGTCCTATGATGCGATTGGAAGCCCGTGAGACAGCACGAA
ACGCCAACTCTGCGGACCTCTCTCGGATGAACACTGAGAACATGAAGTTTGAAGGTGAACATAATGGTGTCCCT
TATGAGGACTTACCAACAGAGAGAGGTGCCGTGGTGTTACATGATGGCTCCGTTCTAAGTGCAAGCAACCCAAT
CAACCCTAAGACTCTAAAAGAGTTCTCCGAGGTTGACCCTGAGAAGGCTGCGCGAGGAATCAAACTGGCTGGGT
TCACCGAGATTGGCTTGAAGACCTTGGGGTCTGACGATGCTGACATCCGTAGAGTGGCTATCGACCTCGTTCGC
TCTCCTACTGGTATGCAGTCTGGTGCCTCAGGTAAGTTCGGTGCAACAGCTTCTGACATCCATGAGAGACTTCA
TGGTACTGACCAGCGTACTTATAATGACTTGTACAAAGCAATGTCTGACGCTATGAAAGACCCTGAGTTCTCTA
CTGGCGGCGCTAAGATGTCCCGTGAAGAAACTCGATACACTATCTACCGTAGAGCGGCACTAGCTATTGAGCGT
CCAGAACTACAGAAGGCACTCACTCCGTCTGAGAGAATCGTTATGGACATCATTAAGCGTCACTTTGACACCAA
GCGTGAACTTATGGAAAACCAGCAATATTCGGTAACACAAAGGCTGTGAGTATCTTCCCTGAGAGTCGCCACA
AAGGTACTTACGTTCCTCACGTATATGACCGTCATGCCAAGGCGCTGATGATTCAACGCTACGGTGCCGAAGGT
TTGCAGGAAGGGATTGCCCGCTCATGGATGAACAGCTACGTCTCCAGACCTGAGGTCAAGGCCAGAGTCGATGA
GATGCTTAAGGAATTACACGGGGTGAAGGAAGTAACACCAGAGATGGTAGAGAAGTACGCTATGGATAAGGCTT
ATGGTATCTCCCACTCAGACCAGTTCACCAACAGTTCCATAATAGAAGAGAACATTGAGGGCTTAGTAGGTATC
GAGAATAACTCATTCCTTGAGGCACGTAACTTGTTTGATTCGGACCTATCCATCACTATGCCAGACGGACAGCA
ATTCTCAGTGAATGACCTAAGGGACTTCGATATGTTCCGCATCATGCCAGCGTATGACCGCCGTGTCAATGGTG
ACATCGCCATCATGGGGTCTACTGGTAAAACCACTAAGGAACTTAAGGATGAGATTTTGGCTCTCAAAGCGAAA
GCTGAGGGAGACGGTAAGAAGACTGGCGAGGTACATGCTTTAATGGATACCGTTAAGATTCTTACTGGTCGTGC
TAGACGCAATCAGGACACTGTGTGGGAAACCTCACTGCGTGCCATCAATGACCTAGGGTTCTTCGCTAAGAACG
CCTACATGGGTGCTCAGAACATTACGGAGATTGCTGGGATGATTGTCACTGGTAACGTTCGTGCTCTAGGGCAT
GGTATCCCAATTCTGCGTGATACACTCTACAAGTCTAAACCAGTTTCAGCTAAGGAACTCAAGGAACTCCATGC
GTCTCTGTTCGGGAAGGAGGTGGACCAGTTGATTCGGCCTAAACGTGCTGACATTGTGCAGCGCCTAAGGGAAG
CAACTGATACCGGACCTGCCGTGGCGAACATCGTAGGGACCTTGAAGTATTCAACACAGGAACTGGCTGCTCGC
TCTCCGTGGACTAAGCTACTGAACGGAACCACTAACTACCTTCTGGATGCTGCGCGTCAAGGTATGCTTGGGGA
TGTTATTAGTGCCACCCTAACAGGTAAGACTACCCGCTGGGAGAAGAAGGCTTCCTTCGTGGTGCCTCCGTAA
CTCCTGAGCAGATGCTGGCATCAAGTCTCTCATCAAGGAACATATGGTACGCGGTGAGGACGGGAAGTTTACC
GTTAAGGACAAGCAAGCGTTCTCTATGGACCCACGGGCTATGGACTTATGGAGACTGGCTGACAAGGTAGCTGA
TGAGGCAATGCTGCGTCCACATAAGGTGTCCTTACAGGATTCCCATGCGTTCGGAGCACTAGGTAAGATGGTTA
TGCAGTTTAAGTCTTTCACTATCAAGTCCCTTAACTCTAAGTTCCTGCGAACCTTCTATGATGGATACAAGAAC
AACCGAGCGATTGACGCTGCGCTGAGCATCATCACCTCTATGGGTCTCGCTGGTGGTTTCTATGCTATGGCTGC
ACACGTCAAAGCATACGCTCTGCCTAAGGAGAAACGTAAGGAGTACTTGGAGCGTGCACTGGACCCAACCATGA
TTGCCCACGCTGCGTTATCTCGTAGTTCTCAATTGGGTGCTCCTTTGGCTATGGTTGACCTAGTTGGTGGTGTT
TTAGGGTTCGAGTCCTCCAAGATGGCTCGCTCTACGATTCTACCTAAGGACACCGTGAAGGAACGTGACCCAAA
CAAACCGTACACCTCTAGAGAGGTAATGGGCGCTATGGGTTCAAACCTTCTGGAACAGATGCCTTCGGCTGGCT
TTGTGGCTAACGTAGGGGCTACCTTAATGAATGCTGCTGGCGTGGTCAACTCACCTAATAAAGCAACCGAGCAG
GACTTCATGACTGGTCTTATGAACTCCACAAAAGAGTTAGTACCGAACGACCCATTGACTCAACAGCTTGTGTT
GAAGATTTATGAGGCGAACGGTGTTAACTTGAGGGAGCGTAGGAAATAATACGACTCACTATAGGGAGAGGCGA
AATAATCTTCTCCCTGTAGTCTCTTAGATTTACTTTAAGGAGGTCAAATGGCTAACGTAATTAAAACCGTTTTG
ACTTACCAGTTAGATGGCTCCAATCGTGATTTTAATATCCCGTTTGAGTATCTAGCCCGTAAGTTCGTAGTGGT
```

FIG. 14J

```
AACTCTTATTGGTGTAGACCGAAAGGTCCTTACGATTAATACAGACTATCGCTTTGCTACACGTACTACTATCT
CTCTGACAAAGGCTTGGGGTCCAGCCGATGGCTACACGACCATCGAGTTACGTCGAGTAACCTCCACTACCGAC
CGATTGGTTGACTTTACGGATGGTTCAATCCTCCGCGCGTATGACCTTAACGTCGCTCAGATTCAAACGATGCA
CGTAGCGGAAGAGGCCCGTGACCTCACTACGGATACTATCGGTGTCAATAACGATGGTCACTTGGATGCTCGTG
GTCGTCGAATTGTGAACCTAGCGAACGCCGTGGATGACCGCGATGCTGTTCCGTTTGGTCAACTAAAGACCATG
AACCAGAACTCATGGCAAGCACGTAATGAAGCCTTACAGTTCCGTAATGAGGCTGAGACTTTCAGAAACCAAGC
GGAGGGCTTTAAGAACGAGTCCAGTACCAACGCTACGAACACAAAGCAGTGGCGCGATGAGACCAAGGGTTTCC
GAGACGAAGCCAAGCGGTTCAAGAATACGGCTGGTCAATACGCTACATCTGCTGGGAACTCTGCTTCCGCTGCG
CATCAATCTGAGGTAAACGCTGAGAACTCTGCCACAGCATCCGCTAACTCTGCTCATTTGGCAGAACAGCAAGC
AGACCGTGCGGAACGTGAGGCAGACAAGCTGGAAAATTACAATGGATTGGCTGGTGCAATTGATAAGGTAGATG
GAACCAATGTGTACTGGAAAGGAAATATTCACGCTAACGGGCGCCTTTACATGACCACAAACGGTTTTGACTGT
GGCCAGTATCAACAGTTCTTTGGTGGTGTCACTAATCGTTACTCTGTCATGGAGTGGGGAGATGAGAACGGATG
GCTGATGTATGTTCAACGTAGAGAGTGGACAACAGCGATAGGCGGTAACATCCAGTTAGTAGTAAACGGACAGA
TCATCACCCAAGGTGGAGCCATGACCGGTCAGCTAAAATTGCAGAATGGGCATGTTCTTCAATTAGAGTCCGCA
TCCGACAAGGCGCACTATATTCTATCTAAAGATGGTAACAGGAATAACTGGTACATTGGTAGAGGGTCAGATAA
CAACAATGACTGTACCTTCCACTCCTATGTACATGGTACGACCTTAACACTCAAGCAGGACTATGCAGTAGTTA
ACAAACACTTCCACGTAGGTCAGGCCGTTGTGGCCACTGATGGTAATATTCAAGGTACTAAGTGGGGAGGTAAA
TGGCTGGATGCTTACCTACGTGACAGCTTCGTTGCGAAGTCCAAGGCGTGGACTCAGGTGTGGTCTGGTAGTGC
TGGCGGTGGGGTAAGTGTGACTGTTTCACAGGATCTCCGCTTCCGCAATATCTGGATTAAGTGTGCCAACAACT
CTTGGAACTTCTTCCGTACTGGCCCCGATGGAATCTACTTCATAGCCTCTGATGGTGGATGGTTACGATTCCAA
ATACACTCCAACGGTCTCGGATTCAAGAATATTGCAGACAGTCGTTCAGTACCTAATGCAATCATGGTGGAGAA
CGAGTAATTGGTAAATCACAAGGAAAGACGTGTAGTCCACGGATGGACTCTCAAGGAGGTACAAGGTGCTATCA
TTAGACTTTAACAACGAATTGATTAAGGCTGCTCCAATTGTTGGGACGGGTGTAGCAGATGTTAGTGCTCGACT
GTTCTTTGGGTTAAGCCTTAACGAATGGTTCTACGTTGCTGCTATCGCCTACACAGTGGTTCAGATTGGTGCCA
AGGTAGTCGATAAGATGATTGACTGGAAGAAAGCCAATAAGGAGTGATATGTATGGAAAAGGATAAGAGCCTTA
TTACATTCTTAGAGATGTTGGACACTGCGATGGCTCAGCGTATGCTTGCGGACCTTTCGGACCATGAGCGTCGC
TCTCCGCAACTCTATAATGCTATTAACAAACTGTTAGACCGCCACAAGTTCCAGATTGGTAAGTTGCAGCCGGA
TGTTCACATCTTAGGTGGCCTTGCTGGTGCTCTTGAAGAGTACAAAGAGAAAGTCGGTGATAACGGTCTTACGG
ATGATGATATTTACACATTACAGTGATATACTCAAGGCCACTACAGATAGTGGTCTTTATGGATGTCATTGTCT
ATACGAGATGCTCCTACGTGAAATCTGAAAGTTAACGGGAGGCATTATGCTAGAATTTTACGTAAGCTAATCC
CTTGGGTTCTCGCTGGGATGCTATTCGGGTTAGGATGGCATCTAGGGTCAGACTCAATGGACGCTAAATGGAAA
CAGGAGGTACACAATGAGTACGTTAAGAGAGTTGAGGCTGCGAAGAGCACTCAAAGAGCAATCGATGCGGTATC
TGCTAAGTATCAAGAAGACCTTGCCGCGCTGGAAGGGAGCACTGATAGGATTATTTCTGATTTGCGTAGCGACA
ATAAGCGGTTGCGCGTCAGAGTCAAAACTACCGGAACCTCCGATGGTCAGTGTGGATTCGAGCCTGATGGTCGA
GCCGAACTTGACGACCGAGATGCTAAACGTATTCTCGCAGTGACCCAGAAGGGTGACGCATGGATTCGTGCGTT
ACAGGATACTATTCGTGAACTGCAACGTAAGTAGGAAATCAAGTAAGGAGGCAATGTGTCTACTCAATCCAATC
GTAATGCGCTCGTAGTGGCGCAACTGAAAGGAGACTTCGTGGCGTTCCTATTCGTCTTATGGAAGGCGCTAAAC
CTACCGGTGCCCACTAAGTGTCAGATTGACATGGCTAAGGTGCTGGCGAATGGAGACAACAAGAAGTTCATCTT
ACAGGCTTTCCGTGGTATCGGTAAGTCGTTCATCACATGTGCGTTCGTTGTGTGGTCCTTATGGAGAGACCCTC
AGTTGAAGATACTTATCGTATCAGCCTCTAAGGAGCGTGCAGACGCTAACTCCATCTTTATTAAGAACATCATT
GACCTGCTGCCATTCCTATCTGAGTTAAAGCCAAGACCCGGACAGCGTGACTCGGTAATCAGCTTTGATGTAGG
CCCAGCCAATCCTGACCACTCTCCTAGTGTGAAATCAGTAGGTATCACTGGTCAGTTAACTGGTAGCCGTGCTG
ACATTATCATTGCGGATGACGTTGAGATTCCGTCTAACAGCGCAACTATGGGTGCCCGTGAGAAGCTATGGACT
CTGGTTCAGGAGTTCGCTGCGTTACTTAAACCGCTGCCTTCCTCTCGCGTTATCTACCTTGGTACACCTCAGAC
AGAGATGACTCTCTATAAGGAACTTGAGGATAACCGTGGGTACACAACCATTATCTGGCCTGCTCTGTACCCAA
GGACACGTGAAGAGAACCTCTATTACTCACAGCGTCTTGCTCCTATGTTACGCGCTGAGTACGATGAGAACCCT
GAGGCACTTGCTGGGACTCCAACAGACCCAGTGCGCTTTGACCGTGATGACCTGCGCAGCGTGAGTTGGAATA
CGGTAAGGCTGGCTTTACGCTACAGTTCATGCTTAACCCTAACCTTAGTGATGCCGAGAAGTACCCGCTGAGGC
TTCGTGACGCTATCGTAGCGGCCTTAGACTTAGAGAAGGCCCCAATGCATTACCAGTGGCTTCCGAACCGTCAG
AACATCATTGAGGACCTTCCTAACGTTGGCCTTAAGGGTGATGACCTGCATACGTACCACGATTGTTCCAACAA
CTCAGGTCAGTACCAACAGAAGATTCTGGTCATTGACCCTAGTGGTCGCGGTAAGGACGAAACAGGTTACGCTG
TGCTGTACACACTGAACGGTTACATCTACCTTATGGAAGCTGGAGGTTTCCGTGATGGCTACTCCGATAAGACC
CTTGAGTTACTCGCTAAGAAGGCAAAGCAATGGGGAGTCCAGACGGTTGTCTACGAGAGTAACTTCGGTGACGG
TATGTTCGGTAAGGTATTCAGTCCTATCCTTCTTAAACACCACAACTGTGCGATGGAAGAGATTCGTGCCCGTG
```

```
GTATGAAAGAGATGCGTATTTGCGATACCCTTGAGCCAGTCATGCAGACTCACCGCCTTGTAATTCGTGATGAG
GTCATTAGGGCCGACTACCAGTCCGCTCGTGACGTAGACGGTAAGCATGACGTTAAGTACTCGTTGTTCTACCA
GATGACCCGTATCACTCGTGAGAAAGGCGCTCTGGCTCATGATGACCGATTGGATGCCCTTGCGTTAGGCATTG
AGTATCTCCGTGAGTCCATGCAGTTGGATTCCGTTAAGGTCGAGGGTGAAGTACTTGCTGACTTCCTTGAGGAA
CACATGATGCGTCCTACGGTTGCTGCTACGCATATCATTGAGATGTCTGTGGGAGGAGTTGATGTGTACTCTGA
GGACGATGAGGGTTACGGTACGTCTTTCATTGAGTGGTGATTTATGCATTAGGACTGCATAGGGATGCACTATA
GACCACGGATGGTCAGTTCTTTAAGTTACTGAAAAGACACGATAAATTAATACGACTCACTATAGGGAGAGGAG
GGACGAAAGGTTACTATATAGATACTGAATGAATACTTATAGAGTGCATAAAGTATGCATAATGGTGTACCTAG
AGTGACCTCTAAGAATGGTGATTATATTGTATTAGTATCACCTTAACTTAAGGACCAACATAAAGGGAGGAGAC
TCATGTTCCGCTTATTGTTGAACCTACTGCGGCATAGAGTCACCTACCGATTTCTTGTGGTACTTTGTGCTGCC
CTTGGGTACGCATCTCTTACTGGAGACCTCAGTTCACTGGAGTCTGTCGTTTGCTCTATACTCACTTGTAGCGA
TTAGGGTCTTCCTGACCGACTGATGGCTCACCGAGGGATTCAGCGGTATGATTGCATCACACCACTTCATCCCT
ATAGAGTCAAGTCCTAAGGTATACCCATAAAGAGCCTCTAATGGTCTATCCTAAGGTCTATACCTAAAGATAGG
CCATCCTATCAGTGTCACCTAAAGAGGGTCTTAGAGAGGGCCTATGGAGTTCCTATAGGGTCCTTTAAAATATA
CCATAAAATCTGAGTGACTATCTCACAGTGTACGGACCTAAAGTTCCCCCATAGGGGGTACCTAAAGCCCAGC
CAATCACCTAAAGTCAACCTTCGGTTGACCTTGAGGGTTCCCTAAGGGTTGGGGATGACCCTTGGGTTTGTCTT
TGGGTGTTACCTTGAGTGTCTCTCTGTGTCCCT
```

*FIG. 14K*

>T7_Swa1_Nanoluc_Insert_sequence Enterobacteria phage T7, complete genome (SEQ ID NO: 6)

CTTTAAGACCCTTAAGTGTTAATTAGAGATTTAAGGAGATTCA
ACATGGTCTTCACACTCGAAGATTTCGTTGGGGACTGGCGA
CAGACAGCCGGCTACAACCTGGACCAAGTCCTTGAACAGG
GAGGTGTGTCCAGTTTGTTTCAGAATCTCGGGGTGTCCGTA
ACTCCGATCCAAAGGATTGTCCTGAGCGGTGAAAATGGGCT
GAAGATCGACATCCATGTCATCATCCCGTATGAAGGTCTGAG
CGGCGACCAAATGGGCCAGATCGAAAAATTTTTAAGGTGG
TGTACCCTGTGGATGATCATCACTTTAAGGTGATCCTGCACTA
TGGCACACTGGTAATCGACGGGGTTACGCCGAACATGATCG
ACTATTTCGGACGGCCGTATGAAGGCATCGCCGTGTTCGAC
GGCAAAAGATCACTGTAACAGGGACCCTGTGGAACGGCA
ACAAAATTATCGACGAGCGCCTGATCAACCCCGACGGCTCC
CTGCTGTTCCGAGTAACCATCAACGGAGTGACCGGCTGGC
GGCTGTGCGAACGCATTCTGGCGTAAAGGAGGTAAACATAT
GACCATGATTACGGATTCACTGGCCGTCGTTTTACAACGTCG
TGACTGGGAAAACCCTGGCGTTACCCAACTTAATCGCCTTG
CAGCACATCCCCCTTTCGCCAGCTGGCGTAATAGCGAAGAG
GCCCGCACCGATCGCCCTTCCCAACAGTTGCGCAGCCTGA
ATGGCGAATGGTAAAATTAAAGAATTACTAAGAGAGGACTTT
AAGTATGCGTAAC

SEQUENCE LISTING

```
<160> NUMBER OF SEQ ID NOS: 6

<210> SEQ ID NO 1
<211> LENGTH: 814
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
cctctagaaa taattttgtt taactttaag aaggagatat acatatggtc ttcacactcg      60
aagatttcgt tggggactgg cgacagacag ccggctacaa cctggaccaa gtccttgaac     120
agggaggtgt gtccagtttg tttcagaatc tcggggtgtc cgtaactccg atccaaagga     180
ttgtcctgag cggtgaaaat gggctgaaga tcgacatcca tgtcatcatc ccgtatgaag     240
gtctgagcgg cgaccaaatg ggccagatcg aaaaaatttt taaggtggtg taccctgtgg     300
```

| | |
|---|---|
| atgatcatca ctttaaggtg atcctgcact atggcacact ggtaatcgac ggggttacgc | 360 |
| cgaacatgat cgactatttc ggacggccgt atgaaggcat cgccgtgttc gacggcaaaa | 420 |
| agatcactgt aacagggacc ctgtggaacg gcaacaaaat tatcgacgag cgcctgatca | 480 |
| accccgacgg ctccctgctg ttccgagtaa ccatcaacgg agtgaccggc tggcggctgt | 540 |
| gcgaacgcat tctggcgtaa aggaggtaaa catatgacca tgattacgga ttcactggcc | 600 |
| gtcgttttac aacgtcgtga ctgggaaaac cctggcgtta cccaacttaa tcgccttgca | 660 |
| gcacatcccc ctttcgccag ctggcgtaat agcgaagagg cccgcaccga tcgcccttcc | 720 |
| caacagttgc gcagcctgaa tggcgaatgg taaaagagg aggtatacaa tggctagcat | 780 |
| gactggtgga cagcaaatgg gtactaacca aggt | 814 |

<210> SEQ ID NO 2
<211> LENGTH: 41369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

| | |
|---|---|
| tctcacagtg tacggaccta agttccccc atagggggta cctaaagccc agccaatcac | 60 |
| ctaaagtcaa ccttcggttg accttgaggg ttccctaagg gttggggatg acccttgggt | 120 |
| ttgtctttgg gtgttacctt gagtgtctct ctgtgtccct atctgttaca gtctcctaaa | 180 |
| gtatcctcct aaagtcacct cctaacgtcc atcctaaagc caacacctaa agcctacacc | 240 |
| taaagaccca tcaagtcaac gcctatctta agtttaaaac ataaagacca gacctaaaga | 300 |
| ccagacctaa agacactaca taagaccag acctaaagac gccttgttgt tagccataaa | 360 |
| gtgataacct ttaatcattg tctttattaa tacaactcac tataaggaga gacaacttaa | 420 |
| agagacttaa aagattaatt taaaatttat caaaaagagt attgacttaa agtctaacct | 480 |
| ataggatact tacagccatc gagagggaca cggcgaatag ccatcccaat cgacaccggg | 540 |
| gtcaaccgga taagtagaca gcctgataag tcgcacgaaa acaggtatt gacaacatga | 600 |
| agtaacatgc agtaagatac aaatcgctag gtaacactag cagcgtcaac cgggcgcaca | 660 |
| gtgccttcta ggtgacttaa gcgcaccacg gcacataagg tgaaacaaaa cggttgacaa | 720 |
| catgaagtaa acacggtacg atgtaccaca tgaaacgaca gtgagtcacc acactgaaag | 780 |
| gtgatgcggt ctaacgaaac ctgacctaag acgctcttta acaatctggt aaatagctct | 840 |
| tgagtgcatg actagcggat aactcaaggg tatcgcaagg tgccctttat gatattcact | 900 |
| aataactgca cgaggtaaca caagatggct atgtctaaca tgacttacaa caacgttttc | 960 |
| gaccacgctt acgaaatgct gaaagaaaac atccgttatg atgacatccg tgacactgat | 1020 |
| gacctgcacg atgctattca catggctgcc gataatgcag ttccgcacta ctacgctgac | 1080 |
| atctttagcg taatggcaag tgagggcatt gaccttgagt cgaagactc tggtctgatg | 1140 |
| cctgacacca aggacgtaat ccgcatcctg caagcgcgta tctatgagca attaacgatt | 1200 |
| gacctctggg aagacgcaga agacttgctc aatgaatact tggaggaagt cgaggagtac | 1260 |
| gaggaggatg aagagtaatg tctactacca acgtgcaata cggtctgacc gctcaaactg | 1320 |
| tactttcta tagcgacatg gtgcgctgtg gctttaactg gtcactcgca atggcacagc | 1380 |
| tcaaagaact gtacgaaaac aacaggcaa tagctttaga atctgctgag tgatagactc | 1440 |
| aaggtcgctc ctagcgagtg gccttatga ttatcacttt acttatgagg gagtaatgta | 1500 |

```
tatgcttact atcggtctac tcaccgctct aggtctagct gtaggtgcat cctttgggaa      1560
ggctttaggt gtagctgtag gttcctactt taccgcttgc atcatcatag gaatcatcaa      1620
aggggcacta cgcaaatgat gaagcactac gttatgccaa tccacacgtc aacggggca      1680 accgtatgta cacctgatgg gttcgcaatg aaacaacgaa tcgaacgcct taagcgtgaa      1740
ctccgcatta accgcaagat taacaagata ggttccggct atgacagaac gcactgatgg      1800
cttaaagaaa ggttatatgc ccaatggcac actatacgct gcaaatcggc gaatagtgag      1860
aacttggcga gagaacaacc tcgaacgccg caaggacaag agagggcggc gtggcataga      1920
cgaaaggaaa aggttaaagc caagaaactc gccgcacttg aacaggcact agccaacaca      1980
ctgaacgcta tctcataacg aacataaagg acacaatgca atgaacatta ccgacatcat      2040
gaacgctatc gacgcaatca agcactgcc aatctgtgaa cttgacaagc gtcaaggtat      2100
gcttatcgac ttactggtcg agatggtcaa cagcgagacg tgtgatggcg agctaaccga      2160
actaaatcag gcacttgagc atcaagattg gtggactacc ttgaagtgtc tcacggctga      2220
cgcagggttc aagatgctcg gtaatggtca cttctcggct gcttatagtc acccgctgct      2280
acctaacaga gtgattaagg tgggctttaa gaaagaggat tcaggcgcag cctataccgc      2340
attctgccgc atgtatcagg gtcgtcctgg tatccctaac gtctacgatg tacagcgcca      2400
cgctggatgc tatacggtgg tacttgacgc acttaaggat tgcgagcgtt tcaacaatga      2460
tgcccattat aaatacgctg agattgcaag cgacatcatt gattgcaatt cggatgagca      2520
tgatgagtta actggatggg atggtgagtt tgttgaaact tgtaaactaa tccgcaagtt      2580
ctttgagggc atcgcctcat tcgacatgca tagcgggaac atcatgttct caaatggaga      2640
cgtaccatac atcaccgacc cggtatcatt ctcgcagaag aaagacggtg gcgcattcag      2700
catcgaccct gaggaactca tcaaggaagt cgaggaagtc gcacgacaga aagaaattga      2760
ccgcgctaag gcccgtaaag aacgtcacga ggggcgctta gaggcacgca gattcaaacg      2820
tcgcaaccgc aaggcacgta aagcacacaa agctaagcgc gaaagaatgc ttgctgcgtg      2880
gcgatgggct gaacgtcaag aacggcgtaa ccatgaggta gctgtagatg tactaggaag      2940
aaccaataac gctatgctct gggtcaacat gttctctggg gactttaagg cgcttgagga      3000
acgaatcgcg ctgcactggc gtaatgctga ccggatggct atcgctaatg gtcttacgct      3060
caacattgat aagcaacttg acgcaatgtt aatgggctga tagtcttatc ttacaggtca      3120
tctgcgggtg gcctgaatag gtacgattta ctaactggaa gaggcactaa atgaacacga      3180
ttaacatcgc taagaacgac ttctctgaca tcgaactggc tgctatcccg ttcaacactc      3240
tggctgacca ttacggtgag cgtttagctc gcgaacagtt ggcccttgag catgagtctt      3300
acgagatggg tgaagcacgc ttccgcaaga tgtttgagcg tcaacttaaa gctggtgagg      3360
ttgcggataa cgctgccgcc aagcctctca tcactaccct actccctaag atgattgcac      3420
gcatcaacga ctggtttgag gaagtgaaag ctaagcgcgg caagcgcccg acagccttcc      3480
agttcctgca agaaatcaag ccggaagccg tagcgtacat caccattaag accactctgg      3540
cttgcctaac cagtgctgac aatacaaccg ttcaggctgt agcaagcgca atcggtcggg      3600
ccattgagga cgaggctcgc ttcggtcgta tccgtgacct tgaagctaag cacttcaaga      3660
aaaacgttga ggaacaactc aacaagcgcg tagggcacgt ctacaagaaa gcatttatgc      3720
aagttgtcga ggctgacatg ctctctaagg gtctactcgg tggcgaggcg tggtcttcgt      3780
ggcataagga agactctatt catgtaggag tacgctgcat cgagatgctc attgagtcaa      3840
ccggaatggt tagcttacac cgccaaaatg ctggcgtagt aggtcaagac tctgagacta      3900
```

```
tcgaactcgc acctgaatac gctgaggcta tcgcaacccg tgcaggtgcg ctggctggca    3960
tctctccgat gttccaacct tgcgtagttc ctcctaagcc gtggactggc attactggtg    4020
gtggctattg gctaacggt cgtcgtcctc tggcgctggt gcgtactcac agtaagaaag    4080
cactgatgcg ctacgaagac gtttacatgc ctgaggtgta caaagcgatt aacattgcgc    4140
aaaacaccgc atggaaaatc aacaagaaag tcctagcggt cgccaacgta atcaccaagt    4200
ggaagcattg tccggtcgag acatccctg cgattgagcg tgaagaactc ccgatgaaac    4260
cggaagacat cgacatgaat cctgaggctc tcaccgcgtg gaaacgtgct gccgctgctg    4320
tgtaccgcaa ggacaaggct cgcaagtctc gccgtatcag ccttgagttc atgcttgagc    4380
aagccaataa gtttgctaac cataaggcca tctggttccc ttacaacatg gactggcgcg    4440
gtcgtgttta cgctgtgtca atgttcaacc cgcaaggtaa cgatatgacc aaaggactgc    4500
ttacgctggc gaaaggtaaa ccaatcggta aggaaggtta ctactggctg aaaatccacg    4560
gtgcaaactg tgcgggtgtc gataaggttc cgttccctga gcgcatcaag ttcattgagg    4620
aaaaccacga gaacatcatg gcttgcgcta agtctccact ggagaacact tggtgggctg    4680
agcaagattc tccgttctgc ttccttgcgt tctgctttga gtacgctggg gtacagcacc    4740
acggcctgag ctataactgc tcccttccgc tggcgtttga cgggtcttgc tctggcatcc    4800
agcacttctc cgcgatgctc cgagatgagg taggtggtcg cgcggttaac ttgcttccta    4860
gtgaaaccgt tcaggacatc tacgggattg ttgctaagaa agtcaacgag attctacaag    4920
cagacgcaat caatgggacc gataacgaag tagttaccgt gaccgatgag aacactggtg    4980
aaatctctga gaaagtcaag ctgggcacta aggcactggc tggtcaatgg ctggcttacg    5040
gtgttactcg cagtgtgact aagcgttcag tcatgacgct ggcttacggg tccaaagagt    5100
tcggcttccg tcaacaagtg ctggaagata ccattcagcc agctattgat tccggcaagg    5160
gtctgatgtt cactcagccg aatcaggctg ctggatacat ggctaagctg atttgggaat    5220
ctgtgagcgt gacggtggta gctgcggttg aagcaatgaa ctggcttaag tctgctgcta    5280
agctgctggc tgctgaggtc aaagataaga agactggaga gattcttcgc aagcgttgcg    5340
ctgtgcattg ggtaactcct gatggtttcc ctgtgtggca ggaatacaag aagcctattc    5400
agacgcgctt gaacctgatg ttcctcggtc agttccgctt acagcctacc attaacacca    5460
acaaagatag cgagattgat gcacacaaac aggagtctgg tatcgctcct aactttgtac    5520
acagccaaga cggtagccac cttcgtaaga ctgtagtgtg ggcacacgag aagtacggaa    5580
tcgaatcttt tgcactgatt cacgactcct tcggtaccat tccggctgac gctgcgaacc    5640
tgttcaaagc agtgcgcgaa actatggttg acacatatga gtcttgtgat gtactggctg    5700
atttctacga ccagttcgct gaccagttgc acgagtctca attggacaaa atgccagcac    5760
ttccggctaa aggtaacttg aacctccgtg acatcttaga gtcggacttc gcgttcgcgt    5820
aacgccaaat caatacgact cactatagag ggacaaactc aaggtcattc gcaagagtgg    5880
cctttatgat tgaccttctt ccggttaata cgactcacta taggagaacc ttaaggttta    5940
actttaagac ccttaagtgt taattagaga tttaggagat tcaacatggt cttcacactc    6000
gaagatttcg ttggggactg cgacagaca gccggctaca acctggacca agtccttgaa    6060
cagggaggtg tgtccagttt gtttcagaat ctcgggtgt ccgtaactcc gatccaaagg    6120
attgtcctga gcggtgaaaa tgggctgaag atcgacatcc atgtcatcat cccgtatgaa    6180
ggtctgagcg gcgaccaaat gggccagatc gaaaaaattt ttaaggtggt gtaccctgtg    6240
```

```
gatgatcatc actttaaggt gatcctgcac tatggcacac tggtaatcga cggggttacg    6300
ccgaacatga tcgactattt cggacggccg tatgaaggca tcgccgtgtt cgacggcaaa    6360
aagatcactg taacagggac cctgtggaac ggcaacaaaa ttatcgacga gcgcctgatc    6420
aaccccgacg gctccctgct gttccgagta accatcaacg gagtgaccgg ctggcggctg    6480
tgcgaacgca ttctggcgta aaggaggtaa acatatgacc atgattacgg attcactggc    6540
cgtcgtttta caacgtcgtg actgggaaaa ccctggcgtt acccaactta atcgccttgc    6600
agcacatccc cctttcgcca gctggcgtaa tagcgaagag gcccgcaccg atcgcccttc    6660
ccaacagttg cgcagcctga atggcgaatg gaaattaaag aattactaag agaggacttt    6720
aagtatgcgt aacttcgaaa agatgaccaa acgttctaac cgtaatgctc gtgacttcga    6780
ggcaaccaaa ggtcgcaagt tgaataagac taagcgtgac cgctctcaca gcgtagctg     6840
ggagggtcag taagatggga cgtttatata gtggtaatct ggcagcattc aaggcagcaa    6900
caaacaagct gttccagtta gacttagcgg tcatttatga tgactggtat gatgcctata    6960
caagaaaaga ttgcatacgg ttacgtattg aggacaggag tggaaacctg attgatacta    7020
gcaccttcta ccaccacgac gaggacgttc tgttcaatat gtgtactgat tggttgaacc    7080
atatgtatga ccagttgaag gactggaagt aatacgactc agtatagggga caatgcttaa    7140
ggtcgctctc taggagtggc cttagtcatt taaccaatag gagataaaca ttatgatgaa    7200
cattaagact aacccgttta aagccgtgtc tttcgtagag tctgccatta agaaggctct    7260
ggataacgct gggtatctta tcgctgaaat caagtacgat ggtgtacgcg gaacatctg     7320
cgtagacaat actgctaaca gttactggct ctctcgtgta tctaaaacga ttccggcact    7380
ggagcactta acgggtttg atgttcgctg gaagcgtcta ctgaacgatg accgttgctt     7440
ctacaaagat ggctttatgc ttgatgggga actcatggtc aagggcgtag actttaacac    7500
agggtccggc ctactgcgta ccaaatggac tgacacgaag aaccaagagt ccatgaaga    7560
gttattcgtt gaaccaatcc gtaagaaaga taaagttccc tttaagctgc acactggaca    7620
ccttcacata aaactgtacg ctatcctccc gctgcacatc gtggagtctg agaagactg     7680
tgatgtcatg acgttgctca tgcaggaaca cgttaagaac atgctgcctc tgctacagga    7740
atacttccct gaaatcgaat ggcaagcggc tgaatcttac gaggtctacg atatggtaga    7800
actacagcaa ctgtacgagc agaagcgagc agaaggccat gagggtctca ttgtgaaaga    7860
cccgatgtgt atctataagc gcggtaagaa atctggctgg tggaaaatga aacctgagaa    7920
cgaagctgac ggtatcattc agggtctggt atggggtaca aaaggtctgg ctaatgaagg    7980
taaagtgatt ggttttgagg tgcttcttga gagtggtcgt ttagttaacg ccacgaatat    8040
ctctcgcgcc ttaatggatg agttcactga gacagtaaaa gaggccaccc taagtcaatg    8100
gggattcttt agcccatacg gtattggcga caacgatgct tgtactatta acccttacga    8160
tggctgggcg tgtcaaatta gctacatgga ggaaacacct gatggctctt gcggcacccc   8220
atcgttcgta atgttccgtg gcaccgagga caaccctcaa gagaaaatgt aatcacactg    8280
gctcaccttc gggtgggcct ttctgcgttt ataaggagac actttatgtt taagaaggtt    8340
ggtaaattcc ttgcggcttt ggcagctatc ctgacgcttg cgtatattct gcggtatac    8400
cctcaagtag cactagtagt agttggcgct tgttacttag cggcagtgtg tgcttgcgtg    8460
tggagtatag ttaactggta atacgactca ctaaaggagg tacacaccat gatgtactta    8520
atgccattac tcatcgtcat tgtaggatgc cttgcgctcc actgtagcga tgatgatatg    8580
ccagatggtc acgcttaata cgactcacta aaggagacac tatatgtttc gacttcatta    8640
```

```
caacaaaagc gttaagaatt tcacggttcg ccgtgctgac cgttcaatcg tatgtgcgag    8700
cgagcgccga gctaagatac ctcttattgg taacacagtt cctttggcac cgagcgtcca    8760
catcattatc acccgtggtg actttgagaa agcaatagac aagaaacgtc cggttcttag    8820
tgtggcagtg acccgcttcc cgttcgtccg tctgttactc aaacgaatca aggaggtgtt    8880
ctgatgggac tgttagatgg tgaagcctgg gaaaagaaa acccgccagt acaagcaact    8940
gggtgtatag cttgcttaga gaaagatgac cgttatccac acacctgtaa caaggagct    9000 aacgatatga ccgaacgtga acaagagatg atcattaagt tgatagacaa taatgaaggt    9060
cgcccagatg atttgaatgg ctgcggtatt ctctgctcca atgtcccttg ccacctctgc    9120
cccgcaaata acgatcaaaa gataaccttag ggtgaaatcc gagcgatgga cccacgtaaa    9180
ccacatctga ataaacctga ggtaactcct acagatgacc agccttccgc tgagacaatc    9240
gaaggtgtca ctaagccttc ccactacatg ctgtttgacg acattgaggc tatcgaagtg    9300
attgctcgtt caatgaccgt tgagcagttc aagggatact gcttcggtaa catcttaaag    9360
tacagactac gtgctggtaa gaagtcagag ttagcgtact tagagaaaga cctagcgaaa    9420
gcagacttct ataagaaact cttttgagaaa cataaggata aatgttatgc ataacttcaa    9480
gtcaacccca cctgccgaca gcctatctga tgacttcaca tcttgctcag agtggtgccg    9540
aaagatgtgg gaagagacat tcgacgatgc gtacatcaag ctgtatgaac tttggaaatc    9600
gagaggtcaa tgactatgtc aaacgtaaat acaggttcac ttagtgtgga caataagaag    9660
ttttgggcta ccgtagagtc ctcggagcat tccttcgagg ttccaatcta cgctgagacc    9720
ctagacgaag ctctggagtt agccgaatgg caatacgttc cggctggctt tgaggttact    9780
cgtgtgcgtc cttgtgtagc accgaagtaa tacgactcac tattagggaa gactccctct    9840
gagaaaccaa acgaaaccta aaggagatta acattatggc taagaagatt ttcacctctg    9900
cgctgggtac cgctgaacct tacgcttaca tcgccaagcc ggactacggc aacgaagagc    9960
gtggctttgg gaaccctcgt ggtgtctata agttgacct gactattccc aacaaagacc    10020
cgcgctgcca gcgtatggtc gatgaaatcg tgaagtgtca cgaagaggct tatgctgctg    10080
ccgttgagga atacgaagct aatccacctg ctgtagctcg tggtaagaaa ccgctgaaac    10140
cgtatgaggg tgacatgccg ttcttcgata cggtgacgg tacgactacc tttaagttca    10200
aatgctacgc gtctttccaa gacaagaaga ccaaagagac caagcacatc aatctggttg    10260
tggttgactc aaaaggtaag aagatggaag acgttccgat tatcggtggt ggctctaagc    10320
tgaaagttaa atattctctg gttccataca agtggaacac tgctgtaggt gcgagcgtta    10380
agctgcaact ggaatccgtg atgctggtcg aactggctac ctttggtggc ggtgaagacg    10440
attgggctga cgaagttgaa gagaacggct atgttgcctc tggttctgcc aaagcgagca    10500
aaccacgcga cgaagaaagc tgggacgaag acgacgaaga gtccgaggaa gcagacgaag    10560
acggagactt ctaagtggaa ctgcgggaga aaatccttga gcgaatcaag gtgacttcct    10620
ctgggtgttg ggagtggcag ggcgctacga acaataaagg gtacgggcag gtgtggtgca    10680
gcaataccgg aaaggttgtc tactgtcatc gcgtaatgtc taatgctccg aaaggttcta    10740
ccgtcctgca ctcctgtgat aatccattat gttgtaccc tgaacaccta tccataggaa    10800
ctccaaaaga gaactccact gacatggtaa ataagggtcg ctcacacaag gggtataaac    10860
tttcagacga agacgtaatg gcaatcatgg agtccagcga gtccaatgta tccttagctc    10920
gcacctatgg tgtctcccaa cagactattt gtgatatacg caaagggagg cgacatggca    10980
```

```
ggttacggcg ctaaaggaat ccgaaaggtt ggagcgtttc gctctggcct agaggacaag   11040
gtttcaaagc agttggaatc aaaaggtatt aaattcgagt atgaagagtg gaaagtgcct   11100
tatgtaattc cggcgagcaa tcacacttac actccagact tcttacttcc aaacggtata   11160
ttcgttgaga caaagggtct gtgggaaagc gatgatagaa agaagcactt attaattagg   11220
gagcagcacc ccgagctaga catccgtatt gtcttctcaa gctcacgtac taagttatac   11280
aaaggttctc caacgtctta tggagagttc tgcgaaaagc atggtattaa gttcgctgat   11340
aaactgatac ctgctgagtg gataaaggaa cccaagaagg aggtcccctt tgatagatta   11400
aaaaggaaag gaggaaagaa ataatggctc gtgtacagtt taaacaacgt gaatctactg   11460
acgcaatctt tgttcactgc tcggctacca agccaagtca gaatgttggt gtccgtgaga   11520
ttcgccagtg gcacaaagag cagggttggc tcgatgtggg ataccacttt atcatcaagc   11580
gagacggtac tgtggaggca ggacgagatg agatggctgt aggctctcac gctaagggtt   11640
acaaccacaa ctctatcggc gtctgccttg ttggtggtat cgacgataaa ggtaagttcg   11700
acgctaactt tacgccagcc caaatgcaat cccttcgctc actgcttgtc acactgctgg   11760
ctaagtacga aggcgctgtg cttcgcgccc atcatgaggt ggcgccgaag gcttgccctt   11820
cgttcgacct taagcgttgg tgggagaaga acgaactggt cacttctgac cgtggataat   11880
taattgaact cactaaaggg agaccacagc ggtttccctt tgttcgcatt ggaggtcaaa   11940
taatgcgcaa gtcttataaa caattctata aggctccgag gaggcatatc caagtgtggg   12000
aggcagccaa tgggcctata ccaaaaggtt attatataga ccacattgac ggcaatccac   12060
tcaacgacgc cttagacaat ctccgtctgg ctctcccaaa agaaaactca tggaacatga   12120
agactccaaa gagcaatacc tcaggactaa agggactgag ttggagcaag gaaagggaga   12180
tgtggagagg cactgtaaca gctgagggta acagcataa ctttcgtagt agagatctat   12240
tggaagtcgt tgcgtggatt tatagaacta ggagggaatt gcatggacaa ttcgcacgat   12300
tccgatagtg tatttctttta ccacattcct tgtgacaact gtgggagtag tgatgggaac   12360
tcgctgttct ctgacggaca cacgttctgc tacgtatgcg agaagtggac tgctggtaat   12420
gaagacacta agagagggc ttcaaaacgg aaaccctcag gaggtaaacc aatgacttac   12480
aacgtgtgga acttcgggga atccaatgga cgctactccg cgttaactgc gagaggaatc   12540
tccaaggaaa cctgtcagaa ggctggctac tggattgcca agtagacgg tgtgatgtac   12600
caagtggctg actatcggga ccagaacggc aacattgtga gtcagaaggt tcgagataaa   12660
gataagaact ttaagaccac tggtagtcac aagagtgacg ctctgttcgg gaagcacttg   12720
tggaatggtg gtaagaagat tgtcgttaca gaaggtgaaa tcgacatgct taccgtgatg   12780
gaacttcaag actgtaagta tcctgtagtg tcgttgggtc acggtgcctc tgccgctaag   12840
aagacatgcg ctgccaacta cgaatacttt gaccagttcg aacagattat cttaatgttc   12900
gatatggaca agcagggcg caaagcagtc gaagaggctg cacaggttct acctgctggt   12960
aaggtacgag tggcagttct tccgtgtaag gatgcaaacg agtgtcacct aaatggtcac   13020
gaccgtgaaa tcatggagca agtgtggaat gctggtcctt ggattcctga tggtgtggta   13080
tcggctcttt cgttacgtga acgaatccgt gagcacctat cgtccgagga atcagtaggt   13140
ttacttttca gtggctgcac tggtatcaac gataagacct taggtgcccg tggtggtgaa   13200
gtcattatgg tcacttccgg ttccggtatg ggtaagtcaa cgttcgtccg tcaacaagct   13260
ctacaatggg gcacagcgat gggcaagaag gtaggcttag cgatgcttga ggagtccgtt   13320
gaggagaccg ctgaggacct tataggtcta cacaaccgtg tccgactgag acaatccgac   13380
```

```
tcactaaaga gagagattat tgagaacggt aagttcgacc aatggttcga tgaactgttc   13440
ggcaacgata cgttccatct atatgactca ttcgccgagg ctgagacgga tagactgctc   13500
gctaagctgg cctacatgcg ctcaggcttg ggctgtgacg taatcattct agaccacatc   13560
tcaatcgtcg tatccgcttc tggtgaatcc gatgagcgta agatgattga caacctgatg   13620
accaagctca aagggttcgc taagtcaact ggggtggtgc tggtcgtaat tgtcaccttt   13680
aagaacccag acaaaggtaa agcacatgag gaaggtcgcc ccgtttctat tactgaccta   13740
cgtggttctg gcgcactacg ccaactatct gatactatta ttgcccttga gcgtaatcag   13800
caaggcgata tgcctaacct tgtcctcgtt cgtattctca agtgccgctt tactggtgat   13860
actggtatcg ctggctacat ggaatacaac aaggaaaccg gatggcttga accatcaagt   13920
tactcagggg aagaagagtc acactcagag tcaacagact ggtccaacga cactgacttc   13980
tgacaggatt cttgatgact ttccagacga ctacgagaag tttcgctgga gagtcccatt   14040
ctaatacgac tcactaaagg agacacacca tgttcaaact gattaagaag ttaggccaac   14100
tgctggttcg tatgtacaac gtggaagcca agcgactgaa cgatgaggct cgtaaagagg   14160
ccacacagtc acgcgctctg gcgattcgct ccaacgaact ggctgacagt gcatccacta   14220
aagttaccga ggctgcccgt gtggcaaacc aagctcaaca gctttccaaa ttctttgagt   14280
aatcaaacag gagaaaccat tatgtctaac gtagctgaaa ctatccgtct atccgataca   14340
gctgaccagt ggaaccgtcg agtccacatc aacgttcgca acggtaaggc gactatggtt   14400
taccgctgga aggactctaa gtcctctaag aatcacactc agcgtatgac gttgacagat   14460
gagcaagcac tgcgtctggt caatgcgctt accaaagctg ccgtgacagc aattcatgaa   14520
gctggtcgcg tcaatgaagc tatggctatc ctcgacaaga ttgataacta agagtggtat   14580
cctcaaggtc gccaaagtgg tggccttcat gaatactatt cgactcacta taggagatat   14640
taccatgcgt gaccctaaag ttatccaagc agaaatcgct aaactggaag ctgaactgga   14700
ggacgttaag taccatgaag ctaagactcg ctccgctgtt cacatcttga agaacttagg   14760
ctggacttgg acaagacaga ctggctggaa gaaaccagaa gttaccaagc tgagtcataa   14820
ggtgttcgat aaggacacta tgacccacat caaggctggt gattgggtta aggttgacat   14880
gggagttgtt ggtggatacg gctacgtccg ctcagttagt ggcaaatatg cacaagtgtc   14940
atacatcaca ggtgttactc cacgcggtgc aatcgttgcc gataagacca acatgattca   15000
cacaggtttc ttgacagttg tttcatatga agagattgtt aagtcacgat aatcaatagg   15060
agaaatcaat atgatcgttt ctgacatcga agctaacgcc ctcttagaga gcgtcactaa   15120
gttccactgc ggggttatct acgactactc caccgctgag tacgtaagct accgtccgag   15180
tgacttcggt gcgtatctgg atgcgctgga agccgaggtt gcacgaggcg gtcttattgt   15240
gttccacaac ggtcacaagt atgacgttcc tgcattgacc aaaactggcaa agttgcaatt   15300 gaaccgagag ttccaccttc ctcgtgagaa ctgtattgac acccttgtgt tgtcacgttt   15360
gattcattcc aacctcaagg acaccgatat gggtcttctg cgttccggca agttgcccgg   15420
aaaacgcttt gggtctcacg ctttggaggc gtggggttat cgcttaggcg agatgaaggg   15480
tgaatacaaa gacgactta agcgtatgct tgaagagcag ggtgaagaat acgttgacgg   15540
aatggagtgg tggaacttca acgaagagat gatggactat aacgttcagg acgttgtggt   15600
aactaaagct ctccttgaga agctactctc tgacaaacat tacttccctc ctgagattga   15660
ctttacggac gtaggataca ctacgttctg gtcagaatcc cttgaggccg ttgacattga   15720
```

-continued

```
acatcgtgct gcatggctgc tcgctaaaca agagcgcaac gggttcccgt ttgacacaaa  15780
agcaatcgaa gagttgtacg tagagttagc tgctcgccgc tctgagttgc tccgtaaatt  15840
gaccgaaacg ttcggctcgt ggtatcagcc taaaggtggc actgagatgt tctgccatcc  15900
gcgaacaggt aagccactac ctaaatacccc tcgcattaag acacctaaag ttggtggtat  15960
ctttaagaag cctaagaaca aggcacagcg agaaggccgt gagccttgcg aacttgatac  16020
ccgcgagtac gttgctggtg ctccttacac cccagttgaa catgttgtgt ttaacccttc  16080
gtctcgtgac cacattcaga agaaactcca agaggctggg tgggtcccga ccaagtacac  16140
cgataagggt gctcctgtgg tggacgatga ggtactcgaa ggagtacgtg tagatgaccc  16200
tgagaagcaa gccgctatcg acctcattaa agagtacttg atgattcaga agcgaatcgg  16260
acagtctgct gagggagaca aagcatggct tcgttatgtt gctgaggatg gtaagattca  16320
tggttctgtt aaccctaatg gagcagttac gggtcgtgcg acccatgcgt tcccaaacct  16380
tgcgcaaatt ccgggtgtac gttctcctta tggagagcag tgtcgcgctg cttttggcgc  16440
tgagcaccat ttggatggga taactggtaa gccttgggtt caggctggca tcgacgcatc  16500
cggtcttgag ctacgctgct tggctcactt catggctcgc tttgataacg gcgagtacgc  16560
tcacgagatt cttaacggcg acatccacac taagaaccag atagctgctg aactacctac  16620
ccgagataac gctaagacgt tcatctatgg gttcctctat ggtgctggtg atgagaagat  16680
tggacagatt gttggtgctg gtaaagagcg cggtaaggaa ctcaagaaga aattccttga  16740
gaacaccccc gcgattgcag cactccgcga gtctatccaa cagacacttg tcgagtcctc  16800
tcaatgggta gctggtgagc aacaagtcaa gtggaaacgc cgctggatta aggtctggaa  16860
tggtcgtaag gtacacgttc gtagtcctca cgctgccttg aatacccttac tgcaatctgc  16920 tggtgctctc atctgcaaac tgtggattat caagaccgaa gagatgctcg tagagaaagg  16980
cttgaagcat ggctgggatg ggactttgc gtacatggca tgggtacatg atgaaatcca  17040
agtaggctgc cgtaccgaag agattgctca ggtggtcatt gagaccgcac aagaagcgat  17100
gcgctgggtt ggagaccact ggaacttccg gtgtcttctg gataccgaag gtaagatggg  17160
tcctaattgg gcgatttgcc actgatacag gaggctactc atgaacgaaa gacacttaac  17220
aggtgctgct tctgaaatgc tagtagccta caaatttacc aaagctgggt acactgtcta  17280
ttaccctatg ctgactcaga gtaaagagga cttggttgta tgtaaggatg gtaaatttag  17340
taaggttcag gttaaaacag ccacaacggt tcaaaccaac acaggagatg ccaagcaggt  17400
taggctaggt ggatgcggta ggtccgaata taaggatgga gactttgaca ttcttgcggt  17460
tgtggttgac gaagatgtgc ttatttcac atgggacgaa gtaaaaggta agacatccat  17520
gtgtgtcggc aagagaaaca aaggcataaa actataggag aaattattat ggctatgaca  17580
aagaaattta agtgtccctt cgacgttacc gcaaagatgt cgtctgacgt tcaggcaatc  17640
ttagagaaag atatgctgca tctatgtaag caggtcggct caggtgcgat tgtcccccaat  17700 ggtaaacaga aggaaatgat tgtccagttc ctgacacacg gtatgaaggg attgatgaca  17760
ttcgtagtac gtacatcatt tcgtgaggcc attaaggaca tgcacgaaga gtatgcagat  17820
aaggactctt tcaaacaatc tcctgcaaca gtacgggagg tgttctgatg tctgactacc  17880
tgaaagtgct gcaagcaatc aaaagttgcc ctaagacttt ccagtccaac tatgtacgga  17940
acaatgcgag cctcgtagcg gaggccgctt cccgtggtca catctcgtgc ctgactacta  18000
gtggacgtaa cggtggcgct tgggaaatca ctgcttccgg tactcgcttt ctgaaacgaa  18060
tgggaggatg tgtctaatgt ctcgtgacct tgtgactatt ccacgcgatg tgtggaacga  18120
```

```
tatacagggc tacatcgact ctctggaacg tgagaacgat agccttaaga atcaactaat    18180
ggaagctgac gaatacgtag cggaactaga ggagaaactt aatggcactt cttgaccttA    18240
aacaattcta tgagttacgt gaaggctgcg acgacaaggg tatccttgtg atggacggcg    18300
actggctggt cttccaagct atgagtgctg ctgagtttga tgcctcttgg gaggaagaga    18360
tttggcaccg atgctgtgac cacgctaagg cccgtcagat tcttgaggat tccattaagt    18420
cctacgagac ccgtaagaag gcttgggcag gtgctccaat tgtccttgcg ttcaccgata    18480
gtgttaactg gcgtaaagaa ctggttgacc cgaactataa ggctaaccgt aaggccgtga    18540
agaaacctgt agggtacttt gagttccttg atgctctctt tgagcgcgaa gagttctatt    18600
gcatccgtga gcctatgctt gagggtgatg acgttatggg agttattgct tccaatccgt    18660
ctgccttcgg tgctcgtaag gctgtaatca tctcttgcga taaggacttt aagaccatcc    18720
ctaactgtga cttcctgtgg tgtaccactg gtaacatcct gactcagacc gaagagtccg    18780
ctgactggtg gcacctcttc cagaccatca agggtgacat cactgatggt tactcaggga    18840
ttgctggatg gggtgatacc gccgaggact tcttgaataa cccgttcata accgagccta    18900
aaacgtctgt gcttaagtcc ggtaagaaca aaggccaaga ggttactaaa tgggttaaac    18960
gcgaccctga gcctcatgag acgctttggg actgcattaa gtccattggc gcgaaggctg    19020
gtatgaccga agaggatatt atcaagcagg gccaaatggc tcgaatccta cggttcaacg    19080
agtacaactt tattgacaag gagatttacc tgtggagacc gtagcgtata ttggtctggg    19140
tctttgtgtt ctcggagtgt gcctcatttc gtggggcctt tgggacttag ccagaataat    19200
caagtcgtta cacgacacta agtgataaac tcaaggtccc taaattaata cgactcacta    19260
tagggagata ggggccttta cgattattac tttaagattt aactctaaga ggaatcttta    19320
ttatgttaac acctattaac caattactta agaaccctaa cgatattcca gatgtacctc    19380
gtgcaaccgc tgagtatcta caggttcgat tcaactatgc gtacctcgaa gcgtctggtc    19440
atataggact tatgcgtgct aatggttgta gtgaggccca catcttgggt ttcattcagg    19500
gcctacagta tgcctctaac gtcattgacg agattgagtt acgcaaggaa caactaagag    19560
atgatgggga ggattgacac tatgtgtttc tcaccgaaaa ttaaaactcc gaagatggat    19620
accaatcaga ttcgagccgt tgagccagcg cctctgaccc aagaagtgtc aagcgtggag    19680
ttcggtgggt cttctgatga gacggatacc gagggcaccg aagtgtctgg acgcaaaggc    19740
ctcaaggtcg aacgtgatga ttccgtagcg aagtctaaag ccagcggcaa tggctccgct    19800
cgtatgaaat cttccatccg taagtccgca tttggaggta agaagtgatg tctgagttca    19860
catgtgtgga ggctaagagt cgcttccgtg caatccggtg gactgtggaa cacct tgggt    19920 tgcctaaagg attcgaagga cactttgtgg gctacagcct ctacgtagac gaagtgatgg    19980
acatgtctgg ttgccgtgaa gagtacattc tggactctac cggaaaacat gtagcgtact    20040
tcgcgtggtg cgtaagctgt gacattcacc acaaaggaga cattctggat gtaacgtccg    20100
ttgtcattaa tcctgaggca gactctaagg gcttacagcg attcctagcg aaacgcttta    20160
agtaccttgc ggaactccac gattgcgatt gggtgtctcg ttgtaagcat gaaggcgaga    20220
caatgcgtgt atactttaag gaggtataag ttatgggtaa gaaagttaag aaggccgtga    20280
agaaagtcac caagtccgtt aagaaagtcg ttaaggaagg ggctcgtccg gttaaacagg    20340
ttgctggcgg tctagctggt ctggctggtg gtactggtga agcacagatg gtggaagtac    20400
cacaagctgc cgcacagatt gttgacgtac ctgagaaaga ggtttccact gaggacgaag    20460
```

```
cacagacaga aagcggacgc aagaaagctc gtgctggcgg taagaaatcc ttgagtgtag   20520
cccgtagctc cggtggcggt atcaacattt aatcaggagg ttatcgtgga agactgcatt   20580
gaatggaccg gaggtgtcaa ctctaagggt tatggtcgta agtgggttaa tggtaaactt   20640
gtgactccac ataggcacat ctatgaggag acatatggtc cagttccaac aggaattgtg   20700
gtgatgcata tctgcgataa ccctaggtgc tataacataa agcaccttac gcttggaact   20760
ccaaaggata attccgagga catggttacc aaaggtagac aggctaaagg agaggaacta   20820
agcaagaaac ttacagagtc agacgttctc gctatacgct cttcaacctt aagccaccgc   20880
tccttaggag aactgtatgg agtcagtcaa tcaaccataa cgcgaatact acagcgtaag   20940
acatggagac acatttaatg gctgagaaac gaacaggact tgcggaggat ggcgcaaagt   21000
ctgtctatga gcgtttaaag aacgaccgtg ctccctatga gacacgcgct cagaattgcg   21060
ctcaatatac catcccatca ttgttcccta aggactccga taacgcctct acagattatc   21120
aaactccgtg gcaagccgtg ggcgctcgtg gtctgaacaa tctagcctct aagctcatgc   21180
tggctctatt ccctatgcag acttggatgc gacttactat atctgaatat gaagcaaagc   21240
agttactgag cgaccccgat ggactcgcta aggtcgatga gggcctctcg atggtagagc   21300
gtatcatcat gaactacatt gagtctaaca gttaccgcgt gactctcttt gaggctctca   21360
aacagttagt cgtagctggt aacgtcctgc tgtacctacc ggaaccggaa gggtcaaact   21420
ataatcccat gaagctgtac cgattgtctt cttatgtggt ccaacgagac gcattcggca   21480
acgttctgca aatggtgact cgtgaccaga tagcttttgg tgctctccct gaggacatcc   21540
gtaaggctgt agaaggtcaa ggtggtgaga agaaagctga tgagacaatc gacgtgtaca   21600
ctcacatcta tctggatgag gactcaggtg aatacctccg atacgaagag gtcgagggta   21660
tggaagtcca aggctccgat gggacttatc ctaaagaggc ttgcccatac atcccgattc   21720
ggatggtcag actagatggt gaatcctacg gtcgttcgta cattgaggaa tacttaggtg   21780
acttacggtc ccttgaaaat ctccaagagg ctatcgtcaa gatgtccatg attagctcta   21840
aggttatcgg cttagtgaat cctgctggta tcacccagcc acgccgactg accaaagctc   21900
agactggtga cttcgttact ggtcgtccag aagacatctc gttcctccaa ctggagaagc   21960
aagcagactt tactgtagct aaagccgtaa gtgacgctat cgaggctcgc ctttcgtttg   22020
cctttatgtt gaactctgcg gttcagcgta caggtgaacg tgtgaccgcc gaagagattc   22080
ggtatgtagc ttctgaactt gaagatactt taggtggtgt ctactctatc ctttctcaag   22140
aattacaatt gcctctggta cgagtgctct tgaagcaact acaagccacg caacagattc   22200
ctgagttacc taaggaagcc gtagagccaa ccattagtac aggtctggaa gcaattggtc   22260
gaggacaaga ccttgataag ctggagcggt gtgtcactgc gtgggctgca ctggcaccta   22320
tgcgggacga ccctgatatt aaccttgcga tgattaagtt acgtattgcc aacgctatcg   22380
gtattgacac ttctggtatt ctactcaccg aagaacagaa gcaacagaag atggcccaac   22440
agtctatgca aatgggtatg gataatggtg ctgctgcgct ggctcaaggt atggctgcac   22500
aagctacagc ttcacctgag gctatggctg ctgccgctga ttccgtaggt ttacagccgg   22560
gaatttaata cgactcacta tagggagacc tcatctttga aatgagcgat gacaagaggt   22620
tggagtcctc ggtcttcctg tagttcaact ttaaggagac aataataatg gctgaatcta   22680
atgcagacgt atatgcatct tttggcgtga actccgctgt gatgtctggt ggttccgttg   22740
aggaacatga gcagaacatg ctggctcttg atgttgctgc ccgtgatggc gatgatgcaa   22800
tcgagttagc gtcagacgaa gtggaaacag aacgtgacct gtatgacaac tctgacccgt   22860
```

```
tcggtcaaga ggatgacgaa ggccgcattc aggttcgtat cggtgatggc tctgagccga   22920
ccgatgtgga cactggagaa gaaggcgttg agggcaccga aggttccgaa gagtttaccc   22980
cactgggcga gactccagaa gaactggtag ctgcctctga gcaacttggt gagcacgaag   23040
agggcttcca agagatgatt aacattgctg ctgagcgtgg catgagtgtc gagaccattg   23100
aggctatcca gcgtgagtac gaggagaacg aagagttgtc cgccgagtcc tacgctaagc   23160
tggctgaaat tggctacacg aaggctttca ttgactcgta tatccgtggt caagaagctc   23220
tggtggagca gtacgtaaac agtgtcattg agtacgctgg tggtcgtgaa cgttttgatg   23280
cactgtataa ccaccttgag acgcacaacc ctgaggctgc acagtcgctg gataatgcgt   23340
tgaccaatcg tgacttagcg accgttaagg ctatcatcaa cttggctggt gagtctcgcg   23400
ctaaggcgtt cggtcgtaag ccaactcgta gtgtgactaa tcgtgctatt ccggctaaac   23460
ctcaggctac caagcgtgaa ggctttgcgg accgtagcga gatgattaaa gctatgagtg   23520
accctcggta tcgcacagat gccaactatc gtcgtcaagt cgaacagaaa gtaatcgatt   23580
cgaacttctg atagacttcg aaattaatac gactcactat agggagacca caacggtttc   23640
cctctagaaa taattttgtt taactttaag aaggagatat acatatggag gagattcaac   23700
atggtcttca cactcgaaga tttcgttggg gactggcgac agacagccgg ctacaacctg   23760
gaccaagtcc ttgaacaggg aggtgtgtcc agtttgtttc agaatctcgg ggtgtccgta   23820
actccgatcc aaaggattgt cctgagcggt gaaaatgggc tgaagatcga catccatgtc   23880
atcatcccgt atgaaggtct gagcggcgac caaatgggcc agatcgaaaa aattttaag    23940 gtggtgtacc ctgtggatga tcatcacttt aaggtgatcc tgcactatgg cacactggta   24000
atcgacgggg ttacgccgaa catgatcgac tatttcggac ggccgtatga aggcatcgcc   24060
gtgttcgacg gcaaaaagat cactgtaaca gggaccctgt ggaacggcaa caaattatc    24120 gacgagcgcc tgatcaaccc cgacggctcc ctgctgttcc gagtaaccat caacggagtg   24180
accggctggc ggctgtgcga acgcattctg gcgtaaagga ggtaaacata tgaccatgat   24240
tacggattca ctggccgtcg tttttacaacg tcgtgactgg gaaaaccctg gcgttaccca   24300
acttaatcgc cttgcagcac atccccctt cgccagctgg cgtaatagcg aagaggcccg    24360
caccgatcgc ccttcccaac agttgcgcag cctgaatggc gaatggcatg actggtggac   24420
agcaaatggg tactaaccaa ggtaaaggtg tagttgctgc tggagataaa ctggcgttgt   24480
tcttgaaggt atttggcggt gaagtcctga ctgcgttcgc tcgtacctcc gtgaccactt   24540
ctcgccacat ggtacgttcc atctccagcg gtaaatccgc tcagttccct gttctgggtc   24600
gcactcaggc agcgtatctg gctccgggcg agaacctcga cgataaacgt aaggacatca   24660
aacacaccga gaaggtaatc accattgacg gtctcctgac ggctgacgtt ctgatttatg   24720
atattgagga cgcgatgaac cactacgacg ttcgctctga gtataccctct cagttgggtg   24780 aatctctggc gatggctgcg gatggtgcgg ttctggctga gattgccggt ctgtgtaacg   24840
tggaaagcaa atataatgag aacatcgagg gcttaggtac tgctaccgta attgagacca   24900
ctcagaacaa ggccgcactt accgaccaag ttgcgctggg taaggagatt attgcggctc   24960
tgactaaggc tcgtgcggct ctgaccaaga actatgttcc ggctgctgac cgtgtgttct   25020
actgtgaccc agatagctac tctgcgattc tggcagcact gatgccgaac gcagcaaact   25080
acgctgctct gattgaccct gagaagggtt ctatccgcaa cgttatgggc tttgaggttg   25140
tagaagttcc gcacctcacc gctggtggtg ctggtaccgc tcgtgagggc actactggtc   25200
```

```
agaagcacgt cttccctgcc aataaaggtg agggtaatgt caaggttgct aaggacaacg    25260
ttatcggcct gttcatgcac cgctctgcgg taggtactgt taagctgcgt gacttggctc    25320
tggagcgcgc tcgccgtgct aacttccaag cggaccagat tatcgctaag tacgcaatgg    25380
gccacggtgg tcttcgccca gaagctgctg gtgcagtggt tttcaaagtg gagtaatgct    25440
gggggtggcc tcaacggtcg ctgctagtcc cgaagaggcg agtgttactt caacagaaga    25500
aaccttaacg ccagcacagg aggccgcacg cacccgcgct gctaacaaag cccgaaagga    25560
agctgagttg gctgctgcca ccgctgagca ataactagca taaccccttg gggcctctaa    25620
acgggtcttg aggggttttt tgctgaaagg aggaactata tgcgctcata cgatatgaac    25680
gttgagactg ccgctgagtt atcagctgtg aacgacattc tggcgtctat cggtgaacct    25740
ccggtatcaa cgctggaagg tgacgctaac gcagatgcag cgaacgctcg gcgtattctc    25800
aacaagatta accgacagat tcaatctcgt ggatggacgt tcaacattga ggaaggcata    25860
acgctactac ctgatgttta ctccaacctg attgtataca gtgacgacta tttatcccta    25920
atgtctactt ccggtcaatc catctacgtt aaccgaggtg gctatgtgta tgaccgaacg    25980
agtcaatcag accgctttga ctctggtatt actgtgaaca ttattcgtct ccgcgactac    26040
gatgagatgc ctgagtgctt ccgttactgg attgtcacca aggcttcccg tcagttcaac    26100
aaccgattct ttggggcacc ggaagtagag ggtgtactcc aagaagagga agatgaggct    26160
agacgtctct gcatggagta tgagatggac tacggtgggt acaatatgct ggatggagat    26220
gcgttcactt ctggtctact gactcgctaa cattaataaa taaggaggct ctaatggcac    26280
tcattagcca atcaatcaag aacttgaagg gtggtatcag ccaacagcct gacatccttc    26340
gttatccaga ccaagggtca cgccaagtta acggttggtc ttcggagacc gagggcctcc    26400
aaaagcgtcc acctcttgtt ttcttaaata cacttggaga caacggtgcg ttaggtcaag    26460
ctccgtacat ccacctgatt aaccgagatg agcacgaaca gtattacgct gtgttcactg    26520
gtagcggaat ccgagtgttc gacctttctg gtaacgagaa gcaagttagg tatcctaacg    26580
gttccaacta catcaagacc gctaatccac gtaacgacct gcgaatggtt actgtagcag    26640
actatacgtt catcgttaac cgtaacgttg ttgcacagaa gaacacaaag tctgtcaact    26700
taccgaatta caaccctaat caagacggat tgattaacgt tcgtggtggt cagtatggta    26760
gggaactaat tgtacacatt aacggtaaag acgttgcgaa gtataagata ccagatggta    26820
gtcaacctga acacgtaaac aatacggatg cccaatggtt agctgaagag ttagccaagc    26880
agatgcgcac taacttgtct gattggactg taaatgtagg gcaagggttc atccatgtga    26940
ccgcacctag tggtcaacag attgactcct tcacgactaa agatggctac gcagaccagt    27000
tgattaaccc tgtgacccac tacgctcagt cgttctctaa gctgccacct aatgctccta    27060
acggctacat ggtgaaaatc gtaggggacg cctctaagtc tgccgaccag tattacgttc    27120
ggtatgacgc tgagcggaaa gtttggactg agactttagg ttggaacact gaggaccaag    27180
ttctatggga aaccatgcca cacgctcttg tgcgagccgc tgacggtaat ttcgacttca    27240
agtggcttga gtggtctcct aagtcttgtg gtgacgttga caccaaccct tggccttctt    27300
ttgttggttc aagtattaac gatgtgttct cttccgtaa ccgcttagga ttccttagtg    27360
gggagaacat catattgagt cgtacagcca aatacttcaa cttctaccct gcgtccattg    27420
cgaaccttag tgatgacgac cctatagacg tagctgtgag taccaaccga atagcaatcc    27480
ttaagtacgc cgttccgttc tcagaagagt tactcatctg gtccgatgaa gcacaattcg    27540
tcctgactgc ctcgggtact ctcacatcta agtcggttga gttgaaccta acgacccagt    27600
```

```
ttgacgtaca ggaccgagcg agaccttttg ggattgggcg taatgtctac tttgctagtc    27660
cgaggtccag cttcacgtcc atccacaggt actacgctgt gcaggatgtc agttccgtta    27720
agaatgctga ggacattaca tcacacgttc ctaactacat ccctaatggt gtgttcagta    27780
tttgcggaag tggtacggaa aacttctgtt cggtactatc tcacggggac cctagtaaaa    27840
tcttcatgta caaattcctg tacctgaacg aagagttaag gcaacagtcg tggtctcatt    27900
gggactttgg ggaaaacgta caggttctag cttgtcagag tatcagctca gatatgtatg    27960
tgattcttcg caatgagttc aatacgttcc tagctagaat ctctttcact aagaacgcca    28020
ttgacttaca gggagaaccc tatcgtgcct ttatggacat gaagattcga tacacgattc    28080
ctagtggaac atacaacgat gacacattca ctacctctat tcatattcca acaatttatg    28140
gtgcaaactt cgggagggge aaaatcactg tattggagcc tgatggtaag ataaccgtgt    28200
ttgagcaacc tacggctggg tggaatagcg acccttggct gagactcagc ggtaacttgg    28260
agggacgcat ggtgtacatt gggttcaaca ttaacttcgt atatgagttc tctaagttcc    28320
tcatcaagca gactgccgac gacgggtcta cctccacgga agacattggg cgcttacagt    28380
tacgccgagc gtgggttaac tacgagaact ctggtacgtt tgacatttat gttgagaacc    28440
aatcgtctaa ctggaagtac acaatggctg gtgcccgatt aggctctaac actctgaggg    28500
ctgggagact gaacttaggg accggacaat atcgattccc tgtggttggt aacgccaagt    28560
tcaacactgt atacatcttg tcagatgaga ctacccctct gaacatcatt gggtgtggct    28620
gggaaggtaa ctacttacgg agaagttccg gtatttaatt aaatattctc cctgtggtgg    28680
ctcgaaatta atacgactca ctatagggag aacaatacga ctacgggagg gttttcttat    28740
gatgactata agacctacta aaagtacaga ctttgaggta ttcactccgg ctcaccatga    28800
cattcttgaa gctaaggctg ctggtattga gccgagtttc cctgatgctt ccgagtgtgt    28860
cacgttgagc ctctatgggt tccctctagc tatcggtggt aactgcgggg accagtgctg    28920
gttcgttacg agcgaccaag tgtggcgact tagtggaaag gctaagcgaa agttccgtaa    28980
gttaatcatg gagtatcgcg ataagatgct tgagaagtat gatactcttt ggaattacgt    29040
atgggtaggc aatacgtccc acattcgttt cctcaagact atcggtgcgg tattccatga    29100
agagtacaca cgagatggtc aatttcagtt atttacaatc acgaaaggag gataaccata    29160
tgtgttgggc agccgcaata cctatcgcta tatctggcgc tcaggctatc agtggtcaga    29220
acgctcaggc caaaatgatt gccgctcaga ccgctgctgg tcgtcgtcaa gctatggaaa    29280
tcatgaggca gacgaacatc cagaatgctg acctatcgtt gcaagctcga agtaaacttg    29340
aggaagcgtc cgccgagttg acctcacaga acatgcagaa ggtccaagct attgggtcta    29400
tccgagcggg tatcggagag agtatgcttg aaggttcctc aatggaccgc attaagcgag    29460
tcacagaagg acagttcatt cgggaagcca atatggtaac tgagaactat cgccgtgact    29520
accaagcaat cttcgcacag caacttggtg gtactcaaag tgctgcaagt cagattgacg    29580
aaatctataa gagcgaacag aaacagaaga gtaagctaca gatggttctg gacccactgg    29640
ctatcatggg gtcttccgct gcgagtgctt acgcatccgg tgcgttcgac tctaagtcca    29700
caactaaggc acctattgtt gccgctaaag gaaccaagac ggggaggtaa tgagctatga    29760
gtaaaattga atctgcccct caagcggcac aaccgggact ctctcggtta cgtggtggtg    29820
ctggaggtat gggctatcgt gcagcaacca ctcaggccga acagccaagg tcaagcctat    29880
tggacaccat tggtcggttc gctaaggctg gtgccgatat gtataccgct aaggaacaac    29940
```

```
gagcacgaga cctagctgat gaacgctcta acgagattat ccgtaagctg acccctgagc    30000
aacgtcgaga agctctcaac aacgggaccc ttctgtatca ggatgaccca tacgctatgg    30060
aagcactccg agtcaagact ggtcgtaacg ctgcgtatct tgtggacgat gacgttatgc    30120
agaagataaa agagggtgtc ttccgtactc gcgaagagat ggaagagtat cgccatagtc    30180
gccttcaaga gggcgctaag gtatacgctg agcagttcgg catcgaccct gaggacgttg    30240
attatcagcg tggtttcaac ggggacatta ccgagcgtaa catctcgctg tatggtgcgc    30300
atgataactt cttgagccag caagctcaga agggcgctat catgaacagc cgagtggaac    30360
tcaacggtgt ccttcaagac cctgatatgc tgcgtcgtcc agactctgct gacttctttg    30420
agaagtatat cgacaacggt ctggttactg gcgcaatccc atctgatgct caagccacac    30480
agcttataag ccaagcgttc agtgacgctt ctagccgtgc tggtggtgct gacttcctga    30540
tgcgagtcgg tgacaagaag gtaacactta acggagccac tacgacttac cgagagttga    30600
ttggtgagga acagtggaac gctctcatgg tcacagcaca acgttctcag tttgagactg    30660
acgcgaagct gaacgagcag tatcgcttga agattaactc tgcgctgaac caagaggacc    30720
caaggacagc ttgggagatg cttcaaggta tcaaggctga actagataag gtccaacctg    30780
atgagcagat gacaccacaa cgtgagtggc taatctccgc acaggaacaa gttcagaatc    30840
agatgaacgc atggacgaaa gctcaggcca aggctctgga cgattccatg aagtcaatga    30900
acaaacttga cgtaatcgac aagcaattcc agaagcgaat caacggtgag tgggtctcaa    30960
cggattttaa ggatatgcca gtcaacgaga acactggtga gttcaagcat agcgatatgg    31020
ttaactacgc caataagaag ctcgctgaga ttgacagtat ggacattcca gacggtgcca    31080
aggatgctat gaagttgaag taccttcaag cggactctaa ggacggagca ttccgtacag    31140
ccatcggaac catggtcact gacgctggtc aagagtggtc tgccgctgtg attaacggta    31200
agttaccaga acgaacccca gctatggatg ctctgcgcag aatccgcaat gctgaccctc    31260
agttgattgc tgcgctatac ccagaccaag ctgagctatt cctgacgatg gacatgatgg    31320
acaagcaggg tattgaccct caggttattc ttgatgccga ccgactgact gttaagcggt    31380
ccaaagagca acgctttgag gatgataaag cattcgagtc tgcactgaat gcatctaagg    31440
ctcctgagat tgcccgtatg ccagcgtcac tgcgcgaatc tgcacgtaag atttatgact    31500
ccgttaagta tcgctcgggg aacgaaagca tggctatgga gcagatgacc aagttcctta    31560
aggaatctac ctacacgttc actggtgatg atgttgacgg tgataccgtt ggtgtgattc    31620
ctaagaatat gatgcaggtt aactctgacc cgaaatcatg ggagcaaggt cgggatattc    31680
tggaggaagc acgtaaggga atcattgcga gcaacccttg gataaccaat aagcaactga    31740
ccatgtattc tcaaggtgac tccatttacc ttatggacac cacaggtcaa gtcagagtcc    31800
gatacgacaa agagttactc tcgaaggtct ggagtgagaa ccagaagaaa ctcgaagaga    31860
aagctcgtga gaaggctctg gctgatgtga acaagcgagc acctatagtt gccgctacga    31920
aggcccgtga agctgctgct aaacgagtcc gagagaaacg taaacagact cctaagttca    31980
tctacggacg taaggagtaa ctaaaggcta cataaggagg ccctaaatgg ataagtacga    32040
taagaacgta ccaagtgatt atgatggtct gttccaaaag gctgctgatg caacgggggt    32100
ctcttatgac cttttacgta agtcgcttg  acagaatca cgatttgtgc ctacagcaaa    32160
atctaagact ggaccattag gcatgatgca atttaccaag gcaaccgcta aggccctcgg    32220
tctgcgagtt accgatggtc cagacgacga ccgactgaac cctgagttag ctattaatgc    32280
tgccgctaag caacttgcag gtctggtagg gaagtttgat ggcgatgaac tcaaagctgc    32340
```

```
ccttgcgtac aaccaaggcg agggacgctt gggtaatcca caacttgagg cgtactctaa   32400
gggagacttc gcatcaatct ctgaggaggg acgtaactac atgcgtaacc ttctggatgt   32460
tgctaagtca cctatggctg gacagttgga aacttttggt ggcataaccc caaagggtaa   32520
aggcattccg gctgaggtag gattggctgg aattggtcac aagcagaaag taacacagga   32580
acttcctgag tccacaagtt ttgacgttaa gggtatcgaa caggaggcta cggcgaaacc   32640
attcgccaag gacttttggg agacccacgg agaaacactt gacgagtaca acagtcgttc   32700
aaccttcttc ggattcaaaa atgctgccga agctgaactc tccaactcag tcgctgggat   32760
ggctttccgt gctggtcgtc tcgataatgg ttttgatgtg tttaaagaca ccattacgcc   32820
gactcgctgg aactctcaca tctggactcc agaggagtta gagaagattc gaacagaggt   32880
taagaaccct gcgtacatca acgttgtaac tggtggttcc cctgagaacc tcgatgacct   32940
cattaaattg gctaacgaga actttgagaa tgactcccgc gctgccgagg ctggcctagg   33000
tgccaaactg agtgctggta ttattggtgc tggtgtggac ccgcttagct atgttcctat   33060
ggtcggtgtc actggtaagg gctttaagtt aatcaataag gctcttgtag ttggtgccga   33120
aagtgctgct ctgaacgttg catccgaagg tctccgtacc tccgtagctg gtggtgacgc   33180
agactatgcg ggtgctgcct taggtggctt tgtgtttggc gcaggcatgt ctgcaatcag   33240
tgacgctgta gctgctggac tgaaacgcag taaaccagaa gctgagttcg acaatgagtt   33300
catcggtcct atgatgcgat tggaagcccg tgagacagca cgaaacgcca actctgcgga   33360
cctctctcgg atgaacactg agaacatgaa gtttgaaggt gaacataatg gtgtcccttta  33420 tgaggactta ccaacagaga gaggtgccgt ggtgttacat gatggctccg ttctaagtgc   33480
aagcaaccca atcaacccta agactctaaa agagttctcc gaggttgacc ctgagaaggc   33540
tgcgcgagga atcaaactgg ctgggttcac cgagattggc ttgaagacct tggggtctga   33600
cgatgctgac atccgtagag tggctatcga cctcgttcgc tctcctactg gtatgcagtc   33660
tggtgcctca ggtaagttcg gtgcaacagc ttctgacatc catgagagac ttcatggtac   33720
tgaccagcgt acttataatg acttgtacaa agcaatgtct gacgctatga aagaccctga   33780
gttctctact ggcggcgcta agatgtcccg tgaagaaact cgatacacta tctaccgtag   33840
agcggcacta gctattgagc gtccagaact acagaaggca ctcactccgt ctgagagaat   33900
cgttatggac atcattaagc gtcactttga caccaagcgt gaacttatgg aaacccagc   33960 aatattcggt aacacaaagg ctgtgagtat cttccctgag agtcgccaca aaggtactta   34020
cgttcctcac gtatatgacc gtcatgccaa ggcgctgatg attcaacgct acggtgccga   34080
aggtttgcag gaagggattg cccgctcatg gatgaacagc tacgtctcca gacctgaggt   34140
caaggccaga gtcgatgaga tgcttaagga attacgcggg gtgaaggaag taacaccaga   34200
gatggtagag aagtacgcta tggataaggc ttatggtatc tcccactcag accagttcac   34260
caacagttcc ataatagaag agaacattga gggcttagta ggtatcgaga ataactcatt   34320
ccttgaggca cgtaacttgt ttgattcgga cctatccatc actatgccag acggacagca   34380
attctcagtg aatgacctaa gggacttcga tatgttccgc atcatgccag cgtatgaccg   34440
ccgtgtcaat ggtgacatcg ccatcatggg gtctactggt aaaaccacta aggaacttaa   34500
ggatgagatt ttggctctca aagcgaaagc tgagggagac ggtaagaaga ctggcgaggt   34560
acatgcttta atggataccg ttaagattct tactggtcgt gctagacgca atcaggacac   34620
tgtgtgggaa acctcactgc gtgccatcaa tgacctaggg ttcttcgcta agaacgccta   34680
```

```
catgggtgct cagaacatta cggagattgc tgggatgatt gtcactggta acgttcgtgc    34740
tctagggcat ggtatcccaa ttctgcgtga tacactctac aagtctaaac cagtttcagc    34800
taaggaactc aaggaactcc atgcgtctct gttcgggaag gaggtggacc agttgattcg    34860
gcctaaacgt gctgacattg tgcagcgcct aagggaagca actgataccg gacctgccgt    34920
ggcgaacatc gtagggacct tgaagtattc aacacaggaa ctggctgctc gctctccgtg    34980
gactaagcta ctgaacggaa ccactaacta ccttctggat gctgcgcgtc aaggtatgct    35040
tggggatgtt attagtgcca ccctaacagg taagactacc cgctgggaga agaaggctt    35100 ccttcgtggt gcctccgtaa ctcctgagca gatggctggc atcaagtctc tcatcaagga    35160
acatatggta cgcggtgagg acgggaagtt taccgttaag gacaagcaag cgttctctat    35220
ggacccacgg gctatggact tatgagact ggctgacaag gtagctgatg aggcaatgct    35280
gcgtccacat aaggtgtcct tacaggattc ccatgcgttc ggagcactag gtaagatggt    35340
tatgcagttt aagtctttca ctatcaagtc ccttaactct aagttcctgc gaaccttcta    35400
tgatggatac aagaacaacc gagcgattga cgctgcgctg agcatcatca cctctatggg    35460
tctcgctggt ggtttctatg ctatggctgc acacgtcaaa gcatacgctc tgcctaagga    35520
gaaacgtaag gagtacttgg agcgtgcact ggacccaacc atgattgccc acgctgcgtt    35580
atctcgtagt tctcaattgg gtgctccttt ggctatggtt gacctagttg gtggtgtttt    35640
agggttcgag tcctccaaga tggctcgctc tacgattcta cctaaggaca ccgtgaagga    35700
acgtgaccca aacaaaccgt acacctctag agaggtaatg ggcgctatgg gttcaaacct    35760
tctggaacag atgccttcgg ctggctttgt ggctaacgta ggggctacct taatgaatgc    35820
tgctggcgtg gtcaactcac ctaataaagc aaccgagcag gacttcatga ctggtcttat    35880
gaactccaca aaagagttag taccgaacga cccattgact caacagcttg tgttgaagat    35940
ttatgaggcg aacggtgtta acttgaggga gcgtaggaaa taatacgact cactataggg    36000
agaggcgaaa taatcttctc cctgtagtct cttagattta cttaaggag gtcaaatggc    36060 taacgtaatt aaaaccgttt tgacttacca gttagatggc tccaatcgtg attttaatat    36120
cccgtttgag tatctagccc gtaagttcgt agtggtaact cttattggtg tagaccgaaa    36180
ggtccttacg attaatacag actatcgctt tgctacacgt actactatct ctctgacaaa    36240
ggcttggggt ccagccgatg gctacacgac catcgagtta cgtcgagtaa cctccactac    36300
cgaccgattg gttgacttta cggatggttc aatcctccgc gcgtatgacc ttaacgtcgc    36360
tcagattcaa acgatgcacg tagcggaaga ggccgtgac ctcactacgg atactatcgg    36420
tgtcaataac gatggtcact tggatgctcg tggtcgtcga attgtgaacc tagcgaacgc    36480
cgtggatgac cgcgatgctg ttccgtttgg tcaactaaag accatgaacc agaactcatg    36540
gcaagcacgt aatgaagcct tacagttccg taatgaggct gagactttca gaaaccaagc    36600
ggagggcttt aagaacgagt ccagtaccaa cgctacgaac acaaagcagt ggcgcgatga    36660
gaccaagggt ttccgagacg aagccaagcg gttcaagaat acggctggtc aatacgctac    36720
atctgctggg aactctgctt ccgctgcgca tcaatctgag gtaaacgctg agaactctgc    36780
cacagcatcc gctaactctg ctcatttggc agaacagcaa gcagaccgtg cggaacgtga    36840
ggcagacaag ctggaaaatt acaatggatt ggctggtgca attgataagg tagatggaac    36900
caatgtgtac tggaaaggaa atattcacgc taacgggcgc ctttacatga ccacaaacgg    36960
ttttgactgt ggccagtatc aacagttctt tggtggtgtc actaatcgtt actctgtcat    37020
ggagtgggga gatgagaacg gatggctgat gtatgttcaa cgtagagagt ggacaacagc    37080
```

```
gataggcggt aacatccagt tagtagtaaa cggacagatc atcacccaag gtggagccat   37140
gaccggtcag ctaaaattgc agaatgggca tgttcttcaa ttagagtccg catccgacaa   37200
ggcgcactat attctatcta aagatggtaa caggaataac tggtacattg gtagagggtc   37260
agataacaac aatgactgta ccttccactc ctatgtacat ggtacgacct taacactcaa   37320
gcaggactat gcagtagtta acaaacactt ccacgtaggt caggccgttg tggccactga   37380
tggtaatatt caaggtacta agtggggagg taaatggctg gatgcttacc tacgtgacag   37440
cttcgttgcg aagtccaagg cgtggactca ggtgtggtct ggtagtgctg gcggtggggt   37500
aagtgtgact gtttcacagg atctccgctt ccgcaatatc tggattaagt gtgccaacaa   37560
ctcttggaac ttcttccgta ctggccccga tggaatctac ttcatagcct ctgatggtgg   37620
atggttacga ttccaaatac actccaacgg tctcggattc aagaatattg cagacagtcg   37680
ttcagtacct aatgcaatca tggtggagaa cgagtaattg gtaaatcaca aggaaagacg   37740
tgtagtccac ggatggactc tcaaggaggt acaaggtgct atcattagac tttaacaacg   37800
aattgattaa ggctgctcca attgttggga cgggtgtagc agatgttagt gctcgactgt   37860
tctttgggtt aagccttaac gaatggttct acgttgctgc tatcgcctac acagtggttc   37920
agattggtgc caaggtagtc gataagatga ttgactggaa gaaagccaat aaggagtgat   37980
atgtatggaa aaggataaga gccttattac attcttagag atgttggaca ctgcgatggc   38040
tcagcgtatg cttgcggacc tttcggacca tgagcgtcgc tctccgcaac tctataatgc   38100
tattaacaaa ctgttagacc gccacaagtt ccagattggt aagttgcagc cggatgttca   38160
catcttaggt ggccttgctg gtgctcttga agagtacaaa gagaaagtcg gtgataacgg   38220
tcttacggat gatgatattt acacattaca gtgatatact caaggccact acagatagtg   38280
gtctttatgg atgtcattgt ctatacgaga tgctcctacg tgaaatctga agttaacgg   38340 gaggcattat gctagaattt ttacgtaagc taatcccttg ggttctcgct gggatgctat   38400
tcgggttagg atggcatcta gggtcagact caatggacgc taaatggaaa caggaggtac   38460
acaatgagta cgttaagaga gttgaggctg cgaagagcac tcaaagagca atcgatgcgg   38520
tatctgctaa gtatcaagaa gaccttgccg cgctggaagg gagcactgat aggattattt   38580
ctgatttgcg tagcgacaat aagcggttgc gcgtcagagt caaaactacc ggaacctccg   38640
atggtcagtg tggattcgag cctgatggtc gagccgaact tgacgaccga gatgctaaac   38700
gtattctcgc agtgacccag aagggtgacg catggattcg tgcgttacag gatactattc   38760
gtgaactgca acgtaagtag gaaatcaagt aaggaggcaa tgtgtctact caatccaatc   38820
gtaatgcgct cgtagtggcg caactgaaag gagacttcgt ggcgttccta ttcgtcttat   38880
ggaaggcgct aaacctaccg gtgcccacta agtgtcagat tgacatggct aaggtgctgg   38940
cgaatggaga caacaagaag ttcatcttac aggctttccg tggtatcggt aagtcgttca   39000
tcacatgtgc gttcgttgtg tggtccttat ggagagaccc tcagttgaag atacttatcg   39060
tatcagcctc taaggagcgt gcagacgcta actccatctt tattaagaac atcattgacc   39120
tgctgccatt cctatctgag ttaaagccaa gacccggaca gcgtgactcg gtaatcagct   39180
ttgatgtagg cccagccaat cctgaccact ctcctagtgt gaaatcagta ggtatcactg   39240
gtcagttaac tggtagccgt gctgacatta tcattgcgga tgacgttgag attccgtcta   39300
acagcgcaac tatgggtgcc cgtgagaagc tatggactct ggttcaggag ttcgctgcgt   39360
tacttaaacc gctgccttcc tctcgcgtta tctaccttgg tacacctcag acagagatga   39420
```

```
ctctctataa ggaacttgag gataaccgtg ggtacacaac cattatctgg cctgctctgt    39480
acccaaggac acgtgaagag aacctctatt actcacagcg tcttgctcct atgttacgcg    39540
ctgagtacga tgagaaccct gaggcacttg ctgggactcc aacagaccca gtgcgctttg    39600
accgtgatga cctgcgcgag cgtgagttgg aatacggtaa ggctggcttt acgctacagt    39660
tcatgcttaa ccctaacctt agtgatgccg agaagtaccc gctgaggctt cgtgacgcta    39720
tcgtagcggc cttagactta gagaaggccc caatgcatta ccagtggctt ccgaaccgtc    39780
agaacatcat tgaggacctt cctaacgttg gccttaaggg tgatgacctg catacgtacc    39840
acgattgttc caacaactca ggtcagtacc aacagaagat tctggtcatt gaccctagtg    39900
gtcgcggtaa ggacgaaaca ggttacgctg tgctgtacac actgaacggt tacatctacc    39960
ttatggaagc tggaggtttc cgtgatggct actccgataa gacccttgag ttactcgcta    40020
agaaggcaaa gcaatgggga gtccagacgg ttgtctacga gagtaacttc ggtgacggta    40080
tgttcggtaa ggtattcagt cctatccttc ttaaacacca caactgtgcg atggaagaga    40140
ttcgtgcccg tggtatgaaa gagatgcgta tttgcgatac ccttgagcca gtcatgcaga    40200
ctcaccgcct tgtaattcgt gatgaggtca ttagggccga ctaccagtcc gctcgtgacg    40260
tagacggtaa gcatgacgtt aagtactcgt tgttctacca gatgacccgt atcactcgtg    40320
agaaaggcgc tctggctcat gatgaccgat tggatgccct tgcgttaggc attgagtatc    40380
tccgtgagtc catgcagttg gattccgtta aggtcgaggg tgaagtactt gctgacttcc    40440
ttgaggaaca catgatgcgt cctacggttg ctgctacgca tatcattgag atgtctgtgg    40500
gaggagttga tgtgtactct gaggacgatg agggttacgg tacgtctttc attgagtggt    40560
gatttatgca ttaggactgc atagggatgc actatagacc acggatggtc agttctttaa    40620
gttactgaaa agacacgata aattaatacg actcactata gggagaggag ggacgaaagg    40680
ttactatata gatactgaat gaatacttat agagtgcata agtatgcat aatggtgtac    40740 ctagagtgac ctctaagaat ggtgattata ttgtattagt atcaccttaa cttaaggacc    40800
aacataaagg gaggagactc atgttccgct tattgttgaa cctactgcgg catagagtca    40860
cctaccgatt tcttgtggta ctttgtgctg cccttgggta cgcatctctt actggagacc    40920
tcagttcact ggagtctgtc gtttgctcta tactcacttg tagcgattag ggtcttcctg    40980
accgactgat ggctcaccga gggattcagc ggtatgattg catcacacca cttcatccct    41040
atagagtcaa gtcctaaggt atacccataa agagcctcta atggtctatc ctaaggtcta    41100
tacctaaaga taggccatcc tatcagtgtc acctaaagag ggtcttagag agggcctatg    41160
gagttcctat agggtccttt aaaatatacc ataaaaatct gagtgactat ctcacagtgt    41220
acggacctaa agttcccca taggggtac ctaaagccca gccaatcacc taaagtcaac    41280
cttcggttga ccttgagggt tccctaaggg ttggggatga cccttgggtt tgtctttggg    41340
tgttaccttg agtgtctctc tgtgtccct                                     41369
```

<210> SEQ ID NO 3
<211> LENGTH: 1044
<212> TYPE: DNA
<213> ORGANISM: Artificial Sequence
<220> FEATURE:
<223> OTHER INFORMATION: Description of Artificial Sequence: Synthetic
       polynucleotide

<400> SEQUENCE: 3

```
caacgtcgtg ccatgaagaa accttctgca tcttctgcgt aaagaggaga tatacaatgg      60
```

```
tcttcacact cgaagatttc gttggggact ggcgacagac agccggctac aacctggacc    120
aagtccttga acagggaggt gtgtccagtt tgtttcagaa tctcggggtg tccgtaactc    180
cgatccaaag gattgtcctg agcggtgaaa atgggctgaa gatcgacatc catgtcatca    240
tcccgtatga aggtctgagc ggcgaccaaa tgggccagat cgaaaaaatt tttaaggtgg    300
tgtaccctgt ggatgatcat cactttaagg tgatcctgca ctatggcaca ctggtaatcg    360
acggggttac gccgaacatg atcgactatt cggacggcc gtatgaaggc atcgccgtgt    420
tcgacggcaa aaagatcact gtaacaggga ccctgtggaa cggcaacaaa attatcgacg    480
agcgcctgat caaccccgac ggctccctgc tgttccgagt aaccatcaac ggagtgaccg    540
gctggcggct gtgcgaacgc attctggcgt aagcaggtta atatcttagt ataaacaagg    600
gcagacttag gtttgtcctt agtgtattcc aaaggaggta acatgctgaa agatggttgg    660
gtttcatatg accctacaga ccctaagaat tggctacagg ttatcgctat agcttgtgca    720
ggtagcctat ggctgccct gatgtattca ttatggatgt acacaaagta accaaagtca    780
aaattttgat gtaggcgtgt gtcagctctc tcgccctcgc cctcgccggg ttgtccccat    840
agggtggcct gagggaatcc gtcttcgacg ggcagggctg atgtactcct tgtctagtac    900
aagggaggcg gagggaacgc ctagggaggc ctaggaatgg cttagtggtg acaaggtga    960 ttaccttagt gaagcctctt agtgcattcc tgaggccatt cagggcgttt atgagggatt    1020
gacagggtgt gagggcgtgg gcta                                          1044
```

<210> SEQ ID NO 4
<211> LENGTH: 44915
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

```
tcgccctcgc cctcgccggg ttgtccccat agggtggcct gagggaatcc gtcttcgacg     60
ggcagggctg atgtactcct tgtctagtac aagggaggcg gagggaacgc ctagggaggc    120
ctaggaatgg cttagtggtg acaaggtga ttaccttagt gaagcctctt agtgcattcc    180
tgaggccatt cagggcgttt atgagggatt gacagggtgt gagggcgtgg gctatctgtt    240
cctttgctcc tcacttcgtt cgtcgctgcg gtagcctgat gtgtaccta ggttattcct    300 tgatggatag cttaggttag ccttagtgga ttaccttagt taaagcctta gtgcttcact    360
tagtatcagc ttagtagtgt accttagtaa gtcttagtgt cttctcttag tgattgcaca    420
tgcaagcatg taagatgcta ataggtcgcg gtcggcagac cgctaaagaa agagaatggt    480
aataagatgc agtaggagga acaccagaag cctagccaac ctaagctatc ctagctctat    540
atctattgct tttccttagt ctaacacgtt agacaaccta tcttattctt agtgatggta    600
acttagtgtt gacaagataa tcttagtgta atactatgca tcacgtaggc ggtgctgagg    660
cacctagtag ccagctagta aggcatacga agagactagc gcttacattg ctctttaaca    720
atttgcttag tgtaacctat gtatgccgtg gttaactact tattgaatga ggtattaact    780
atgacattaa ataaccgtga actgtccgtt ctcttcactc tgttgtgcta catgattcgt    840
aacaacgaat tacttacaga tgatgagtta gccttgtatc accgctttct taacgaaggt    900
tggaccgata cagttaatca ataccgtaac atgatagatg agttgaggga gggtaaataa    960
tgtatcaaca tgaggtattc tttgaatcag ctagcgaagc tattcgcttc cgtgatgata    1020
```

```
tgatgcaagc tggtgtaggc gttgatgtgt atcactattt gatagattac gacactgaat    1080
atcaccgagt taccttagta tctgagtatg acaaccaagt cattactgag tatctaggca    1140
gtgaagatta cgattacgat gaagtaatca cgacaaatct ctaaattaac tgttgacagc    1200
cacggcatac aaggttacat taagcatcaa gacggcgacg tctttaaaca tcccgctctt    1260
taacaatacg gtttgtgtct tgataggcta actaactaac taaggtaatt atcatgaaag    1320
ggttaatttg tgtagaacgt atggtcaatg gtaaacttga atattacca ctggaaaacc    1380 aatctagctt caaagagtgg tatggctgtt tctcactgat ttaaggtaaa ggctggcact    1440
agtcagccta tcaaggcgca aaccaagctc tttaacaatt tggatggtag cttcttagtc    1500
tggataggtt aaacctagga gattctcttg agtctcctat aatgtaacct aactaactaa    1560
atgaggatta aatcatggaa cgcaatgcta acgcttacta caaccttctg gctgcaactg    1620
ttgaagcatt caacgagcgt attcagtttg atgagattcg cgaaggtgat gattactctg    1680
atgcactaca tgaggttgta gacagcaatg ttccagttta ttacagcgaa atctttacag    1740
tgatggctgc tgatggtatt gatgttgatt ttgaggatgc tggtttgatt cctgacacga    1800
aggatgtaac caagattcta caagctcgca tctatgaagc tctttataat gatgtaccaa    1860
atgacagcga tgtagtttgg tgtgaaggcg aagaagagga agaataagga tggaaaagca    1920
atataacttt atcttttcag acggtgtaac cctgaagtgt tccctacgat tcgcacaaat    1980
tcgtgaggaa gtactaggca ctacatacaa actatttagc tgcactata agagaaggct    2040 taacaaggcg ttactaaggt agcgcctgat taaactttca cttactagga gttgagatta    2100
tgaaaacctt gattggatgc ttcttgttgg cttctcttgc tctggcattt accgctaaag    2160
ctggttatga cgcttataaa gtagaacaag cccagcaaga ctgggccaaa aaaaagttca    2220
acttgtgcag caagagcaac acctacgagt actgcaacaa acactaaga cacttatgga    2280 aagagtaact agcctatagc ccacctgagt gggctatgtg atatttactt aacactatat    2340
aaggtgatta ctatgactac tgaaaacacc ctcgtgtctg tccgtgaagc tgcaaccgct    2400
gaaatcaagc aacatttaga caatatcggc acttcttaca tcaaagtagg ggcttgtctg    2460
aatgagttac gcggagactt tgaaggtcaa aaagagtttt tagcctatgt tgaagcagag    2520
tttgccatta agaaggcaca atgttacaag ctgatgagtg tagcccgtgt ctttgaaggc    2580
gatgatcgct ttaaaggcgt ggcgatgcgt gtaatgctgg cgcttgttcc tttcgctgat    2640
gaaaatataa tcatggagaa ggccgcagaa ctcgccgcaa atggcaagct ggacactaat    2700
gccgtaaacg ccctgattga acctaagaaa gagtcaaagg ccgaaacggt acaatctaag    2760
gctgagacag taaaaccgca ggagaacgcg actgagtccg cagaatcaca tgaaatgcaa    2820
gcgccgcagg tagtgccacc cgcgagcgag caggagtccg acgaatcagc accttgggaa    2880
gaggaaagca aaccggaagc gccaaaggca gctccgatgg ataacacggc taatactgag    2940
aatgccgcta ttgctggtct gctggcacaa attaaagcac tgactgagca attacaggca    3000
gccaatgacc gcatcgcctc cttaagtagc gcacgcgaaa gcaagaaggc atccgcacct    3060
atgctgccgc agttcaaatc ttcctgcttc tacgctcgct taggcttgag cgcggaggag    3120
gcaacgaaga aaacagcagt taacaaggca cgccgcgaac tggttaagct gggatacggt    3180
gaaggccatg aggcatggcc cttaatctct gaggcagtag aagagttgac taagtaacct    3240
tatcggtggc atcttcttag gtgtcaccta ttaaggtttc tttcactagg agtaaacaag    3300
atgcaaggcc tacacgctat tcaacttcaa cttgaagaag aaatgtttaa cggcggtatc    3360
cgtcgctttg aagcggacca acaacgccag attgcatccg gtaatgaatc agacacggca    3420
```

```
tggaatcgcc gcttattgtc cgagttaatc gcgccaatgg ctgaaggtat tcaggcatac    3480
aaggaagagt atgaaggtaa aagaggccgt gcaccgcgtg cattagcttt cattaactgc    3540
gtagaaaacg aagtggcagc atatatcacg atgaaaatcg ttatggatat gctgaacacg    3600
gatgtaacct tgcaggctat agccatgaat gtagctgacc gcattgagga ccaagtacgt    3660
tttagcaagc tggaaggtca cgccgccaaa tactttgaaa aagttaagaa gtcacttaag    3720
gcaagtaaga ctaaatcata tcgccatgcg cacaacgtag cggtagtggc tgagaagtca    3780
gtagctgacc gtgacgctga tttctcccgc tgggaggcat ggcctaaaga caccttgctg    3840
caaattggga tgaccttgct tgaaatctta gagaatagcg tattcttcaa cgggcaacct    3900
gtcttcctcc gcaccttgcg cactaatggc ggcaaacatg gtgtttacta cctacagact    3960
agtgaacacg taggtgagtg gataactgca ttcaaagagc acgtagcgca actgagtcct    4020
gcctatgctc cttgcgtcat ccctccgcgt ccgtgggtat cacctttaa cggcggtttc    4080 cacactgaga aagtagcaag ccgtattcgt ctggtaaaag gaaaccgcga acacgtccgc    4140
aagctgacca aaaagcaaat gccagaggtt tacaaggctg ttaacgcgtt gcaggcgact    4200
aaatggcagt taacaagga agttttacag gttgtggaag acgtcatccg tctagaccta    4260
ggttatggtg taccttcctt taaaccactc attgaccgcg agaacaagcc agctaatcca    4320
gtgccgctag aatttcagca cctacggggc cgtgaactga agaaatgct tacgccggaa    4380 caatggcaag cctttatcaa ctggaaaggt gaatgtacta agctgtacac cgctgaaact    4440
aagcgcggaa gcaaatcggc ggcaaccgtt cgcatggttg gtcaggcccg taaatatagc    4500
cagttcgacg caatctactt cgtgtatgca ctggacagcc gcagccgcgt ctacgcgcaa    4560
tctagcacac tctcaccgca atcaaatgac ttgggcaagg ccttgctccg ttttaccgaa    4620
gggcagcgtc ttgatagcgc tgaggcgctt aagtggtttt tggtgaacgg ggctaataac    4680 tgggggttggg ataagaaaac ttttgacgtg cgcaccgcta acgtgctgga tagtgaattt    4740
caagacatgt gccgcgacat tgcagcggat ccgctgacct tcactcaatg ggtaaatgcc    4800
gactcccctt acggcttcct tgcatggtgc tttgaatatg cgcgttatct ggatgcactg    4860
gatgaaggca cgcaagacca attcatgacg cacctcccag tccatcaaga tggtagttgt    4920
tctggtatcc agcactacag tgctatgcta cgcgatgcag taggtgcgaa agcagtaaac    4980
cttaagccct ctgactctcc tcaagatatt tatggtgccg ttgcgcaggt agtaattcag    5040
aagaattatg catacatgaa tgcagaggat gcggaaacct tcacttctgg cagcgtgact    5100
ttaacaggtg cggagctgcg tagtatggct agtgcgtggg atatgatagg aatcactcgc    5160
ggcctgacca aaaagcccgt aatgacacta ccttatggca gcacacgtct aacctgccgt    5220
gagtcagtga ttgattatat cgttgattta aagaaaaag aggcccaacg ggctattgcg    5280
gaagggcgta ccgccaatcc tgtacaccct tttgataatg accgtaaaga cagcctgaca    5340
cctagcgcag cttataacta tatgacagct ttaatctggc cttctatttc ggaagtggtt    5400
aaagccccta tagtggcaat gaaaatgatt cgtcagcttg cccgtttcgc agctaaaagg    5460
aatgaaggct tagagtatac cctgcctact ggcttcatct tgcaacaaaa gattatggct    5520
actgatatgc tccgcgtatc tacttgcttg atgggagaaa tcaagatgag ctacagatt    5580 gaaacagacg tagtggatga acggcaatg atgggcgctg ctgctcctaa ctttgtgcat    5640
ggtcatgatg ccagccacct tatcttaaca gtctgcgacc ttgttgataa agggattaca    5700
tctatcgcag ttattcatga ctcttttggc actcatgcag gccgtacagc cgaccttcgt    5760
```

```
gatagcttaa gggcagaaat ggtgaagatg tatcaaggcc gtaatgcact gcaaagcctg      5820
ctagatgagc acgaagaacg ctggttagtt gataccggaa tacaagtacc agagcaaggg      5880
gagtttgacc ttaacgaaat cttagtttca gactattgct tcgcataata ttaataggcc      5940
attccttcgg gagtggcctt tcttttacct actacctgta acatttcatt aacataaaag      6000
tgtctcacat gtgagactta tttaccggac actataggat agccgtcgga gacgggaaag      6060
aaagggaaga taaaggatat aaaggaagta ataggtatta aaggttatat aggttatcta      6120
ggaataccta ttaccttctt ccttcctctt attaccactc agaggaaggg cagacctagg      6180
ttgtctcaca tgtgagactt cgtatttacc ggacagtata gataagatta actcactttg      6240
gagatttaac catgcgcaac tttgagaaga tggcccgtaa agctaaccgt tttgacatgg      6300
aagaggggca gaagaaaggc aagaagctga ataagcctgt ccgtgaccgt gcatctaaac      6360
gcgctgcgtg ggagttctaa gttatggcta ttattcagaa tgtaccgtgt cctgcctgtc      6420
aaaagaatgg acatgatatt actggcaacc atctcatgat atttgatgat ggtgccggct      6480
actgtaatcg tggacacttt catgataatg gtagaccttg ctatcacaag ccggaaggtg      6540
gcatcgagat aaccgagtta tctattactg gcaatatcaa atatacacct tctcaattca      6600
aagaaatgga aaggaaggg aagataagcg accctaaatt acgtgccatc gcacttggtg      6660
gtatgcgtat gaaagaccgt tgggaggtca tgaatgaaca agaaagggca gagcaagaag      6720
cagagtggaa acttgatgtt gaatggttcc tcacgcttaa gcgtaagaac cttgtttcca      6780
ggcacattcg cggcgacatt tgcgcattgt atgatgtacg tgttgggcac gatgaagagg      6840
gtagagtctc acggcattac tatccgcgct tcgaaaaagg tgagctagta ggcgctaagt      6900
gtcgcacatt acctaaagat tttaagtttg gtcatttagg taaactcttt ggtatgcaag      6960
atcttttcgg tatgaatact ttgtctcacg tgttagacaa gggaagacga aaggattgct      7020
tgctcattgt cggcggcgaa ctggatgcac tagcagcgca gcagatgctc cttgattctg      7080
ccaagggtac taagtgggaa ggccagccat accatgtatg gtctgtcaac aaaggcgagt      7140
cttgccttga agagatagtg cagaaccgtg agcatatcgc ccaattcaag aagattatat      7200
ggggttttga tggagatgag gtagggcaga agcagaatca gcaagcggct cgcctgtttc      7260
ctggtaaatc ctatatcctt gaataccct ctggttgcaa agatgctaac aaggcattga      7320
tggctggcaa ggctaaagaa tttgtagatg catggtttaa tgccaagtca tctgatgaag      7380 tcttggtag ccagattaaa tctatcgcat ctcaaaggga taagctcaag gctgcacgtc      7440
cagagcaagg actgtcatgg ccttggccta agctgaacaa ggtaacgcta ggtattcgta      7500
agaaccagct tatcattgta ggtgcagggt ctggtgtagg taagactgag ttccttcgtg      7560
aagtagttaa gcacctcatt gaagaacacg gtgaatctgt aggcatcatt tctacagaag      7620
acccgatggt caaggtgtcc cgtgctttta tcggcaagtg gattgataag cgtattgagt      7680
tacctccaac caacgacccg aaagaagacg gataccgtga ggtgttcgac tataccgagg      7740
aagaagctaa cgccgccatt gattatgtag ctgatacagg taagctgttt gtagctgacc      7800
tagagggtga ctattcgatg gaaaaggtag agcaaacttg cctagagttt gaggctatgg      7860
gtatttctaa tatcatcatt gataacttaa cggggattaa attagatgag cgtgcttttg      7920
gtgggaaggt tggtgcactt gatgaatgcg tcaagcggat tggtactatc aaagaccgac      7980
acccggttac tatattcctt gtatcacacc ttacacgtcc tccggcaaac cgtacccaac      8040 acgaagaagtg tggcgaagtt atcctttctg acttccgagg ctcaggcgct atcggattct      8100
gggcatctta cgccttgggg attgagcgta atacaagagc tgaaacgctt gacgaaagga      8160
```

```
ctaccacgta catctcatgt gtcaaagacc gcgaccaagg tatctacact ggaaccaagg   8220
tcatgcttaa gggtgacatt caaaccggac gtttaatgga accacaagcc cgtactaagt   8280
catttgatac aggtgaagca aggcaacaag aagtaccaga tttaccggat actatagaag   8340
agactacctt cgatgaagaa agtgagttct gattagtgta tttatcaggc ttgtctcaca   8400
tgtgagacag gctcttatta agtacattaa ataactggag attgattatg tataacttag   8460
tgttgaatgt aggtgacttt gtacgcaaca tcaagaaaga ttcaagtcgc tatctttgcc   8520
gtggtgttgt aaccttttgta ggtgagaacc tgtattatgt agaatatcgc agtggtgtta   8580
agcaatatta ccacaagaag acagcacata aatatcttga aaagattgta gagataaaca   8640
atcaatgtaa gtgcatacat gatgaggttt gcgataaatg tgctcgccag atgcttaaga   8700
atttcctagc tcctctttat tatggtgctg gtcctcaaac actagcagag tgcatggcag   8760
aaaagaaaac cacactcaag aaagagcgtc gcaatgtaat cactggtaag actcaaagtg   8820
agatgattaa gcaatgtggc actgcattag gtgttacaca gtttaatact cgtgcattgg   8880
gtaaatccac aggacaagct atggtaaaga ttggagaagc catgatgcat ccaaatgtac   8940
ctgtgcgaat catggatgtt gaccatgcaa tcacagaaca aggtacgcaa cgacgtgtaa   9000
ttaataagca ttttgccgac actatagaag gcattattcg taagcaaggg ttgaaaggtc   9060
ttcacatctt aaatggtgaa gaattactgt acctacctat cgttactgaa gaaacatacg   9120
tgaatatcta aggagttaat catgactaag gtattaattt atatgcgtgg acctcataaa   9180
tgctatgcag ttgtagcacc aaatggtgtt aagccttatc gtacttcaaa aagattggca   9240
ttaataggtg ctagtagtag tgcaagtttc caaatggaac tttttggtca ttggactgaa   9300
aggcaattcc gtgaggattt taaagtcatt ggcagcttca tggtgaaata tgcagaataa   9360
acatagtctt agaatgttcg atggtcatga aaacctgcaa gccaagatta ctaaccaagc   9420
cttcctgttc gcacagttaa ctatggctga ggctaagaag aatagtctca ctcgtgaaca   9480
ggttatcaag gaggccactt gggaaccaca ccaaggtaaa tatatgggcc acaaattaac   9540
tgtaacacgc agtcgataag tcaagggttg tccaacgtgt tggacagcct ttcatcatat   9600
tgattgggag gtattaaatg actaagttta ctatgcaaga cctcattaaa ttacgtgatg   9660
aaatagaatc accggaagtt aatacagagt ttcactacat tgatccacga gataaacgag   9720
agattcctga ttatcagatt gagacggagt taatgtatga agattattga ttggaagaag   9780
gaagcagaag gccgtatcct agtgatggat gcggaggcta aaggcctgct gggtgctatc   9840
cgctacggtc atcgtgaaga tgtacacatt atttgctgca tggacttgct caccactgag   9900
gagttcctct tcttcgaccc atatgagatg cgtgaccctg aagcaaggga acacttgaaa   9960
gagtgggaag gccatcaaga tgggaccttg gttgatggtg ttaacttcct aaagcactgt  10020
gaagccatcg tctcacagaa cttcctaggc tatgacgggc ttctctttga gaaagccttc  10080
cctgacatct ggaagggatt taactacacc gagaggcgcg gcaagggcag actacgtgct  10140
gacttgtgtc cggtacgcgt catggatacg ctggtcatga gtcgcctgtt aaacccagat  10200
agacgccttc ctccgcaagc atatgccaaa ggtatgggta acgttgcccc tcactcaatt  10260
gaggcgcacg gcattcgtat aggccgttat aagccggaga acgaggattg gtctaaacta  10320
actgaccaca tggtacatcg tgtacgcgag gacgtggcga taggccgtga cctattcctc  10380 tggctatttta acgagaatg gacggagcac aaacgccgtg gcgtgaataa acgcactggc  10440
ctaggtattg agacagcctt ccacatggag tccattgtga cgctggagat gagccgtcag  10500
```

```
gccgagcgtg gattccgtct ggatatagat aaagcattag cacgatgcga ggaattggac   10560
gctaagattg atgagacagt cgcagcgttc cgtccgcaca tgcctatgcg tatcaagtct   10620 aaaccttta  aaccggaaga aaagaatgaa gtatgccaac gcgcaaatga gtatggagct   10680
agcaacaata tacctactgt ccttgacccc tctcactttc ttcacgcaga gagacgagga   10740
gatcgcaaga cagtatggag tgtcactact aagtctggtg attggtcggc tagcgtcaag   10800
aaagactttc ctcaccttag aggaaaccgt aatgacacgc caagtgtcaa gtggattggc   10860
gcttactcgc ctgttacttt cgaagagatt cccttgggta acagggatac agttaagcaa   10920
gtgctctatg attatggatg gaaaggtgtt gaatttaacg ataccgagca agcgcatctc   10980
gatgagcatg gcgtattacc caagccttgg agtgggaaga taaatgaaaa gtcccttact   11040
ttatggcaag agagagccgc acgtgaaggt aaaacagtcc ctgattggtg cttgggtatc   11100
gctgcatggt acatactcgt atcccgtcgt ggtcagatcc tcaaccgtgg tgacgttgaa   11160
gccttcgacc agaaggggt  gtggccttcg caagctggta tacgaaagtg tcgcggcctt   11220
gtacctgtag catttaacaa ggagttagga atcaatgcgc agcaatacta cgaaaggtac   11280
ggatgctggc ctacgtcaga caaggatgac ggagaatggc gtgtgccagc tattgctatt   11340
agtattggaa cttctacgtt ccgtatgcgt catcgtaacg tggttaatat tcctgcccgt   11400
ggcttgtatc ctttacgtga tttattcata gcagggaaag gcaagctaat ccttggttgt   11460
gacggtgcag gtcttgaact gcgtgtcctg tctcacttca tgaatgaccc tgagtaccaa   11520
gagattgtac tgcacggtga tattcatacg cataaccaga tgaaggctgg tcttcctaag   11580
cgtgatatgg cgaagacatt tatatatgcc ttcctatatg ggtctggtat agctaaccat   11640
gcagcagtat gtggtgttac tgaggaagaa atggaggaag ttgtggcaag atttgaggtt   11700
gaactaccat ctcttgcacg tcttcgtgag aatgttatcg cacaaggtaa caagtttggc   11760
tacctacaag cacctgatgg tcattgggt cgcatccgta tgtctggtgg tgaacttaaa   11820
gaacacacta tgcttaacgt actactccag atgactggtt ctctgtgtat gaaatacgca   11880
ttggtcagag cgtttgcagt gatgcgcaag gaaggtgtgg ccttagatag catgggaaac   11940
ccttgcggta tagctaacgt gcacgatgaa atccagatgg aagtccctga agatgaggtc   12000
ttgtatctca actacgactt gccttteace ttagaagggt tcgaaacaga gaaggctgct   12060
gtgaaagcag tgttcgatgc agaggagaaa cgtgttcatg tggattctga aggacgtatg   12120
tggtctgctg caaatctcgt tagtgttgat gctggtgtac ttcattgcca gcgtcgttat   12180
caccgtgcag gcatatcat  tgccgacgca atgacctggg cgggtcagta cctgaagatg   12240
cgttgtccga tggcaggtga gtataagatt ggtgcaagtt ggaaggaaac acactgatgg   12300
acaggtttga tattgtttgc ctattctcta ccttctttct tatattcctt atgcttgctt   12360
gctatggaag tatgcgatta gatatacctg atgaagagga gggttacgat tgatgcaggc   12420
atcttttatt attcttggag tcatattatt tatggtagta ttctgggctt tctctggcat   12480
tgacccagat tgtgatggta actacgactg agttatactc aaggtcactt acgagtggcc   12540
tttatgaata acttattcct acttattttg tctaacatga tttactggac actatagaag   12600
gaaagcatag gtaatctagg tttataaggt agtataggta attaagtaaa tataggagat   12660
ataaatatgt ctatggtaac tactctggta ttcgtggctc aatactttcg tggtcttgct   12720
aataagttca agtccaaggc tatcaaagct attgaggctc gcatcgaagc agtacaggca   12780
gagcaagtta aagttgaaga acatcgtagt tctcaaatga ttgactgtca taaccgctac   12840
tatgcatctc gtgatgaact aaatgcacgt caagtcaaag aggtagaaga tatgctggca   12900
```

```
cgtcaccagc aagagcgtga cagcctgaaa gctgaatttg aagagaacaa ggcatcaatt    12960
gctcttgtac atcaagctgc atctgacagt ctgaagaaag agattgttat gctggaaatc    13020
gaactggata acctgaccaa ataagggggg gttatgatgg aagaagtaat tcaagctaaa    13080
catgtaggta ttatctttcg cgatctagag cagcgtaaag ttgcaggtca tactcgtctg    13140
gctaaagagg aagacaccgc aatcactact gtagaacaag cagatgccta tcgtggacca    13200
gagttcactc aaggtgaaac ttgtcaccaa ttgagcctat caatttgtga cactatggct    13260
attgtaaatg tgcaagaagt cgaagagggt gagtgtgtca gttacatcta ccctttagat    13320
actattgcac gcattaaggt aatccataag taattactag acactataga acaataggtc    13380
ggcttagttc ggcctatgat tgtaaagtgt tgttgatgtt gaaccattgt gcatcttgca    13440
caacccgata ccgtataggg ctttctagtg agtacatgct tgtgctcagt acaaagctaa    13500
ctgacaatag gagactaaat aaatggcacg tggtgatttt gattttggtg ctcaggttac    13560
taaatctgaa ggtaaagtct ttaagaatcc agaagtaggt gatcatgaag cagtaatctc    13620
tggcatcatt catgttggtt ccttccaaga catctttaag aaaggtaata ccactgaagt    13680
taagaagcca gcaaactttg ttctggttaa gattgtcctg atgggtgacg atgcaagaa    13740 cgaagatggt tctcgcatgg aacaatggat ggctgtgcct ctgaagtctg gtgataaggc    13800
aacactgact aagttcctga atgcagttga ccctaaagag ttgctgggtg cttcgatga    13860 tttcattggt gaatgcctga ctgcaacgat ggtcggttct ggtgataaga atgacgatgg    13920
ctcattcaag tatgttaact ggaagggatt tggtggtatg ccggacaagc tgaagaaact    13980
ggtcattgct caggttgaag aggaaggtct gtctatgaca ggtcacatta ccttcgacaa    14040
gctgaccaaa gaaatccttg atgacatccc agccaacttg gtgcgtcaat acttcctgaa    14100
cgagacgcct cgtggtaaga acctgtctgt tgctggttct cacgtagaag caatcattaa    14160
agctgctcgt gaagaagacc cagaatgaa gaaggctaag aagaaagacg aggaagatgc    14220
taccccagct aatcgtaaat ctctggatac tggtgagtct gttccacagg aagtacctga    14280
agcagaagat actcctgcac cggagatgga tgaggacgcg gaatattaag agaaaaggat    14340
gaaagtacaa atcgtaaccc tgcactgcaa gaaaggaatt acaactcttg gcggcaacac    14400
tttccactcc ttctctgaag gggacacata tgccgacctg cactacatct ggcgcgacgg    14460
acagcacgtg gtgaactaca gcgacccagc tacggggaaa cgccacggcg tatcgcttcc    14520
ggcgcatgac attgctcagg tgaacacagt tttataaagt ctcacgtgtg agacaaatcg    14580
gtgtccggta tttactggac actatagaag agaagaattt taatcggcga taatgccata    14640
accaacaaaa ggagaattta atatgttcaa gattgaaact atcgtaaacc gtgttgttaa    14700
aggtgctgct ctggtatccg ttgagtcttt cattatcgtc gatgaaactg atcaactggt    14760
agctggtact aaggcttacg ataccgtga agaagctcag gctaagattg acagcatggg    14820
taacttcgct gctggtctgg agttcgctcg tgcttgcttc cctgagcagg ctgacaaagc    14880
tcagattggt aaggctaata tcgtagctga atatctggat tgggttgctg ctggtaaacc    14940
agtgaaagaa gttaaggctg ctgaagaagc tgaagctcca gcagaagaag tagctgcacc    15000
ggaaactccg gtaagtgaag aggaagaatt ttgataatag caggtgttgc ctctgttagt    15060
cctagctgac tatcacgctc acctcatcta atgccctgtc tgccttagtg taggcagggt    15120
cttttgcgta atagttattg gagaatgaat tatgccgact attgaatctc gaattgaact    15180
ggacattagc tacaatgcaa tcaccagaca gtatattggg gttgcctatg attacaaaac    15240
```

```
tggtgagaag ctagtggagg tgagacaatg ggatgactat tggttaagac agaacctcca   15300
tgatgcggtg tcctccttcc tgaaggagtg gcctacatgc gaccaaactt cgacttcgga   15360
gctacagtat cggaagacaa taacctgttg ctgtggccaa ctgaaggtaa tcgaatcgct   15420
ttaatagatg ctgatatgtt accttacatc atagggtata caatcagtga tatgacttat   15480
gtacgagcca caactcgtgt taagtcaggg caagtcccct caatcaaaga tacacctgag   15540
tgtaagcaag cgtgtgaccg tgtgaactcc ttgcttaact cttgggtgta tgcagcagaa   15600
tgtgatgcag ctaagttgtt catgacgaaa tcagaagcta acttccgtgt ccgcctagca   15660
ttcaccaagc cttataaagg tcaacgtaag accgagaagc ctccattctt ctatgaattg   15720
cgagagcatc tcttagaggt tcacggtgca atcttggcag atggagagga agcagatgac   15780
ctcatgagta tcgcacaatg ggacagccac cgccgcttcc agcaagatac aggtaacgag   15840
ttccctatcg gtagtccaga gcataaagca ttctctgata cttgcatcgt ttccttggat   15900
aaggatttga tgattgttcc cggttggcat ctacagccgg tcaagagaa gaaatgggta    15960 gagcctatgg gttggcttga gctacgccgt aaggctaatg gcaagtcaa agatctaaaa    16020 ggtgctggcc tcatgttcca ctatgcacag atgattatcg gtgatgatat tgataactat   16080
gctggcatac caggtcgtgg tgctaaatat gcctatgatc ttctcaaaga ttgtaagaca   16140
gagaaagagt tgtacatggc agtgctgggt gcttacaagg ctaagttcgg catggacaa    16200 gttaaaatta gaattaccg aggtggttat cgtatcggca aagcctttga cctaatgctt    16260
gagtgtggtc gcttatctca catggcaaga ttcaagggtg atatatggcg agccgataag   16320
aacccaatct tgtggggaga tgatgcgaa tggttagcaa attaaaatca tcggaggtgg    16380
cagcttataa gaaggaattg ctagataagc aaggatggaa atgccctctg tgtggcggca   16440
gtctcaaagc tgtcacacct gtaaaccgtg tacttgacca tgaccatgag acaggattct   16500
gccgcgctgt tgtatgccga ggctgcaatg gtgcggaagg gaagattaag ggtgttatct   16560
ctggttatgg taaggctggt aacaaccgtt acttccagct tcaatggtta gagcgactat   16620
atgaatactg gaagttacat agtacgcctc agacagataa gttatatcac aaacatcaaa   16680
cggaggcaga gaagcgcgag gctaagaacc gtaaggcacg ccttgcttat gcaagaaaga   16740
aggaggttaa agttgggtaa gctgcgcagc ttgtacaaag actccgaggt acttgatgca   16800
atcgagcaag ctaccgacga gaaggtaat gttaactaca atgagatggc acgtgtatta    16860
tcgtgtcata ctgtgggtaa gaagattacc cgccagttgg ctcgatactg gcatggtcaa   16920
ttcaagaaga ccaagaagaa tggtgattac taccagaccc ttctgcaaga agataagcgt   16980
atcaaagaag agcgtaagct caggactcct gaccgctacg aggatttggc tattgtgcca   17040
ttgcctgact cgcctcatcg aagtgtactg gtgatccctg atactcatgc acccttatgag  17100 cacccagata ccctagagtt ccttgcagcc gtggcagcac gttaccgtcc agacacagtg   17160
gtacacctag gagatgaggc agacaaacat gccctgtcat tccacgattc ggacccaaat   17220
ctggatagtg ctggcatgga gttagagaag gctcgtatct tcatgcacaa attgcacaag   17280
atgttccctg tgatgcgcct gtgtcactct aaccacggct ctatgcactt ccgtaaggca   17340
agcgccaaag gcatccctgt gcaatacctg cgcacctatc gtgaagtctt cttcccgcag   17400
ggaggtggcg accagtggga ttggcaacat acgcacgtcc ttgagttgcc gaatggtgaa   17460
caagtggcat tcaagcatca acctgctggc tctgtcctag cagatgcagc gcatgagcgt   17520
atgaaccttg tgtgtggtca cttgcacggt aagatgtctg tggagtacgc acgtaataca   17580
catgaacagt attgggctgt gcaaggtggc tgcttaattg atgagtcatc ccgtgcattt   17640
```

```
gcctatggtc gtgagtctaa atacaagcca gcattaggtt gtgtggtcat tctggagggt    17700
gtgcctcaca ttgtcccgat gcaaaccaat agcgacaacc gttggattgg caagatttag    17760
ttgacactat agaacaaagg gctaggtaag actttatcgg ctggcgtatc caaatgatat    17820
tgcactagcc cttgattgta tagtgaatgg aggattcaat atgtcacact atgaatgtaa    17880
gaagtgtcat aagcgttatg attactgtac ttgtggtcaa gagaaaacat cttttaaagt    17940
tggagacaag gtatttcgta atgaaaaaga ttcgattcct tggaatcaat actgcaaaga    18000
agctggtatt gaccctgata gccctgtaac catagatgat attgatggca ttaacttgtg    18060 cttttcgtgag gtgaggggta caggttggga ttccaaaaaa ttcaaacttg catctgataa    18120
gttagacaac aatatggtaa ttaagcctaa gcactacgag ttctttgatg gcgtagaggc    18180
aatcactatc attgcccgca gtatgaccga gaagcaattc gctggctatt gcatgggtaa    18240
tgctttgaag taccgtctac gtgcaggtaa gaagttcaac actgaagaag acctgaagaa    18300
agcagattac tacaaagagt tattccagaa gcatcgtcac gaatgtattg atgaggatat    18360
ttgatatgaa tatctttgag ttcctaggtc ttccagaaga ccaccgcaat cacccattca    18420
tgctggtgaa gcatcgcggt gaagttcctg agaagaaatt aacttttcca tgttatgcac    18480
aggtgaaacg agatggtatc ttttctgctg ttgttgttcg cactgatggt gtcgttggca    18540
tttttggtcg cactggtaag aaattggcaa acactgaagg actcgaacaa gcctttgcta    18600
cctttccggt tggcatttat cttggtgagc ttcagtctat ggccattgat atctaccttg    18660
aggcaatctc tggggttgtg aaccccaatc gcactgagcc acttgatttc ataggccagc    18720
agattaaaga caacctgtat atcgacttct tcgatatgtt aactattaag gcattccatg    18780
atggattcac tgatgtttct tatctcaaac gttacgatgc tttacatcgt cgtatcggcg    18840
ctcatcttag cgggtgcaac gctatccttc ctatcactcc ttgccataat gagcgagaag    18900
ttgaagcgtt tgcgcaagag caaatagatg caggacgtga gggtgctgta ttcaaactgg    18960
actgcgatta tgaagcagga cacaaaggtt atcgtcagac taaagaagtc cgtaaggtaa    19020
cctatgacct tacttgtatt ggctttgaag aaggtaaagg caaatacaaa ggtaaggtag    19080
ctaacctcat tttcaaatgg aaaggaggca agacaatcaa agctatgtta ggtaagggt    19140 ggactcatgc agatgcagag cagatgttcc acgacattaa acatggtgga cgattgaatg    19200
tcattggtaa aatcttttga gtcaaaggtc ttcaggattc aagcaagggc aacattcgtc    19260
tgcccaaagc gggagaatta agacatgaca aagatgaacc agatttcttt tgatagcatg    19320
aaggcaactc gtgcagttga ggtagcagaa gctatcttcg aaactttatc ctgtggcatg    19380
gaagtgccat atactttact tgctgatgca gaagaacttg gtctttctgt agaagctatc    19440
caagagaagg ttgacgaatt atatggtaca gacgaagaag aaaccgacga tttcatttga    19500
aggaatggag atgcttgaga tgattctcaa gccttcttct cctaaggtga ctaagactca    19560
tgaagagtta atcgttgatg aagttaagcg ttacatcatg gattgtgtca gagcacaact    19620
ggtggtccaa tgatacgtcc agcctccttc ctagatattc ctgagattat aaaccttggg    19680
aataaatatg tggaagagga agtcaaggtt gtagcccacc actcagcctc atggaatgca    19740
gaacaaagtg ccataacctt tgtgcatctc ttaatagaga cccaccactc agcctcatgg    19800
aatgcagaac aaagtgcaca taacctttgt gcatctctta gtagagaaga tttatcccta    19860
tgggttgctg tagatgaagg gcagattgta gggttcctgt gggctggcta tcacgagttg    19920 gcccccttgga cacctgtaag agttgcctct gacattctct tttatattat accagagagg    19980
```

-continued

```
cgaggaacac tacttggtat gcgtctcatc aaagccctaa agcaatgggc tagtgataat   20040
gaatgctctg aggttcgcct gtctatcgcc tctggtatta atgaagaacg tgtcggacgt   20100
atgtataagc gacttggctt tgaaccgttt ggcactgtgt ataacctgaa gttctaagga   20160
gataacatgg gtgttgtaaa gaaagcattt aaggctatcg gtcttgctca agatgcacca   20220
cgtattgaag ccaaagtccc agcacagcag cttgagcgta agcctgagac tgaagctgaa   20280
gatattcaaa ttggtgcagg ggatgatgct actgcatctg caaaaggtaa gcgtggcctt   20340
gtccgtccgg tagcttctag cttgaaggtg taatatgaaa cagagcatag atttggagta   20400
tggaggtaag cggtctaaga tacctaagct atgggagaag ttctccaata acgtagctc    20460 tttccttgat agggcgaagc attactccaa attaaccttg ccctatctga tgaatgacaa   20520
aggtgataac gagacttcgc agaatggatg gcaaggtgta ggtgctcagg caaccaacca   20580
tctagccaac aagctagcgc aagtactatt ccctgcacag cgttccttct tccgtgtaga   20640
cttaactgca caaggtgaga aggttcttaa tcagcgtggc ctgaagaaga cagagctagc   20700
taccatcttc gctcaagtgg aaacacgggc aatgaaagag ttagagcaac gtcaattccg   20760
gcctgctgta gtagaagcat ttaagcatct tattgttgct ggcagctgta tgctatacaa   20820
gccgagcaaa ggtgcaatca gtgctatccc aatgcatcac tacgtagtta accgtgatac   20880
caatggcgac ctgttagaca ttatcttgct acaagagaaa gccttacgta cctttgaccc   20940
agctacacgt gcggtagtag aggttggcct gaaaggtaag aagtgcaagg aagatgcag    21000 cgttaagctg tacacacatg ctaagtatct tggtgatgga ttttgggaac tcaagcaatc   21060
tgctgatgat atccctgtgg gtaaggtgag taaaatcaaa tcagaaaagc tacctttcat   21120
cccattaact tggaagcgaa gctatggtga ggattggggt cgacctcttg cagaggatta   21180
ctccggtgat ttattcgtta tccaattctt atctgaagcg gttgcccgtg gtgctgcgct   21240
gatggcagat atcaagtacc tgattcgtcc tggtgctcaa actgatgttg accactttgt   21300
taactctggc actggtgagg ttgtcactgg tgtagaagaa gacatccata ttgtacagtt   21360
aggtaagtac gcagacctca cacctattag cgcggttcta gaggtataca ctcgccgtat   21420
cggtgttgtc ttcatgatgg agacaatgac acgccgtgac gccgaacgtg ttactgctgt   21480
agaaatccag cgagatgcgt tagagattga gcagaacatg ggtggtgtat actccctctt   21540
tgctactact atgcaatcgc cagtagcgat gtggggtctg ctggaggcag gggagtcctt   21600
cactagtgac ttagtggacc ctgtgattat cacaggtatt gaagctttag gacgcatggc   21660
tgagttggat aaaactggcta actttgctca gtatatgtca ctgccattac aatggcctga   21720
gcctgtccta gctgctgtga atggcctga ctatatggat tgggtgcgtg gtcaaatctc    21780
tgctgaactg ccgttcctta aatcggctga agagatggca caagaacagg aagcacagat   21840
gcaagcacag caagcacaga tgcttgaaga aggtgtggct aaggccgtgc cgggtgtaat   21900
tcaacaagaa cttaaggagg cgtaatgtct ttctcattta ctgaaccgtc aaccactcac   21960
cctactgctg aagagggtcc ggtagaaacc aaggaggtaa caactgatgc tgctactact   22020
gatgctcctg ctgacgctgg cacttctgta caagatgaca atgctggtgc acaacctact   22080
gaagacaccg gaggagaagc ttctggacag ccttcagaaa aaggagacaa tggcggagag   22140
aatggtgaac ctaagccaga tgataccgcg accgacactg aggaagtgca atacttcttc   22200
ggagaacatg aagtaacagt agacatccca caggatgtaa ctgacagcct taaagagaaa   22260
ggcattgatg ccaagcaggt tgccaaggaa ctctattcca aggtggcaa gtttgaactg   22320 tcagatgcaa ccaagcagaa attgtatgat gcttttggca agtttgcggt agatgcttac   22380
```

```
ctatcaggtc taaaggctca aaatgaagcc ttcttcctga agaagccaa cgcagctaaa    22440 gagttggaag cagctaacac ccaacgcttc tctgatgttt ctaaggaaat tggtggcgaa    22500
gaaggttggt cccgtcttga ggagtgggca cttgaagcgc tgtctgatga cgaactaatg    22560
gcattcaatg cggtgatgga atctggcaac cagtacctgc aacaatatgc tgttcgtgaa    22620
ctggagggtc gtcgtaagca ggcacagggg gatgataagc catccctgat tgagccatca    22680
gcacctgcta aggctaatga agagaatggc ccactgacgc gagatcagta cgttcaagca    22740
atcgcaactc ttagccagaa gtacggcaat gaccgtaaag ctatggcaga agctcaggct    22800
aaactggacg cccgtcgccg tgctggcatg gctcgcggta tctaattcag tatttactgg    22860
acactataga agggagaaaa gttctcccta gttatcaatt tgatttataa ggagattata    22920
atacatgtct acaccgaata ctctgactaa cgttgctgta tctgcgtccg gtgaggttga    22980
cagccttctc attgagaagt ttaatggtaa ggtcaatgag cagtacctga aggtgagaa    23040 cattctgtcc tactttgatg tacaaactgt tactggcact aacacagtga gcaacaaata    23100
tttgggcgaa actgagttgc aggtgctagc accgggtcag tcccctaatg ccaccctac    23160 tcaggcggat aaaaaccagt tggtaattga taccactgtc attgctcgta acactgtggc    23220
tcacatccac gatgtacaag gtgacatcga tagcctgaaa ccaaaactgg ctatgaacca    23280
agccaagcaa ctgaaacgtc tggaagacca gatggcaatt cagcagatgc tgttaggcgg    23340
tattgctaac accaaggccg aacgtaacaa gccgcgtgtt aaagggcatg gcttctctat    23400
caacgttaac gtaactgaga gtgaagcact ggctaacccct cagtatgtta tggctgcggt    23460
agagtatgct ctggagcaac agcttgagca ggaagtggac atctctgatg tagctatcat    23520
gatgccgtgg aagttcttca atgctttgcg tgatgcagac cgaattgtag ataagactta    23580
cactatcagc cagtctggtg caaccattaa tggcttcgtt ctctcttctt ataactgccc    23640
tgtgatcccg tctaaccgat tccctacctt cgctcaggat caggctcacc acctgttgtc    23700
taatgaagat aacggctatc gttatgaccc tatcgcagag atgaatggtg cagttgctgt    23760
tctgttcact tccgacgcac tgctggtggg tcgtaccatt gaagtgactg gtgacatctt    23820
ctatgagaag aaagagaaga cttattacat tgacaccttc atggctgagg gtgcaatccc    23880
tgaccgttgg gaagcagtgt ctgtagttac cactaaacgt gatgcaacta ctggtgatgc    23940
tggaggtcct ggtgatgatc acgcaaccgt actggctcgt gcacagcgta aggctgtata    24000
tgtcaaaacc gaaggtgctg cggctgcatt ctctgctgcc ccagcaggta tccaagcgga    24060
agaccttgta gcggcggtac gtgctgtaat ggcaaatgac attaagccga ctgcaatgaa    24120
acctactgag taacacctat gccctatcta ccttgcgtag gtagggttct ttttgttagg    24180
aggattcatg cctgtaatta dacaaaccag taaattagga catatgatgg aagatgtggc    24240
cttccagatt attgatagta agctggaagc ggtaaacttg tgtatgcgag ctattggtcg    24300
tgagggtgtg gattccctcg actcagggga cttgacgca aagatgcaa gcaaaatgat    24360 cgacatcgta tcccagcggt tccagtacaa caaaggaggt ggctggtggt tcaatcgtga    24420
accaaactgg caacttgcac cagacactaa cggtgaagtt aatttaccta caactgcct    24480 agcagtattg cagtgttatg ctttaggtga aagaaagta cctatgacta tgcgagcagg    24540
taagctctac tctacttgga gtcacaacctt tgatatgcgt aagcatgtta atgctaatgg    24600
tatgattcgt cttaccttac tcaccttact accctacgag catctaccta caagtgtaat    24660
gcaggctatt gcctatcaag ctgctgtaga gtttattgtg tctaaggatg cagatcagac    24720
```

```
taagctagcc actgcgcagc agatagccac tcagcttctt atggatgtac aatctgagca    24780
aatgtcacag aagcgattaa acatgctggt acataaccct actcagcgtc agtttggtat    24840
catggctggt ggctctcaga atgtacctgc ttactctcat tcaccttatg agagttgggc    24900
gctccgtccg tgggaggatc gttaatggaa gtacaaggtt cattaggtag acaaatccaa    24960
gggattagcc agcagccgcc agcggtacgc ttggatggtc agtgcacagc tatggttaat    25020
atgatacctg atgtagtgaa tggtactcaa tcacgcatgg gtacaactca tattgcaaag    25080
atacttgatg cggggactga tgacatggct actcatcatt atcgcagagg tgatggtgat    25140
gaagagtatt tcttcacgtt gaagaaagga caagttcctg agatatttga taagtatggg    25200
cgcaaatgta atgtgacttc acaagatgca cctatgacct acctctctga ggttgttaat    25260
ccaagggaag atgtgcaatt catgacgata gctgatgtta cttttcatgct taatcgtagg    25320 aaagtagtta aagctagtag caggaagtca cctaaagttg aaacaaagc cattgtgttt    25380 tgtgcgtatg gtcaatatgg tacatcttat tccattgtaa ttaatggggc caacgctgct    25440
agttttaaaa caccggatgg tggaagtgca gaccatgttg aacaaattcg aactgaacgt    25500
atcacttctg aattgtactc taagttgcag caatggagcg gtgtgagtga ctatgaaata    25560
caaagagacg gtactagtat atttatcgag agacgggatg tgctagctt tacaataaca    25620 accaccgatg gtgcaaaagg taaggactta gtggctatca agaataaagt tagctctact    25680
gacctactcc cttctcgtgc gcctgctggt tataaagtac aagtgtggcc tactggcagc    25740
aaacctgagt ctcgttactg gctgcaagct gagcctaaag agggaaaccct tgtgtcttgg    25800 aaagaaacaa tagctgctga tgtattactt gggtttgata aaggcacaat gccttacatt    25860
attgaacgta cagatatcat caacggcata gctcaattca agataagaca aggtgattgg    25920
gaagatcgta agtagggga tgacttgact aaccctatgc cctcttttat tgatgaggaa    25980
gtaccccaga caataggtgg aatgttcatg gtgcagaacc gcctatgctt tacagcaggt    26040
gaagcggtta ttgcttctcg tacatcatac ttcttcgatt tctttcgtta tacggttatc    26100
tctgcattgg caactgaccc ctttgatatt ttctcagatg ctagtgaagt ctaccagcta    26160
aaacatgcag tgaccttaga tggcgctacc gtgttgttct ctgataagtc acaattcata    26220
ctgccaggcg ataagccttt agagaagtca atgcactgc ttaagcctgt tacaacattt    26280
gaagtgaaca ataaagtgaa gccagtagta actggtgaat cggtaatgtt tgccactaat    26340
gatggttctt actctggtgt acgagagttc tatacagact cttatagtga cactaagaag    26400
gcacaagcaa tcacaagtca tgtgaataaa ctcatcgaag gtaacattac caacatggca    26460
gcaagcacca atgtcaacag gttacttgtc actaccgata agtatcgtaa cataatctac    26520
tgctacgatt ggttatggca aggaacagac cgtgtacaat cagcatggca tgtatggaag    26580
tggcctatag gtacaaaggt gcgaggtatg tttattctg gtgaattact ttacctgctc    26640
cttgagcgag gagatggcgt gtatctggag aagatggaca tgggtgatgc actaacctac    26700
ggtttgaatg accgcatcag aatggatagg caagcagagt tagtcttcaa gcatttcaaa    26760
gcagaagatg aatgggtatc tgagccgctc ccttgggttc ctactaaccc agaactttta    26820
gattgcatct taatcgaggg ttgggattca tatattggcg gctctttctt attcaagtac    26880
aaccctagtg acaatacttt gtctacaacc tttgatatgt atgatgacag ccatgtaaaa    26940
gcgaaggtta ttgttggtca gatttaccct caagagtttg aacctacgcc tgtggttatc    27000
agagacaatc aagaccgtgt atcctacatt gatgtaccag ttgtaggatt ggttcacctt    27060
aatcttgaca tgtaccccga tttctccgta gaagttaaga atgtgaagag tggtaaagta    27120
```

```
cgtagagtat tagcgtcaaa ccgtataggt ggtgctctca ataatacagt aggctatgtt    27180
gaaccgagag aaggtgtctt cagatttcca ctgagagcta agagcacgga tgttgtttat    27240
cgtattattg tagagtcacc tcacacattc cagcttcgtg atattgagtg ggaagggagc    27300
tacaatccaa ccaaaaggag ggtctaatgg ctataggttc agccgttatg ctggtatgt    27360 cttctattgg tagcatgttt gcaggcagtg gtgcagcagc cgctgctgga ggtgctgccg    27420
caggtggcgg aggtttgcta ggttcactag gtggattcct aagtggctct actgctggtt    27480
tctctaatgc tggccttctt ggtgctggcc ttcaagggtt aggcttgatt ggtgatctat    27540
ttggtggaag tgatgaagcc aaggcgatga agaaagcaca agaagagcaa tggcggcagc    27600
agcttattgc tacacaagag gcgtacaaga cagtggcaga cgcagaacgt tctgctgcta    27660
aacaatatca tgcagatgca atcagtaatc aggcttcact gctacagcag cgagcacagg    27720
ttgcattact tgctggggct actggtactg gtggtaattc tgtgtcctct atgcttaatg    27780
acttagcagc agatggcggc aggaaccaga gtactatcat tgataactat agagaatcaga    27840 agattaattt caccaaccag cttaagtcta tccaacgtgg tggtcagatg cagatgcgtg    27900
agtttaagaa gccttctgct atgaataacct tggttaaagg tattccaagt ctggcatctg    27960
cctatgtaac tggtagtaag tctggcaagg cattgggtaa agccttaact gattctcgca    28020
catattcatc tggaacaaga ggtatttaat ggcaattgag cgacaagcag tacaaggtct    28080
gccacaagtg caggccactt ctcctaatgt catgaccttt gcacctcaac aagtgggagg    28140
tgtggaggct ggcgtggctt ctacctccgg tagtaggttt atcgaagacc ttattcgtgc    28200
agcaagcagc gtggctgatg ttaccactgg tatccttaat cagaagattg aggaagataa    28260
ggttgttcaa atggaacggg catataacgg attaatgcct tctgaggatg caactcgtgg    28320
tggcgctcgt gctaacatgc ttgtcaaagc tcaactgcta gctaatgatg aagcagcacg    28380
aatgaaagac atggctactc gtttccaagg aacggatgac gaatggacac aacttatggt    28440
tgactctcgt aatgagatgc agaataagct gttccagcaa taccctgagt tgcaaggtga    28500
caaagatact atgcgtatgg tcactaatgt cttccaagaa cagcagcctc agatttgggc    28560
tacacgaacc cagcataaac ttgaccgtga acaagcagac cgtgaggata cctttgacgg    28620
gcgagtggct tctacttggg attctaatat tgaccctgaa gcctctggct atgctttaca    28680
ggaacgaatc cgcgaaggtc ttactcaagg attactacct gaacagatgt acaagaagtt    28740
agtccagcga gcaatttcac ttgcacaagg cggtgatgtt agcatggctg aagccctgaa    28800
gtatgtgaag gacgataagg gtgttttctgt ttatgctaag aatccacagc ttatcacagc    28860
catcactagt ggtaatgcag tttgggctag gaataatgta gctgatgtaa ctcgtatgtc    28920
tttcgaagtt aaagaatcct accttgcagg tgatttaact gatgaagaat tgttggaacg    28980
agcacagcac attaataatc tgacaggtaa ctctgtcttc tctaatccag aactagaggc    29040
actgatgcgc aacgggcta agcagaatgc agagctaggt gcaatgcagg atatgcgacg    29100
tgagctttac tccgaccgcc tgactggctt ccaaggtaag actgataaag agaagaaggc    29160
ttacattgat gttatcaaac aggatagcca actttatgca gaccagcaaa tcaaacaacg    29220
tggcttggac ccttacagtc aagaggctga agctattcgt ggtgcagtgg aagtgcagcg    29280
cctgcaattc atgaactcca aaggcttagt ggatgatacc tttgagtctc gtatcaaagc    29340
catggaatct atgctatcgc ctgagcactt tgccaagggc gaaccacagg agttgatgac    29400
tattcgccag ttgtgggaac agttaccaga agagagccga ggtgtctttg gtgacacggt    29460
```

```
gaatggctac atggataact acaacactgc actacaaatg ggagagacac ctttgcaggc    29520
tgcaaggttt gcgcgtaaag cacagcagaa attctctcgt actgagaagg aaaccaagaa    29580
gttcaactca gctattggag atgcactgga tgaggtatct ggtgctggct ggtttgatgg    29640
taaaaccgaa gtgtcagact taggtaaagc tattgcggaa aaagagttac gagctaaggc    29700
caatatgttg tggtctagtg gtatgcgtaa catggattcc atcaagaagg ctttaattac    29760
ttggggcaat aaacgctaca ctcaatcaga ggatgcaaag acttccggtg gctatttcat    29820
taaaggtgat tacacttctg catctgatat gcttatgtca gttgggaaag gcgtaaaccc    29880
taccgatgta cctctggcgc ttggtaggta tgtagaaaca cagatgccag aattgaagaa    29940
ggagcttcaa gagggggaaa ctaaagatga tatatacatt gattacaatg aacagaaagg    30000
tactttcgtg attcgtgctg gtgcagcagg tcgccctctt tctggagtaa tccctgtaac    30060
ctctttagat accacttcac tactagattc tgcctatcag aagaaagtag aggaacgaga    30120
taaaggcgag tatgttcacc cgtatcgtac agatattggt gcacaagagc ctatgccagc    30180
taaaccaact gccaaagata ttggtaaatt tggactagct aacttcctca tgtcttctgc    30240
ttttgcttct ggtgagaatc tgccttctaa cttcgagatt aactatcgag gtaatatgca    30300
acaattctat gacaagctag ctatggatga gaataaagat aaagttggct taataaggc     30360 aactggaacc tttactccat ataaagacgc tcacggtgag tctatcggtt acggtcattt    30420
cttaacggaa gaagagaagc gaaacgggta tattaagatt ggcgatgaac tagttcccta    30480
tcgagggtct atgtctcagc ttacagagag caaggctcgc gctcttatgg agcaagatgc    30540
taagaagcat gtgcctccta ctcgtgactg aagattccg tttgaccaga tgcaccctgc     30600
acagcaacgt ggcttgatgg atttaagcta caatttaggt aaaggtggaa tccagaactc    30660
accgcgtgct cttgctgcat tcaaagctgg taagcttacg gagggcttta tcgaaatgct    30720
gggcactgca tcaagtgaag gtaagcgtat tcctggccta ctgaagcgac gcgctgaggc    30780
atacaatatg gcatctgctg gtggtgtgcc taagattacc gaagtggaga ctcgtgaaga    30840
tggctccatg tgggttaggt ttggtggacc tatgccagca ggttctgtct cggcatggac    30900
tcataaacgt attggcgcgg atggttggta tcaggtttat gaggctgcac ctaccaagtt    30960
agctaaagat tctaaggtag gtaaagttaa gttgtagtac ctaactcaag gcttgtctca    31020
catgtgagac aggtctttat gataggcact atggaggaat tatggaacaa gacattaaga    31080
ctaattgggc tggatatgtc cagtctactc ctgagccgtt ttctattgag gcggctccgg    31140
tatcggctcc tacgatacgc cagcgtaatg agttacaaga gcaagttctt gaagctaaag    31200
ctgacgctga tatcttaggt gctgtaggtg ctgccttcca gaatgagtgg ttggcattcg    31260
gaggcaagcg gtggtatgac cgtgccactg ctgatttcac acctcaacca gactttgaga    31320
tacaacctga gcaacgtgaa gcactacgtt tcaaatatgg tacggatatg atgcagacaa    31380
tcactgaggg tgttcgttct gaggatgaat tgaacttccg tattcagaat gcggatgaag    31440
accttgagcg caataagcgc attgctcagg ctggctgggt tggctctgtg gcgacgattg    31500
gcgctgctgt gcttgaccct gtgggatggg ttgcctctat tccaaccggt ggtgccgcta    31560
aagttggact cgtaggccgt gctgtgcgtg gcgctatcgc cgctggcgtg agtaatgccg    31620
ctattgaatc cgtattggtc caaggtgaca tgactcgtga tttagatgac attatggtag    31680
cactgggttc cggtatggct atgggtggcg ttattggcgc tgtagcgcgt ggtagggcca    31740
ctaagctcag tgagcaaggt gatgacaggg ctgctagcat tgtgcgcagt gcagacgcag    31800
gggaccgcta tgttcgtgct gttgccgatg acagtatcgg tgcgatgcgt gttaagggcg    31860
```

```
cagaggttct cactgagggt gtattcgata tctccagtaa gagtgaagac ctactgaaaa   31920
ccttgcaacg agaaggtaat gcgattgata tgacacctcg ccgttgggct ggaactatgt   31980
ctgccctcgg tactgtcgtg cactcatcta aagatgcaag tatccgaggc cttggtgctc   32040
gtctgtttga atccccacaa ggtctaggta tgcagaaggc atctgctagt cttatgcaga   32100
atactaactt aaatcgcctg aaatctgctg atatgaaccg cttcaatgat gggtttgatt   32160
tgtggcttaa agagaataat atcaatccag tagcagggca taccaactct cattatgtac   32220
agcaatacaa tgaaaaggtg tgggaggcag tgcgtattgg catggatgag tctacaccta   32280
aatctatccg catggctgct gagggacaac aggctatgta cagagaggcg ctggctttac   32340
gtcaacgttc tggtgaagcg ggatttgaaa aggtaaaagc cgacaacaaa tatatgcctg   32400
atatctttga tagtatgaaa gccagacgtc aattcgatat gcacgataaa gaagacatca   32460
tcgaactttt ctctcgtgcc taccagaatg gcgctcgtaa gattccaaag gaagcagcag   32520
atgagattgc acgagcacag gtaaatcgcg ttgctgatgc taccttaact ggaaagctta   32580
gttttgaaaa ggcaatgtca ggtcagacta aggcagagta tgaagctatc atgcgtaagg   32640
caggcttcag tgatgaagaa attgaaaaga tgatagaagc tctggataac aaagaaacca   32700
gagataacat ctctaaccga gctaaaatga gtttaggatt agatgttact caagaataca   32760
atggcattcg tatgcgtgac ttcatgaata ccaacgtgga agagctaaca gataactata   32820
tgaaggaagc agcaggtggc gctgcattgg ctcgccaagg cttctctacc tatcaggctg   32880
cacttaatgc aattgacctt gtagagcgaa atgcacgaaa cgcggctaag gatagcaagg   32940
ctagtttggc attagatgaa gagattcgtc agatgcgaga aggtcttcgc ctgattatgg   33000
gcaagtcgat tgatgcagac ccacaggcta tatctactaa gatgatgcgt cgtggtcgtg   33060
atatcacagg tgtgcttcgc ttaggtcaaa tgggcttcgc acagctaggt gaacttgcca   33120
actttatggg tgaatttggt attgctgcaa ctactatggc tttaggtaag caattccgct   33180
tcacctctaa ggcgttgcgt aatggcgatg gcttcttccg agataagaac ttagctgagg   33240
ttgagagaat ggtggggtac attggtgagg ataactggct aacaactaag ggtgcacgtc   33300
ctgatgaatt tggtgatgta accacagtaa gagggatgat ggctcacttt gaccaatcca   33360
tgaactcaat acgtcgtgct caaaccaacc tatcactctt ccgcatggca cagggttctc   33420
tggagcgaat gactaatagg caaatagctt tgtctttcat tgaccacctt gaaggcaaga   33480
agattattcc tcagaagaaa ctggaggaac ttggtcttac tcaggagttc atgactaacc   33540
tacagaagca ctatgatgct aactctaaag gttctggctt gcttggcttt gatacaatgc   33600
cttatgccat gggtgaaact ttagctaatg ctattcgtcg taagtcaggt ctaatcatcc   33660
aacgtaactt cattggtgat gaaggtatct ggatgaacaa agcactaggt aagacatttg   33720
cacagcttaa gtcattctct cttgtatctg gtgagaagca atttggtcga gggattcgcc   33780
acgataaaat tggtcttgct aagaagacag cttacgggtt tgctttgggt tcaatagtgt   33840
atgcggcaaa agcctatgtg aactctattg ggcgagaaga ccaagatgaa tatttggaag   33900
agaagttatc gcctaaaggg ttggccttg gtgcaatggg tatgatgagt acaactgctg   33960
tatttagtct aggtggagat ttcttaggtg gcctaggtgt tctaccttcc gaactcattc   34020
aatcacgcta tgaagcaggt ttccaaagta agggtctgat tgaccaaata cctctggttg   34080
gcgttggtgc agatgcagta aatctggcta actcaatcaa gaagtatgca gaaggtgaca   34140
cagaaggtgt agatatcgct aagcgagcac tccgtcttgt gccacttacc aatataatag   34200
```

```
gtgtccaaaa cgcattgcgt tatggcttag atgaactgga ggattgatga gttatacttt    34260
cacagaacat acagccaatg gtacgcaagt cacctatcct tttagctttg ctggtaggga    34320
taaaggttat cttcgtgcct cagatgtgat agtggagtct cttcaaggta acacttggat    34380
tgaagttaca tctggctggc aactaactgg cacgcaccag attacttttg atgtagcacc    34440
agttgcaggt ttgaagttcc gtattcgaag ggaagtacaa aaagaatatc catacgctga    34500
gtttgaccgt ggtgttacct tggatatgaa gtctttaaat ggttctttca ttcatatact    34560
ggagattaca caggagttac ttgacgggtt ttatccagaa ggatacttca ttaaacagaa    34620
tgtaagctgg ggcggcaata agattactga tttggctgat ggcacaaatc gggagatgc     34680 agtaaataaa gggcagcttg atgccatcga caagaagcat acagattgga acgccaaaca    34740
ggacattgag attgctggcc ttaaggctgg tatgacttct ggtattgcgc acagaactgt    34800
tccttggtac acgatagccc aaggtggtga gatttccgta aaaccacctt atgaatttca    34860
agatgcacta gttttcctta atggggtatt gcagcaccaa attgtaggcg catactctat    34920
aagcaacaac actatcactt tcgcagagcc gcttgtggct ggtacagagg tgtatgtgct    34980
gattggtagt cgtgtggcta catctgaacc taatattcag ttggagttga actttgactt    35040
agtagaaggc caacaagtag tacagattgg ctctgcattt aagtacattg aggtctacct    35100
tgatggatta ttacaaccta aacttgctta tcaggtagac ggtgacattg ttactttctc    35160
agaaagagta ccagaatgcc ggatgactgc taagattatc acagcataag gaggtgggat    35220
gattaactcc gaactggtag atagtggtgt gaagcttgcg ccacctgcac tcatatcagg    35280
tgggtacttc ctcggtatca gttgggataa ttggtgtta atagcaacat tcatttatac     35340
cgtgttgcaa attggggact ggttttataa taagttcaag atttggaggg agaagcgtga    35400
gcgtacacaa taaacatgca gctacagagg acgaggttgg cattctgcat ggtgctatta    35460
ccaaaatctt caataagaaa gcacaggcaa tactggacac tatagaagaa gaccctgatg    35520
cagcattaca tttagtgtct ggtaaggata ttggtgcgat gtgtaagtgg gttcttgata    35580
acggcattac cgccacacct gctgcacagc aggaagagtc caagttatct aagcgcctca    35640
aggctatccg agaggcatcc agtggtaaga taattcaatt cactaaggag gattgatggc    35700
taaggcaaga gaatcacaag cggaggctct tgccagatgg gagatgctac aggagttaca    35760
gcagaccttt ccttacaccg cggaaggttt gcttctcttt gcagatacag ttattcataa    35820
cttaattgca ggcaaccctc atctgattcg tatgcaggcg gatatcttga agttcctatt    35880
ttacggacac aagtaccgcc tcatcgaagc gcctcgtggt atcgctaaga caacactatc    35940
agcaatctat acggtattcc gtattattca tgaaccgcat aagcgtatca tggttgtgtc    36000
ccaaaacgcc aagcgagcag aggaaatcgc aggttgggta gttaaaatct tccgtggctt    36060
agactttctt gagtttatgc tgccggatat ctacgctggg gaccgtgcat ccgttaaggc    36120
gtttgagatt cattcaccc tacgtggtag tgataagtct ccttctgtat cctgttactc     36180
aatcgaagca ggtatgcagg gtgctcgtgc tgatattatt ctagcggatg acgtagagtc    36240
gatgcagaat gctcgtacgg cagcgggccg tgccttgctt gaggagctga ctaaggagtt    36300
tgaatctatc aaccagtttg gggatatcat ttaccttggt acacctcaga acgtaaactc    36360
tatctacaac aacctacctg ctcgtggtta ctctgttcgt atctggactg cgcgttaccc    36420
ttcagtagag caagagcaat gttatggcga cttccttgca cctatgattg ttcaagatat    36480
gaaggacaac ccagcactt  gctcagggta cgggttggat ggtaatagtg gtgcaccttg     36540 tgccctgaa atgtatgatg atgaagtcct gattgagaag gaaatctctc agggtgctgc    36600
```

```
taagttccag cttcagttca tgcttaacac tcgcatgatg gatgctgaca gatacccatt   36660
acgcctgaac aatctaatct tcacctcgtt tggtacagag gaagtccctg tgatgcctac   36720
gtggagtaat gattccataa acatcattgg tgatgcacct aagtatggta acaagcctac   36780
ggatttcatg tacagacctg tagctcgccc atatgaatgg ggtgctgtct cccgcaagat   36840
tatgtatatt gaccctgcgg gtggtggtaa gaacggagat gagacgggtg tagccatcgt   36900
attcctgcac ggcacattca tttatgtgta tcagtgcttt ggtgtacctg gcggataccg   36960
agagtcgtcc ctgaatcgca ttgtgcaggc cgcaaagcag gcgggtgtta aagaggtatt   37020
cattgagaag aactttggtc atggcgcgtt tgaggcggta attaagccgt actttgaacg   37080
agagtggcct gtaactctgg aagaggatta cgccaccgga cagaaagagt tgcgtatcat   37140
tgagacgctg gagccgctca tggcagccca taggcttatc ttcaatgcag agatggtgaa   37200
gtcagacttt gagtcggtac agcactatcc gcttgaacta cgcatgtcct acagtctttt   37260
caatcaaatg tcgaacataa cgattgagaa gaacagcctc cggcacgatg accgcctaga   37320
cgccctgtat ggcgctatac ggcaattaac ttctcagata gactatgacg aggttacacg   37380
gattaatcgc ctcagagcgc aggagatgcg cgattacatc catgctatga acacacctca   37440
tctacgcagg gcaatgctat atggagatta cggtactgag cgaagagtga ccaacacttc   37500
cgtagcgatg cagcagcgag tttacgggca gaactaccga aataaatcgg caagcagaaa   37560
tacactttct gcaaggattt caaggactta ttaattactg gacactatag aaggaaggcc   37620
cagataataa gagaaaataa taggtaatat atatataggt taacctaggt tatataggta   37680
tgccttagta tgggtgtact cctgtacacc ctattcctta ctaccttact atatttacat   37740
aataggagag agacaatggc taatgattat agtagtcaac cattaacagg taagtctaag   37800
agaaagcagg tacaacctgt aagtgaagaa ctaatgcttc cggtgctcaa aaaagaggaa   37860
gttagtaaga aaagcaatgt tattaatgat gccaccaaat caggtaaaca gaaaggggcc   37920
atggtgtgcc ttgaagtgaa aggtggtgta ttgaagattg ctatcgcggt tgatggcaaa   37980
gaagattcag agtggaagtt agtaacagtg gaaccaactg ttaacccagt ttaagataag   38040
gaggaagatt acatggctaa atatggtact acaggttctg ttactggtca ggcttttcga   38100
gtaaaagcag tacaaactat tgcaacggca atcccgatgc ctgttgttaa agaagaagac   38160
cttaagagta aagaccaccc tatcaacatc aaacatttat caggtaaaca gaaaggtgca   38220
atggttgctc ttgagaaagg tgacacaacc ttacatattg ctgttgcacg tggtagtgaa   38280
cccacagacc cttgggatgt aactggtatg gaaaaggacg ctgttactcc agcagggta   38340 taataatgct taataaatac ttcaagcgta aagagtttgc ttgccgttgt gggtgcggta   38400
catccactgt tgatgctgaa ttactacagg tagtcacaga tgtgcgtgag cactttggtt   38460
ctcctgtagt tatcacttcg ggtcatcgct gtgctaagca caatgccaat gtaggtggcg   38520
ctaagaactc catgcatctt actggtaagg ctgctgacat taaagtgtct ggcatattac   38580
cttctgaagt gcataagtat cttactagca aataccaagg caagtatggt ataggtaagt   38640
ataactcctt cactcacatc gatgtacggg atggttgtgc gcgatggtaa gatgtgttga   38700
atggtgtgag cgtatggttg cccaagctgc cgaggatggc aactatgatg actgaagaa   38760 ctactctgac ttgttagctc aatggaaagg gagatgcaat gaaaaagctg tttaagtcta   38820
agaaggttgt aggtgcactg gttgcacttg ttattgctct tgtttctgta ggtcttggtg   38880
tagaccttgg ctctggcacg gaatcctctg tgacagatgt ggtctgccaa gtgatcacct   38940
```

```
gtgaataagt ttctagaagt tctggcaggt cttattggcc tgcttgtctc tgctaagaag   39000
aaacaagaag agaaggaggc acaaagtgaa gcgaatcatg ttagtgacaa cccttctgat   39060
tggttcgctg accacttccg ggtgtcagca ggcgttacca gagaaagcaa tggtgaaacc   39120
tctgaggccg acgctgacgg cagtttacga ggtagacgat aaggtctgct ttagtaagcc   39180
tgacgctaca aaacttggtt tgtacattct ctcgctagaa cgcggataca attaatacat   39240
agctttatgt atcagtgtct tacgatttac tggacactat agaagaggta agatagcgcc   39300
gttcttttga gcggcctatt actagccaat cttcataggg agggttggaa agtaatagga   39360
gatagcatgg ctaaattaac caaacctaat actgaaggaa tcttgcataa aggacaatct   39420
ttgtatgagt accttgatgc gagagtttta acatcaaagc cgtttggtgc tgcaggtgac   39480
gccactactg atgatacgga ggttatagct gcttcattaa actctcagaa agctgtcaca   39540
gtctcagatg gtgtattctc tagctctggt attaacagta attactgtaa cttagacggc   39600
aggggtagtg gcgtgctaag tcaccgttca agtacaggta actacttagt atttaacaat   39660
ctacgtgcag gtcgcttaag taatattacg gtagaaagta ataaggcgac tgatacaact   39720
cagggacagc aggtatccct tgctggtgga agtgatgtta ctgtaagtga cgttaacttc   39780
tcaaacgtta aaggtactgg tttcagttta atcgcatacc ctaatgatgc gccacctgat   39840
ggacttatga ttaaaggcat tcgaggtagc tattccggct atgctactaa taaggcagcc   39900
ggatgcgtac ttgctgattc ctcagttaac tccctcatag ataacgtcat tgctaagaac   39960
taccctcagt tcggagcagt agagttgaaa ggtacagcca gttacaacat agtcagtaat   40020
gttataggga cagattgcca gcatgtaact acaacggca ctgaagggcc aatagctcct   40080
tctaataacc ttatcaaggg ggtgatggct aataacccta agtatgcagc ggttgttgca   40140
ggcaaaggaa gtacgaactt aatctcgac gtgctcgtag attactcaac ttctgatgct   40200
aggcaggctc atggtgttac agtagagggt tctgataacg tcataaataa tgtgcttatg   40260
tcaggatgtg atggtactaa ctctttagga caagggcaga ctgctacaat tgcacgcttt   40320
ataggtacag ctaataacaa ctatgcgtct gtatttccta gctacagtgc tacaggtgtt   40380
attactttcg aatccggctc tacccgtaac ttcgtagagg taaagcaccc tggcaggaga   40440
aacgaccttc tcagttctgc tagtactatt gacggtgcag ctactattga cggcactagt   40500
aatagtaacg tagtgcacgc acctgcctta gggcagtaca taggtagtat gtcaggtagg   40560
ttcgaatggc ggattaagtc catgtcactc ccttcaggcg ttcttacttc tgctgataag   40620
tacagaatgc ttggagatgg tgctgtgtca ttagctgtag gtgggggcac ttcttctcaa   40680
gttcgcctat ttacttctga tggtacttct cggacagtgt ccctcaccaa cggtaacgtg   40740
cgtcttctta ccagtagcac aggcttttg cagttaggtg ctgatgcaat gaccccagac   40800
agtactggta catacgcatt aggttccgcc agccgagcat ggtctggcgg ttttactcaa   40860
gcagcattca ctgttacctc agatgctcgg tgtaaaacag aacctcttac tatctcagat   40920
gccttactgg atgcttggtc tgaagttgac tttgtgcagt ttcagtattt ggatcgtgtt   40980
gaggagaagg gtgcagactc agctagatgg cacttcggta tcatcgctca gcgagctaag   41040
gaggctttcg aacgtcacgg tatagatgca catcgctatg gcttcttgtg cttcgacagt   41100
tgggatgatg tatacgagga agatgccaat ggctctcgta aactgattac accagcaggt   41160
tcccgctacg gtattcgtta cgaggaagta ctgatattag aggctgcgtt gatgcggcgg   41220
actattaagc gtatgcagga agcactagct tccctgcta agtaagcaac aggcagtgcg   41280
taagcactgc ttttagcgca acttttctta aaggttatca cggtggtagc ctttcagaaa   41340
```

```
aggaggttac atgattcaaa gactaggttc ttcattagtt aaattcaaga gtaaaatagc    41400
aggtgcaatc tggcgtaact tggatgacaa gctcaccgag gttgtatcgc ttaaagattt    41460
tggagccaaa ggtgatggta agacaaacga ccaagatgca gtaaatgcag cgatggcttc    41520
aggtaagaga attgacggtg ctggtgctac ttacaaagta tcatctttac ctgatatgga    41580
gcgattctat aacacccgct tcgtatggga acgtttagca ggtcaacctc tttactatgt    41640
gagtaaaggt tttatcaatg gtgaactata taaaatcacg gataacccct attacaatgc    41700
ttggcctcaa gacaaagcgt ttgtatatga gaacgtgata tatgcacctt acatgggtag    41760
tgaccgtcat ggtgttagtc gtctgcatgt atcatgggtt aagtctggtg acgatggtca    41820
aacatggtct actccagagt ggttaactga tctgcatcca gattacccta cagtgaacta    41880
tcattgtatg agtatgggtg tatgtcgcaa ccgtctgttt gccatgattg aaacacgtac    41940
tttagccaag aacaaactaa ccaattgtgc attgtgggat cgccctatgt ctcgtagtct    42000
gcatcttact ggtggtatca ctaaggctgc aaatcagcaa tatgcaacaa tacatgtacc    42060
agatcacgga ctattcgtgg gcgattttgt taacttctct aattctgcgg taacaggtgt    42120
atcaggtgat atgactgttg caacggtaat agataaggac aacttcacgg ttcttacacc    42180
taaccagcag acttcagatt tgaataacgc tggaaagagt tggcacatgg gtacttcttt    42240
ccataagtct ccatggcgta agacagatct tggtctaatc cctagtgtca cagaggtgca    42300
tagctttgct actattgata acaatggctt tgttatgggc tatcatcaag gtgatgtagc    42360
tccacgagaa gttggtcttt tctacttccc tgatgctttc aatagcccat ctaattatgt    42420
tcgtcgtcag ataccatctg agtatgaacc agatgcgtca gagccatgca tcaagtacta    42480
tgacggtgta ttatacctta tcactcgtgg cactcttggt gacagacttg gaagctcttt    42540
gcatcgtagt agagatatag gtcagacttg ggagtcactg agatttccac ataatgttca    42600
tcatactacc ctaccttttg ctaaagtagg agatgacctt attatgtttg gttcagaacg    42660
tgcagaaaat gaatgggaag caggtgcacc agatgatcgt tacaaggcat cttatcctcg    42720
taccttctat gcacgattga atgtaaacaa ttggaatgca gatgatattg aatgggttaa    42780
catcacagac caaatctatc aaggtgacat tgtgaactct agtgtaggtg taggttcggt    42840
agtagttaaa gacagctaca tttactatat cttttggtggc gaaaaccatt tcaacccaat    42900
gacttatggt gacaacaaag gtaaagaccc atttaaaggt catggacacc ctactgatat    42960
atactgctat aagatgcaga ttgcaaatga caatcgtgta tctcgtaagt ttacatatgg    43020
tgcaactccg ggtcaagcta tacctacttt catgggtact gatggaatac gaaatatccc    43080
tgcacctttg tatttctcag ataacattgt tacagaggat actaaagttg gacacttaac    43140
acttaaagca agcacaagtt ccaatatacg atctgaagtg cagatggaag gtgaaatatg    43200
ctttattggc aagtctgttc caaaggacaa cccaactggt caacgtttga ttatttgtgg    43260
tggagaagag acttcgtcct cttcaggtgc acagataact ttgcacggct ctaattcaag    43320
taaggctaat cgtatcactt ataacggaaa tgagcaccta ttccaaggtg caccaatcat    43380
gcctgctgta gataaccagt ttgctgctgg tggacctagt aaccgattca ctaccatcta    43440
cctaggtagt gacccctgtta caacttcaga tgctgaccac aagtacagta tctctagtat    43500
taataccaag gtgttaaagg cttggagcag ggttggtttt aaacagtatg gtttgaatag    43560
tgaagcagag agggaccttg atagcataca cttcggtgtc ttggctcagg atattgtagc    43620
tgcttttgaa gctgaagggt tggatgccat taagtatgga attgtgtcct tcgaagaagg    43680
```

| | | | | | |
|---|---|---|---|---|---|
| taggtacggt | gtgaggtata | gtgaagttct | aatactagag | gctgcttata | ctcgttatcg | 43740 |
| tttagacaag | ttagaggaga | tgtatgccac | taataaaatc | agttaagcaa | gctgctgtac | 43800 |
| tccagaacac | agaagagctt | attcaatcag | gacgtgaccc | taagcaggct | tatgccattg | 43860 |
| ccaaggatgt | tcaacgtcgt | gccatgaaga | aaccttctgc | atcttctgcg | taaagaggag | 43920 |
| atatacaatg | gtcttcacac | tcgaagattt | cgttgggggac | tggcgacaga | cagccggcta | 43980 |
| caacctggac | caagtccttg | aacagggagg | tgtgtccagt | ttgtttcaga | atctcggggt | 44040 |
| gtccgtaact | ccgatccaaa | ggattgtcct | gagcggtgaa | aatgggctga | agatcgacat | 44100 |
| ccatgtcatc | atcccgtatg | aaggtctgag | cggcgaccaa | atgggccaga | tcgaaaaaat | 44160 |
| ttttaaggtg | gtgtaccctg | tggatgatca | tcactttaag | gtgatcctgc | actatggcac | 44220 |
| actggtaatc | gacggggtta | cgccgaacat | gatcgactat | ttcggacggc | cgtatgaagg | 44280 |
| catcgccgtg | ttcgacggca | aaagatcac | tgtaacaggg | accctgtgga | acggcaacaa | 44340 |
| aattatcgac | gagcgcctga | tcaaccccga | cggctccctg | ctgttccgag | taaccatcaa | 44400 |
| cggagtgacc | ggctggcggc | tgtgcgaacg | cattctggcg | taagcaggtt | aatatcttag | 44460 |
| tataaacaag | ggcagactta | ggtttgtcct | tagtgtattc | caaggaggt | aacatgctga | 44520 |
| aagatggttg | ggtttcatat | gaccctacag | accctaagaa | ttggctacag | gttatcgcta | 44580 |
| tagcttgtgc | aggtagccta | ttggctgccc | tgatgtattc | attatggatg | tacacaaagt | 44640 |
| aaccaaagtc | aaaattttga | tgtaggcgtg | tgtcagctct | ctcgccctcg | ccctcgccgg | 44700 |
| gttgtcccca | tagggtggcc | tgagggaatc | cgtcttcgac | gggcagggct | gatgtactcc | 44760 |
| ttgtctagta | caagggaggc | ggagggaacg | cctaggagg | cctaggaatg | gcttagtggt | 44820 |
| ggacaaggtg | attaccttag | tgaagcctct | tagtgcattc | ctgaggccat | tcagggcgtt | 44880 |
| tatgagggat | tgacagggtg | tgagggcgtg | ggcta | | | 44915 |

```
<210> SEQ ID NO 5
<211> LENGTH: 40659
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
```

| | | | | | |
|---|---|---|---|---|---|
| tctcacagtg | tacggaccta | aagttccccc | ataggggggta | cctaaagccc | agccaatcac | 60 |
| ctaaagtcaa | ccttcggttg | accttgaggg | ttccctaagg | gttggggatg | acccttgggt | 120 |
| ttgtctttgg | gtgttacctt | gagtgtctct | ctgtgtccct | atctgttaca | gtctcctaaa | 180 |
| gtatcctcct | aaagtcacct | cctaacgtcc | atcctaaagc | caacacctaa | agcctacacc | 240 |
| taaagaccca | tcaagtcaac | gcctatctta | agtttaaac | ataaagacca | gacctaaaga | 300 |
| ccagacctaa | agacactaca | taaagaccag | acctaaagac | gccttgttgt | tagccataaa | 360 |
| gtgataacct | ttaatcattg | tctttattaa | tacaactcac | tataaggaga | gacaacttaa | 420 |
| agagacttaa | aagattaatt | taaaatttat | caaaaagagt | attgacttaa | agtctaacct | 480 |
| ataggatact | tacagccatc | gagagggaca | cggcgaatag | ccatcccaat | cgacaccggg | 540 |
| gtcaaccgga | taagtagaca | gcctgataag | tcgcacgaaa | acaggtatt | gacaacatga | 600 |
| agtaacatgc | agtaagatac | aaatcgctag | gtaacactag | cagcgtcaac | cgggcgcaca | 660 |
| gtgccttcta | ggtgacttaa | gcgcaccacg | gcacataagg | tgaaacaaaa | cggttgacaa | 720 |
| catgaagtaa | acacggtacg | atgtaccaca | tgaaacgaca | gtgagtcacc | acactgaaag | 780 |

```
gtgatgcggt ctaacgaaac ctgacctaag acgctcttta caatctggt  aaatagctct    840 tgagtgcatg actagcggat aactcaaggg tatcgcaagg tgcccttttat gatattcact   900 aataactgca cgaggtaaca caagatggct atgtctaaca tgacttacaa caacgttttc   960
gaccacgctt acgaaatgct gaaagaaaac atccgttatg atgacatccg tgacactgat  1020
gacctgcacg atgctattca catggctgcc gataatgcag ttccgcacta ctacgctgac  1080
atctttagcg taatggcaag tgagggcatt gaccttgagt cgaagactc  tggtctgatg  1140 cctgacacca aggacgtaat ccgcatcctg caagcgcgta tctatgagca attaacgatt  1200
gacctctggg aagacgcaga agacttgctc aatgaatact tggaggaagt cgaggagtac  1260
gaggaggatg aagagtaatg tctactacca acgtgcaata cggtctgacc gctcaaactg  1320
tacttttcta tagcgacatg gtgcgctgtg gctttaactg gtcactcgca atggcacagc  1380
tcaaagaact gtacgaaaac aacaaggcaa tagctttaga atctgctgag tgatagactc  1440
aaggtcgctc ctagcgagtg gcctttatga ttatcacttt acttatgagg gagtaatgta  1500
tatgcttact atcggtctac tcaccgctct aggtctagct gtaggtgcat cctttgggaa  1560
ggctttaggt gtagctgtag gttcctactt taccgcttgc atcatcatag gaatcatcaa  1620
aggggcacta cgcaaatgat gaagcactac gttatgccaa tccacacgtc caacggggca  1680
accgtatgta cacctgatgg gttcgcaatg aaacaacgaa tcgaacgcct taagcgtgaa  1740
ctccgcatta accgcaagat taacaagata ggttccggct atgacagaac gcactgatgg  1800
cttaaagaaa ggttatatgc ccaatggcac actatacgct gcaaatcggc gaatagtgag  1860
aacttggcga gagaacaacc tcgaacgccg caaggacaag agagggcggc gtggcataga  1920
cgaaaggaaa aggttaaagc caagaaactc gccgcacttg aacaggcact agccaacaca  1980
ctgaacgcta tctcataacg aacataaagg acacaatgca atgaacatta ccgacatcat  2040
gaacgctatc gacgcaatca agcactgcc  aatctgtgaa cttgacaagc gtcaaggtat  2100
gcttatcgac ttactggtcg agatggtcaa cagcgagacg tgtgatgcg  agctaaccga  2160 actaaatcag gcacttgagc atcaagattg gtggactacc ttgaagtgtc tcacggctga  2220
cgcagggttc aagatgctcg gtaatggtca cttctcggct gcttatagtc acccgctgct  2280
acctaacaga gtgattaagg tgggcttta  gaaagaggat tcaggcgcag cctataccgc  2340
attctgccgc atgtatcagg gtcgtcctgg tatccctaac gtctacgatg tacagcgcca  2400
cgctggatgc tatacggtgg tacttgacgc acttaaggat tgcgagcgtt tcaacaatga  2460
tgcccattat aaatacgctg agattgcaag cgacatcatt gattgcaatt cggatgagca  2520
tgatgagtta actggatggg atggtgagtt tgttgaaact tgtaaactaa tccgcaagtt  2580
ctttgagggc atcgcctcat tcgacatgca tagcgggaac atcatgttct caaatggaga  2640
cgtaccatac atcaccgacc cggtatcatt ctcgcagaag aaagacggtg gcgcattcag  2700
catcgaccct gaggaactca tcaaggaagt cgaggaagtc gcacgacaga agaaattga   2760 ccgcgctaag gcccgtaaag aacgtcacga ggggcgctta aggcacgca  gattcaaacg  2820 tcgcaaccgc aaggcacgta agcacacaa  agctaagcgc gaaagaatgc ttgctgcgtg  2880
gcgatgggct gaacgtcaag aacggcgtaa ccatgaggta gctgtagatg tactaggaag  2940
aaccaataac gctatgctct gggtcaacat gttctctggg gactttaagg cgcttgagga  3000
acgaatcgcg ctgcactggc gtaatgctga ccggatggct atcgctaatg gtcttacgct  3060
caacattgat aagcaacttg acgcaatgtt aatgggctga tagtcttatc ttacaggtca  3120
tctgcgggtg gcctgaatag gtacgattta ctaactggaa gaggcactaa atgaacacga  3180
```

```
ttaacatcgc taagaacgac ttctctgaca tcgaactggc tgctatcccg ttcaacactc   3240
tggctgacca ttacggtgag cgtttagctc gcgaacagtt ggcccttgag catgagtctt   3300
acgagatggg tgaagcacgc ttccgcaaga tgtttgagcg tcaacttaaa gctggtgagg   3360
ttgcggataa cgctgccgcc aagcctctca tcactaccct actccctaag atgattgcac   3420
gcatcaacga ctggtttgag gaagtgaaag ctaagcgcgg caagcgcccg acagccttcc   3480
agttcctgca agaaatcaag ccggaagccg tagcgtacat caccattaag accactctgg   3540
cttgcctaac cagtgctgac aatacaaccg ttcaggctgt agcaagcgca atcggtcggg   3600
ccattgagga cgaggctcgc ttcggtcgta tccgtgacct tgaagctaag cacttcaaga   3660
aaaacgttga ggaacaactc aacaagcgcg tagggcacgt ctacaagaaa gcatttatgc   3720
aagttgtcga ggctgacatg ctctctaagg gtctactcgg tggcgaggcg tggtcttcgt   3780
ggcataagga agactctatt catgtaggag tacgctgcat cgagatgctc attgagtcaa   3840
ccggaatggt tagcttacac cgccaaaatg ctggcgtagt aggtcaagac tctgagacta   3900
tcgaactcgc acctgaatac gctgaggcta tcgcaacccg tgcaggtgcg ctggctggca   3960
tctctccgat gttccaacct tgcgtagttc ctcctaagcc gtggactggc attactggtg   4020
gtggctattg ggctaacggt cgtcgtcctc tggcgctggt gcgtactcac agtaagaaag   4080
cactgatgcg ctacgaagac gtttacatgc ctgaggtgta caaagcgatt aacattgcgc   4140
aaaacaccgc atggaaaatc aacaagaaag tcctagcggt cgccaacgta atcaccaagt   4200
ggaagcattg tccggtcgag gacatccctg cgattgagcg tgaagaactc ccgatgaaac   4260
cggaagacat cgacatgaat cctgaggctc tcaccgcgtg gaaacgtgct gccgctgctg   4320
tgtaccgcaa ggacaaggct cgcaagtctc gccgtatcag ccttgagttc atgcttgagc   4380
aagccaataa gtttgctaac cataaggcca tctggttccc ttacaacatg gactggcgcg   4440
gtcgtgttta cgctgtgtca atgttcaacc cgcaaggtaa cgatatgacc aaaggactgc   4500
ttacgctggc gaaaggtaaa ccaatcggta aggaaggtta ctactggctg aaaatccacg   4560
gtgcaaactg tgcgggtgtc gataaggttc cgttccctga gcgcatcaag ttcattgagg   4620
aaaaccacga gaacatcatg gcttgcgcta agtctccact ggagaacact tggtgggctg   4680
agcaagattc tccgttctgc ttccttgcgt tctgctttga gtacgctggg gtacagcacc   4740
acggcctgag ctataactgc tcccttccgc tggcgtttga cgggtcttgc tctggcatcc   4800
agcacttctc cgcgatgctc cgagatgagg taggtggtcg cgcggttaac ttgcttccta   4860
gtgaaaccgt tcaggacatc tacgggattg ttgctaagaa agtcaacgag attctacaag   4920
cagacgcaat caatgggacc gataacgaag tagttaccgt gaccgatgag aacactggtg   4980
aaatctctga gaaagtcaag ctgggcacta aggcactggc tggtcaatgg ctggcttacg   5040
gtgttactcg cagtgtgact aagcgttcag tcatgacgct ggcttacggg tccaaagagt   5100
tcggcttccg tcaacaagtg ctggaagata ccattcagcc agctattgat tccggcaagg   5160
gtctgatgtt cactcagccg aatcaggctg ctggatacat ggctaagctg atttgggaat   5220
ctgtgagcgt gacggtggta gctgcggttg aagcaatgaa ctggcttaag tctgctgcta   5280
agctgctggc tgctgaggtc aaagataaga agactggaga gattcttcgc aagcgttgcg   5340
ctgtgcattg ggtaactcct gatggtttcc ctgtgtggca ggaatacaag aagcctattc   5400
agacgcgctt gaacctgatg ttcctcggtc agttccgctt acagcctacc attaacacca   5460
acaaagatag cgagattgat gcacacaaac aggagtctgg tatcgctcct aactttgtac   5520
```

-continued

```
acagccaaga cggtagccac cttcgtaaga ctgtagtgtg ggcacacgag aagtacggaa    5580 tcgaatctttt tgcactgatt cacgactcct tcggtaccat tccggctgac gctgcgaacc    5640
tgttcaaagc agtgcgcgaa actatggttg acacatatga gtcttgtgat gtactggctg    5700
atttctacga ccagttcgct gaccagttgc acgagtctca attggacaaa atgccagcac    5760
ttccggctaa aggtaacttg aacctccgtg acatcttaga gtcggacttc gcgttcgcgt    5820
aacgccaaat caatacgact cactatagag ggacaaactc aaggtcattc gcaagagtgg    5880
cctttatgat tgaccttctt ccggttaata cgactcacta taggagaacc ttaaggttta    5940
actttaagac ccttaagtgt taattagaga tttaaggaga ttcaacatgg tcttcacact    6000
cgaagatttc gttggggact ggcgacagac agccggctac aacctggacc aagtccttga    6060
acagggaggt gtgtccagtt tgtttcagaa tctcggggtg tccgtaactc cgatccaaag    6120
gattgtcctg agcggtgaaa atgggctgaa gatcgacatc catgtcatca tcccgtatga    6180
aggtctgagc ggcgaccaaa tgggccagat cgaaaaaatt tttaaggtgg tgtaccctgt    6240
ggatgatcat cactttaagg tgatcctgca ctatggcaca ctggtaatcg acggggttac    6300
gccgaacatg atcgactatt tcggacggcc gtatgaaggc atcgccgtgt tcgacggcaa    6360
aaagatcact gtaacaggga ccctgtggaa cggcaacaaa attatcgacg agcgcctgat    6420 caacccccgac ggctccctgc tgttccgagt aaccatcaac ggagtgaccg gctggcggct    6480
gtgcgaacgc attctggcgt aaaggaggta acatatgac catgattacg gattcactgg    6540
ccgtcgtttt acaacgtcgt gactgggaaa accctggcgt tacccaactt aatcgccttg    6600
cagcacatcc ccctttcgcc agctggcgta atagcgaaga ggcccgcacc gatcgccctt    6660
cccaacagtt gcgcagcctg aatggcgaat ggtaaaaatt aaagaattac taagagagga    6720
ctttaagtat gcgtaacttc gaaaagatga ccaaacgttc taaccgtaat gctcgtgact    6780
tcgaggcaac caaaggtcgc aagttgaata agactaagcg tgaccgctct cacaagcgta    6840
gctgggaggg tcagtaagat gggacgtta tatagtggta atctggcagc attcaaggca    6900
gcaacaaaca agctgttcca gttagactta gcggtcattt atgatgactg gtatgatgcc    6960
tatacaagaa aagattgcat acggttacgt attgaggaca ggagtggaaa cctgattgat    7020
actagcacct tctaccacca cgacgaggac gttctgttca atatgtgtac tgattggttg    7080
aaccatatgt atgaccagtt gaaggactgg aagtaatacg actcagtata gggacaatgc    7140
ttaaggtcgc tctctaggag tggccttagt catttaacca ataggagata aacattatga    7200
tgaacattaa gactaacccg tttaaagccg tgtctttcgt agagtctgcc attaagaagg    7260
ctctggataa cgctgggtat cttatcgctg aaatcaagta cgatggtgta cgcgggaaca    7320
tctgcgtaga caatactgct aacagttact ggctctctcg tgtatctaaa acgattccgg    7380
cactggagca cttaaacggg tttgatgttc gctggaagcg tctactgaac gatgaccgtt    7440
gcttctacaa agatggcttt atgcttgatg gggaactcat ggtcaagggc gtagacttta    7500
acacagggtc cggcctactg cgtaccaaat ggactgacac gaagaaccaa gagttccatg    7560
aagagttatt cgttgaacca atccgtaaga aagataaagt tcccctttaag ctgcacactg    7620 gacaccttca cataaaactg tacgctatcc tcccgctgca catcgtggag tctggagaag    7680
actgtgatgt catgacgttg ctcatgcagg aacacgttaa gaacatgctg cctctgctac    7740
aggaatactt ccctgaaatc gaatggcaag cggctgaatc ttacgaggtc tacgatatgg    7800
tagaactaca gcaactgtac gagcagaagc gagcagaagg ccatgagggt ctcattgtga    7860
aagacccgat gtgtatctat aagcgcggta agaaatctgg ctggtggaaa atgaaacctg    7920
```

```
agaacgaagc tgacggtatc attcagggtc tggtatgggg tacaaaaggt ctggctaatg    7980
aaggtaaagt gattggtttt gaggtgcttc ttgagagtgg tcgtttagtt aacgccacga    8040
atatctctcg cgccttaatg gatgagttca ctgagacagt aaaagaggcc accctaagtc    8100 aatgggatt  ctttagccca tacggtattg gcgacaacga tgcttgtact attaacccttt    8160 acgatggctg ggcgtgtcaa attagctaca tggaggaaac acctgatggc tctttgcggc    8220
acccatcgtt cgtaatgttc cgtggcaccg aggacaaccc tcaagagaaa atgtaatcac    8280
actggctcac cttcgggtgg gcctttctgc gtttataagg agacacttta tgtttaagaa    8340
ggttggtaaa ttccttgcgg cttttggcagc tatcctgacg cttgcgtata ttcttgcggt    8400
ataccctcaa gtagcactag tagtagttgg cgcttgttac ttagcggcag tgtgtgcttg    8460
cgtgtggagt atagttaact ggtaatacga ctcactaaag gaggtacaca ccatgatgta    8520
cttaatgcca ttactcatcg tcattgtagg atgccttgcg ctccactgta gcgatgatga    8580
tatgccagat ggtcacgctt aatacgactc actaaaggag acactatatg tttcgacttc    8640
attacaacaa aagcgttaag aatttcacgg ttcgccgtgc tgaccgttca atcgtatgtg    8700
cgagcgagcg ccgagctaag atacctctta ttggtaacac agttcctttg gcaccgagcg    8760
tccacatcat tatcacccgt ggtgactttg agaaagcaat agacaagaaa cgtccggttc    8820
ttagtgtggc agtgacccgc ttcccgttcg tccgtctgtt actcaaacga atcaaggagg    8880
tgttctgatg ggactgttag atggtgaagc ctgggaaaaa gaaaacccgc cagtacaagc    8940
aactgggtgt atagcttgct tagagaaaga tgaccgttat ccacacacct gtaacaaagg    9000
agctaacgat atgaccgaac gtgaacaaga gatgatcatt aagttgatag acaataatga    9060
aggtcgccca gatgatttga atggctgcgg tattctctgc tccaatgtcc cttgccacct    9120
ctgccccgca aataacgatc aaaagataac cttaggtgaa atccgagcga tggacccacg    9180
taaaccacat ctgaataaac ctgaggtaac tcctacagat gaccagcctt ccgctgagac    9240
aatcgaaggt gtcactaagc cttcccacta catgctgttt gacgacattg aggctatcga    9300
agtgattgct cgttcaatga ccgttgagca gttcaaggga tactgcttcg gtaacatctt    9360
aaagtacaga ctacgtgctg gtaagaagtc agagttagcg tacttagaga aagacctagc    9420
gaaagcagac ttctataaag aactctttga gaaacataag gataaatgtt atgcataact    9480
tcaagtcaac cccacctgcc gacagcctat ctgatgactt cacatcttgc tcagagtggt    9540
gccgaaagat gtgggaagag acattcgacg atgcgtacat caagctgtat gaactttgga    9600
aatcgagagg tcaatgacta tgtcaaacgt aaatacaggt tcacttagtg tggacaataa    9660
gaagttttgg gctaccgtag agtcctcgga gcattccttc gaggttccaa tctacgctga    9720
gaccctagac gaagctctgg agttagccga atggcaatac gttccggctg gctttgaggt    9780
tactcgtgtg cgtccttgtg tagcaccgaa gtaatacgac tcactattag ggaagactcc    9840
ctctgagaaa ccaaacgaaa cctaaaggag attaacatta tggctaagaa gattttcacc    9900
tctgcgctgg gtaccgctga accttacgct tacatcgcca agccggacta cggcaacgaa    9960
gagcgtggct ttgggaaccc tcgtggtgtc tataaagttg acctgactat tcccaacaaa   10020
gacccgcgct gccagcgtat ggtcgatgaa atcgtgaagt gtcacgaaga ggcttatgct   10080
gctgccgttg aggaatacga agctaatcca cctgctgtag ctcgtggtaa gaaaccgctg   10140
aaaccgtatg agggtgacat gccgttcttc gataacggtg acggtacgac tacctttaag   10200
ttcaaatgct acgcgtcttt ccaagacaag aagaccaaag agaccaagca catcaatctg   10260
```

```
gttgtggttg actcaaaagg taagaagatg aagacgttc cgattatcgg tggtggctct    10320
aagctgaaag ttaaatattc tctggttcca tacaagtgga acactgctgt aggtgcgagc    10380
gttaagctgc aactggaatc cgtgatgctg gtcgaactgg ctacctttgg tggcggtgaa    10440
gacgattggg ctgacgaagt tgaagagaac ggctatgttg cctctggttc tgccaaagcg    10500
agcaaaccac gcgacgaaga aagctgggac gaagacgacg aagagtccga ggaagcagac    10560
gaagacggag acttctaagt ggaactgcgg gagaaaatcc ttgagcgaat caaggtgact    10620
tcctctgggt gttgggagtg gcagggcgct acgaacaata aagggtacgg gcaggtgtgg    10680
tgcagcaata ccggaaaggt tgtctactgt catcgcgtaa tgtctaatgc tccgaaaggt    10740
tctaccgtcc tgcactcctg tgataatcca ttatgttgta accctgaaca cctatccata    10800
ggaactccaa aagagaactc cactgacatg gtaaataagg gtcgctcaca caaggggtat    10860
aaactttcag acgaagacgt aatggcaatc atggagtcca gcgagtccaa tgtatcctta    10920
gctcgcacct atggtgtctc ccaacagact atttgtgata tacgcaaagg gaggcgacat    10980
ggcaggttac ggcgctaaag gaatccgaaa ggttggagcg tttcgctctg gcctagagga    11040
caaggtttca aagcagttgg aatcaaaagg tattaaattc gagtatgaag agtggaaagt    11100
gccttatgta attccggcga gcaatcacac ttacactcca gacttcttac ttccaaacgg    11160
tatattcgtt gagacaaagg gtctgtggga aagcgatgat agaaagaagc acttattaat    11220
tagggagcag caccccgagc tagacatccg tattgtcttc tcaagctcac gtactaagtt    11280
atacaaaggt tctccaacgt cttatggaga gttctgcgaa aagcatggta ttaagttcgc    11340
tgataaactg atacctgctg agtggataaa ggaacccaag aaggaggtcc cctttgatag    11400
attaaaaagg aaaggaggaa agaaataatg gctcgtgtac agtttaaaca acgtgaatct    11460
actgacgcaa tctttgttca ctgctcggct accaagccaa gtcagaatgt tggtgtccgt    11520
gagattcgcc agtggcacaa agagcagggt tggctcgatg tgggatacca cttatcatc     11580 aagcgagacg gtactgtgga ggcaggacga gatgagatgg ctgtaggctc tcacgctaag    11640
ggttacaacc acaactctat cggcgtctgc cttgttggtg gtatcgacga taaaggtaag    11700
ttcgacgcta actttacgcc agcccaaatg caatcccttc gctcactgct tgtcacactg    11760
ctggctaagt acgaaggcgc tgtgcttcgc gcccatcatg aggtggcgcc gaaggcttgc    11820
ccttcgttcg accttaagcg ttggtgggag aagaacgaac tggtcacttc tgaccgtgga    11880
taattaattg aactcactaa agggagacca cagcggtttc cctttgttcg cattggaggt    11940
caaataatgc gcaagtctta taaacaattc tataaggctc cgaggaggca tatccaagtg    12000
tgggaggcag ccaatgggcc tataccaaaa ggttattata tagaccacat tgacggcaat    12060
ccactcaacg acgccttaga caatctccgt ctggctctcc caaaagaaaa ctcatggaac    12120
atgaagactc caaagagcaa tacctcagga ctaaagggac tgagttggag caaggaaagg    12180
gagatgtgga gaggcactgt aacagctgag ggtaaacagc ataactttcg tagtagagat    12240
ctattggaag tcgttgcgtg gatttataga actaggaggg aattgcatgg acaattcgca    12300
cgattccgat agtgtatttc tttaccacat tccttgtgac aactgtggga gtagtgatgg    12360
gaactcgctg ttctctgacg gacacacgtt ctgctacgta tgcgagaagt ggactgctgg    12420
taatgaagac actaaagaga gggcttcaaa acggaaaccc tcaggaggta aaccaatgac    12480
ttacaacgtg tggaacttcg gggaatccaa tggacgctac tccgcgttaa ctgcgagagg    12540
aatctccaag gaaacctgtc agaaggctgg ctactggatt gccaaagtag acggtgtgat    12600
gtaccaagtg gctgactatc gggaccagaa cggcaacatt gtgagtcaga aggttcgaga    12660
```

```
taaagataag aactttaaga ccactggtag tcacaagagt gacgctctgt tcgggaagca   12720
cttgtggaat ggtggtaaga agattgtcgt tacagaaggt gaaatcgaca tgcttaccgt   12780
gatggaactt caagactgta agtatcctgt agtgtcgttg ggtcacggtg cctctgccgc   12840
taagaagaca tgcgctgcca actacgaata ctttgaccag ttcgaacaga ttatcttaat   12900
gttcgatatg gacgaagcag ggcgcaaagc agtcgaagag gctgcacagg ttctacctgc   12960
tggtaaggta cgagtggcag ttcttccgtg taaggatgca aacgagtgtc acctaaatgg   13020
tcacgaccgt gaaatcatgg agcaagtgtg gaatgctggt ccttggattc ctgatggtgt   13080
ggtatcggct cttccgttac gtgaacgaat ccgtgagcac ctatcgtccg aggaatcagt   13140
aggtttactt ttcagtggct gcactggtat caacgataag accttaggtg cccgtggtgg   13200
tgaagtcatt atggtcactt ccggttccgg tatgggtaag tcaacgttcg tccgtcaaca   13260
agctctacaa tggggcacag cgatgggcaa gaaggtaggc ttagcgatgc ttgaggagtc   13320
cgttgaggag accgctgagg accttatagg tctacacaac cgtgtccgac tgagacaatc   13380
cgactcacta agagagagaa ttattgagaa cggtaagttc gaccaatggt tcgatgaact   13440
gttcggcaac gatacgttcc atctatatga ctcattcgcc gaggctgaga cggatagact   13500
gctcgctaag ctggcctaca tgcgctcagg cttgggctgt gacgtaatca ttctagacca   13560
catctcaatc gtcgtatccg cttctggtga atccgatgag cgtaagatga ttgacaacct   13620
gatgaccaag ctcaaagggt tcgctaagtc aactggggtg gtgctggtcg taatttgtca   13680
ccttaagaac ccagacaaag gtaaagcaca tgaggaaggt cgccccgttt ctattactga   13740
cctacgtggt tctggcgcac tacgccaact atctgatact attattgccc ttgagcgtaa   13800
tcagcaaggc gatatgccta accttgtcct cgttcgtatt ctcaagtgcc gctttactgg   13860
tgatactggt atcgctggct acatggaata caacaaggaa accggatggc ttgaaccatc   13920
aagttactca ggggaagaag agtcacactc agagtcaaca gactggtcca acgacactga   13980
cttctgacag gattcttgat gacttttccag acgactacga gaagtttcgc tggagagtcc   14040
cattctaata cgactcacta aaggagacac accatgttca aactgattaa gaagttaggc   14100
caactgctgg ttcgtatgta caacgtggaa gccaagcgac tgaacgatga ggctcgtaaa   14160
gaggccacac agtcacgcgc tctggcgatt cgctccaacg aactggctga cagtgcatcc   14220
actaaagtta ccgaggctgc ccgtgtggca aaccaagctc aacagctttc caaattcttt   14280
gagtaatcaa acaggagaaa ccattatgtc taacgtagct gaaactatcc gtctatccga   14340
tacagctgac cagtggaacc gtcgagtcca catcaacgtt cgcaacggta aggcgactat   14400
ggtttaccgc tggaaggact ctaagtcctc taagaatcac actcagcgta tgacgttgac   14460
agatgagcaa gcactgcgtc tggtcaatgc gcttaccaaa gctgccgtga cagcaattca   14520
tgaagctggt cgcgtcaatg aagctatggc tatcctcgac aagattgata actaagagtg   14580
gtatcctcaa ggtcgccaaa gtggtggcct tcatgaatac tattcgactc actataggag   14640
atattaccat gcgtgaccct aaagttatcc aagcagaaat cgctaaactg gaagctgaac   14700
tggaggacgt taagtaccat gaagctaaga ctcgctccgc tgttcacatc ttgaagaact   14760
taggctggac ttgacaagga cagactggct ggaagaaacc agaagttacc aagctgagtc   14820
ataaggtgtt cgataaggac actatgaccc acatcaaggc tggtgattgg gttaaggttg   14880
acatgggagt tgttggtgga tacggctacg tccgctcagt tagtggcaaa tatgcacaag   14940
tgtcatacat cacaggtgtt actccacgcg gtgcaatcgt tgccgataag accaacatga   15000
```

```
ttcacacagg tttcttgaca gttgtttcat atgaagagat tgttaagtca cgataatcaa    15060
taggagaaat caatatgatc gtttctgaca tcgaagctaa cgccctctta gagagcgtca    15120
ctaagttcca ctgcggggtt atctacgact actccaccgc tgagtacgta agctaccgtc    15180
cgagtgactt cggtgcgtat ctggatgcgc tggaagccga ggttgcacga ggcggtctta    15240
ttgtgttcca caacggtcac aagtatgacg ttcctgcatt gaccaaactg gcaaagttgc    15300
aattgaaccg agagttccac cttcctcgtg agaactgtat tgacacccct gtgttgtcac    15360
gtttgattca ttccaacctc aaggacaccg atatgggtct tctgcgttcc ggcaagttgc    15420
ccggaaaacg ctttgggtct cacgctttgg aggcgtgggg ttatcgctta ggcgagatga    15480
agggtgaata caaagacgac tttaagcgta tgcttgaaga gcagggtgaa gaatacgttg    15540
acggaatgga gtggtggaac ttcaacgaag agatgatgga ctataacgtt caggacgttg    15600
tggtaactaa agctctcctt gagaagctac tctctgacaa acattacttc cctcctgaga    15660
ttgactttac ggacgtagga tacactacgt tctggtcaga atcccttgag gccgttgaca    15720
ttgaacatcg tgctgcatgg ctgctcgcta acaagagcg caacgggttc ccgtttgaca    15780
caaaagcaat cgaagagttg tacgtagagt tagctgctcg ccgctctgag ttgctccgta    15840
aattgaccga aacgttcggc tcgtggtatc agcctaaagg tggcactgag atgttctgcc    15900
atccgcgaac aggtaagcca ctacctaaat accctcgcat taagacacct aaagttggtg    15960
gtatctttaa gaagcctaag aacaaggcac agcgagaagg ccgtgagcct tgcgaacttg    16020
ataccgcga gtacgttgct ggtgctcctt acaccccagt tgaacatgtt gtgtttaacc    16080
cttcgtctcg tgaccacatt cagaagaaac tccaagaggc tgggtgggtc ccgaccaagt    16140
acaccgataa gggtgctcct gtggtggacg atgaggtact cgaaggagta cgtgtagatg    16200
accctgagaa gcaagccgct atcgacctca ttaaagagta cttgatgatt cagaagcgaa    16260
tcggacagtc tgctgaggga gacaaagcat ggcttcgtta tgttgctgag gatggtaaga    16320
ttcatggttc tgttaaccct aatggagcag ttacgggtcg tgcgacccat gcgttcccaa    16380
accttgcgca aattccgggt gtacgttctc cttatggaga gcagtgtcgc gctgcttttg    16440
gcgctgagca ccatttggat gggataactg gtaagccttg ggttcaggct ggcatcgacg    16500
catccggtct tgagctacgc tgcttggctc acttcatggc tcgctttgat aacggcgagt    16560
acgctcacga gattcttaac ggcgacatcc acactaagaa ccagatagct gctgaactac    16620
ctacccgaga taacgctaag acgttcatct atgggttcct ctatggtgct ggtgatgaga    16680
agattggaca gattgttggt gctggtaaag agcgcggtaa ggaactcaag aagaaattcc    16740
ttgagaacac ccccgcgatt gcagcactcc gcgagtctat ccaacagaca cttgtcgagt    16800
cctctcaatg ggtagctggt gagcaacaag tcaagtggaa acgccgctgg attaaaggtc    16860
tggatggtcg taaggtacac gttcgtagtc ctcacgctgc cttgaatacc ctactgcaat    16920
ctgctggtgc tctcatctgc aaactgtgga ttatcaagac cgaagagatg ctcgtagaga    16980
aaggcttgaa gcatggctgg gatggggact ttgcgtacat ggcatgggta catgatgaaa    17040
tccaagtagg ctgccgtacc gaagagattg ctcaggtggt cattgagacc gcacaagaag    17100
cgatgcgctg ggtggagac cactggaact tccgtgtgtct tctggatacc gaaggtaaga    17160
tgggtcctaa ttgggcgatt tgccactgat acaggaggct actcatgaac gaaagacact    17220
taacaggtgc tgcttctgaa atgctagtag cctacaaatt taccaaagct gggtacactg    17280
tctattaccc tatgctgact cagagtaaag aggacttggt tgtatgtaag gatggtaaat    17340
ttagtaaggt tcaggttaaa acagccacaa cggttcaaac caacacagga gatgccaagc    17400
```

```
aggttaggct aggtggatgc ggtaggtccg aatataagga tggagacttt gacattcttg    17460
cggttgtggt tgacgaagat gtgcttattt tcacatggga cgaagtaaaa ggtaagacat    17520
ccatgtgtgt cggcaagaga aacaaaggca taaaactata ggagaaatta ttatggctat    17580
gacaaagaaa tttaaagtgt ccttcgacgt taccgcaaag atgtcgtctg acgttcaggc    17640
aatcttagag aaagatatgc tgcatctatg taagcaggtc ggctcaggtg cgattgtccc    17700
caatggtaaa cagaaggaaa tgattgtcca gttcctgaca cacggtatgg aaggattgat    17760
gacattcgta gtacgtacat catttcgtga ggccattaag gacatgcacg aagagtatgc    17820
agataaggac tctttcaaac aatctcctgc aacagtacgg gaggtgttct gatgtctgac    17880
tacctgaaag tgctgcaagc aatcaaaagt tgccctaaga ctttccagtc caactatgta    17940
cggaacaatg cgagcctcgt agcggaggcc gcttcccgtg tcacatctc gtgcctgact     18000
actagtggac gtaacggtgg cgcttgggaa atcactgctt ccggtactcg ctttctgaaa    18060
cgaatgggga gatgtgtcta atgtctcgtg accttgtgac tattccacgc gatgtgtgga    18120
acgatataca gggctacatc gactctctgg aacgtgagaa cgatagcctt aagaatcaac    18180
taatggaagc tgacgaatac gtagcggaac tagaggagaa acttaatggc acttcttgac    18240
cttaaacaat tctatgagtt acgtgaaggc tgcgacgaca agggtatcct tgtgatggac    18300
ggcgactggt tggtcttcca agctatgagt gctgctgagt ttgatgcctc ttgggaggaa    18360
gagatttggc accgatgctg tgaccacgct aaggcccgtc agattcttga ggattccatt    18420
aagtcctacg agaccgtaa gaaggcttgg gcaggtgctc caattgtcct tgcgttcacc     18480
gatagtgtta actggcgtaa agaactggtt gacccgaact ataaggctaa ccgtaaggcc    18540
gtgaagaaac ctgtagggta ctttgagttc cttgatgctc tctttgagcg cgaagagttc    18600
tattgcatcc gtgagcctat gcttgagggt gatgacgtta tgggagttat tgcttccaat    18660
ccgtctgcct tcggtgctcg taaggctgta atcatctctt gcgataagga ctttaagacc    18720
atccctaact gtgacttcct gtggtgtacc actggtaaca tcctgactca gaccgaagag    18780
tccgctgact ggtggcacct cttccagacc atcaagggtg acatcactga tggttactca    18840
gggattgctg gatgggtga taccgccgag gacttcttga ataacccgtt cataaccgag    18900
cctaaaacgt ctgtgcttaa gtccggtaag aacaaaggcc aagaggttac taaatgggtt    18960
aaacgcgacc ctgagcctca tgagacgctt tgggactgca ttaagtccat tggcgcgaag    19020
gctggtatga ccgaagagga tattatcaag cagggccaaa tggctcgaat cctacggttc    19080
aacgagtaca actttattga caaggagatt tacctgtgga gaccgtagcg tatattggtc    19140
tgggtctttg tgttctcgga gtgtgcctca tttcgtgggg cctttgggac ttagccagaa    19200
taatcaagtc gttacacgac actaagtgat aaactcaagg tccctaaatt aatacgactc    19260
actatagcga gataggggcc tttacgatta ttactttaag atttaactct aagaggaatc    19320
tttattatgt taacacctat taaccaatta cttaagaacc ctaacgatat tccagatgta    19380
cctcgtgcaa ccgctgagta tctacaggtt cgattcaact atgcgtacct cgaagcgtct    19440
ggtcatatag gacttatgcg tgctaatggt tgtagtgagg cccacatctt gggtttcatt    19500
cagggcctac agtatgcctc taacgtcatt gacgagattt agttacgcaa ggaacaacta    19560
agagatgatg gggaggattg acactatgtg tttctcaccg aaaattaaaa ctccgaagat    19620
ggataccaat cagattcgag ccgttgagcc agcgcctctg acccaagaag tgtcaagcgt    19680
ggagttcggt gggtcttctg atgagacgga taccgagggc accgaagtgt ctggacgcaa    19740
```

```
aggcctcaag gtcgaacgtg atgattccgt agcgaagtct aaagccagcg gcaatggctc    19800
cgctcgtatg aaatcttcca tccgtaagtc cgcatttgga ggtaagaagt gatgtctgag    19860
ttcacatgtg tggaggctaa gagtcgcttc cgtgcaatcc ggtggactgt ggaacacctt    19920
gggttgccta aaggattcga aggacacttt gtgggctaca gcctctacgt agacgaagtg    19980
atggacatgt ctggttgccg tgaagagtac attctggact ctaccggaaa acatgtagcg    20040
tacttcgcgt ggtgcgtaag ctgtgacatt caccacaaag gagacattct ggatgtaacg    20100
tccgttgtca ttaatcctga ggcagactct aagggcttac agcgattcct agcgaaacgc    20160
tttaagtacc ttgcggaact ccacgattgc gattgggtgt ctcgttgtaa gcatgaaggc    20220
gagacaatgc gtgtatactt taaggaggta aagttatgg gtaagaaagt taagaaggcc    20280
gtgaagaaag tcaccaagtc cgttaagaaa gtcgttaagg aagggctcg tccggttaaa    20340 caggttgctg gcggtctagc tggtctggct ggtggtactg gtgaagcaca gatggtggaa    20400
gtaccacaag ctgccgcaca gattgttgac gtacctgaga aagaggtttc cactgaggac    20460
gaagcacaga cagaaagcgg acgcaagaaa gctcgtgctg gcggtaagaa atccttgagt    20520
gtagcccgta gctccggtgg cggtatcaac atttaatcag gaggttatcg tggaagactg    20580
cattgaatgg accggaggtg tcaactctaa gggttatggt cgtaagtggg ttaatggtaa    20640
acttgtgact ccacataggc acatctatga ggagacatat ggtccagttc aacaggaat    20700 tgtggtgatg catatctgcg ataaccctag gtgctataac ataaagcacc ttacgcttgg    20760
aactccaaag gataattccg aggacatggt taccaaaggt agacaggcta aggagagga    20820 actaagcaag aaacttacag agtcagacgt tctcgctata cgctcttcaa ccttaagcca    20880
ccgctcctta ggagaactgt atggagtcag tcaatcaacc ataacgcgaa tactacagcg    20940
taagacatgg agacacattt aatggctgag aaacgaacag gacttgcgga ggatggcgca    21000
aagtctgtct atgagcgttt aaagaacgac cgtgctccct atgagacacg cgctcagaat    21060
tgcgctcaat ataccatccc atcattgttc cctaaggact ccgataacgc ctctacagat    21120
tatcaaactc cgtggcaagc cgtgggcgct cgtggtctga caatctagc ctctaagctc    21180 atgctggctc tattccctat gcagacttgg atgcgactta ctatatctga atatgaagca    21240
aagcagttac tgagcgaccc cgatggactc gctaaggtcg atgagggcct ctcgatggta    21300
gagcgtatca tcatgaacta cattgagtct aacagttacc gcgtgactct ctttgaggct    21360
ctcaaacagt tagtcgtagc tggtaacgtc ctgctgtacc taccggaacc ggaagggtca    21420
aactataatc ccatgaagct gtaccgattg tcttcttatg tggtccaacg agacgcattc    21480
ggcaacgttc tgcaaatggt gactcgtgac cagatagctt ttggtgctct ccctgaggac    21540
atccgtaagg ctgtagaagg tcaaggtggt gagaagaaag ctgatgagac aatcgacgtg    21600
tacactcaca tctatctgga tgaggactca ggtgaatacc tccgatacga agaggtcgag    21660
ggtatggaag tccaaggctc cgatgggact tatcctaaag aggcttgccc atacatcccg    21720
attcggatgg tcagactaga tggtgaatcc tacggtcgtt cgtacattga ggaatactta    21780
ggtgacttac ggtcccttga aaatctccaa gaggctatcg tcaagatgtc catgattagc    21840
tctaaggtta tcggcttagt gaatcctgct ggtatcaccc agccacgccg actgaccaaa    21900
gctcagactg gtgacttcgt tactggtcgt ccagaagaca tctcgttcct ccaactggag    21960
aagcaagcag actttactgt agctaaagcc gtaagtgacg ctatcgaggc tcgcctttcg    22020 tttgcctttta tgttgaactc tgcggttcag cgtacaggtg aacgtgtgac cgccgaagag    22080
attcggtatg tagcttctga acttgaagat actttaggtg gtgtctactc tatcctttct    22140
```

```
caagaattac aattgcctct ggtacgagtg ctcttgaagc aactacaagc cacgcaacag    22200
attcctgagt tacctaagga agccgtagag ccaaccatta gtacaggtct ggaagcaatt    22260
ggtcgaggac aagaccttga taagctggag cggtgtgtca ctgcgtgggc tgcactggca    22320
cctatgcggg acgaccctga tattaacctt gcgatgatta agttacgtat tgccaacgct    22380
atcggtattg acacttctgg tattctactc accgaagaac agaagcaaca gaagatggcc    22440
caacagtcta tgcaaatggg tatggataat ggtgctgctg cgctggctca aggtatggct    22500
gcacaagcta cagcttcacc tgaggctatg gctgctgccg ctgattccgt aggtttacag    22560
ccgggaattt aatacgactc actataggga gacctcatct ttgaaatgag cgatgacaag    22620
aggttggagt cctcggtctt cctgtagttc aactttaagg agacaataat aatggctgaa    22680
tctaatgcag acgtatatgc atcttttggc gtgaactccg ctgtgatgtc tggtggttcc    22740
gttgaggaac atgagcagaa catgctggct cttgatgttg ctcccgtga tggcgatgat    22800 gcaatcgagt tagcgtcaga cgaagtggaa acagaacgtg acctgtatga caactctgac    22860
ccgttcggtc aagaggatga cgaaggccgc attcaggttc gtatcggtga tggctctgag    22920
ccgaccgatg tggacactgg agaagaaggc gttgagggca ccgaaggttc cgaagagttt    22980
accccactgg gcgagactcc agaagaactg gtagctgcct ctgagcaact tggtgagcac    23040
gaagagggct tccaagagat gattaacatt gctgctgagc gtggcatgag tgtcgagacc    23100
attgaggcta tccagcgtga gtacgaggag aacgaagagt tgtccgccga gtcctacgct    23160
aagctggctg aaaattggct acacgaaggct ttcattgact cgtatatccg tggtcaagaa    23220
gctctggtgg agcagtacgt aaacagtgtc attgagtacg ctggtggtcg tgaacgtttt    23280
gatgcactgt ataaccacct tgagacgcac aaccctgagg ctgcacagtc gctggataat    23340
gcgttgacca atcgtgactt agcgaccgtt aaggctatca tcaacttggc tggtgagtct    23400
cgcgctaagg cgttcggtcg taagccaact cgtagtgtga ctaatcgtgc tattccggct    23460
aaacctcagg ctaccaagcg tgaaggcttt gcggaccgta gcgagatgat taaagctatg    23520
agtgaccctc ggtatcgcac agatgccaac tatcgtcgtc aagtcgaaca gaaagtaatc    23580
gattcgaact tctgatagac ttcgaaatta atacgactca ctatagggag accacaacgg    23640
tttccctcta gaaataattt tgtttaactt taagaaggag atatacatat ggctagcatg    23700
actggtggac agcaaatggg tactaaccaa ggtaaaggtg tagttgctgc tggagataaa    23760
ctggcgttgt tcttgaaggt atttggcggt gaagtcctga ctgcgttcgc tcgtacctcc    23820
gtgaccactt ctcgccacat ggtacgttcc atctccagcg gtaaatccgc tcagttccct    23880
gttctgggtc gcactcaggc agcgtatctg gctccgggcg agaacctcga cgataaacgt    23940
aaggacatca aacacaccga gaaggtaatc accattgacg gtctcctgac ggctgacgtt    24000
ctgatttatg atattgagga cgcgatgaac cactacgacg ttcgctctga gtatacctct    24060
cagttgggtg aatctctggc gatggctgcg gatggtgcgg ttctggctga gattgccggt    24120
ctgtgtaacg tggaaagcaa atataatgag aacatcgagg gcttaggtac tgctaccgta    24180
attgagacca ctcagaacaa ggccgcactt accgaccaag ttgcgctggg taaggagatt    24240
attgcggctc tgactaaggc tcgtgcggct ctgaccaaga actatgttcc ggctgctgac    24300
cgtgtgttct actgtgaccc agatagctac tctgcgattc tggcagcact gatgccgaac    24360
gcagcaaact acgctgctct gattgaccct gagaagggtt ctatccgcaa cgttatgggc    24420
tttgaggttg tagaagttcc gcacctcacc gctggtggtg ctggtaccgc tcgtgagggc    24480
```

```
actactggtc agaagcacgt cttccctgcc aataaaggtg agggtaatgt caaggttgct    24540
aaggacaacg ttatcggcct gttcatgcac cgctctgcgg taggtactgt taagctgcgt    24600
gacttggctc tggagcgcgc tcgccgtgct aacttccaag cggaccagat tatcgctaag    24660
tacgcaatgg gccacggtgg tcttcgccca gaagctgctg gtgcagtggt tttcaaagtg    24720
gagtaatgct gggggtggcc tcaacggtcg ctgctagtcc cgaagaggcg agtgttactt    24780
caacagaaga aaccttaacg ccagcacagg aggccgcacg cacccgcgct gctaacaaag    24840
cccgaaagga agctgagttg gctgctgcca ccgctgagca ataactagca taaccccttg    24900
gggcctctaa acgggtcttg aggggttttt tgctgaaagg aggaactata tgcgctcata    24960
cgatatgaac gttgagactg ccgctgagtt atcagctgtg aacgacattc tggcgtctat    25020
cggtgaacct ccggtatcaa cgctggaagg tgacgctaac gcagatgcag cgaacgctcg    25080
gcgtattctc aacaagatta accgacagat tcaatctcgt ggatggacgt tcaacattga    25140
ggaaggcata acgctactac ctgatgttta ctccaacctg attgtataca gtgacgacta    25200
tttatcccta atgtctactt ccggtcaatc catctacgtt aaccgaggtg gctatgtgta    25260
tgaccgaacg agtcaatcag accgctttga ctctggtatt actgtgaaca ttattcgtct    25320
ccgcgactac gatgagatgc ctgagtgctt ccgttactgg attgtcacca aggcttcccg    25380
tcagttcaac aaccgattct ttggggcacc ggaagtagag ggtgtactcc aagaagagga    25440
agatgaggct agacgtctct gcatggagta tgagatggac tacggtgggt acaatatgct    25500
ggatggagat gcgttcactt ctggtctact gactcgctaa cattaataaa taaggaggct    25560
ctaatggcac tcattagcca atcaatcaag aacttgaagg gtggtatcag ccaacagcct    25620
gacatccttc gttatccaga ccaagggtca cgccaagtta acggttggtc ttcggagacc    25680
gagggcctcc aaaagcgtcc acctcttgtt ttcttaaata cacttggaga caacggtgcg    25740
ttaggtcaag ctccgtacat ccacctgatt aaccgagatg agcacgaaca gtattacgct    25800
gtgttcactg gtagcggaat ccgagtgttc gacctttctg gtaacgagaa gcaagttagg    25860
tatcctaacg gttccaacta catcaagacc gctaatccac gtaacgacct gcgaatggtt    25920
actgtagcag actatacgtt catcgttaac cgtaacgttg ttgcacagaa gaacacaaag    25980
tctgtcaact taccgaatta caaccctaat caagacggat tgattaacgt tcgtggtggt    26040
cagtatggta gggaactaat tgtacacatt aacggtaaag acgttgcgaa gtataagata    26100
ccagatggta gtcaacctga acacgtaaac aatacggatg cccaatggtt agctgaagag    26160
ttagccaagc agatgcgcac taacttgtct gattggactg taaatgtagg gcaagggttc    26220
atccatgtga ccgcacctag tggtcaacag attgactcct tcacgactaa agatggctac    26280
gcagaccagt tgattaaccc tgtgacccac tacgctcagt cgttctctaa gctgccacct    26340
aatgctccta acggctacat ggtgaaaatc gtaggggacg cctctaagtc tgccgaccag    26400
tattacgttc ggtatgacgc tgagcggaaa gtttggactg agactttagg ttggaacact    26460
gaggaccaag ttctatggga aaccatgcca cacgctcttg tgcgagccgc tgacggtaat    26520
ttcgacttca gtggcttga gtggtctcct aagtcttgtg gtgacgttga caccaaccct    26580
tggccttctt ttgttggttc aagtattaac gatgtgttct tcttccgtaa ccgcttagga    26640
ttccttagtg gggagaacat catattgagt cgtacagcca aatacttcaa cttctaccct    26700
gcgtccattg cgaaccttag tgatgacgac cctatagacg tagctgtgag taccaaccga    26760
atagcaatcc ttaagtacgc cgttccgttc tcagaagagt tactcatctg gtccgatgaa    26820
gcacaattcg tcctgactgc ctcgggtact ctcacatcta agtcggttga gttgaaccta    26880
```

```
acgacccagt tgacgtaca ggaccgagcg agacctttg ggattgggcg taatgtctac  26940
tttgctagtc cgaggtccag cttcacgtcc atccacaggt actacgctgt gcaggatgtc  27000
agttccgtta agaatgctga ggacattaca tcacacgttc ctaactacat ccctaatggt  27060
gtgttcagta tttgcggaag tggtacgaaa aacttctgtt cggtactatc tcacggggac  27120
cctagtaaaa tcttcatgta caaattcctg tacctgaacg aagagttaag caacagtcg  27180 tggtctcatt gggactttgg ggaaaacgta caggttctag cttgtcagag tatcagctca  27240
gatatgtatg tgattcttcg caatgagttc aatacgttcc tagctagaat ctctttcact  27300
aagaacgcca ttgacttaca gggagaaccc tatcgtgcct ttatggacat gaagattcga  27360
tacacgattc ctagtggaac atacaacgat gacacattca ctacctctat tcatattcca  27420
acaatttatg tgcaaaactt cgggaggggc aaaatcactg tattggagcc tgatggtaag  27480
ataaccgtgt ttgagcaacc tacggctggg tggaatagcg acccttggct gagactcagc  27540
ggtaacttgg agggacgcat ggtgtacatt gggttcaaca ttaacttcgt atatgagttc  27600
tctaagttcc tcatcaagca gactgccgac gacgggtcta cctccacgga agacattggg  27660
cgcttacagt tacgccgagc gtgggttaac tacgagaact ctggtacgtt tgacattat  27720 gttgagaacc aatcgtctaa ctggaagtac acaatggctg gtgcccgatt aggctctaac  27780
actctgaggg ctgggagact gaacttaggg accggacaat atcgattccc tgtggttggt  27840
aacgccaagt tcaacactgt atacatcttg tcagatgaga ctacccctct gaacatcatt  27900
gggtgtggct gggaaggtaa ctacttacgg agaagttccg gtatttaatt aaatattctc  27960
cctgtggtgg ctcgaaatta atacgactca ctataggag aacaatacga ctacgggagg  28020
gttttcttat gatgactata agacctacta aaagtacaga ctttgaggta ttcactccgg  28080
ctcaccatga cattcttgaa gctaaggctg ctggtattga gccgagtttc cctgatgctt  28140
ccgagtgtgt cacgttgagc ctctatgggt tccctctagc tatcggtggt aactgcgggg  28200
accagtgctg gttcgttacg agcgaccaag tgtggcgact tagtggaaag gctaagcgaa  28260
agttccgtaa gttaatcatg gagtatcgcg ataagatgct tgagaagtat gatactcttt  28320
ggaattacgt atgggtaggc aatacgtccc acattcgttt cctcaagact atcggtgcgg  28380
tattccatga agagtacaca cgagatggtc aatttcagtt atttacaatc acgaaaggag  28440
gataaccata tgtgttgggc agccgcaata cctatcgcta tatctggcgc tcaggctatc  28500
agtggtcaga acgctcaggc caaaatgatt gccgctcaga ccgctgctgg tcgtcgtcaa  28560
gctatggaaa tcatgaggca gacgaacatc cagaatgctg acctatcgtt gcaagctcga  28620
agtaaacttg aggaagcgtc cgccgagttg acctcacaga acatgcagaa ggtccaagct  28680
attgggtcta tccgagcggc tatcggagag agtatgcttg aaggttcctc aatgaccgc  28740 attaagcgag tcacagaagg acagttcatt cgggaagcca atatggtaac tgagaactat  28800
cgccgtgact accaagcaat cttcgcacag caacttggtg gtactcaaag tgctgcaagt  28860
cagattgacg aaatctataa gagcgaacag aaacagaaga gtaagctaca gatggttctg  28920
gacccactgg ctatcatggg gtcttccgct gcgagtgctt acgcatccgg tgcgttcgac  28980
tctaagtcca caactaaggc acctattgtt gccgctaaag aaccaagac ggggaggtaa  29040 tgagctatga gtaaaattga atctgccctt caagcggcac aaccgggact ctctcggtta  29100
cgtggtggtg ctgaggtat gggctatcgt gcagcaacca ctcaggccga acagccaagg  29160
tcaagcctat tggacaccat tggtcggttc gctaaggctg gtgccgatat gtataccgct  29220
```

| | |
|---|---|
| aaggaacaac gagcacgaga cctagctgat gaacgctcta acgagattat ccgtaagctg | 29280 |
| acccctgagc aacgtcgaga agctctcaac aacgggaccc ttctgtatca ggatgaccca | 29340 |
| tacgctatgg aagcactccg agtcaagact ggtcgtaacg ctgcgtatct tgtggacgat | 29400 |
| gacgttatgc agaagataaa agagggtgtc ttccgtactc gcgaagagat ggaagagtat | 29460 |
| cgccatagtc gccttcaaga gggcgctaag gtatacgctg agcagttcgg catcgaccct | 29520 |
| gaggacgttg attatcagcg tggtttcaac ggggacatta ccgagcgtaa catctcgctg | 29580 |
| tatggtgcgc atgataactt cttgagccag caagctcaga agggcgctat catgaacagc | 29640 |
| cgagtggaac tcaacggtgt ccttcaagac cctgatatgc tgcgtcgtcc agactctgct | 29700 |
| gacttctttg agaagtatat cgacaacggt ctggttactg gcgcaatccc atctgatgct | 29760 |
| caagccacac agcttataag ccaagcgttc agtgacgctt ctagccgtgc tggtggtgct | 29820 |
| gacttcctga tgcgagtcgg tgacaagaag gtaacactta acggagccac tacgacttac | 29880 |
| cgagagttga ttggtgagga acagtggaac gctctcatgg tcacagcaca acgttctcag | 29940 |
| tttgagactg acgcgaagct gaacgagcag tatcgcttga agattaactc tgcgctgaac | 30000 |
| caagaggacc caaggacagc ttgggagatg cttcaaggta tcaaggctga actagataag | 30060 |
| gtccaacctg atgagcagat gacaccacaa cgtgagtggc taatctccgc acaggaacaa | 30120 |
| gttcagaatc agatgaacgc atggacgaaa gctcaggcca aggctctgga cgattccatg | 30180 |
| aagtcaatga acaaacttga cgtaatcgac aagcaattcc agaagcgaat caacggtgag | 30240 |
| tgggtctcaa cggattttaa ggatatgcca gtcaacgaga acactggtga gttcaagcat | 30300 |
| agcgatatgg ttaactacgc caataagaag ctcgctgaga ttgacagtat ggacattcca | 30360 |
| gacggtgcca aggatgctat gaagttgaag taccttcaag cggactctaa ggacggagca | 30420 |
| ttccgtacag ccatcggaac catggtcact gacgctggtc aagagtggtc tgccgctgtg | 30480 |
| attaacggta agttaccaga acgaacccca gctatggatg ctctgcgcag aatccgcaat | 30540 |
| gctgaccctc agttgattgc tgcgctatac ccagaccaag ctgagctatt cctgacgatg | 30600 |
| gacatgatgg acaagcaggg tattgaccct caggttattc ttgatgccga ccgactgact | 30660 |
| gttaagcggt ccaaagagca acgctttgag gatgataaag cattcgagtc tgcactgaat | 30720 |
| gcatctaagg ctcctgagat tgcccgtatg ccagcgtcac tgcgcgaatc tgcacgtaag | 30780 |
| atttatgact ccgttaagta tcgctcgggg aacgaaagca tggctatgga gcagatgacc | 30840 |
| aagttcctta aggaatctac ctacacgttc actggtgatg atgttgacgg tgataccgtt | 30900 |
| ggtgtgattc ctaagaatat gatgcaggtt aactctgacc cgaaatcatg ggagcaaggt | 30960 |
| cgggatattc tggaggaagc acgtaaggga atcattgcga gcaacccttg gataaccaat | 31020 |
| aagcaactga ccatgtattc tcaaggtgac tccatttacc ttatggacac cacaggtcaa | 31080 |
| gtcagagtcc gatacgacaa agagttactc tcgaaggtct ggagtgagaa ccagaagaaa | 31140 |
| ctcgaagaga aagctcgtga gaaggctctg gctgatgtga acaagcgagc acctatagtt | 31200 |
| gccgctacga aggcccgtga agctgctgct aaacagagtcc gagagaaacg taaacagact | 31260 |
| cctaagttca tctacggacg taaggagtaa ctaaaggcta cataaggagg ccctaaatgg | 31320 |
| ataagtacga taagaacgta ccaagtgatt atgatggtct gttccaaaag gctgctgatg | 31380 |
| ccaacggggt ctcttatgac cttttacgta agtcgcttg acagaatca cgatttgtgc | 31440 |
| ctacagcaaa atctaagact ggaccattag gcatgatgca atttaccaag gcaaccgcta | 31500 |
| aggccctcgg tctgcgagtt accgatggtc cagacgacga ccgactgaac cctgagttag | 31560 |
| ctattaatgc tgccgctaag caacttgcag gtctggtagg gaagtttgat ggcgatgaac | 31620 |

```
tcaaagctgc ccttgcgtac aaccaaggcg agggacgctt gggtaatcca caacttgagg    31680
cgtactctaa gggagacttc gcatcaatct ctgaggaggg acgtaactac atgcgtaacc    31740
ttctggatgt tgctaagtca cctatggctg acagttgga aacttttggt ggcataaccc     31800
caaagggtaa aggcattccg gctgaggtag gattggctgg aattggtcac aagcagaaag    31860
taacacagga acttcctgag tccacaagtt ttgacgttaa gggtatcgaa caggaggcta    31920
cggcgaaacc attcgccaag gacttttggg agacccacgg agaaacactt gacgagtaca    31980
acagtcgttc aaccttcttc ggattcaaaa atgctgccga agctgaactc tccaactcag    32040
tcgctgggat ggctttccgt gctggtcgtc tcgataatgg ttttgatgtg tttaaagaca    32100
ccattacgcc gactcgctgg aactctcaca tctggactcc agaggagtta gagaagattc    32160
gaacagaggt taagaaccct gcgtacatca acgttgtaac tggtggttcc cctgagaacc    32220
tcgatgacct cattaaattg gctaacgaga actttgagaa tgactcccgc gctgccgagg    32280
ctggcctagg tgccaaactg agtgctggta ttattggtgc tggtgtggac ccgcttagct    32340
atgttcctat ggtcggtgtc actggtaagg gctttaagtt aatcaataag gctcttgtag    32400
ttggtgccga aagtgctgct ctgaacgttg catccgaagg tctccgtacc tccgtagctg    32460
gtggtgacgc agactatgcg ggtgctgcct taggtggctt tgtgtttggc gcaggcatgt    32520
ctgcaatcag tgacgctgta gctgctggac tgaaacgcag taaaccagaa gctgagttcg    32580
acaatgagtt catcggtcct atgatgcgat tggaagcccg tgagacagca cgaaacgcca    32640
actctgcgga cctctctcgg atgaacactg agaacatgaa gtttgaaggt gaacataatg    32700
gtgtccctta tgaggactta ccaacagaga gaggtgccgt ggtgttacat gatggctccg    32760
ttctaagtgc aagcaaccca atcaacccta agactctaaa agagttctcc gaggttgacc    32820
ctgagaaggc tgcgcgagga atcaaactgg ctgggttcac cgagattggc ttgaagacct    32880
tggggtctga cgatgctgac atccgtagag tggctatcga cctcgttcgc tctcctactg    32940
gtatgcagtc tggtgcctca ggtaagttcg gtgcaacagc ttctgacatc catgagagac    33000
ttcatggtac tgaccagcgt acttataatg acttgtacaa agcaatgtct gacgctatga    33060
aagaccctga gttctctact ggcggcgcta agatgtcccg tgaagaaact cgatacacta    33120
tctaccgtag agcggcacta gctattgagc gtccagaact acagaaggca ctcactccgt    33180
ctgagagaat cgttatggac atcattaagc gtcactttga caccaagcgt gaacttatgg    33240
aaaacccagc aatattcggt aacacaaagg ctgtgagtat cttccctgag agtcgccaca    33300
aaggtactta cgttcctcac gtatatgacc gtcatgccaa ggcgctgatg attcaacgct    33360
acggtgccga aggtttgcag gaagggattg cccgctcatg gatgaacagc tacgtctcca    33420
gacctgaggt caaggccaga gtcgatgaga tgcttaagga attcacgggt gtgaaggaag    33480
taacaccaga gatggtagag aagtacgcta tggataaggc ttatggtatc tcccactcag    33540
accagttcac caacagttcc ataatagaag agaacattga gggcttagta ggtatcgaga    33600
ataactcatt ccttgaggca cgtaacttgt ttgattcgga cctatccatc actatgccag    33660
acggacagca attctcagtg aatgacctaa gggacttcga tatgttccgc atcatgccag    33720
cgtatgaccg ccgtgtcaat ggtgacatcg ccatcatggg gtctactggt aaaaccacta    33780
aggaacttaa ggatgagatt ttggctctca aagcgaaagc tgagggagac ggtaagaaga    33840
ctggcgaggt acatgcttta atggataccg ttaagattct tactggtcgt gctagacgca    33900
atcaggacac tgtgtgggaa acctcactgc gtgccatcaa tgacctaggg ttcttcgcta    33960
```

```
agaacgccta catgggtgct cagaacatta cggagattgc tgggatgatt gtcactggta    34020
acgttcgtgc tctagggcat ggtatcccaa ttctgcgtga tacactctac aagtctaaac    34080
cagtttcagc taaggaactc aaggaactcc atgcgtctct gttcgggaag gaggtggacc    34140
agttgattcg gcctaaacgt gctgacattg tgcagcgcct aagggaagca actgataccg    34200
gacctgccgt ggcgaacatc gtagggacct tgaagtattc aacacaggaa ctggctgctc    34260
gctctccgtg gactaagcta ctgaacggaa ccactaacta ccttctggat gctgcgcgtc    34320
aaggtatgct tggggatgtt attagtgcca ccctaacagg taagactacc cgctgggaga    34380
aagaaggctt ccttcgtggt gcctccgtaa ctcctgagca gatggctggc atcaagtctc    34440
tcatcaagga acatatggta cgcggtgagg acgggaagtt taccgttaag gacaagcaag    34500
cgttctctat ggacccacgg gctatggact tatggagact ggctgacaag gtagctgatg    34560
aggcaatgct gcgtccacat aaggtgtcct tacaggattc ccatgcgttc ggagcactag    34620
gtaagatggt tatgcagttt aagtctttca ctatcaagtc ccttaactct aagttcctgc    34680
gaaccttcta tgatggatac aagaacaacc gagcgattga cgctgcgctg agcatcatca    34740
cctctatggg tctcgctggt ggtttctatg ctatggctgc acacgtcaaa gcatacgctc    34800
tgcctaagga gaaacgtaag gagtacttgg agcgtgcact ggacccaacc atgattgccc    34860
acgctgcgtt atctcgtagt tctcaattgg gtgctccttt ggctatggtt gacctagttg    34920
gtggtgtttt agggttcgag tcctccaaga tggctcgctc tacgattcta cctaaggaca    34980
ccgtgaagga acgtgaccca aacaaaccgt acacctctag agaggtaatg ggcgctatgg    35040
gttcaaacct tctggaacag atgccttcgg ctggctttgt ggctaacgta ggggctacct    35100
taatgaatgc tgctggcgtg gtcaactcac ctaataaagc aaccgagcag gacttcatga    35160
ctggtctat gaactccaca aaagagttag taccgaacga cccattgact caacagcttg    35220
tgttgaagat ttatgaggcg aacggtgtta acttgaggga gcgtaggaaa taatacgact    35280
cactataggg agaggcgaaa taatcttctc cctgtagtct cttagattta ctttaaggag    35340
gtcaaatggc taacgtaatt aaaaccgttt tgacttacca gttagatggc tccaatcgtg    35400
atttaatat cccgtttgag tatctagccc gtaagttcgt agtggtaact cttattggtg    35460
tagaccgaaa ggtccttacg attaatacag actatcgctt tgctacacgt actactatct    35520
ctctgacaaa ggcttggggt ccagccgatg gctacacgac catcgagtta cgtcgagtaa    35580
cctccactac cgaccgattg gttgacttta cggatggttc aatcctccgc gcgtatgacc    35640
ttaacgtcgc tcagattcaa acgatgcacg tagcggaaga ggcccgtgac ctcactacgg    35700
atactatcgg tgtcaataac gatggtcact tggatgctcg tggtcgtcga attgtgaacc    35760
tagcgaacgc cgtggatgac cgcgatgctg ttccgtttgg tcaactaaag accatgaacc    35820
agaactcatg gcaagcacgt aatgaagcct tacagttccg taatgaggct gagactttca    35880
gaaaccaagc ggagggcttt aagaacgagt ccagtaccaa cgctacgaac acaaagcagt    35940
ggcgcgatga gaccaagggt ttccgagacg aagccaagcg gttcaagaat acggctggtc    36000
aatacgctac atctgctggg aactctgctt ccgctgcgca tcaatctgag gtaaacgctg    36060
agaactctgc cacagcatcc gctaactctg ctcatttggc agaacagcaa gcagaccgtg    36120
cggaacgtga ggcagacaag ctggaaaatt acaatggatt ggctggtgca attgataagg    36180
tagatgaac caatgtgtac tggaaaggaa atattcacgc taacgggcgc ctttacatga    36240
ccacaaacgg ttttgactgt ggccagtatc aacagttctt tggtggtgtc actaatcgtt    36300
actctgtcat ggagtgggga gatgagaacg gatggctgat gtatgttcaa cgtagagagt    36360
```

```
ggacaacagc gataggcggt aacatccagt tagtagtaaa cggacagatc atcacccaag   36420
gtggagccat gaccggtcag ctaaaattgc agaatgggca tgttcttcaa ttagagtccg   36480
catccgacaa ggcgcactat attctatcta aagatggtaa caggaataac tggtacattg   36540
gtagagggtc agataacaac aatgactgta ccttccactc ctatgtacat ggtacgacct   36600
taacactcaa gcaggactat gcagtagtta acaaacactt ccacgtaggt caggccgttg   36660
tggccactga tggtaatatt caaggtacta agtggggagg taaatggctg gatgcttacc   36720
tacgtgacag cttcgttgcg aagtccaagg cgtggactca ggtgtggtct ggtagtgctg   36780
gcggtggggt aagtgtgact gtttcacagg atctccgctt ccgcaatatc tggattaagt   36840
gtgccaacaa ctcttggaac ttcttccgta ctggccccga tggaatctac ttcatagcct   36900
ctgatggtgg atggttacga ttccaaatac actccaacgg tctcggattc aagaatattg   36960
cagacagtcg ttcagtacct aatgcaatca tggtggagaa cgagtaattg gtaaatcaca   37020
aggaaagacg tgtagtccac ggatggactc tcaaggaggg acaaggtgct atcattagac   37080
tttaacaacg aattgattaa ggctgctcca attgttggga cgggtgtagc agatgttagt   37140
gctcgactgt tctttgggtt aagccttaac gaatggttct acgttgctgc tatcgcctac   37200
acagtggttc agattggtgc caaggtagtc gataagatga ttgactggaa gaaagccaat   37260
aaggagtgat atgtatggaa aaggataaga gccttattac attcttagag atgttggaca   37320
ctgcgatggc tcagcgtatg cttgcggacc tttcggacca tgagcgtcgc tctccgcaac   37380
tctataatgc tattaacaaa ctgttagacc gccacaagtt ccagattggt aagttgcagc   37440
cggatgttca catcttaggt ggccttgctg gtgctcttga agagtacaaa gagaaagtcg   37500
gtgataacgg tcttacggat gatgatattt acacattaca gtgatatact caaggccact   37560
acagatagtg gtctttatgg atgtcattgt ctatacgaga tgctcctacg tgaaatctga   37620
aagttaacgg gaggcattat gctagaattt ttacgtaagc taatcccttg ggttctcgct   37680
gggatgctat tcgggttagg atggcatcta gggtcagact caatggacgc taaatggaaa   37740
caggaggtac acaatgagta cgttaagaga gttgaggctg cgaagagcac tcaaagagca   37800
atcgatgcgg tatctgctaa gtatcaagaa gaccttgccg cgctggaagg gagcactgat   37860
aggattattt ctgatttgcg tagcgacaat aagcggttgc gcgtcagagt caaaactacc   37920
ggaacctccg atggtcagtg tggattcgag cctgatggtc gagccgaact tgacgaccga   37980
gatgctaaac gtattctcgc agtgacccag aagggtgacg catggattcg tgcgttacag   38040
gatactattc gtgaactgca acgtaagtag gaaatcaagt aaggaggcaa tgtgtctact   38100
caatccaatc gtaatgcgct cgtagtggcg caactgaaag gagacttcgt ggcgttccta   38160
ttcgtcttat ggaaggcgct aaacctaccg gtgcccacta agtgtcagat tgacatggct   38220
aaggtgctgg cgaatggaga caacaagaag ttcatcttac aggctttccg tggtatcggt   38280
aagtcgttca tcacatgtgc gttcgttgtg tggtccttat ggagagaccc tcagttgaag   38340
atacttatcg tatcagcctc taaggagcgt gcagacgcta actccatctt tattaagaac   38400
atcattgacc tgctgccatt cctatctgag ttaaagccaa gacccggaca gcgtgactcg   38460
gtaatcagct ttgatgtagg cccagccaat cctgaccact ctcctagtgt gaaatcagta   38520
ggtatcactg gtcagttaac tggtagccgt gctgacatta tcattgcgga tgacgttgag   38580
attccgtcta acagcgcaac tatgggtgcc cgtgagaagc tatggactct ggttcaggag   38640
ttcgctgcgt tacttaaacc gctgccttcc tctcgcgtta tctaccttgg tacacctcag   38700
```

```
acagagatga ctctctataa ggaacttgag gataaccgtg ggtacacaac cattatctgg   38760
cctgctctgt acccaaggac acgtgaagag aacctctatt actcacagcg tcttgctcct   38820
atgttacgcg ctgagtacga tgagaaccct gaggcacttg ctgggactcc aacagaccca   38880
gtgcgctttg accgtgatga cctgcgcgag cgtgagttgg aatacggtaa ggctggcttt   38940
acgctacagt tcatgcttaa ccctaacctt agtgatgccg agaagtaccc gctgaggctt   39000
cgtgacgcta tcgtagcggc cttagactta gagaaggccc caatgcatta ccagtggctt   39060
ccgaaccgtc agaacatcat tgaggacctt cctaacgttg gccttaaggg tgatgacctg   39120
catacgtacc acgattgttc caacaactca ggtcagtacc aacagaagat tctggtcatt   39180
gaccctagtg gtcgcggtaa ggacgaaaca ggttacgctg tgctgtacac actgaacggt   39240
tacatctacc ttatggaagc tggaggtttc cgtgatggct actccgataa gacccttgag   39300
ttactcgcta agaaggcaaa gcaatgggga gtccagacgg ttgtctacga gagtaacttc   39360
ggtgacggta tgttcggtaa ggtattcagt cctatccttc ttaaacacca caactgtgcg   39420
atggaagaga ttcgtgcccg tggtatgaaa gagatgcgta tttgcgatac ccttgagcca   39480
gtcatgcaga ctcaccgcct tgtaattcgt gatgaggtca ttagggccga ctaccagtcc   39540
gctcgtgacg tagacggtaa gcatgacgtt aagtactcgt tgttctacca gatgacccgt   39600
atcactcgtg agaaaggcgc tctggctcat gatgaccgat tggatgccct tgcgttaggc   39660
attgagtatc tccgtgagtc catgcagttg gattccgtta aggtcgaggg tgaagtactt   39720
gctgacttcc ttgaggaaca catgatgcgt cctacggttg ctgctacgca tatcattgag   39780
atgtctgtgg gaggagttga tgtgtactct gaggacgatg agggttacgg tacgtctttc   39840
attgagtggt gatttatgca ttaggactgc atagggatgc actatagacc acggatggtc   39900
agttctttaa gttactgaaa agacacgata aattaatacg actcactata gggagaggag   39960
ggacgaaagg ttactatata gatactgaat gaatacttat agagtgcata aagtatgcat   40020
aatggtgtac ctagagtgac ctctaagaat ggtgattata ttgtattagt atcaccttaa   40080
cttaaggacc aacataaagg gaggagactc atgttccgct tattgttgaa cctactgcgg   40140
catagagtca cctaccgatt tcttgtggta cttttgtgctg cccttgggta cgcatctctt   40200
actggagacc tcagttcact ggagtctgtc gtttgctcta tactcacttg tagcgattag   40260
ggtcttcctg accgactgat ggctcaccga gggattcagc ggtatgattg catcacacca   40320
cttcatccct atagagtcaa gtcctaaggt atacccataa agagcctcta atggtctatc   40380
ctaaggtcta tacctaaaga taggccatcc tatcagtgtc acctaaagag ggtcttagag   40440
agggcctatg gagttcctat agggtccttt aaaatatacc ataaaaatct gagtgactat   40500
ctcacagtgt acggacctaa agttccccca taggggtac ctaaagccca gccaatcacc   40560
taaagtcaac cttcggttga ccttgagggt tccctaaggg ttggggatga cccttgggtt   40620
tgtctttggg tgttaccttg agtgtctctc tgtgtccct                          40659
```

<210> SEQ ID NO 6
<211> LENGTH: 796
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

```
ctttaagacc cttaagtgtt aattagagat ttaaggagat tcaacatggt cttcacactc        60
```

```
-continued gaagatttcg ttggggactg gcgacagaca gccggctaca acctggacca agtccttgaa    120
cagggaggtg tgtccagttt gtttcagaat ctcggggtgt ccgtaactcc gatccaaagg    180
attgtcctga gcggtgaaaa tgggctgaag atcgacatcc atgtcatcat cccgtatgaa    240
ggtctgagcg gcgaccaaat gggccagatc gaaaaaattt ttaaggtggt gtaccctgtg    300
gatgatcatc actttaaggt gatcctgcac tatggcacac tggtaatcga cggggttacg    360
ccgaacatga tcgactattt cggacggccg tatgaaggca tcgccgtgtt cgacggcaaa    420
aagatcactg taacagggac cctgtggaac ggcaacaaaa ttatcgacga gcgcctgatc    480
aaccccgacg gctccctgct gttccgagta accatcaacg gagtgaccgg ctggcggctg    540
tgcgaacgca ttctggcgta aaggaggtaa acatatgacc atgattacgg attcactggc    600
cgtcgtttta caacgtcgtg actgggaaaa ccctggcgtt acccaactta atcgccttgc    660
agcacatccc cctttcgcca gctggcgtaa tagcgaagag gcccgcaccg atcgcccttc    720
ccaacagttg cgcagcctga atggcgaatg gtaaaaatta aagaattact aagagaggac    780
tttaagtatg cgtaac                                                    796
```

BACTERIA IDENTIFICATION AND ANTIBIOTIC SUSCEPTIBILITY PROFILING DEVICE

CROSS-REFERENCE TO RELATED APPLICATIONS

This application claims the benefit of and priority to U.S. Application No. 62/314,163, filed Mar. 28, 2016, the contents of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Jun. 7, 2017, is named 102590-0557 SL.txt and is 169,985 bytes in size.

TECHNICAL FIELD

The present technology relates generally to bacteria identification and antibiotic susceptibility profiling devices and uses thereof.

BACKGROUND

The following description of the background of the present technology is provided simply as an aid in understanding the present technology and is not admitted to describe or constitute prior art to the present technology.

Bacterial infections may complicate a patient's existing medical condition, and in some cases, may lead to death. Patients suffering from various bacterial infections often present with similar symptoms, thus making it difficult to accurately identify and characterize the bacterial species or strain responsible for the infection. Accurate identification of the bacteria through conventional lab tests can be challenging and may require incubation periods of up to several days. Additionally, some bacterial strains are not amenable to culturing and in vitro analysis in light of their fastidious nature. In other situations, the observable behavior of some bacterial strains is not readily distinguishable from others. Moreover, individual strains of a particular bacterial species may exhibit resistance to otherwise effective antibiotics.

Early and accurate identification of the bacterial strain(s) responsible for a patient's illness and determining its susceptibility to various antibiotics is an important aspect of the treatment selection decision process.

SUMMARY OF THE DISCLOSURE

According to one aspect of the disclosure, a system includes microfluidic cartridge. The microfluidic cartridge can include an inlet that is configured to receive a sample. The sample can include bacterial cells and blood that includes plasma and a plurality of formed elements. The microfluidic cartridge can also include a separator. The separator can include a first outlet and a second outlet. The separator can be configured to flow the bacterial cells and the plasma into the first outlet and the plurality of formed elements of the blood into the second outlet. The system can include a reservoir that is configured to incubate the bacterial cells. The reservoir can be coupled with the first outlet of the microfluidic channel. The reservoir can be configured to receive at least one recombinant detector bacteriophage that includes a reporter gene. The system can include an optical detector that is configured to detect a signal generated by the expression of the reporter gene responsive to the bacterial cells being infected with the recombinant detector bacteriophage.

The microfluidic cartridge can include a concentrator that is coupled with the first outlet of the separator. The separator can be configured to collect the bacterial cells and flow the bacterial cells through a third outlet. The microfluidic cartridge can include a microfluidic channel that is coupled with the third outlet of the separator. The microfluidic channel can include a fourth outlet. The system can also include a counter that is configured to count a number of the bacterial cells as the bacterial cells flow through the microfluidic channel.

In some implementations, the microfluidic cartridge is removable. The microfluidic cartridge can be disposable. The microfluidic cartridge can include polystyrene.

In some implementations, the system can include an acoustic wave generator. The acoustic wave generator can be configured to generate a standing acoustic wave across the separator of the microfluidic cartridge. The standing acoustic wave can have a frequency between about 0.85 MHz and about 1.1 MHz.

The signal generated by the expression of the reporter gene can be visible through a wall of the reservoir. The signal can include at least one of a luminescent signal, a fluorescent signal, or a chromagraphic signal.

The system can include a plurality of reservoirs that are coupled with the fourth outlet. Each of the plurality of reservoirs can be configured to receive a different recombinant detector bacteriophage. The counter can be one of a laser-based flow cytometer or an impedance-based flow cytometer.

According to another aspect of the disclosure, a microfluidic system includes an inlet that is configured to receive a sample. The sample can include bacterial cells and blood. The blood can include plasma and a plurality of formed elements. The microfluidic system can include a separator that includes a first outlet and a second outlet. The separator can be configured to flow the bacterial cells and the plasma into the first outlet and the plurality of formed elements of the blood into the second outlet. The microfluidic system can include a reservoir that is configured to incubate the bacterial cells. The reservoir can be coupled with the first outlet and can be configured to receive at least one bacteriophage.

The microfluidic system can include a concentrator that is coupled with the first outlet of the separator. The concentrator can be configured to collect the bacterial cells and flow the bacterial cells through a third outlet. The microfluidic system can include a microfluidic channel that is coupled with the third outlet of the concentrator. The microfluidic channel can include a fourth outlet.

In some implementations, the microfluidic system is disposable. The dimensions of the microfluidic channel are substantially monocellular. The microfluidic system can include a plurality of reservoirs that are coupled with the fourth outlet. Each of the plurality of incubation reservoirs can be configured to receive a different bacteriophage. The microfluidic system can include polystyrene.

According to another aspect of the disclosure a method can include receiving a sample. The sample can include bacterial cells and blood. The sample can be received at an inlet of a microfluidic system. The blood can include plasma and a plurality of formed elements. The method can include separating, by a separator, the bacterial cells the sample. The bacterial cells can flow into a first outlet of the separator. The formed elements can flow into a second outlet of the separator. The method can include receiving a test solution that can include at least one recombinant detector bacteriophage that includes a reporter gene. The method can also include detecting a signal that is generated by the expression of the reporter gene responsive to the bacterial cells being infected with the recombinant detector bacteriophage.

In some implementations, the method can include collecting the bacterial cells in an incubation reservoir. The test solution can be introduced into the incubation reservoir. The bacterial cells can then be incubated for a predetermined amount of time.

In some implementations, the method can include introducing an antibiotic into the microfluidic system. The method can also include introducing a lysis reagent into the microfluidic system. Some reagents may be pre-loaded and stored in the cartridge prior to introducing the sample.

In some implementations, the method can include applying a standing acoustic wave across the separator of the microfluidic system. The standing acoustic wave can drive the formed elements towards an aggregation axis of the separator of the microfluidic system.

The method can include counting a number of the bacterial cells flowing through a microfluidic channel coupled with the first outlet with one of a laser-based flow cytometer or an impedance-based flow cytometer. The method can include concentrating the bacterial cells within a concentrator of the microfluidic system. The concentrator can be coupled between the separator and the microfluidic channel. The signal generated by the expression of the reporter gene can include at least one of a luminescent signal, a fluorescent signal, or a chromagraphic signal.

BRIEF DESCRIPTION OF THE DRAWINGS

The skilled artisan will understand that the figures, described herein, are for illustration purposes only. It is to be understood that in some instances various aspects of the described implementations may be shown exaggerated or enlarged to facilitate an understanding of the described implementations. In the drawings, like reference characters generally refer to like features, functionally similar and/or structurally similar elements throughout the various drawings. The drawings are not necessarily to scale, emphasis instead being placed upon illustrating the principles of the teachings. The drawings are not intended to limit the scope of the present teachings in any way. The system and method may be better understood from the following illustrative description with reference to the following drawings in which:

FIG. 4 shows the heterologous nucleic acid sequence that was inserted near the NheI site in the recombinant detector T7 phage (SEQ ID NO: 1).

FIGS. 5A, 5B, 5C, 5D, 5E, 5F, 5G, 5H, 5I, 5J, and 5K show the complete genome sequence of the recombinant detector phage strain DLPECO2, which contains a double insertion of the NanoLuc® reporter gene (SEQ ID NO: 2).

FIG. 12 shows the heterologous nucleic acid sequence that was inserted into the recombinant detector K1-5 phage disclosed herein (SEQ ID NO: 3).

FIG. 13A, 13B, 13C, 13D, 13E, 13F, 13G, 13H, 13I, and 13J show the complete genome sequence of the recombinant detector K1-5 phage disclosed herein (SEQ ID NO: 4).

FIG. 14A, 14B, 14C, 14D, 14E, 14F, 14G, 14H, 14I, 14J, and 14K show the complete genome sequence of the recombinant detector phage strain DLPECO1, which contains a single insertion of the NanoLuc® reporter gene (SEQ ID NO: 5).

FIG. 15 shows the heterologous nucleic acid sequence that was inserted near the SwaI site in the recombinant detector T7 phage (SEQ ID NO: 6).

DETAILED DESCRIPTION

Figure 1:
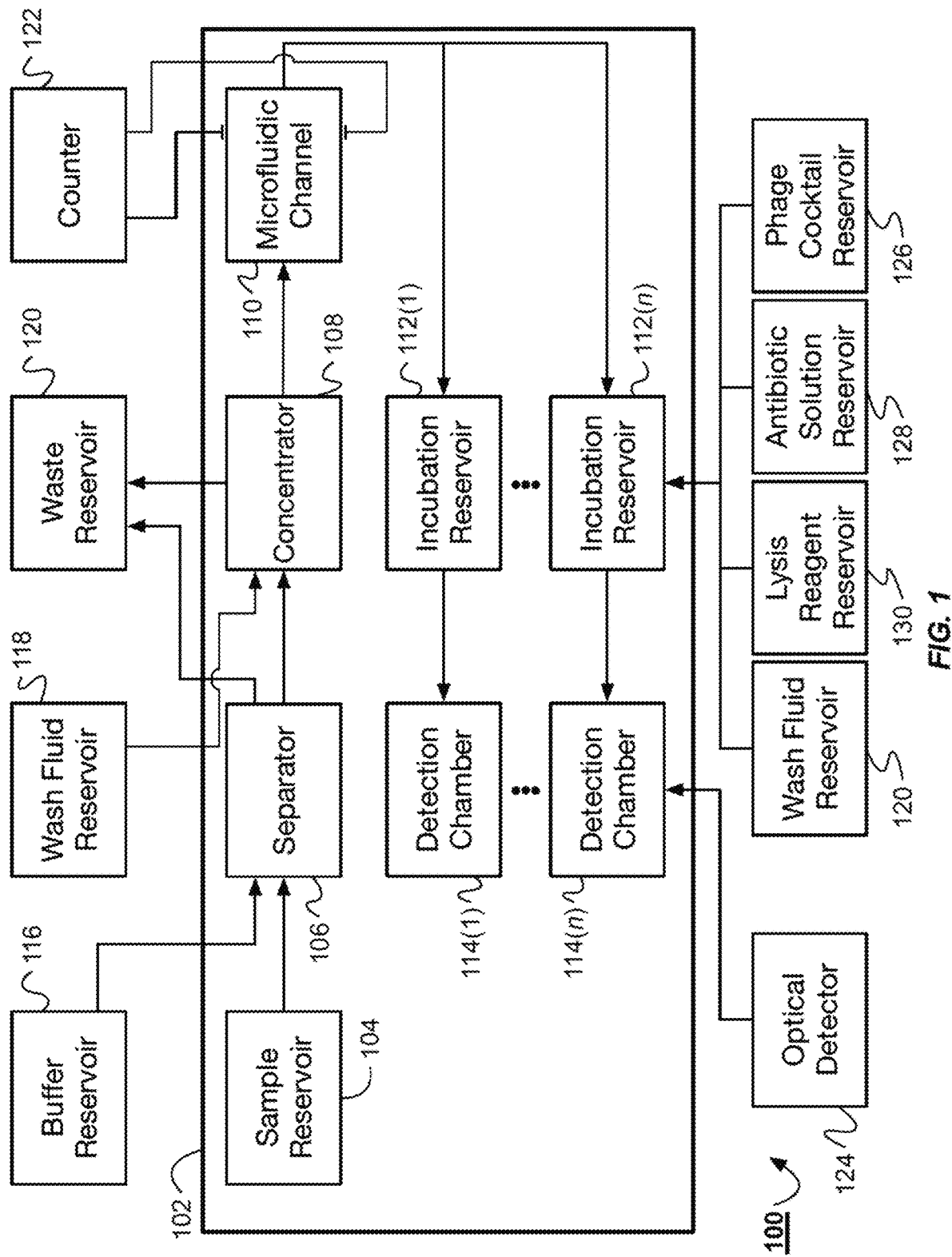
FIG. 1 illustrates a block diagram of an example system for bacteria identification and antibiotic susceptibility profiling.

It is to be appreciated that certain aspects, modes, embodiments, variations and features of the present methods are described below in various levels of detail in order to provide a substantial understanding of the present technology.

In practicing the present methods, many conventional techniques in molecular biology, protein biochemistry, cell biology, microbiology and recombinant DNA are used. See, e.g., Sambrook and Russell eds. (2001) *Molecular Cloning: A Laboratory Manual*, 3rd edition; the series Ausubel et al. eds. (2007) *Current Protocols in Molecular Biology*; the series *Methods in Enzymology* (Academic Press, Inc., N.Y.); MacPherson et al. (1991) *PCR 1: A Practical Approach* (IRL Press at Oxford University Press); MacPherson et al. (1995)

PCR 2: *A Practical Approach*; Harlow and Lane eds. (1999) *Antibodies, A Laboratory Manual*; Freshney (2005) *Culture of Animal Cells: A Manual of Basic Technique,* 5th edition; Gait ed. (1984) *Oligonucleotide Synthesis*; U.S. Pat. No. 4,683,195; Hames and Higgins eds. (1984) *Nucleic Acid Hybridization*; Anderson (1999) *Nucleic Acid Hybridization*; Hames and Higgins eds. (1984) *Transcription and Translation; Immobilized Cells and Enzymes* (IRL Press (1986)); Perbal (1984)*A Practical Guide to Molecular Cloning*; Miller and Calos eds. (1987) *Gene Transfer Vectors for Mammalian Cells* (Cold Spring Harbor Laboratory); Makrides ed. (2003) *Gene Transfer and Expression in Mammalian Cells*; Mayer and Walker eds. (1987) *Immunochemical Methods in Cell and Molecular Biology* (Academic Press, London); and Herzenberg et al. eds (1996) *Weir's Handbook of Experimental Immunology*.

A. DEFINITIONS

Unless defined otherwise, all technical and scientific terms used herein generally have the same meaning as commonly understood by one of ordinary skill in the art to which this technology belongs. As used in this specification and the appended claims, the singular forms "a", "an" and "the" include plural referents unless the content clearly dictates otherwise. For example, reference to "a cell" includes a combination of two or more cells, and the like. Generally, the nomenclature used herein and the laboratory procedures in cell culture, molecular genetics, organic chemistry, analytical chemistry and nucleic acid chemistry and hybridization described below are those well-known and commonly employed in the art.

As used herein, "$\mu$" is the signal separation between untreated bacterial host cells infected with a recombinant detector phage and antibiotic-treated bacterial host cells infected with a recombinant detector phage ($\mu$=signal of untreated recombinant detector phage-infected host cells/signal of antibiotic treated recombinant detector phage-infected host cells). In some embodiments, a $\mu$ greater than or equal to 2 is indicative of antibiotic sensitivity for a given bacterial host.

As used herein, the terms "about" and "substantially" in reference to a number is generally taken to include numbers that fall within a range of 1%, 5%, or 10% in either direction (greater than or less than) of the number unless otherwise stated or otherwise evident from the context (except where such number would be less than 0% or exceed 100% of a possible value).

As used herein, "bacteriophage" or "phage" refers to a virus that infects bacteria. Bacteriophages are obligate intracellular parasites that multiply inside bacteria by co-opting some or all of the host biosynthetic machinery (i.e., viruses that infect bacteria). Though different bacteriophages may contain different materials, they all contain nucleic acid and protein, and can under certain circumstances be encapsulated in a lipid membrane. Depending upon the phage, the nucleic acid can be either DNA or RNA (but not both).

As used herein, the term "effective amount" refers to a quantity sufficient to achieve a desired effect, e.g., an amount of recombinant detector bacteriophage which results in the identification of bacteria and/or identification of antibiotic susceptibility. The amount of a recombinant detector bacteriophage contacted with a sample will depend on the degree, type, and severity of the bacterial infection. The skilled artisan will be able to determine appropriate dosages depending on these and other factors.

As used herein, "expression" includes one or more of the following: transcription of the gene into precursor mRNA; splicing and other processing of the precursor mRNA to produce mature mRNA; mRNA stability; translation of the mature mRNA into protein (including codon usage and tRNA availability); and glycosylation and/or other modifications of the translation product, if required for proper expression and function.

As used herein, "heterologous nucleic acid sequence" is any sequence placed at a location in the genome where it does not normally occur. A heterologous nucleic acid sequence may comprise a sequence that does not naturally occur in a bacteriophage, or it may comprise only sequences naturally found in the bacteriophage, but placed at a non-normally occurring location in the genome. In some embodiments, the heterologous nucleic acid sequence is not a natural phage sequence. In other embodiments, the heterologous nucleic acid sequence is a sequence that occurs naturally in the genome of a wild-type phage but is then relocated to another site where it does not naturally occur, rendering it a heterologous sequence at that new site.

As used herein, a "host cell" is a bacterial cell that can be infected by a phage to yield progeny phage particles. A host cell can form phage particles from a particular type of phage genomic DNA. In some embodiments, the phage genomic DNA is introduced into the host cell by infecting the host cell with a phage. In some embodiments, the phage genomic DNA is introduced into the host cell using transformation, electroporation, or any other suitable technique. In some embodiments, the phage genomic DNA is substantially pure when introduced into the host cell. In some embodiments, the phage genomic DNA is present in a vector when introduced into the host cell. The definition of host cell varies from one phage to another. For example, *E. coli* may be the natural host cell for a particular type of phage, but *K. pneumoniae* is not.

As used herein, the term "isolated" refers to a substance or entity that has been separated from at least some of the components with which it was associated when initially produced (whether in nature or in an experimental setting). Isolated substances and/or entities may be separated from at least about 10%, about 20%, about 30%, about 40%, about 50%, about 60%, about 70%, about 80%, about 90%, or more of the other components with which they were initially associated. In some embodiments, isolated substances and/or entities are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components.

As used herein, a "phage genome" includes naturally occurring phage genomes and derivatives thereof. Generally, the derivatives possess the ability to propagate in the same hosts as the naturally occurring phage. In some embodiments, the only difference between a naturally occurring phage genome and a derivative phage genome is at least one of a deletion and an addition of nucleotides from at least one end of the phage genome (if the genome is linear) or at least one point in the genome (if the genome is circular).

As used herein, the term "polynucleotide" or "nucleic acid" means any RNA or DNA, which may be unmodified or modified RNA or DNA. Polynucleotides include, without limitation, single- and double-stranded DNA, DNA that is a mixture of single- and double-stranded regions, single- and double-stranded RNA, RNA that is mixture of single- and double-stranded regions, and hybrid molecules comprising DNA and RNA that may be single-stranded or, more typically, double-stranded or a mixture of single- and double-stranded regions. In addition, polynucleotide refers to triple-stranded regions comprising RNA or DNA or both RNA and DNA. The term polynucleotide also includes DNAs or RNAs containing one or more modified bases and DNAs or RNAs with backbones modified for stability or for other reasons.

As used herein, the term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the material is derived from a cell so modified. Thus, for example, recombinant cells express genes that are not found within the native (non-recombinant) form of the cell or express native genes that are otherwise abnormally expressed, under expressed or not expressed at all.

As used herein, a "recombinant detector bacteriophage" or "recombinant detector phage" or "RDB" means a bacteriophage whose genomic DNA comprises a heterologous nucleic acid that encodes a bioluminescent protein, a fluorescent protein, a chromogenic protein, or any combination thereof.

As used herein, "T" refers to the luminescent signal produced by bacterial host cells infected with a recombinant detector bacteriophage divided by the background signal, wherein the background signal is defined by the Lower Limit of Detection (LLoD), which equals 3× the standard deviation added to a negative control (i.e., recombinant detector phage strain in the absence of bacterial host cells). In some embodiments, a T greater than or equal to 2 is indicative of the presence of a bacterial species that is targeted by the recombinant detector bacteriophage.

As used herein, the terms "individual", "patient", or "subject" are used interchangeably and refer to an individual organism, a vertebrate, a mammal, or a human. In certain embodiments, the individual, patient or subject is a human.

As used herein, "a sub-sample" refers to one or more samples containing bacterial cells that are derived from a test sample obtained from a subject. In some embodiments, the sub-sample is void of non-bacterial cells (e.g., human cells). In some embodiments, the sub-sample contains lysed human cells.

As used herein, "test sample" refers to a sample taken from a subject that is to be assayed for the presence of bacteria and/or for the antibiotic susceptibility of bacteria present in the sample. In some implementations, the test sample is blood, sputum, mucus, lavage, or saliva. In some implementations, the test sample is a swab from a subject.

B. BACTERIOPHAGE

Bacteriophage are obligate intracellular parasites that multiply inside bacteria by co-opting some or all of the host biosynthetic machinery. Phages contain nucleic acid and protein, and may be enveloped by a lipid membrane. Depending upon the phage, the nucleic acid genome can be either DNA or RNA but not both, and can exist in either circular or linear forms. The size of the phage genome varies depending upon the phage. The simplest phages have genomes that are only a few thousand nucleotides in size, while the more complex phages may contain more than 100,000 nucleotides in their genome, and in rare instances more than 1,000,000. The number and amount of individual types of protein in phage particles will vary depending upon the phage. The proteins function in infection and to protect the nucleic acid genome from environmental nucleases.

Phage genomes come in a variety of sizes and shapes (e.g., linear or circular). Most phages range in size from 24-200 nm in diameter. The capsid is composed of many copies of one or more phage proteins, and acts as a protective envelope around the phage genome. Many phages have tails attached to the phage capsid. The tail is a hollow tube through which the phage nucleic acid passes during infection. The size of the tail can vary and some phages do not even have a tail structure. In the more complex phages, the tail is surrounded by a contractile sheath which contracts during infection of the bacterial host cell. At the end of the tail, phages have a base plate and one or more tail fibers attached to it. The base plate and tail fibers are involved in the binding of the phage to the host cell.

Lytic or virulent phages are phages which can only multiply in bacteria and lyse the bacterial host cell at the end of the life cycle of the phage. The lifecycle of a lytic phage begins with an eclipse period. During the eclipse phase, no infectious phage particles can be found either inside or outside the host cell. The phage nucleic acid takes over the host biosynthetic machinery and phage specific mRNAs and proteins are produced. Early phage mRNAs code for early proteins that are needed for phage DNA synthesis and for shutting off host DNA, RNA and protein biosynthesis. In some cases, the early proteins actually degrade the host chromosome. After phage DNA is made late mRNAs and late proteins are made. The late proteins are the structural proteins that comprise the phage as well as the proteins needed for lysis of the bacterial cell. In the next phase, the phage nucleic acid and structural proteins are assembled and infectious phage particles accumulate within the cell. The bacteria begin to lyse due to the accumulation of the phage lysis protein, leading to the release of intracellular phage particles. The number of particles released per infected cell can be as high as 1000 or more. Lytic phage may be enumerated by a plaque assay. The assay is performed at a low enough concentration of phage such that each plaque arises from a single infectious phage. The infectious particle that gives rise to a plaque is called a PFU (plaque forming unit).

Lysogenic phages are those that can either multiply via the lytic cycle or enter a quiescent state in the host cell. In the quiescent state, the phage genome exists as a prophage (i.e., it has the potential to produce phage). In most cases, the phage DNA actually integrates into the host chromosome and is replicated along with the host chromosome and passed on to the daughter cells. The host cell harboring a prophage is not adversely affected by the presence of the prophage and the lysogenic state may persist indefinitely. The lysogenic state can be terminated upon exposure to adverse conditions. Conditions which favor the termination of the lysogenic state include: desiccation, exposure to UV or ionizing radiation, exposure to mutagenic chemicals, etc. Adverse conditions lead to the production of proteases (rec A protein), the expression of the phage genes, reversal of the integration process, and lytic multiplication.

In some embodiments, a phage genome comprises at least 5 kilobases (kb), at least 10 kb, at least 15 kb, at least 20 kb, at least 25 kb, at least 30 kb, at least 35 kb, at least 40 kb, at least 45 kb, at least 50 kb, at least 55 kb, at least 60 kb, at least 65 kb, at least 70 kb, at least 75 kb, at least 80 kb, at least 85 kb, at least 90 kb, at least 95 kb, at least 100 kb, at least 105 kb, at least 110 kb, at least 115 kb, at least 120 kb, at least 125 kb, at least 130 kb, at least 135 kb, at least 140 kb, at least 145 kb, at least 150 kb, at least 175 kb, at least 200 kb, at least 225 kb, at least 250 kb, at least 275 kb, at least 300 kb, at least 325 kb, at least 350 kb, at least 375 kb, at least 400 kb, at least 425 kb, at least 450 kb, at least 475 kb, or at least 500 kb of nucleic acids.

Phage groups include Myoviridae, Siphoviridae, Podoviridae, Lipothrixviridae, Rudiviridae, Ampullaviridae, Bucaudaviridae, Clavaviridae, Corticoviridae, Cystoviridae, Fuselloviridae, Globuloviriade, Guttaviridae, Inoviridae, Leviviridae, Mircoviridae, Plasmaviridae, and Tectiviridae.

C. RECOMBINANT DETECTOR BACTERIOPHAGES OF THE PRESENT TECHNOLOGY

The genomes of the recombinant detector bacteriophages of the present technology comprise a heterologous nucleic acid that encodes a bioluminescent protein, a fluorescent protein, a chromogenic protein, or any combination thereof (collectively known as "reporter genes"). In some embodiments, the encoded gene product(s) produces a detectable signal upon exposure to the appropriate stimuli, and the resulting signal permits detection of bacterial host cells infected by the recombinant detector phage. In certain embodiments, the protein encoded by the heterologous nucleic acid serves as a marker that can be identified by screening bacterial host cells infected by a recombinant detector phage comprising the heterologous nucleic acid sequence. In some embodiments, the heterologous nucleic acid sequence further comprises sequences naturally found in the bacteriophage, but placed at a non-normally occurring location in the genome.

In some embodiments, the recombinant detector phage genome comprises one, two, three, four, or five reporter genes. In some embodiments, the recombinant detector phage genome comprises two or more reporter genes. The reporter genes may be identical or different.

Fluorescent proteins include but are not limited to blue/UV fluorescent proteins (for example, TagBFP, Azurite, EBFP2, mKalama1, Sirius, Sapphire, and T-Sapphire), cyan fluorescent proteins (for example, ECFP, Cerulean, SCFP3A, mTurquoise, monomeric Midoriishi-Cyan, TagCFP, and mTFP1), green fluorescent proteins (for example, EGFP, Emerald, Superfolder GFP, Monomeric Azami Green, TagGFP2, mUKG, and mWasabi), yellow fluorescent proteins (for example, EYFP, Citrine, Venus, SYFP2, and TagYFP), orange fluorescent proteins (for example, Monomeric Kusabira-Orange, mKOK, mKO2, mOrange, and mOrange2), red fluorescent proteins (for example, mRaspberry, mCherry, mStrawberry, mTangerine, tdTomato, TagRFP, TagRFP-T, mApple, dsRed, and mRuby), far-red fluorescent proteins (for example, mPlum, HcRed-Tandem, mKate2, mNeptune, and NirFP), near-IR fluorescent proteins (for example, TagRFP657, IFP1.4, and iRFP), long stokes-shift proteins (for example, mKeima Red, LSS-mKate1, and LSS-mKate2), photoactivatable fluorescent proteins (for example, PA-GFP, PAmCherry1, and PATagRFP), photoconvertible fluorescent proteins (for example, Kaede (green), Kaede (red), KikGR1 (green), KikGR1 (red), PS-CFP2, PS-CFP2, mEos2 (green), mEos2 (red), PSmOrange, and PSmOrange), fluorescein, rhodamine, and photoswitchable fluorescent proteins (for example, Dronpa).

Examples of bioluminescent proteins are aequorin (derived from the jellyfish *Aequorea victoria*) and luciferases (including luciferases derived from firefly and *Renilla*, nanoluciferase, red luciferase, luxAB, and the like). Examples of chemiluminescent protein include β-galactosidase, horseradish peroxidase (HRP), and alkaline phosphatase.

In some embodiments, the recombinant detector bacteriophage belongs to a phage type selected from the group consisting of T3, T7, M6, K11, F92, K1-5, and K1F.

In certain embodiments, the recombinant detector bacteriophage comprises the nucleic acid sequence of SEQ ID NO: 1. In other embodiments, the recombinant detector bacteriophage comprises the nucleic acid sequence of SEQ ID NO: 2. In some embodiments, the recombinant detector bacteriophage comprises the nucleic acid sequence of SEQ ID NO: 2.

In some embodiments, the recombinant detector bacteriophage comprises the nucleic acid sequence of SEQ ID NO: 3. See FIG. 12. In certain embodiments, the recombinant detector bacteriophage comprises the nucleic acid sequence of SEQ ID NO: 4. See FIGS. 13A-13J. In other embodiments, the recombinant detector bacteriophage comprises the nucleic acid sequence of SEQ ID NO: 5. See FIGS. 14A-14K.

D. SYSTEM FOR BACTERIAL IDENTIFICATION

As an overview, the system for bacterial identification can be a single, self-contained, point-of-care or lab-based diagnostic system. The system can be used to detect foreign agents, such as bacteria, within blood or other samples. The system can receive as input the blood or other samples and output an indication of whether, and to what degree, the foreign agent is present in the sample. The system can reduce the time scale for bacteria detection to a few hours and serve as a point-of-care diagnostic tool within hospital, lab, and other medical factilities. As described further below, the system can include disposable microfluidic cartridges that are removable from the system and can be replaced between tests. The microfluidic cartridges can receive a sample, such as a blood sample, that is suspected of containing bacterial cells and separate the bacterial cells from the blood sample. Once the bacterial cells are separated from the blood, the system can introduce the RDBs into the system. The RDB can include one or more reporter genes. When the RDB comes into contact with a specified bacterial cell type, the RDB can infect the bacterial cells with the reporter gene. Once infected, the bacterial cells can then express the reporter gene. The system can detect a signal generated responsive to the expression of the reporter gene with an optical detector. The signal can include luminescence, fluorescence, or chromagraphic signals generated in response to the expressed reporter gene. The system can display or otherwise report out the signal as an indication of the presence of the foreign agent.

FIG. 1 illustrates a block diagram of an example system 100. The system 100 can be a bacteria identification and antibiotic susceptibility profiling device that uses the above described RDBs. The system 100 can be a single, self-contained system that is housed as a single unit that is a point-of-care or lab-based system. The system 100 can include a microfluidic cartridge 102. The microfluidic cartridge 102 includes a microfluidic cartridge 102 that is coupled with a separator 106. The microfluidic cartridge 102 also includes a concentrator 108 and a microfluidic channel 110. The output of the microfluidic channel 110 feeds into the incubation reservoirs 112(1)-112(n) (collectively referred to as the incubation reservoirs 112). Each of the incubation reservoirs 112 can be coupled with a respective one of the detection chambers 114(1)-114(n) (collectively referred to as the detection chambers 114). When two elements of the microfluidic cartridge 102 are coupled with one another, the coupling can be direct or indirect. For example, the reservoirs 112 are coupled with both the microfluidic channel 110 through a direct coupling and to the concentrator 108 indirectly via the microfluidic channel 110.

The system 100 can also include one or more buffer reservoirs 116, wash fluid reservoirs 118, and waste reservoirs 120. The system 100 can include a counter 122 and an optical detector 124. The system 100 can include a phage cocktail reservoir 126, an antibiotic solution reservoir 128, and a lysis reagent reservoir 130.

The system 100 can include the microfluidic cartridge 102. The components of the microfluidic cartridge 102 are described further in relation to FIG. 2A. The microfluidic cartridge 102 can be contained within a cartridge. The cartridges can be a removeable and disposable. For example, a new cartridge can be used for each patient such that the components of the system 100 do not have to be sterilized between samples. Containing the fluids within the cartridge can increase throughput of the system 100 because after the completion of a test, the cartridge can be replaced and a second sample can be processed through the system 100.

The cartridge containing the components of the microfluidic cartridge 102 can include polystyrene. The cartridge can include other thermoplastics, such as, acrylic (polymethylmethacrylate), polysulfone, polycarbonate, polyethylene, polypropylene, cyclic olefin copolymer, silicone, liquid crystal polymer, and polyvinylidene fluoride. In some implementations, the cartridge can include glass. The cartridge of the microfluidic cartridge 102 can be manufactured using a number of manufacturing techniques, including, but not limited to, milling, injection molding, embossing, and etching.

The microfluidic cartridge 102 can include a sample reservoir 104. The sample reservoir 104 can be an inlet configured to receive a sample of whole blood. For example, the sample can be contained in a blood collection tube and is pumped through the microfluidic cartridge 102 via a tube connected to the microfluidic cartridge 102 at the inlet. The whole blood sample can include plasma, a plurality of formed elements, and bacteria. The formed elements of the blood can include red blood cells, white blood cells, and platelets. The sample reservoir 104 can be well configured to hold between about 1 mL and about 15 mL, Between about 2 mL and about 12 mL, between about 3 mL and about 10 mL, or between about 5 mL and about 10 mL.

The microfluidic cartridge 102 can include the separator 106. The separator 106 can include an inlet coupled with the sample reservoir 104. The separator 106 can include two or more outlets. Fluid containing waste can be driven to one of the outlets and fluid containing the bacteria can be driven to a different one of the outlets. The separator 106 can use inertial, hydrodynamic, dielectrophoretic, magnetic, surface capture, acoustic separation, and size exclusion devices to separate the bacteria from the formed elements of the blood. For example, the separator 106 can be an acoustic separation device. The system 100 can include an acoustic wave generator that generates a standing acoustic wave across a flow channel of the separator 106. The standing acoustic wave can drive the formed elements and the bacteria toward an alignment axis of the flow channel. The alignment axis of the separator 106 can be location of the positive or negative node of the standing wave within the flow channel. In some implementations, the formed elements are driven toward the alignment axis. In other implementations, the formed elements and the bacteria are driven toward the alignment axis. In these implementations, the formed elements and the bacteria can be driven toward the alignment axis at different rates such that the bacteria and formed elements can be separated based on the distance they have been driven toward the alignment axis. The flow channel of the separator 106 can have a width between about 0.2 mm and about 1 mm, between about 0.2 mm and about 0.8 mm, between about 0.4 mm and about 0.6 mm, or between about 0.4 mm and about 0.5 mm. The flow channel of the separator 106 can have a height between about 0.2 mm and about 1 mm, between about 0.2 mm and about 0.8 mm, between about 0.2 mm and about 0.6 mm, or between about 0.2 mm and about 0.4 mm.

The microfluidic cartridge 102 can include the concentrator 108. The concentrator 108 can be coupled with an outlet of the separator 106. The concentrator 108 can be coupled to the outlet of the separator 106 through which the bacteria exits the separator 106. The bacteria can exit the separator 106 in a fluid flow that can include the bacteria, plasma, and buffer fluid. The concentrator 108 can concentrate the bacteria within the fluid flow. For example, the fluid flow entering the concentrator 108 can enter the concentrator 108 with a bacteria concentration between about 1 and about 100 colony forming units (cfu)/mL. The fluid flow exiting the concentrator 108 can exit the concentrator 108 with a bacteria concentration between about 5 and about 5000 cfu/mL. The concentrator 108 can increase the bacteria concentration within the exiting fluid flow by a factor of between about 5 and about 100×. The concentrated fluid flow generated by the concentrator 108 exits the concentration portion of the microfluidic cartridge 102 through an outlet and can enter a microfluidic channel 110.

The microfluidic cartridge 102 can include the microfluidic channel 110. The microfluidic channel 110 can narrow to a height and width such that substantially only one bacterial cell can pass through the microfluidic channel 110 at a time. The dimensions of the microfluidic channel 110 can be referred to as monocellular as the microfluidic channel 110 can enable substantially only one cell to flow through the microfluidic channel 110 at a time. The system 100 can serve as an interface to the counter 122.

The microfluidic cartridge 102 can include the incubation reservoirs 112. The microfluidic cartridge 102 can include between 1 and about 384, between about 1 and about 96, between about 1 and about 50, between about 1 and about 24, or between about 1 and about 6 incubation reservoirs 112. The fluid exiting the microfluidic channel 110 can enter the incubation reservoirs 112. For example, each of the incubation reservoirs 112 can be coupled to the outlet of the microfluidic channel 110 such that an substantially equal amount of the fluid exiting the microfluidic channel 110 enters each of the incubation reservoirs 112. In some implementations, different amounts of fluid exiting the microfluidic channel 110 can flow into each of the respective incubation reservoirs 112. Flow channel dimensioning or valves can be used to control the amount of fluid that flows into each of the incubation reservoirs 112. For example, the sizes of the flow channels coupling the incubation reservoirs 112 with the microfluidic channel 110 can be narrowed (e.g., the resistance to flow is increased) such that less fluid flows through the narrowed flow channels and into the respective incubation reservoirs 112. The incubation reservoirs 112 to receive a relatively greater amount of fluid can be coupled with the microfluidic channel 110 with wider flow channels (having less resistance to flow) such that a relatively greater amount of fluid flows through the flow channels and into the respective incubation reservoirs 112. In other implementations, a flow meter and valves can be used to control the amount of fluid flowing into each of the incubation reservoirs 112. In another example, the incubation reservoirs 112 can be manufactured to house different amounts of fluid such that when the incubation reservoir 112 is full no additional fluid can flow into the incubation reservoir 112. In some implementations, one or more walls (e.g., the ceiling) of the incubation reservoirs 112 is clear such that luminescence is visible through the wall of the incubation reservoirs 112.

The incubation reservoirs 112 can be environmentally controlled chambers configured to allow for the survival of bacteriophages and the bacteria within the fluid from the microfluidic channel 110. The controller can also include a controller to control environmental conditions within the incubation reservoir 112, such as the temperature level, humidity level, and other conditions within the incubation reservoirs 112. In some implementations, each of the incubation reservoirs 112 can be assigned a unique chamber code that can be encoded as a barcode. The unique chamber code can enable each of the sub-samples from the microfluidic channel 110 to be automatically tracked. In some implementations, each of the incubation reservoirs 112 can be maintained under different environmental conditions (e.g., different temperatures and humidity levels) relative to each other. In some arrangements, the incubation reservoirs 112 can include a perfusion system. The perfusion system can include a plurality of microfluidic flow channels and pumps. The perfusion system can supply the sub-samples and bacteriophages with growth medium and other cell culture fluids (e.g., fluids that contain nutrients for the survival of the samples and bacteriophages). The culture fluids can be perfused into the wells containing the samples and bacteriophages at predetermined intervals or continuously. In some implementations, the incubation reservoirs 112 can be open to the external environment. In these implementations, the incubation reservoirs 112 can be sealed with a gas permeable membrane such that gases can move into and out of the incubation reservoirs 112. In these implementations, the microfluidic channel 110 can temporally move the microfluidic cartridge 102 into an incubator. The environment within each of the incubation reservoirs 112 can be substantially the same as the environment within the incubator. The microfluidic cartridge 102 can be stored within the incubator for a predetermined amount of time during the incubation phase.

The system 100 can also include a plurality of reservoirs coupled with each of the incubation reservoirs 112. In addition to growth medium reservoirs, a phage cocktail reservoir 126, an antibiotic solution reservoir 128, a lysis reagent reservoir 130, and a washer fluid reservoir 120 can be coupled with each of the incubation reservoirs 112 (collectively referred to as the reservoirs). The incubation reservoirs 112 can each be coupled with reservoirs containing the same composition of fluids or with different compositions of fluid. For example, each of the incubation reservoirs 112 can be coupled to a different antibiotic solution reservoir 128 that includes a different antibiotic solution. In some implementations, in addition to or in place of one or more of the reservoirs coupled to the incubation reservoirs 112, the incubation reservoirs 112 can be prefilled with the fluid from one or more of the reservoirs. For example, the system 100 may not include the antibiotic solution reservoirs and each of the incubation reservoirs 112 can be prefilled with a different antibiotic solution. In some implementations, a dried or powdered form of the fluid stored within each of the reservoirs can be prefilled into the incubation reservoirs 112.

The microfluidic cartridge 102 can include the detection chambers 114. The detection chambers 114 can include one or more visually clear walls that enable luminesce to be viewed through the wall. In some implementations, the detection chamber 114 can be the incubation reservoir 112. For example, the sub-samples can remain within the incubation reservoir 112 when viewed by the optical detector 124. The detection chamber 114 can include a bacteria trap, such as a filter, that can entrap bacterial cells and enhance the detection of an amount of light detected by the optical detector 124 as the bacterial cells are concentrated onto the bacteria trap.

Outside of the microfluidic cartridge 102, the system 100 can include the counter 122. The counter 122 can count cells as they pass through the microfluidic channel 110. The counter 122 can identify or otherwise classify the cells that pass through the microfluidic channel 110. For example, the incubation reservoir 112 can count and classify cells flowing through the microfluidic channel 110 as bacterial cells or red blood cells. In some implementations, the counter 122 can be one of a laser-based flow cytometer or an impedance-based flow cytometer. The counter 122 can include a transmitter and a receiver on either side of the microfluidic channel 110. For a laser-based flow cytometer, the transmitter can a laser and the receiver can be a photo-detector. For an impedance-based flow cytometer, the transmitter and receiver can each be electrodes that measure the impedance across the width of the microfluidic channel 110.

In some implementations, the counter 122 can be coupled with a controller that controls one or more valves leading to each of the incubation reservoirs 112. Based on the cellular count generated by the counter 122, the controller can control the number of cells in each of the incubation reservoirs 112. For example, the controller can open a valve to the first incubation reservoir 112 while the cell count is below n cells (where n is the number of cells desired to be in each of the incubation reservoirs 112). While the cell count is below n, the controller can close the valves to each of the other incubation reservoirs 112. Once the cell count reaches n, the controller can close the first valve and open the second valve. The open second valve can enable fluid to flow into the incubation reservoir 112(2). Once the cell count reaches 2n, the controller can close the second valve and open the third valve. The process can continue until the controller has filled each of the incubation reservoirs 112 with n cells.

The optical detector 124 can detect and measure a signal generated in response to the expression of the reporter gene. The signal can include a luminescent, fluorescent, or chromagraphic signal generated by the reporter gene. The system 100 can include a single optical detector 124. In this configuration, each of the detection chambers 114 are sequentially placed (e.g., by a robotic arm) in the optical detector's viewing field and signal generated by the reporter genes within the respective detection chamber 114 is measured. In other implementations, the system 100 can include a plurality of optical detectors. For example, the system 100 can include a separate optical detector for each of the detection chambers 114. The optical detector 124 can provide the detected signal to a controller that can determine if bacteria is present in the signal. For example, the controller can determine if the signal is above a predetermined threshold. If the signal is above the predetermined threshold then the controller can signal to a user, via a display or printout, that bacterial cells were present in the sample. The controller can also indicate the type of bacterial cells that are present based on from which of the detection chambers 114 the signal was detected. In other implementations, the controller can display the value of the signal in addition to or in place of the binary yes/no to the presence of the bacterial cells. The value of the signal can be an indication of the amount the reporter gene was expressed, which can serve as a proxy for the amount of bacterial cells present in the sample.

The system 100 can include a wave generator. The microfluidic cartridge 102 can be positioned to sit atop the wave generator. The wave generator can generate and impose a standing acoustic wave on the separator 106. The wave generator can generate the standing acoustic wave transverse to the flow of the fluid through the separator 106. The standing acoustic wave can drive fluid constituents (e.g., bacteria and formed elements) towards or away from the walls of the separator 106. The standing acoustic wave can drive the bacteria and formed elements towards one or more aggregation axes. The wave generator can be a bulk piezoelectric acoustic transducer. The wave generator can generate a standing acoustic wave with a frequency between about 0.5 MHz and about 1.5 MHz, between about 0.7 MHz and about 1.2 MHz, or between about 0.85 MHz and about 1.1 MHz.

In some implementations, the frequency of the standing acoustic wave is selected responsive to the dimensions of the separator 106. For example, the width of a portion of the flow channel within the separator 106 (e.g., a portion of the aggregation channel) can be equal to about half the wavelength of the acoustic wave in the fluid. In other implementations, the wavelength of the acoustic wave can be between about 1 and about 5 times, between about 2 and about 4, or between about 3 and about 4 times larger than the interior width of the separator's aggregation channel.

Figure 2A:
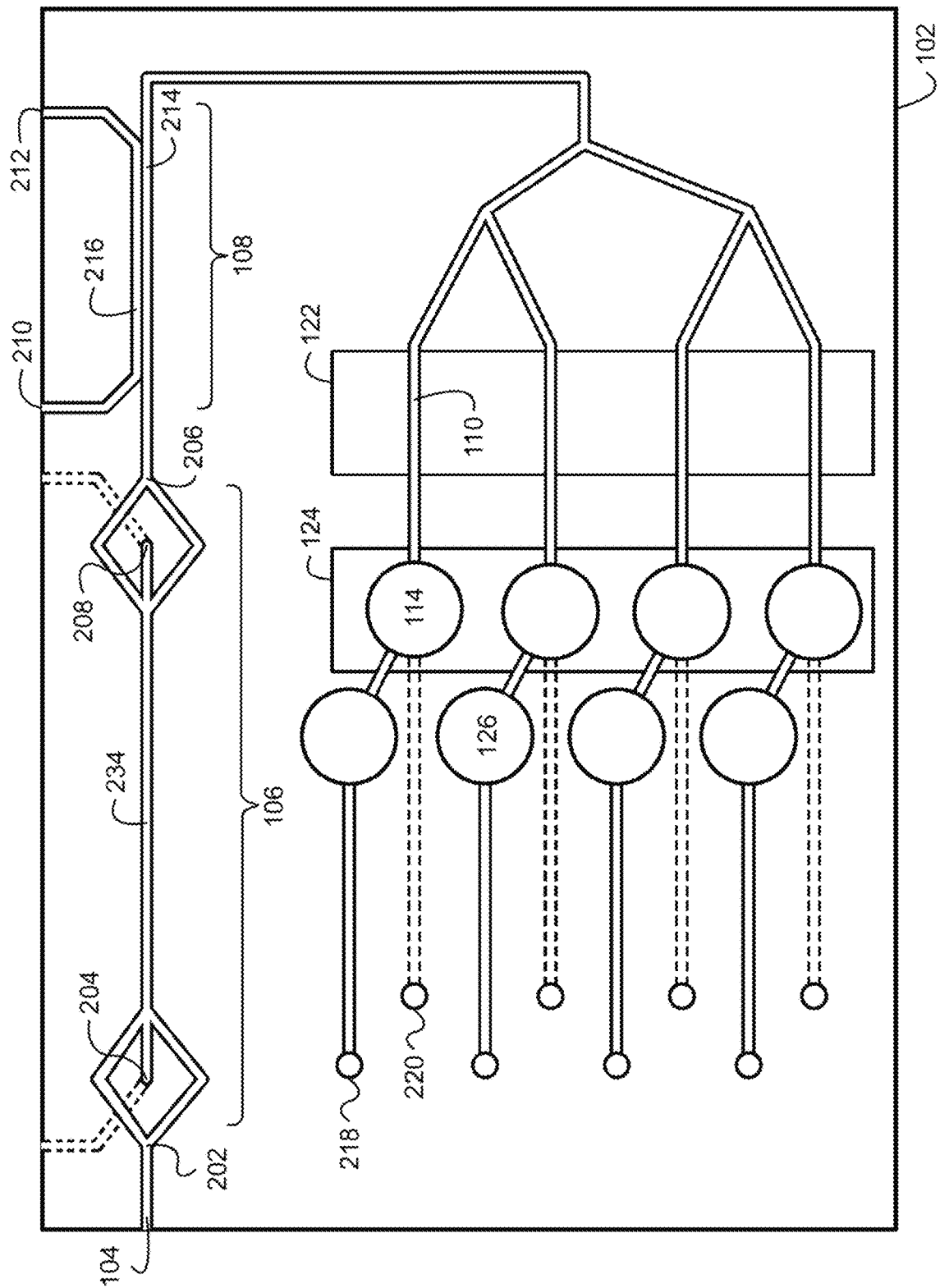
FIG. 2A illustrates a schematic of an example microfluidic cartridge for use in the system illustrated in FIG. 1.

FIG. 2A illustrates a schematic of an example microfluidic cartridge 102. The microfluidic cartridge 102 can include a substrate that defines the plurality of components (e.g., the microfluidic channels) of the microfluidic cartridge 102. In some implementations, the substrate includes rigid materials such as silicon, glass, metals, or other materials that establish a high acoustic contrast between the fluid flowing though the channels of the microfluidic cartridge 102 and the substrate. In other implementations, the substrate includes relatively more elastic materials, which establish a lower acoustic contrast between the fluid flowing the through the channels of the substrate and the substrate. These materials can include thermoplastics, such as, polystyrene, acrylic (polymethylmethacrylate), polysulfone, poly-carbonate, polyethylene, polypropylene, cyclic olefin copolymer, silicone, liquid crystal polymer, and polyvinylidene fluoride.

The sample can be loaded into the microfluidic cartridge 102 at the sample reservoir 104, which can be an inlet to the microfluidic cartridge 102. The sample can enter a first inlet 202 of the separator 106. A co-flow buffer can enter the separator 106 through a second inlet 204 of the separator 106. A standing acoustic wave can be applied across the separator's aggregation channel 234. The standing acoustic wave can drive the particles (e.g. the formed elements of a blood sample) within the sample toward an aggregation axis of the separator 106. The standing acoustic wave can also drive bacterial cells toward the aggregation axis, but at a rate slower than the other particles within the sample. The bacterial cells can exit the separator 106 through a first outlet 206 and the particles can exit the separator 106 through a second outlet 208 as waste. The concentrator 108 is coupled with the first outlet 206 of the separator 106. The concentrator 108 can include a first microfluidic channel 214 that is separated from a second microfluidic channel 216 by a permeable membrane or filter. The second microfluidic channel 216 can have an inlet 210 and an outlet 212 through which a wash fluid is pumped. The bacterial cells exiting the separator 106 can be captured on the membrane between the first microfluidic channel 214 and the second microfluidic channel 216. The bacterial cells can be capture on the membrane when a pressure differential between the fluids flowing within the first microfluidic channel 214 and the second microfluidic channel 216 drives fluid from the first microfluidic channel 214 into the second microfluidic channel 216. The membrane, having a pore size less than the size of the bacterial cells, captures the bacterial cells. The bacterial cells can be released from the membrane by reversing the pressure differential such that fluid is driven from the second microfluidic channel 216 into the first microfluidic channel 214.

The concentrator 108 may use acoustic, optical, dielectrophoretic, or other means to capture and retain bacterial cells as they flow through it. The concentrator may use a surface coating comprising a ligand that preferentially binds bacteria to a surface until released by a liquid reagent.

As illustrated in FIG. 2A, the sample is divided into four sub-samples. The sub-samples pass into four separate microfluidic channels 110, which serve as an interface to the counter 122. The counter 122 can be separate from the microfluidic cartridge 102, but the microfluidic cartridge 102 can be machined such that the counter 122 can be seated onto, or otherwise interface with, the microfluidic cartridge 102. The counter 122 can count the number of bacterial cells passing through each of the microfluidic channels 110. From the microfluidic channels 110, the sub-samples can pass into a respective detection chamber 114. A phage cocktail reservoir 126 can be coupled with each of the detection chambers 114. The phage cocktail reservoir 126 can contain the RDB. The reservoir 126 can contain an antibiotic. Fluids can be pumped into and out of the detection chambers 114 and phage cocktail reservoirs 126 through respective ports 218 and 220. One or more ports can be coupled with the inlets, outlet, and ports of the microfluidic cartridge 102. For example, a first pump can be coupled with the second outlet 208, a second pump can be coupled with the outlet 212 of the concentrator 108, and third pump can be coupled with ports 218 and 220.

In some implementations, the system can include an optical detector positioned to detect the reporter molecules released into the channels coupled to the ports 220. For example, after incubation with the RBD, a lysis agent may be added to reservoirs 112 such that reporter molecules flow to a port 220 while other cellular fragments are retained by a filter. The optical detector measures the net signal released from the reservoir and passing a detection point positioned in the channel connected to the port 220 of the incubation reservoirs.

Figure 2B:
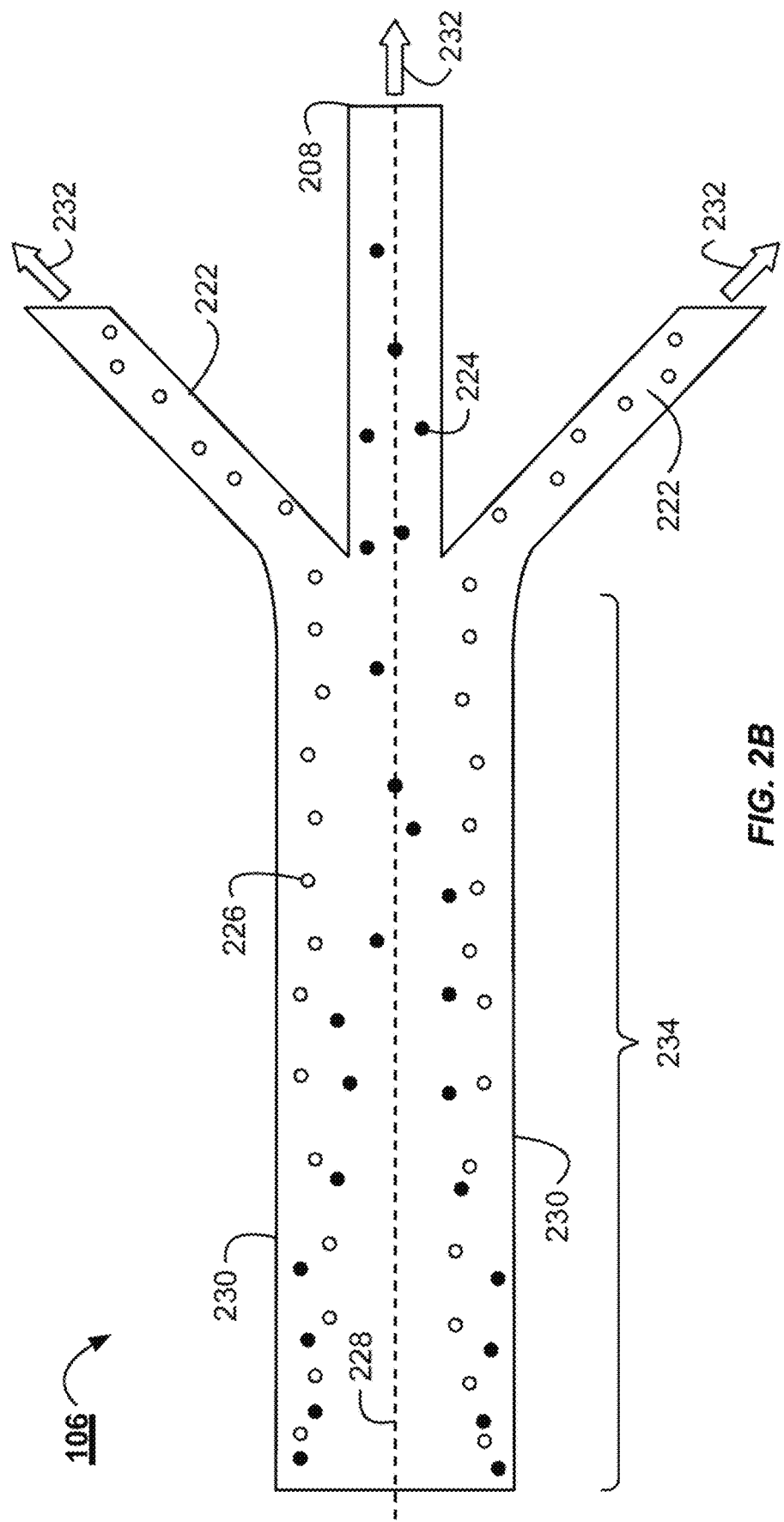
FIG. 2B illustrates the outlet portion of the separator illustrated in FIG. 2A.

FIG. 2B illustrates the outlet portion of the separator 106 that includes the second outlet 208. The legs 222 of the aggregation channel 234 are coupled with the first outlet 206 of the separator 106. At the second inlet 204 a buffer is introduced along the aggregation axis 228 of the separator 106. The arrows 232 illustrate the direction of flow through the separator 106. The sample is introduced via inlets near the walls 230 of the separator 106. The sample containing, for example, bacterial cells 226 and formed elements 224 initially flow along the length of the separator 106 near the walls 230. In the presence of the standing acoustic wave, the formed elements 224 are driven towards the aggregation axis 228. The formed elements 224 exit the separator 106 via the second outlet 208. The bacterial cells 226 remain sufficiently close to the walls 230 such that they exit the separator 106 via the legs 222 and the first outlet 206.

Figure 3:
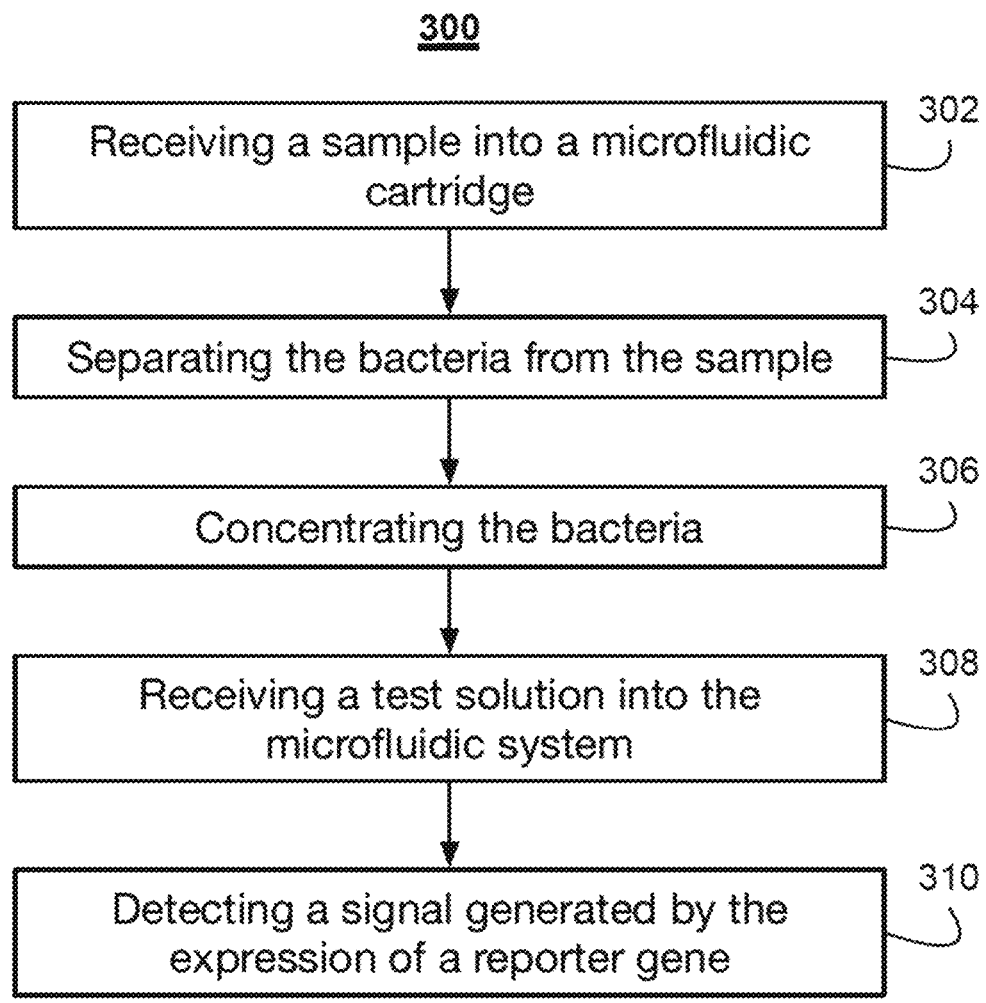
FIG. 3 illustrates a flow diagram of an example method for detecting bacterial cells in a sample using the example system illustrated in FIG. 1.

FIG. 3 illustrates a flow diagram of an example method 300 for detecting bacteria in a sample. The method 300 can include receiving a sample into a microfluidic cartridge (step 302). The method 300 can include separating the bacteria from the sample (step 304). The method 300 can include concentrating the bacteria within the portion of the sample exiting the separator (step 306). The method 300 can also include receiving a test solution into the microfluidic cartridge (step 308). The method 300 can include detecting a signal generated by the expression of the reporter gene (step 310).

As set forth above, the method 300 can include receiving a sample into a microfluidic cartridge (step 302). The microfluidic cartridge can be similar to the microfluidic cartridges described above in relation to FIGS. 2 and 3. The microfluidic cartridge can be a component of a singularly house, bacteria identification system similar to the system described above in relation to FIG. 1. The sample can be a collection of bodily fluid or tissue containing a plurality of living cells. The sample may be received as a result of a blood draw, a biopsy, a tissue swab, or other similar sample gathering procedure. The sample can be maintained in one or more containers under conditions sufficient for cells contained within to survive outside of the subject's body (e.g., under controlled temperature, moisture, and pH conditions). The sample can be cultured to provide a larger overall sample size before the sample is provided to the microfluidic cartridge. The samples can be assigned unique codes (e.g., a barcode or QR code) sufficient to distinguish the received sample from other patient samples. The unique codes may be provided on microfluidic cartridges, vials, containers, dishes, or other such patient sample storage devices. The sample can be a blood sample that is suspected of including bacteria. The sample can be whole blood that includes plasma and formed elements in addition to the possible bacteria. The whole blood can also include antibodies, free proteins, electrolytes and other components. The sample can also be any other fluids suspected of including bacteria. The sample can be between about 1 mL and about 20 mL. Once the sample is loaded into an inlet reservoir of the microfluidic cartridge, a pump can flow the sample from the inlet reservoir to and through a separator. Once the microfluidic cartridge receives the sample, one or more pumps can pump the sample (or a portion thereof) into a separator.

The method 300 can include separating the bacteria from the sample (step 304). A separator can separate the bacterial cells in the test sample from other components in the sample, such as the formed elements and other components disposed therein (e.g., antibodies, free proteins, electrolytes). In some implementations, these components can cause complications in the later detection steps of the method 300. For example, immune system components (e.g., antibodies) in the sample may interfere with the operation of bacteriophages. The bacterial cells can be separated from the sample by any of a number of particle separation procedures, including particle centrifugation, adhesion, acoustophoresis, or via the use of harmonics. The separator can be an acoustic separator. In these implementations, a standing acoustic wave can be applied across a fluid channel within the separator. The standing acoustic wave can drive the formed elements and bacteria toward aggregation axes within the separator. For example, the standing acoustic wave can drive the formed elements towards an aggregation axis near the center of fluid channel in the separator. A first set of outlets positioned near the wall of the fluid channel can collect the bacteria since the standing acoustic wave did not drive the bacteria sufficiently close to the aggregation axis. A second outlet positioned in the center of the fluid channel and in line with the aggregation axis can collect the formed elements.

The method 300 can include concentrating the bacteria within the portion of the sample exiting the separator (step 306). As described above, the bacterial cells can exit the separator mixed with the diluted plasma from the sample. The concentrator can concentrate the bacterial cells before the bacterial cells are provided to subsequent steps of the method 300. In one implementation, the fluid exiting the separator can enter a first flow channel that is separated from a second flow channel by a filter. Initially, the pressure within the second flow channel can be less than the pressure within the first flow channel such that the bacterial cells are driven toward the filter. The filter, having a pore size less than the size of the bacterial cells can capture the bacterial cells. After a predetermined amount of time, the pressure is increased in the second flow channel. The increase in pressure in the second flow channel can drive fluid from the second channel and into the first channel via the membrane. The reverse in fluid flow from the second flow channel to the first flow channel can dislodge the bacterial cells from the filter and provide a concentrated release of bacterial cells into the first flow channel.

The method 300 can include counting the bacterial cells. The bacterial cells can flow into a microfluidic channel that has substantially monocellular dimensions such that only one bacterial cell can flow through the microfluidic channel at a time. As the bacterial cells flow through the microfluidic channel a cell counter, such as a flow cytometer, can count the number of bacterial cells and determine the number of bacterial cells flowing through the microfluidic channel at any given time. A controller can be coupled with the cell counter and a plurality of valves. The valves can control the flow of the sample into incubation reservoirs. The controller can be configured to generate sub-samples from the sample flowing through the microfluidic channel. Each of the sub-samples can be provided to the incubation reservoirs. The controller can serially fill each of the incubation reservoirs such that they each receive substantially the same number of bacterial cells based on the counting made by the cell counter. For example, as counted by the cell counter, the controller can open and close valves such that the first 100 bacterial cells are provided to a first incubation chamber, a second 100 bacterial cells are provided to a second incubation chamber, and so on. Providing substantially the same number of bacterial cells to each of the incubation reservoirs can reduce cell clumping and provide more consistent results between the incubation reservoirs.

Once in the incubation reservoirs, the system can add a media fluid to each of the incubation reservoirs. The media fluid can be configured to provide a replacement environment for the bacterial cells, which can accommodate requirements of the bacterial cells such as moisture, pH, and osmotic balance to continue surviving outside of the body of the patient.

The method 300 can also include receiving a test solution into the microfluidic cartridge (step 308). The test solution can include a RDB. The RDB can include one or more reporter genes. The reporter genes can generate luminescent proteins, fluorescent proteins, or chromatographic proteins. The test solution can be introduced into the incubation reservoirs containing each of the sub-samples. The bacterial cells in the incubation reservoirs are contacted with a given test solution in a manner that can enable the bacterial cells to be exposed to and come into contact with the bacteriophages in the test solution. For example, a RDB portion of the test solution can be stored within a phage cocktail reservoir coupled with the microfluidic cartridge. At a predetermined time the system can flow the test solution from the reservoir and into one of the incubation reservoirs. Upon contact, the RDBs can have an opportunity to attempt to recognize their corresponding bacteria types within the sub-sample. In the event that a RDB identifies its corresponding bacteria type in the sub-sample, the RDB can infect the bacteria and deliver the genetic reporter gene payload into the bacteria. At which point, the bacterial cell can begin synthesizing the reporter proteins. In some implementations, the RDB from multiple RDBs can be combined with the sub-samples of bacterial cells. In some such implementations, each of the RDBs can include a distinct type of reporter gene. For example, a first RDB can include a first type of reporter gene (e.g., coding for biofluorescence) and a second RDB can include a different, second type of reporter gene (e.g., coding for bioluminescence). In such an example, two different types of bacterial cells can be identified in the same sub-sample (e.g., by detecting and measuring both light and fluorescence).

In some implementations, the test solution can include multiple solutions. The multiple solutions of the test solution can be administered to the incubation reservoirs at the same time or the multiple solutions can be delivered to the incubation reservoirs as a series of solutions over a period of time. For example, the above-described RDB can be administered to the incubation reservoirs. After a predetermined incubation time, a second solution can be administered to the incubation reservoirs 112. The second solution in the test solution can be different than the first solution of the test solution. For example, the second solution in the test solution can be an antibiotic solution from one of the above-described antibiotic reservoirs. The applied antibiotics can correspond to the bacteria type targeted by the RDB applied above. In some arrangements, each of the sub-samples can be tested for antibiotic susceptibility, except for a control sample (if any). The sub-samples can be subjected to a different type of antibiotic. For example, a first sub-sample can serve as a control, and no antibiotics can be applied to it. A second sub-sample that is to be tested for antibiotic susceptibility is subjected to a first antibiotic (e.g., a broad spectrum antibiotic), a third sub-sample that is to be tested for antibiotic susceptibility is subjected to a second antibiotic (e.g., distinct from the first antibiotic, for example another broad spectrum antibiotic or a narrower spectrum antibiotic), and a fourth sub-sample that is to be tested for antibiotic susceptibility is subjected to a third antibiotic (e.g., distinct from the first and second antibiotic). In some such arrangements, multiple trials are performed for each control sample and each antibiotic (e.g., the first antibiotic is applied to ten sub-samples that are to be tested for antibiotic susceptibility, the second antibiotic is applied to another ten sub-samples that are to be tested for antibiotic susceptibility). In addition, in some arrangements, sub-samples that are to be tested for antibiotic susceptibility may be subjected to varying dosage strengths of the same antibiotic (e.g., 5 mg of the first antibiotic is applied to five sub-samples, 25 mg of the first antibiotic is applied to another five sub-samples). Each of the antibiotics can be associated with a unique code (e.g., as expressed as a bar code or a QR code on an antibiotic container) identifying each particular antibiotic.

The method 300 can include detecting a signal generated by the expression of the reporter gene (step 310). In some implementations, the expression can be detected when the sample is within the incubation reservoirs. In other implementations, the sample can be pumped into a detection chamber and the expression can be monitored when the sample is in the detection chamber. The reporter gene can be detected a predetermined amount of time after the application of the test solution or solutions. In some implementations, reporter gene expression conditions can be applied to the sample during and/or prior to the detection of the reporter gene. The expression conditions provided can correspond to the type of reporter genes applied to the sample. For example, where bioluminescent genes were applied, low levels of light and an energy source (e.g., nutrients and co-factors) are provided to the sample. As another example, where biofluorescent genes were used, wavelengths of light expected to cause corresponding biofluorescent proteins to fluoresce are provided to the sample. Other arrangements depending on the type of reporter genes assembled may be used as well. The expression can be detected by the system's optical detector.

The method 300 can also include quantifying the reporter gene expression. The amount of reporter gene expression can be quantified based on the presence of corresponding reporter proteins. Where bacteria corresponding to the bacteriophages in the RDBs applied are present in the sample, reporter genes will be delivered into bacterial cells and the reporter proteins will be synthesized within the bacterial cells. In turn, where those bacterial cells are absent, reporter proteins will not be synthesized. For example, where the reporter gene codes for a bioluminescent protein, any light provided by the corresponding patient sample may be measured to quantify reporter gene expression. Reporter gene expression may be quantified on a per-cell basis (e.g., where bacterial cells are counted) or on a bulk expression basis (e.g., where an overall amount of bioluminescent light is determined). The presence (or lack thereof) of the bacterial cells can be reported or otherwise displayed to a user. The presence of the bacteria can be reported to the user as positive (bacteria is present) or negative (bacteria is not present) result. In some implementations, the report can also include an indication of the quantify of reporter gene expression, which provides an indication of the number of bacterial cells present in the sample.

In some implementations, the method 300 can include determining the antibiotic susceptibility of the bacterial cells. The amount quantified amount of reporter gene expression can be used to determine the antibiotic susceptibility. For example, reporter gene expression in a control sub-sample may be used as a baseline to indicate the extent to which a targeted bacteria is present among the sub-samples to be tested for antibiotic susceptibility. As such, the comparative level of gene expression among the other sub-samples to be tested for antibiotic susceptibility may indicate the extent to which a given antibiotic has killed or otherwise deactivated bacteria in a given sub-sample. Where reporter gene expression remains at a level comparable to the control sample, antibiotic susceptibility may be low. In turn, where reporter gene expression is low or nonexistent, antibiotic susceptibility may be high.

E. BACTERIAL IDENTIFICATION AND ANTIBIOTIC SUSCEPTIBILITY PROFILING METHODS OF THE PRESENT TECHNOLOGY

Accurate identification of bacterial species within a biological sample informs the selection of suitable therapies for treating bacterial infections. Recombinant detector bacteriophages disclosed herein may be used to identify bacteria present within a biological sample (e.g., whole blood, plasma, serum). The recombinant detector bacteriophages can be used alone or in combination with the system described above in relation to Section D. Such methods entail contacting the biological sample with a recombinant detector bacteriophage disclosed herein, and detecting the presence of bacterial host cells infected by the recombinant detector phage, wherein the recombinant detector phage comprises a heterologous nucleic acid that encodes a detectable gene product, thereby leading to the identification of bacteria present within the biological sample.

Additionally or alternatively, the recombinant detector bacteriophages disclosed herein, may be used in methods for profiling antibiotic susceptibility of bacteria present within a biological sample (e.g., whole blood, plasma, serum). The profiling of antibiotic susceptibility can be used alone or in combination with the system described above in relation to Section D. These methods include (a) contacting the biological sample with an antibiotic and a recombinant detector bacteriophage disclosed herein, (b) detecting the presence of bacterial host cells infected by the recombinant detector phage, wherein the recombinant detector phage comprises a heterologous nucleic acid that encodes a detectable gene product, and (c) determining that the antibiotic is effective in inhibiting the bacteria present in the biological sample when the number of recombinant detector phage infected bacterial host cells is reduced relative to that observed in an untreated control sample.

In one aspect, the present disclosure provides a method for identifying at least one bacterial strain or species in a test sample obtained from a subject comprising (a) separating bacterial cells isolated from the test sample into one or more sub-samples, (b) contacting each sub-sample with one or more recombinant detector bacteriophages disclosed herein, wherein each recombinant detector bacteriophage comprises a heterologous nucleic acid encoding one or more reporter genes, and (c) identifying at least one bacterial strain or species in the test sample by detecting the expression of the one or more reporter genes of the one or more recombinant detector bacteriophages. The identification of at least one bacterial strain or species in a test sample can be done alone or in combination with the system described above in relation to Section D. In certain embodiments, the nucleic acid sequence of the one or more recombinant detector bacteriophages is selected from the group consisting of SEQ ID NO: 1, SEQ ID NO: 2, SEQ ID NO: 2, SEQ ID NO: 3, SEQ ID NO: 4, SEQ ID NO: 5, and SEQ ID NO: 6. In certain embodiments, the method for identifying at least one bacterial strain or species in a test sample does not require the culturing of bacterial cells from the test sample or a sub-sample.

In some embodiments, identification of at least one bacterial strain or species includes detecting the expression of the one or more reporter genes of the one or more recombinant detector bacteriophages, e.g., detection of green fluorescence indicates the presence of bacterial species A whereas detection of blue fluorescence indicates the presence of bacterial species B. In some embodiments, the absence of at least one bacterial strain or species is identified by the lack of detectable expression of the one or more reporter genes of the one or more recombinant detector bacteriophages, e.g., undetectable expression of green fluorescence indicates the lack of bacterial species A in a test sample or sub-sample. These methods can be used alone or in combination with the devices described above in Section D.

In some embodiments, the one or more recombinant detector bacteriophages infect a single species of bacteria. In certain embodiments, the one or more recombinant detector bacteriophage infect two or more species of bacteria. By way of example, but not by way of limitation, in some embodiments, the species of bacteria that are infected include *Pseudomonas aeruginosa, Escherichia coli, Staphylococcus aureus, Klebsiella pneumoniae, Yersinia pestis, Bacillus anthraces, Burkholderia mallei*, and *Franciscella tularensis*. These methods can be used alone or in combination with the devices described above in Section D.

In some embodiments, the one or more recombinant detector bacteriophages that infect two or more species of bacteria comprise different reporter genes, wherein the recombinant detector bacteriophages that infect the same species of bacteria comprise the same reporter gene(s). These methods can be used alone or in combination with the devices described above in Section D.

In some embodiments, detection of the expression of the reporter gene is detection of the gene product itself, e.g., a fluorescent protein. In some embodiments, detection of the expression of the reporter gene is detection of an enzymatic reaction requiring the expression of the reporter gene, e.g., expression of luciferase to catalyze luciferin to produce light. These methods can be used alone or in combination with the devices described above in Section D.

In some embodiments, the expression of the one or more reporter genes is detected in about 5, 10, 15, 20, 25, 30, 35, 40, 45, 50, 55, 60, 65, 70, 75, 80, 85, 90 minutes or any time between any two of the preceding values after contacting a sub-sample with the one or more recombinant detector bacteriophages disclosed herein. These methods can be used alone or in combination with the devices described above in Section D.

In another aspect, the present disclosure provides a method for determining the antibiotic susceptibility of a bacterial strain or species in a test sample obtained from a subject comprising (a) separating bacterial cells isolated from the test sample into a plurality of sub-samples, (b) contacting the plurality of sub-samples with a recombinant detector bacteriophage disclosed herein and at least one antibiotic, wherein the recombinant detector bacteriophage comprises a heterologous nucleic acid encoding a reporter gene, and (c) detecting the expression of the reporter gene of the recombinant detector bacteriophage in the presence of each antibiotic. In some embodiments, the method further comprises determining that the bacterial strain or species in the test sample is susceptible to an antibiotic if the reporter gene expression of the recombinant detector bacteriophage in the antibiotic treated sub-sample is decreased relative to that observed in a control sub-sample that is not treated with the antibiotic. In other embodiments, the method further comprises determining that the bacterial strain or species in the test sample is resistant to an antibiotic if the reporter gene expression of the recombinant detector bacteriophage in the antibiotic treated sub-sample is comparable to that observed in a control sub-sample that is not treated with the antibiotic. In certain embodiments, the nucleic acid sequence of the recombinant detector bacteriophage is selected from the group consisting of SEQ ID NO: 1, SEQ ID NO: 2, SEQ ID NO: 2, SEQ ID NO: 3, SEQ ID NO: 4, SEQ ID NO: 5, SEQ ID NO: 6. In certain embodiments, the method for determining the antibiotic susceptibility of a bacterial strain or species in a test sample does not require the culturing of bacterial cells from a test sample or a sub-sample. These methods can be used alone or in combination with the devices described above in Section D.

In some embodiments, the at least one antibiotic is one or more of rifampicin, tetracycline, levofloxacin, and ampicillin. Examples of other antibiotics include penicillin G, methicillin, oxacillin, amoxicillin, cefadroxil, ceforanid, cefotaxime, ceftriaxone, doxycycline, minocycline, amikacin, gentamycin, kanamycin, neomycin, streptomycin, tobramycin, azithromycin, clarithromycin, erythromycin, ciprofloxacin, lomefloxacin, norfloxacin, chloramphenicol, clindamycin, cycloserine, isoniazid, rifampin, teicoplanin, quinupristin/dalfopristin, linezolid, pristinamycin, ceftobiprole, ceftaroline, dalbavancin, daptomycin, mupirocin, oritavancin, tedizolid, telavancin, tigecycline, ceftazidime, cefepime, piperacillin, ticarcillin, virginiamycin, netilmicin, paromomycin, spectinomycin, geldanamycin, herbimycin, rifaximin, loracarbef, ertapenem, doripenem, imipenem/cilastatin, meropenem, cefazolin, cefalotin, cephalexin, cefaclor, cefamandole, cefoxitin, cefprozil, cefuroxime, cefixime, cefdinir, cefditoren, cefoperazone, cefpodoxime, ceftibuten, ceftizoxime, lincomycin, dirithromycin, roxithromycin, troleandomycin, telithromycin, spiramycin, aztreonam, furazolidone, nitrofurantoin, posizolid, radezolid, torezolid, azlocillin, carbenicillin, cloxacillin, dicloxacillin, flucloxacillin, mezlocillin, nafcillin, penicillin V, temocillin, bacitracin, colistin, polymyxin B, enoxacin, gatifloxacin, gemifloxacin, moxifloxacin, nalidixic acid, ofloxacin, trovafloxacin, grepafloxacin, sparfloxacin, temafloxacin, mafenide, sulfacetamide, sulfadiazine, silver sulfadiazine, sulfadimethoxine, sulfamethizole, sulfamethoxazole, sulfanilimide, sulfasalazine, sulfisoxazole, trimethoprim-sulfamethoxazole (Co-trimoxazole) (TMP-SMX), sulfonamidochrysoidine, demeclocycline, oxytetracycline, clofazimine, dapsone, capreomycin, ethambutol, ethionamide, pyrazinamide, rifabutin, rifapentine, arsphenamine, fosfomycin, fusidic acid, metronidazole, platensimycin, thiamphenicol, tinidazole, trimethoprim(Bs) and vancomycin.

In some embodiments of the method, the differences in the reporter gene expression of the recombinant detector bacteriophage observed in the antibiotic treated sub-sample and the untreated control sub-sample is defined as μ.

Additionally or alternatively, in some embodiments of the method, the expression of the reporter gene is detected in about 5, 10, 15, 20, 25, 30, 35, 40, 45, 50, 55, 60, 65, 70, 75, 80, 85, 90 minutes or any time between any two of the preceding values after contacting a sub-sample with a recombinant detector bacteriophage disclosed herein.

In some embodiments, two or more sub-samples are tested for antibiotic susceptibility in series. In some embodiments, two or more sub-samples are tested for antibiotic susceptibility in parallel. In some embodiments, one or more sub-samples are tested for antibiotic susceptibility in a running assay (where resistance or sensitivity to one antibiotic is determined and the resistance or sensitivity to a second, third, fourth, fifth, etc., antibiotic is being assayed).

In some embodiments of the methods disclosed herein, isolating bacterial cells from a test sample includes incubating the test sample with distilled water to form a mixture, centrifuging the mixture to form a pellet that includes bacterial cells, and re-suspending the pellet to form a bacterial suspension comprising isolated bacterial cells after discarding the supernatant. The pellet may be re-suspended in a phosphate buffer. In some embodiments, the bacterial suspension is divided into one or more sub-samples.

In certain embodiments of the methods disclosed herein, mixing the test sample with distilled water will lead to the lysis of cells that lack cell walls (e.g., mammalian cells and red blood cells) while leaving cells with cell walls (e.g., bacteria) intact. Without wishing to be bound by theory, in some embodiments, the removal of cells that lack cell walls enhances the detection of reporter gene expression in bacterial cells infected with a recombinant detector bacteriophage, as intact non-bacterial cells (e.g., red blood cells) may quench reporter gene expression.

In some embodiments of the methods of the present technology, the mixture is about 90% distilled water and 10% test sample, about 80% distilled water and 20% test sample, about 70% distilled water and 30% test sample, about 60% distilled water and 40% test sample, about 50% distilled water and 50% test sample, about 40% distilled water and 60% test sample, about 30% distilled water and 70% test sample, about 20% distilled water and 80% sample, or about 10% distilled water and 90% test sample.

In some embodiments of the methods disclosed herein, the mixture is incubated for 1, 2, 3, 4, 5, 6, 7, 8, 9, 10, 11, 12, 13, 14, or 15 minutes, or any time between two of the previously listed time points. Additionally or alternatively, in certain embodiments of the methods disclosed herein, the mixture is centrifuged for 1, 2, 3, 4, 5, 6, 7, 8, 9, 10, 11, 12, 13, 14, or 15 minutes, or any time between two of the previously listed time points.

Additionally or alternatively, in certain embodiments of the methods disclosed herein, each of the one or more sub-samples comprise between about 5 to 500, about 10 to 400, about 20 to 300, about 30 to 300, about 40 to 200 or about 50 to 100 bacterial cells. In some embodiments of the methods disclosed herein, each of the one or more sub-samples comprises between about 100 to 10,000, about 200 to 9,000, about 300 to 8,000, about 400 to 7,000, about 500 to 6,000, about 600 to 5,000, about 700 to 4,000, about 800 to 3,000, about 900 to 2,000, or about 1,000 to 1,500 bacterial cells.

In any of the above embodiments of the methods of the present technology, the test sample is blood, sputum, mucus, lavage, saliva, or a swab obtained from the subject.

In some embodiments of the methods disclosed herein, the test sample is obtained from a mammal, including, for example, farm animals, such as sheep, pigs, cows, and horses; pet animals, such as dogs and cats; and laboratory animals, such as rats, mice and rabbits. In one embodiment, the mammal is a human.

F. KITS

The present technology provides kits for bacteria identification and antibiotic susceptibility profiling.

In one aspect, the kits of the present technology comprise one or more coded/labeled vials that contain a plurality of the recombinant detector bacteriophages disclosed herein, and instructions for use. In certain embodiments, the plurality of the recombinant detector bacteriophages comprise one or more nucleic acid sequences selected from the group consisting of SEQ ID NO: 1, SEQ ID NO: 2, SEQ ID NO: 2, SEQ ID NO: 3, SEQ ID NO: 4, SEQ ID NO: 5, and SEQ ID NO: 6.

In some embodiments, each coded/labeled vial containing a plurality of recombinant detector bacteriophages corresponds to a different bacteriophage type. In other embodiments, each coded/labeled vial containing a plurality of recombinant detector bacteriophages corresponds to the same bacteriophage type. In some embodiments, each phage vial is assigned a unique code that identifies the recombinant detector bacteriophage in the phage vial, or the types of bacteria that the recombinant detector bacteriophage strain infects. The unique code can be encoded by a machine discernible pattern, such as a bar code, a QR code, an alphanumeric string, or any other pattern that can be discerned by a reader. Each unique code may be shown as, for example, a bar code sticker on a vial or container storing a corresponding recombinant detector phage sample. In some embodiments, the kit is stored under conditions that permit the preservation of the recombinant detector bacteriophages for extended periods, such as under bacteriophage-specific, controlled temperature, moisture, and pH conditions.

Additionally or alternatively, in some embodiments, the kits further comprise vials containing natural or non-natural bacterial host cells. In some embodiments, the bacterial host cells are *E. coli*. In certain embodiments, the bacterial host cells are *E. coli* strain DH10B.

The kits may also comprise software for automated analysis, containers, packages such as packaging intended for commercial sale and the like.

The kit may further comprise one or more of: wash buffers and/or reagents, hybridization buffers and/or reagents, labeling buffers and/or reagents, and detection means. The buffers and/or reagents are usually optimized for the particular detection technique for which the kit is intended. Protocols for using these buffers and reagents for performing different steps of the procedure may also be included in the kit. Further optional components of the kits may include expression media for gene products encoded by the recombinant detector phages disclosed herein, such as a medium containing nutrients and cofactors for bioluminescence, devices such as a lamp configured to illuminate at specific wavelengths of light to detect biofluorescence, and devices such as a photometer or photodetector.

Additionally or alternatively, the kits disclosed herein may also include coded and labeled vials that contain a plurality of antibiotics. In some embodiments, the plurality of antibiotics comprises one or more of rifampicin, tetracycline, levofloxacin, and ampicillin. Other examples of antibiotics include penicillin G, methicillin, oxacillin, amoxicillin, cefadroxil, ceforanid, cefotaxime, ceftriaxone, doxycycline, minocycline, amikacin, gentamycin, kanamycin, neomycin, streptomycin, tobramycin, azithromycin, clarithromycin, erythromycin, ciprofloxacin, lomefloxacin, norfloxacin, chloramphenicol, clindamycin, cycloserine, isoniazid, rifampin, teicoplanin, quinupristin/dalfopristin, linezolid, pristinamycin, ceftobiprole, ceftaroline, dalbavancin, daptomycin, mupirocin, oritavancin, tedizolid, telavancin, tigecycline, ceftazidime, cefepime, piperacillin, ticarcillin, virginiamycin, netilmicin, paromomycin, spectinomycin, geldanamycin, herbimycin, rifaximin, loracarbef, ertapenem, doripenem, imipenem/cilastatin, meropenem, cefazolin, cefalotin, cephalexin, cefaclor, cefamandole, cefoxitin, cefprozil, cefuroxime, cefixime, cefdinir, cefditoren, cefoperazone, cefpodoxime, ceftibuten, ceftizoxime, lincomycin, dirithromycin, roxithromycin, troleandomycin, telithromycin, spiramycin, aztreonam, furazolidone, nitrofurantoin, posizolid, radezolid, torezolid, azlocillin, carbenicillin, cloxacillin, dicloxacillin, flucloxacillin, mezlocillin, nafcillin, penicillin V, temocillin, bacitracin, colistin, polymyxin B, enoxacin, gatifloxacin, gemifloxacin, moxifloxacin, nalidixic acid, ofloxacin, trovafloxacin, grepafloxacin, sparfloxacin, temafloxacin, mafenide, sulfacetamide, sulfadiazine, silver sulfadiazine, sulfadimethoxine, sulfamethizole, sulfamethoxazole, sulfanilimide, sulfasalazine, sulfisoxazole, trimethoprim-sulfamethoxazole (Co-trimoxazole) (TMP-SMX), sulfonamidochrysoidine, demeclocycline, oxytetracycline, clofazimine, dapsone, capreomycin, ethambutol, ethionamide, pyrazinamide, rifabutin, rifapentine, arsphenamine, fosfomycin, fusidic acid, metronidazole, platensimycin, thiamphenicol, tinidazole, trimethoprim(Bs) and vancomycin.

G. EXAMPLES

Example 1: Use of Recombinant Detector Bacteriophage Strain T7 NanoLuc® in Detecting Bacteria and Determining Antibiotic Susceptibility Profile This Example demonstrates that the recombinant detector bacteriophage strains disclosed herein are useful in methods for bacteria identification and antibiotic susceptibility profiling.

FIG. 4 shows a heterologous nucleic acid sequence that was inserted near the NheI site in the recombinant detector T7 bacteriophage (SEQ ID NO: 1). FIG. 15 shows the heterologous nucleic acid sequence that was inserted near the SwaI site in the recombinant detector T7 phage (SEQ ID NO: 6). The complete genome sequence of the DLPECO2 strain, a recombinant T7 phage that contains a double insertion of the NanoLuc® reporter gene, is shown in FIGS. 5A-5K (SEQ ID NO: 2).

T7 bacteriophage DNA was extracted from a clarified phage lysate using the Zymo ZR Viral DNA Kit (Cat no. D3015) (Zymo Research, Irvine, Calif.). About 100 ng of T7 phage DNA was digested with the restriction enzyme SwaI (NEB R0604) (New England Biolabs, Ipswich, Mass.) according to the manufacturer's specifications. A gBlock (synthesized by Integrated DNA Technologies, Coralville, Iowa) containing the NanoLuc® gene surrounded by 60 bp of homology to the viral genome was inserted into the SwaI cut site by Gibson Assembly® (New England Biolabs, Ipswich, Mass.).

2 µl of the resulting T7/NanoLuc® fusion product was electroporated into NEB100 cells (NEB C3030K) (New England Biolabs, Ipswich, Mass.). Cells were plated on LB agar with a 0.65% soft agar overlay. After incubation at 37° C. overnight, isolated plaques were selected and screened for NanoLuc® insertion via PCR using primers that flanked the NanoLuc® insertion site. After a recombinant T7 phage with a single NanoLuc® insertion at the SwaI site was isolated, a second NanoLuc® insertion was made at the NheI restriction site (NEB R0131) (New England Biolabs, Ipswich, Mass.) using the cloning protocol outlined above. After incubation at 37° C. overnight, isolated plaques were selected and screened for the second NanoLuc® insertion via PCR using primers that flanked the second NanoLuc® insertion site (i.e., spanned the junction between NanoLuc® and phage genomic DNA).

Figure 6:
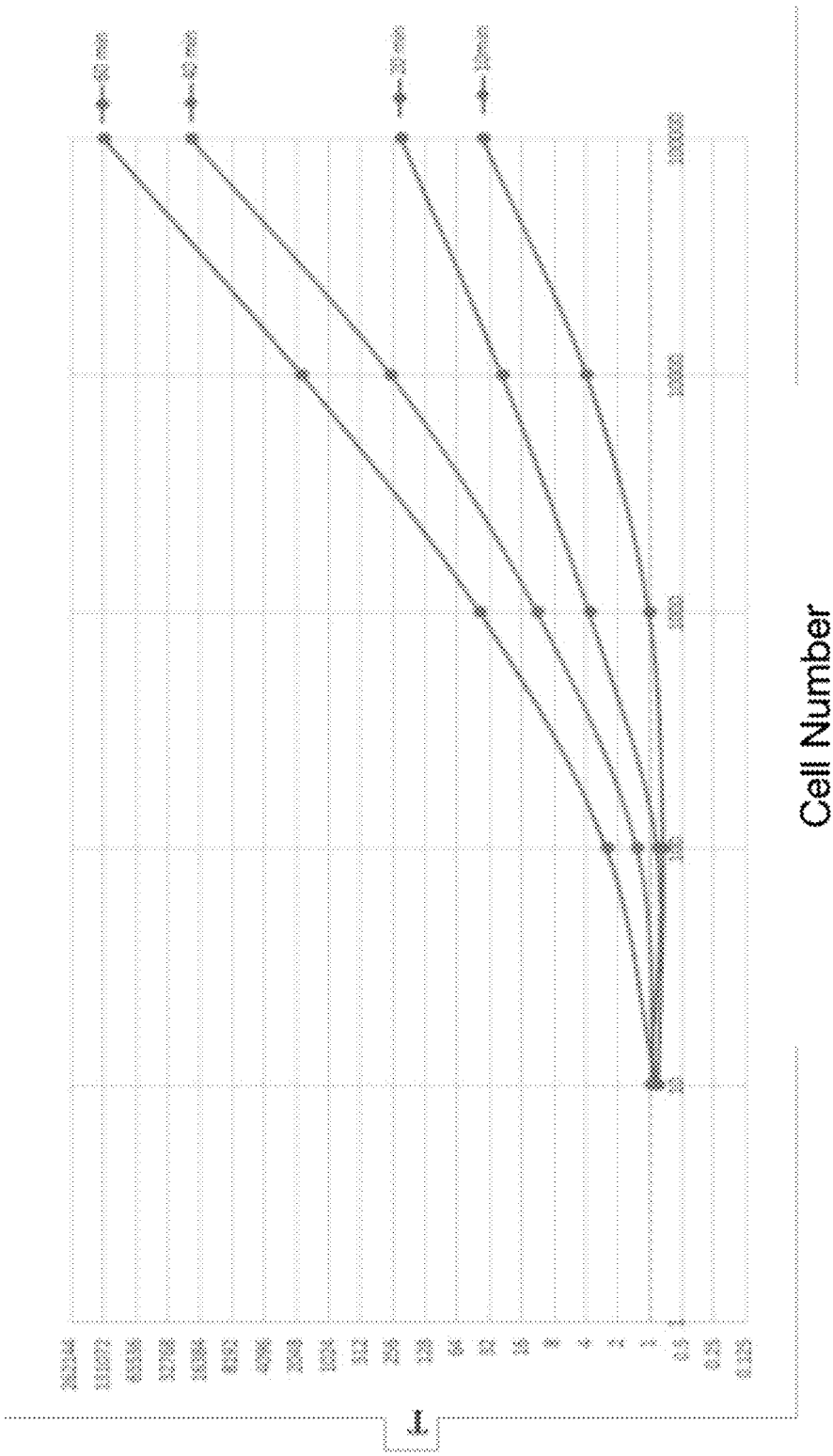
FIG. 6 shows the relative light units (RLU) produced by bacterial host cells infected with the recombinant detector phage strain DLPECO2 over time at different bacterial host cell concentrations. Signal at 10, 20, 40, and 60 minutes after contact with the recombinant detector bacteriophage was measured. Detection of NanoLuc® expression is defined as T.

NanoLuc® production was evaluated by infecting bacterial host cells with recombinant detector phage strain DLPECO2 and measuring luminescence between 10-60 minutes at different bacterial host cell concentrations. FIG. 6 demonstrates that the intensity of the NanoLuc® signal produced by bacterial host cells infected with the recombinant detector phage strain DLPECO2 was dependent on bacterial cell concentration and time.

Figure 11:
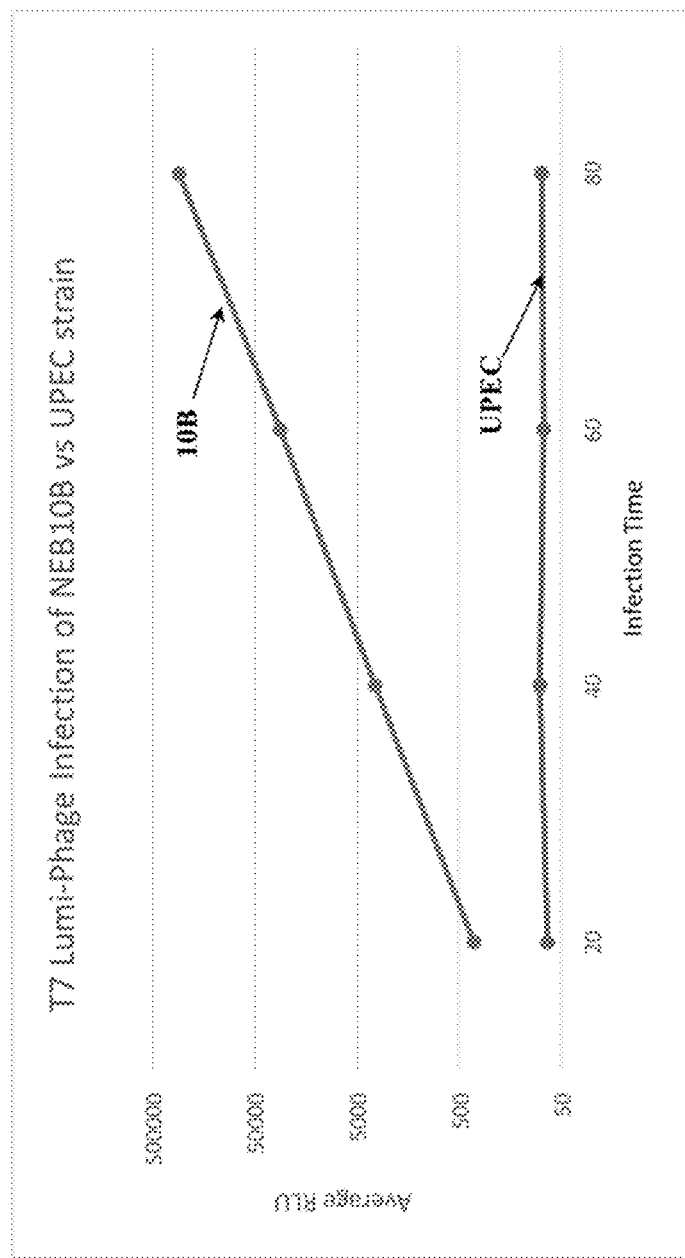
FIG. 11 shows the specific host range of the recombinant detector phage strain DLPECO2.

To ensure that NanoLuc® production was specific to a bacterial host cell that could be infected by T7 phage, DH10B cells (which are the normal T7 host) were infected in parallel with the uropathogenic *E. coli* strain UPEC, which cannot be infected by T7. FIG. 11 shows that luminescence was detected in the infected DH10B cells, whereas no luminescence was detected in UPEC. These results demonstrate that the recombinant detector bacteriophage strains disclosed herein are useful in methods for bacteria identification.

| Strain Name | Phage Type | Phage Family | Heterologous reporter | Host Range | Modifications to Phage Genomes |
|---|---|---|---|---|---|
| DLPECO2 | T7 | Podoviridae | Nanoluciferase | K12 E. coli | NheI insertion into DLPECO1 |

Figure 7:
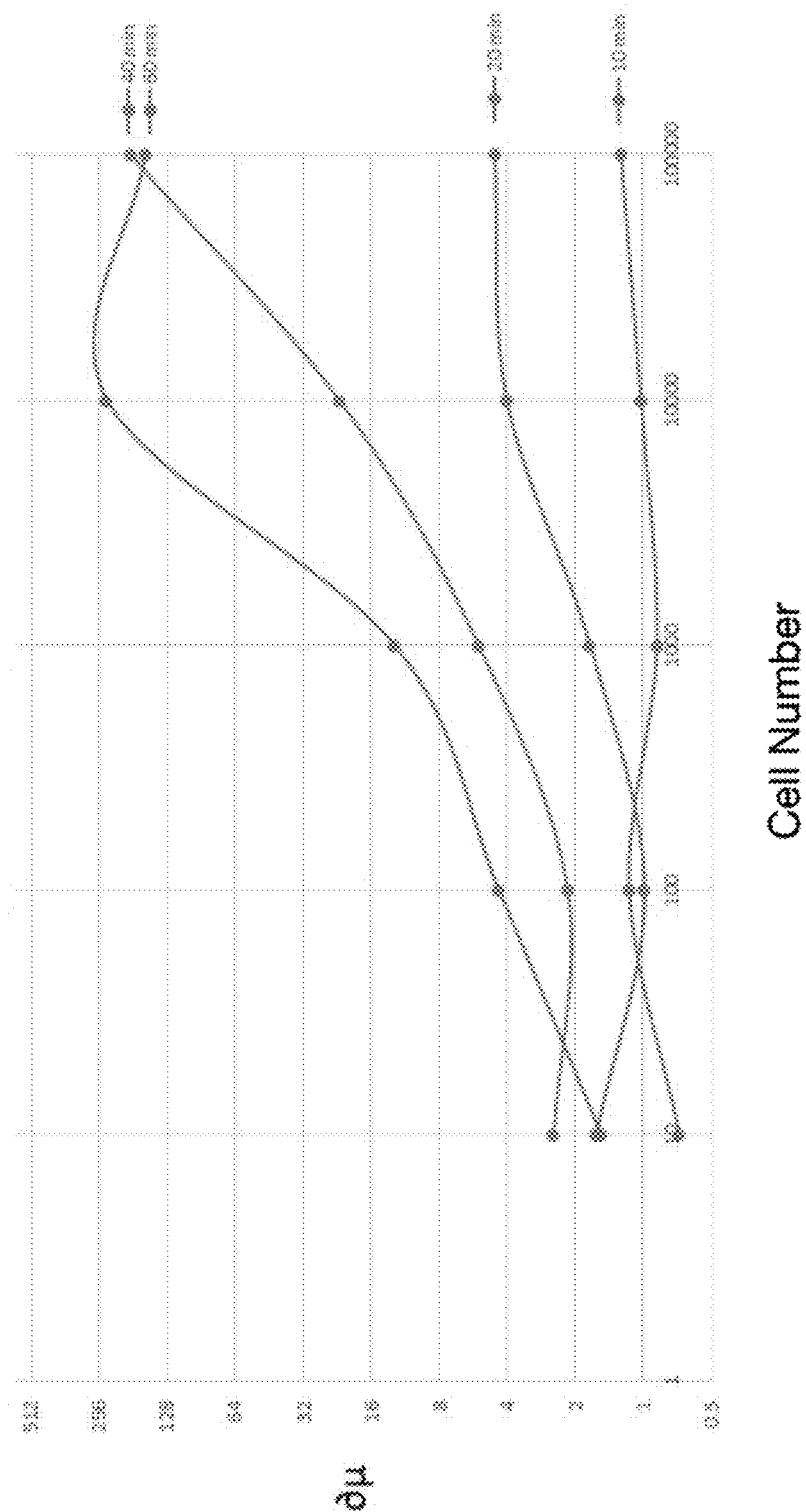
FIG. 7 shows the signal separation between a sensitive and a resistant *Escherichia coli* (*E. coli*) strain infected with the recombinant detector phage strain DLPECO2 (represented as δμ) after treatment with rifampicin, an RNA synthesis inhibitor. Signal at 10, 20, 40, and 60 minutes after contact with the recombinant detector bacteriophage was measured.
Figure 8:
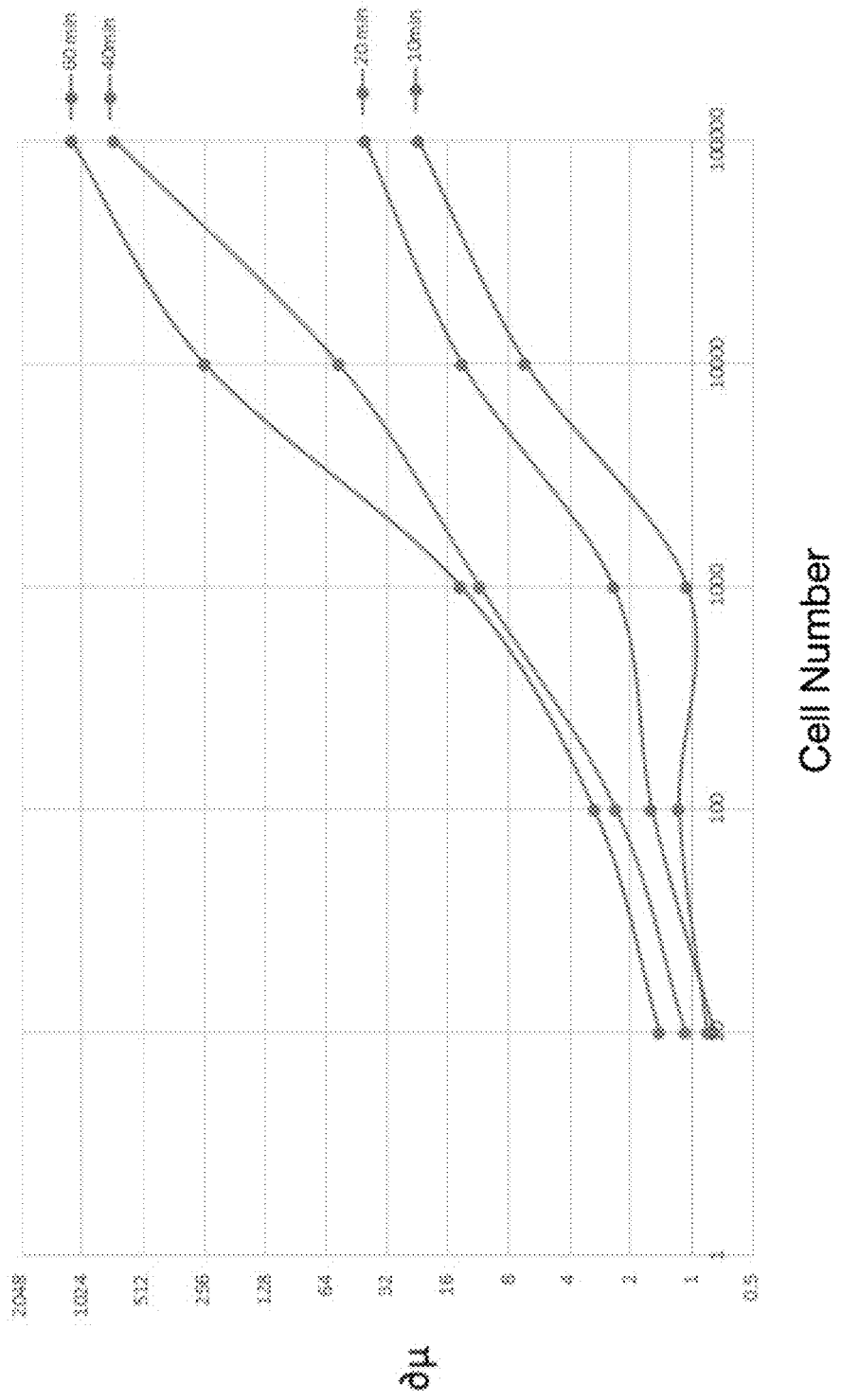
FIG. 8 shows the signal separation between a sensitive and a resistant *E. coli* strain (represented as δμ) infected with the recombinant detector phage strain DLPECO2 after treatment with tetracycline, a protein synthesis inhibitor. Signal at 10, 20, 40, and 60 minutes after contact with the recombinant detector bacteriophage was measured.

FIG. 7 shows the signal separation between a sensitive and a resistant E. coli strain infected with the recombinant detector phage strain DLPECO2 (represented as δμ) after treatment with rifampicin, an RNA synthesis inhibitor. FIG. 8 shows the signal separation between a sensitive and a resistant E. coli strain (represented as δμ) infected with the recombinant detector phage strain DLPECO2 after treatment with tetracycline, a protein synthesis inhibitor.

Figure 9:
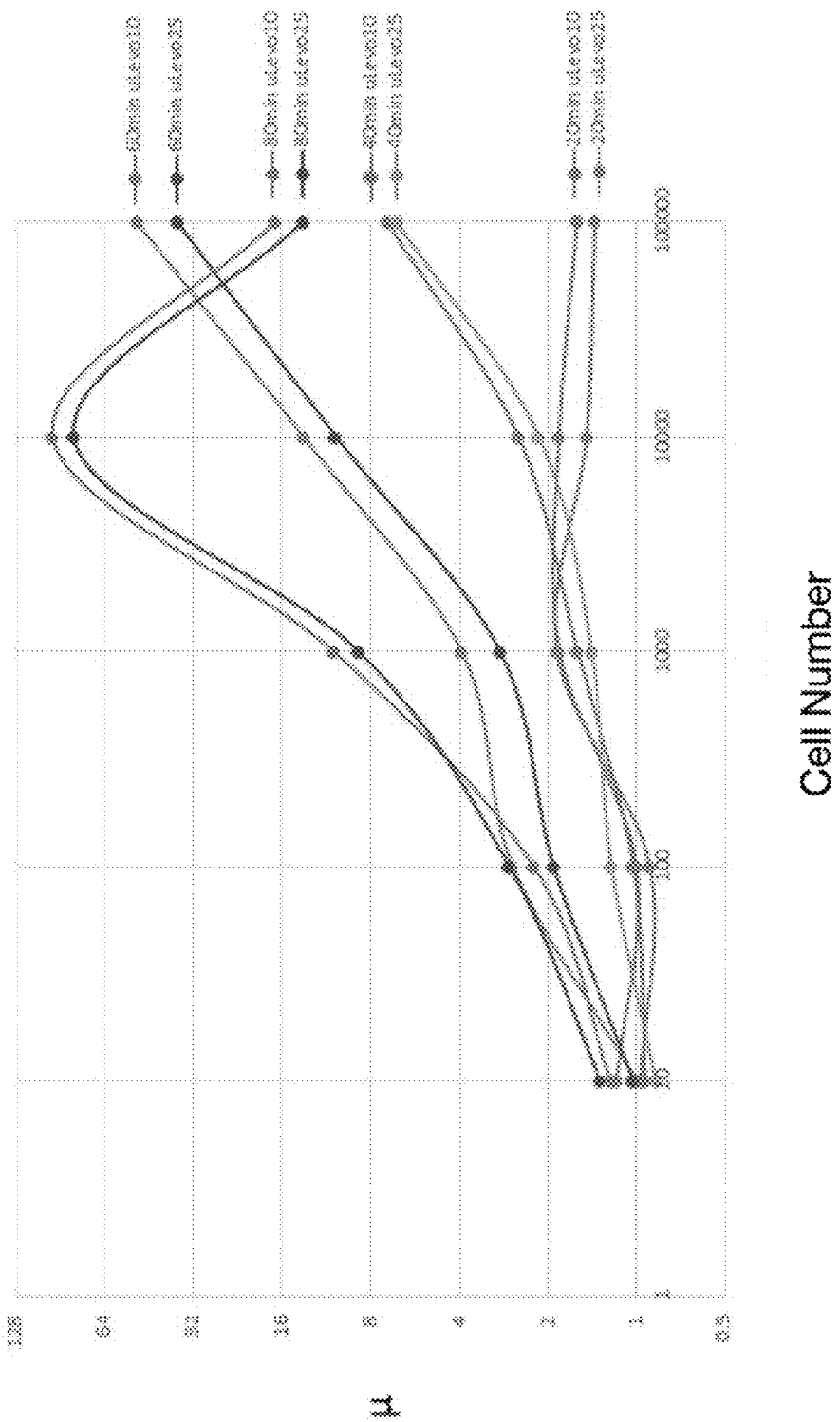
FIG. 9 shows the signal separation between untreated bacterial cells and treated bacterial cells (10 or 25 μg/ml levofloxacin) infected with the recombinant detector phage strain DLPECO2 (designated as μ). Signal at 20, 40, 60, and 80 minutes after contact with the recombinant detector bacteriophage at each levofloxacin concentration was measured.
Figure 10:
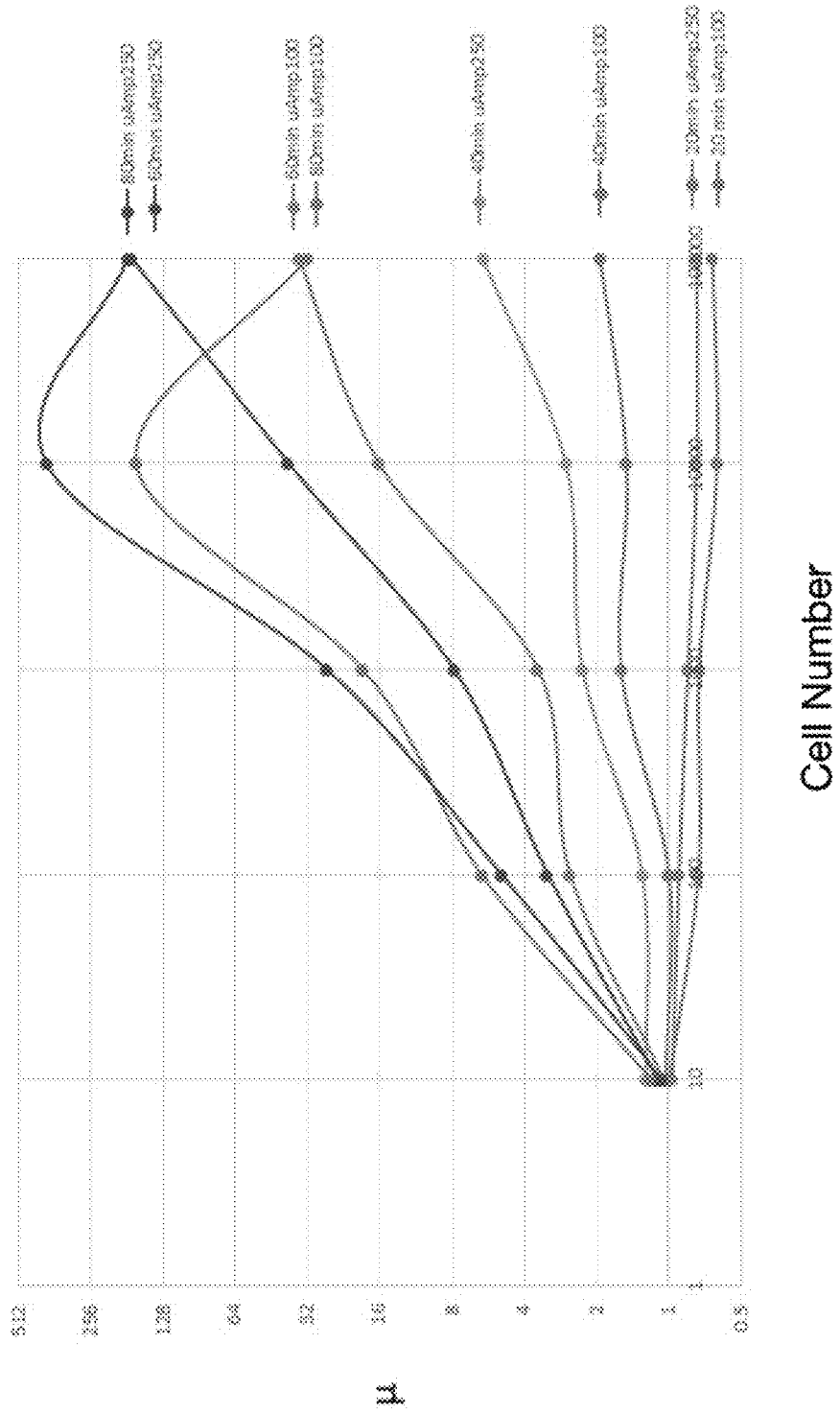
FIG. 10 shows the signal separation between untreated bacterial cells and treated bacterial cells (100 or 250 μg/ml ampicillin) infected with the recombinant detector phage strain DLPECO2 (designated as μ). Signal at 20, 40, 60, and 80 minutes after contact with the recombinant detector bacteriophage at each ampicillin concentration was measured.

FIG. 9 shows the signal separation between untreated bacterial cells and treated bacterial cells (10 or 25 μg/ml levofloxacin) infected with the recombinant detector phage strain DLPECO2 (designated as μ). FIG. 10 shows the signal separation between untreated bacterial cells and treated bacterial cells (100 or 250 μg/ml ampicillin) infected with the recombinant detector phage strain DLPECO2 (designated as μ).

Taken together, FIGS. 6-10 demonstrate that the recombinant detector bacteriophage strains disclosed herein are useful in methods for antibiotic susceptibility profiling.

Accordingly, the methods disclosed herein are useful in methods for bacteria identification and antibiotic susceptibility profiling.

H. EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

What is claimed:

1. A method comprising:
providing a microfluidic cartridge comprising:
a separator comprising a collection outlet and a waste outlet, and configured to direct bacterial cells and plasma of a blood sample to flow into the collection outlet, and to direct other components of the blood sample to flow into the waste outlet,
a plurality of incubation reservoirs configured to be fluidically coupled with the collection outlet and with a plurality of detection chambers of the microfluidic cartridge, and
a phage reservoir fluidically coupled to one or more of the plurality of incubation reservoirs, the phage reservoir storing a test solution comprising at least one recombinant detector bacteriophage comprising a reporter gene;
receiving, at an inlet of the microfluidic cartridge, the blood sample comprising the bacterial cells, the plasma, and a plurality of the other components;
separating, by the separator of the microfluidic cartridge, the bacterial cells of the blood sample into the collection outlet of the separator and the plurality of the other components into the waste outlet of the separator;
causing a portion of the bacterial cells to flow with a portion of the plasma into at least one of the plurality of incubation reservoirs of the microfluidic cartridge;
causing the test solution comprising the at least one recombinant detector bacteriophage comprising the reporter gene to flow from the phage reservoir of the microfluidic cartridge into at least one of the plurality of incubation reservoirs; and
detecting a signal generated by an expression of the reporter gene responsive to the bacterial cells being infected with the at least one recombinant detector bacteriophage.

2. The method of claim 1, further comprising:
collecting the bacterial cells in the plurality of incubation reservoirs of the microfluidic cartridge;
introducing the test solution into the plurality of incubation reservoirs of the microfluidic cartridge;
incubating the bacterial cells for a predetermined amount of time; and
causing the portion of the bacterial cells to flow from the plurality of incubation reservoirs of the microfluidic cartridge into the plurality of detection chambers of the microfluidic cartridge.

3. The method of claim 1, further comprising:
introducing an antibiotic into the microfluidic cartridge; and
introducing a lysis reagent into the microfluidic cartridge.

4. The method of claim 1, further comprising:
applying an acoustic wave across the separator of the microfluidic cartridge, the acoustic wave driving the plurality of the other components towards an aggregation axis of the separator of the microfluidic cartridge.

5. The method of claim 1, further comprising counting a number of the bacterial cells flowing through a microfluidic channel of the microfluidic cartridge coupled with the collection outlet with one of a laser-based flow cytometer or an impedance-based flow cytometer.

6. The method of claim 5, further comprising concentrating the bacterial cells within a concentrator of the microfluidic cartridge coupled between the separator and the microfluidic channel.

7. The method of claim 1, wherein the signal generated by the expression of the reporter gene comprises at least one of a luminescent signal, a fluorescent signal, or a chromagraphic signal.

8. The method of claim 1, further comprising entrapping a plurality of the bacterial cells in one or more of the plurality of detection chambers, and detecting an amount of light when the plurality of the bacterial cells are entrapped.

9. The method of claim 3, further comprising enhancing detection of expression of the reporter gene by removing non-bacterial cells which lack cell walls.

10. The method of claim 6, further comprising:
causing the bacterial cells concentrated within the concentrator to exit the concentrator and enter the microfluidic channel,
wherein the concentrator is configured to increase a bacterial concentration within an existing fluid flow by a factor of between about 5 and about 100.

11. The method of claim 4, wherein:
the separator includes:
- an aggregation channel structured such that the aggregation axis extends along at least a portion of the aggregation channel, and
- legs bifurcated from the aggregation channel, and the method further comprises causing the bacterial cells to exit the separator through the collection outlet and the legs.

* * * * *